US011965209B2

(12) United States Patent
Thisted et al.

(10) Patent No.: US 11,965,209 B2
(45) Date of Patent: Apr. 23, 2024

(54) METHOD FOR OBTAINING STRUCTURAL INFORMATION CONCERNING AN ENCODED MOLECULE AND METHOD FOR SELECTING COMPOUNDS

(71) Applicant: NUEVOLUTION A/S, Copenhagen (DK)

(72) Inventors: Thomas Thisted, Frederikssund (DK); Mikkel Dybro Lundorf, Copenhagen (DK); Per-Ola Freskgard, Norrkorping (SE); Torben Ravn Rasmussen, Ballerup (DK)

(73) Assignee: NUEVOLUTION A/S, Copenhagen (DK)

( * ) Notice: Subject to any disclaimer, the term of this patent is extended or adjusted under 35 U.S.C. 154(b) by 59 days.

(21) Appl. No.: 17/470,923

(22) Filed: Sep. 9, 2021

(65) Prior Publication Data

US 2022/0205027 A1    Jun. 30, 2022

Related U.S. Application Data

(63) Continuation of application No. 10/572,644, filed as application No. PCT/DK2004/000630 on Sep. 17, 2004, now Pat. No. 11,118,215.

(60) Provisional application No. 60/509,268, filed on Oct. 8, 2003, provisional application No. 60/504,748, filed on Sep. 22, 2003.

(30) Foreign Application Priority Data

Sep. 18, 2003 (DK) .......................... PA 2003 01356
Oct. 8, 2003 (DK) .......................... PA 2003 01485

(51) Int. Cl.
*C12Q 1/6837* (2018.01)
*C12N 15/10* (2006.01)
*C12Q 1/6811* (2018.01)

(52) U.S. Cl.
CPC ....... *C12Q 1/6837* (2013.01); *C12N 15/1068* (2013.01); *C12Q 1/6811* (2013.01)

(58) Field of Classification Search
CPC . C12Q 1/6837; C12Q 1/6811; C12N 15/1068
See application file for complete search history.

(56) References Cited

U.S. PATENT DOCUMENTS

| | | |
|---|---|---|
| 4,822,731 A | 4/1989 | Watson et al. |
| 5,013,830 A | 5/1991 | Ohtsuka et al. |
| 5,047,519 A | 9/1991 | Hobbs, Jr. et al. |
| 5,324,829 A | 6/1994 | Bahl et al. |
| 5,432,272 A | 7/1995 | Benner |
| 5,437,977 A | 8/1995 | Segev |
| 5,449,613 A | 9/1995 | Dordick et al. |
| 5,451,503 A | 9/1995 | Hogan et al. |
| 5,473,060 A | 12/1995 | Gryaznov et al. |
| 5,474,796 A | 12/1995 | Brennan |
| 5,476,930 A | 12/1995 | Letsinger et al. |
| 5,503,805 A | 4/1996 | Sugarman et al. |
| 5,571,677 A | 11/1996 | Gryaznov |
| 5,571,903 A | 11/1996 | Gryaznov |
| 5,573,905 A | 11/1996 | Lerner et al. |
| 5,604,097 A | 2/1997 | Brenner |
| 5,635,400 A | 6/1997 | Brenner |
| 5,639,603 A | 6/1997 | Dower et al. |
| 5,643,722 A | 7/1997 | Rothschild et al. |

(Continued)

FOREIGN PATENT DOCUMENTS

| | | |
|---|---|---|
| DE | 196 46 372 | 6/1997 |
| DE | 196 42 751 | 4/1998 |

(Continued)

OTHER PUBLICATIONS

Ligase, Answers.com: http://www.answers.com/topic/ligase, [accessed Dec. 10, 2009].

(Continued)

*Primary Examiner* — Sahana S Kaup
(74) *Attorney, Agent, or Firm* — Merchant & Gould P.C.

(57) ABSTRACT

In one aspect, the present invention relates to a method for obtaining structural information about an encoded molecule. The encoded molecule may be produced by a reaction of a plurality of chemical entities and may be capable of being connected to an identifier oligonucleotide containing codons informative of the identity of the chemical entities which have participated in the formation of the encoded molecule. In a certain embodiment, primers are designed complementary to the codons appearing on the identifier oligonucleotide, and the presence, absence or relative abundance of a codon is evaluated by mixing a primer with the identifier oligonucleotide in the presence of a polymerase and substrate (deoxy)ribonucleotide triphosphates measuring the extension reaction. In another aspect, the invention provides a method for selecting compounds which binds to a target. More specifically, the invention relates to a method in which a target associated with an oligonucleotide initially is mixed with a library of complexes, each complex comprising a display molecule and an oligonucleotide identifying said display molecule. Next, due an increased proximity, the target oligonucleotide is coupled to the identifier oligonucleotide of complexes having a display molecule with affinity towards the target. In a final stage the coupled nucleotides are analyzed to deduce at least the identity of the display molecule.

20 Claims, 14 Drawing Sheets

Specification includes a Sequence Listing.

(56) References Cited

U.S. PATENT DOCUMENTS

| | | | |
|---|---|---|---|
| 5,646,265 A | 7/1997 | McGee |
| 5,654,413 A | 8/1997 | Brenner |
| 5,656,739 A | 8/1997 | Cubicciotti |
| 5,663,046 A | 9/1997 | Baldwin et al. |
| 5,665,975 A | 9/1997 | Kedar |
| 5,670,633 A | 9/1997 | Cook et al. |
| 5,681,943 A | 10/1997 | Letsinger et al. |
| 5,684,169 A | 11/1997 | Hamada et al. |
| 5,686,243 A | 11/1997 | Royer et al. |
| 5,708,153 A | 1/1998 | Dower et al. |
| 5,723,320 A | 3/1998 | Dehlinger |
| 5,723,598 A * | 3/1998 | Lerner .................. C07H 21/00 530/335 |
| 5,739,314 A | 4/1998 | Roy et al. |
| 5,739,386 A | 4/1998 | Holmes et al. |
| 5,741,643 A | 4/1998 | Gryaznov et al. |
| 5,763,175 A | 6/1998 | Brenner |
| 5,763,263 A | 6/1998 | Dehlinger |
| 5,770,358 A | 6/1998 | Dower et al. |
| 5,770,455 A | 6/1998 | Cargill et al. |
| 5,780,613 A | 7/1998 | Letsinger et al. |
| 5,789,162 A | 8/1998 | Dower et al. |
| 5,789,172 A | 8/1998 | Still et al. |
| 5,795,976 A | 8/1998 | Oefner et al. |
| 5,804,563 A | 9/1998 | Still et al. |
| 5,817,795 A | 10/1998 | Gryaznov et al. |
| 5,824,471 A | 10/1998 | Mashal et al. |
| 5,830,658 A | 11/1998 | Gryaznov |
| 5,840,485 A | 11/1998 | Lebl et al. |
| 5,843,650 A | 12/1998 | Segev |
| 5,843,701 A | 12/1998 | Gold et al. |
| 5,846,719 A | 12/1998 | Brenner et al. |
| 5,849,482 A | 12/1998 | Meyer, Jr. |
| 5,880,972 A | 3/1999 | Horlbeck |
| 5,910,408 A | 6/1999 | Szostak |
| 5,942,609 A | 8/1999 | Hunkapiller |
| 5,948,648 A | 9/1999 | Khan et al. |
| 6,001,579 A | 12/1999 | Still et al. |
| 6,056,926 A | 5/2000 | Sugarman et al. |
| 6,060,596 A | 5/2000 | Lerner et al. |
| 6,087,112 A | 7/2000 | Dale |
| 6,090,912 A | 7/2000 | Lebl et al. |
| 6,096,500 A | 8/2000 | Oprandy et al. |
| 6,096,875 A | 8/2000 | Khan et al. |
| 6,127,533 A | 10/2000 | Cook et al. |
| 6,132,970 A | 10/2000 | Stemmer |
| 6,140,489 A | 10/2000 | Brenner |
| 6,140,493 A | 10/2000 | Dower et al. |
| 6,143,497 A | 11/2000 | Dower et al. |
| 6,143,503 A | 11/2000 | Baskerville et al. |
| 6,150,516 A | 11/2000 | Brenner et al. |
| 6,165,717 A | 12/2000 | Dower et al. |
| 6,165,778 A | 12/2000 | Kedar |
| 6,172,214 B1 | 1/2001 | Brenner |
| 6,194,550 B1 | 2/2001 | Gold |
| 6,197,555 B1 | 3/2001 | Khan et al. |
| 6,207,446 B1 | 3/2001 | Szostak et al. |
| 6,210,900 B1 | 4/2001 | Yamashita et al. |
| 6,232,066 B1 | 5/2001 | Felder et al. |
| 6,235,475 B1 | 5/2001 | Brenner et al. |
| 6,235,889 B1 | 5/2001 | Ulanovsky |
| 6,248,568 B1 | 6/2001 | Khan et al. |
| 6,274,385 B1 | 8/2001 | Hochlowski et al. |
| 6,287,765 B1 | 9/2001 | Cubicciotti |
| 6,297,053 B1 | 10/2001 | Stemmer |
| 6,306,587 B1 | 10/2001 | Royer et al. |
| 6,352,828 B1 | 3/2002 | Brenner |
| 6,416,949 B1 | 7/2002 | Dower et al. |
| 6,429,300 B1 | 8/2002 | Kurz et al. |
| 6,479,264 B1 | 11/2002 | Louwrier |
| 6,503,759 B1 | 1/2003 | Still et al. |
| 6,514,736 B1 | 2/2003 | Erlich et al. |
| 6,537,776 B1 | 3/2003 | Short |
| 6,593,088 B1 | 7/2003 | Saito et al. |
| 6,613,508 B1 | 9/2003 | Ness et al. |
| 6,620,584 B1 | 9/2003 | Chee et al. |
| 6,620,587 B1 | 9/2003 | Taussig et al. |
| 6,780,981 B1 | 8/2004 | Southern et al. |
| 6,936,477 B2 | 8/2005 | Still et al. |
| 7,070,928 B2 | 7/2006 | Liu et al. |
| 7,223,545 B2 | 5/2007 | Liu et al. |
| 7,413,854 B2 | 8/2008 | Pedersen et al. |
| 7,442,160 B2 | 10/2008 | Liu et al. |
| 7,479,472 B1 | 1/2009 | Harbury et al. |
| 7,491,494 B2 | 2/2009 | Liu et al. |
| 7,557,068 B2 | 7/2009 | Liu et al. |
| 7,704,925 B2 | 4/2010 | Gouliaev et al. |
| 7,727,713 B2 | 6/2010 | Pedersen et al. |
| 7,771,935 B2 | 8/2010 | Liu et al. |
| 7,915,201 B2 | 3/2011 | Franch et al. |
| 7,998,904 B2 | 8/2011 | Liu et al. |
| 8,206,901 B2 | 6/2012 | Freskgard et al. |
| 2002/0048760 A1 | 4/2002 | Drmanac et al. |
| 2002/0055125 A1 | 5/2002 | Charych et al. |
| 2002/0064779 A1 * | 5/2002 | Landegren .......... G01N 33/542 435/7.1 |
| 2002/0072887 A1 | 6/2002 | Szalma et al. |
| 2002/0081714 A1 | 6/2002 | Jain et al. |
| 2002/0115068 A1 | 8/2002 | Tomlinsen et al. |
| 2002/0127598 A1 | 9/2002 | Zhou et al. |
| 2002/0142335 A1 | 10/2002 | Strittmatter et al. |
| 2002/0147133 A1 | 10/2002 | Briesewitz et al. |
| 2003/0004122 A1 | 1/2003 | Beigelman et al. |
| 2003/0050453 A1 | 3/2003 | Sorge |
| 2003/0113738 A1 | 6/2003 | Liu et al. |
| 2003/0182068 A1 | 9/2003 | Battersby et al. |
| 2003/0186233 A1 | 10/2003 | Chesnut et al. |
| 2003/0187240 A1 | 10/2003 | Cook et al. |
| 2004/0049008 A1 | 3/2004 | Pedersen et al. |
| 2004/0110213 A1 | 6/2004 | Namsaraev |
| 2004/0161741 A1 | 8/2004 | Rabani et al. |
| 2004/0185484 A1 | 9/2004 | Costa et al. |
| 2004/0191812 A1 | 9/2004 | Davydova et al. |
| 2004/0197804 A1 | 10/2004 | Keefe et al. |
| 2004/0197845 A1 | 10/2004 | Hassibi et al. |
| 2004/0209282 A1 | 10/2004 | Ault-Riche et al. |
| 2005/0025766 A1 | 2/2005 | Liu et al. |
| 2005/0042669 A1 | 2/2005 | Liu et al. |
| 2005/0130173 A1 | 6/2005 | Leamon et al. |
| 2005/0142583 A1 | 6/2005 | Liu et al. |
| 2005/0158765 A1 | 7/2005 | Morgan et al. |
| 2005/0170376 A1 | 8/2005 | Liu et al. |
| 2006/0099592 A1 | 5/2006 | Freskgard et al. |
| 2006/0121470 A1 | 6/2006 | Pedersen |
| 2006/0234231 A1 | 10/2006 | Freskgard et al. |
| 2006/0246450 A1 | 11/2006 | Franch et al. |
| 2006/0269920 A1 | 11/2006 | Freskgard et al. |
| 2006/0292603 A1 | 12/2006 | Gouliaev et al. |
| 2007/0026397 A1 | 2/2007 | Freskgard et al. |
| 2007/0042401 A1 | 2/2007 | Morgan et al. |
| 2007/0224607 A1 | 9/2007 | Morgan et al. |
| 2008/0193983 A1 | 8/2008 | Gouliaev et al. |
| 2008/0305957 A1 | 12/2008 | Thisted et al. |
| 2009/0035824 A1 | 2/2009 | Liu et al. |
| 2009/0143232 A1 | 6/2009 | Pedersen et al. |
| 2009/0149347 A1 | 6/2009 | Liu et al. |
| 2009/0239211 A1 | 9/2009 | Freskgard et al. |
| 2009/0264300 A1 | 10/2009 | Franch et al. |
| 2010/0016177 A1 | 1/2010 | Pedersen et al. |
| 2011/0230419 A1 | 9/2011 | Lundorf et al. |
| 2012/0028812 A1 | 2/2012 | Freskgard et al. |

FOREIGN PATENT DOCUMENTS

| | | |
|---|---|---|
| EP | 0 324 616 B1 | 7/1989 |
| EP | 0542770 | 5/1993 |
| EP | 0 604 552 B1 | 7/1994 |
| EP | 0 643 778 B1 | 3/1995 |
| EP | 0 695 305 B1 | 2/1996 |
| EP | 0766826 | 4/1997 |
| EP | 0 773 227 A1 | 5/1997 |
| EP | 0 776 330 B1 | 6/1997 |
| EP | 0778280 | 6/1997 |
| EP | 0879219 | 11/1998 |

(56) References Cited

FOREIGN PATENT DOCUMENTS

| | | |
|---|---|---|
| EP | 0962527 | 12/1999 |
| EP | 1324045 | 7/2003 |
| EP | 1402024 | 3/2004 |
| EP | 1483585 | 12/2004 |
| EP | 1514938 | 3/2005 |
| EP | 1 533 385 A1 | 5/2005 |
| EP | 1828381 | 9/2007 |
| EP | 1832567 | 9/2007 |
| EP | 2305808 | 4/2011 |
| JP | 05292967 | 11/1993 |
| JP | 08000268 | 1/1996 |
| WO | WO 90/05785 A1 | 5/1990 |
| WO | WO 91/05058 A1 | 4/1991 |
| WO | WO 1991/19818 | 12/1991 |
| WO | WO 1992/00091 | 1/1992 |
| WO | WO 1992/02536 | 2/1992 |
| WO | WO 1992/22875 | 12/1992 |
| WO | WO 93/03172 A1 | 2/1993 |
| WO | WO 1993/06121 | 4/1993 |
| WO | WO 1994/08051 | 4/1994 |
| WO | WO 1994/13623 | 6/1994 |
| WO | WO 1994/24143 | 10/1994 |
| WO | WO 1995/04160 | 2/1995 |
| WO | WO 1995/06293 | 3/1995 |
| WO | WO 95/12608 A1 | 5/1995 |
| WO | WO 1996/03418 | 2/1996 |
| WO | WO 96/09316 A1 | 3/1996 |
| WO | WO 96/12014 A1 | 4/1996 |
| WO | WO 1996/11878 | 4/1996 |
| WO | WO 1996/24061 | 8/1996 |
| WO | WO 1996/24847 | 8/1996 |
| WO | WO 96/35699 A1 | 11/1996 |
| WO | WO 1996/40201 | 12/1996 |
| WO | WO 1996/41011 | 12/1996 |
| WO | WO 1997/04131 | 2/1997 |
| WO | WO 1997/004131 | 2/1997 |
| WO | WO 1997/11958 | 4/1997 |
| WO | WO 1997/19039 | 5/1997 |
| WO | WO 1997/27317 | 7/1997 |
| WO | WO 1997/35198 | 9/1997 |
| WO | WO 1998/01562 | 1/1998 |
| WO | WO 98/31700 A1 | 7/1998 |
| WO | WO 1998/47613 | 10/1998 |
| WO | WO 98/56904 A1 | 12/1998 |
| WO | WO 1998/58256 | 12/1998 |
| WO | WO 1999/42605 | 8/1999 |
| WO | WO 99/51773 A1 | 10/1999 |
| WO | WO 1999/51546 | 10/1999 |
| WO | WO 1999/64378 | 12/1999 |
| WO | WO 00/21909 A2 | 4/2000 |
| WO | WO 00/23456 A1 | 4/2000 |
| WO | WO 2000/020639 | 4/2000 |
| WO | WO 2000/23458 | 4/2000 |
| WO | WO 202000023548 | 4/2000 |
| WO | WO 2000/24882 | 5/2000 |
| WO | WO 00/32823 A1 | 6/2000 |
| WO | WO 2000/40695 | 7/2000 |
| WO | WO 00/47775 A1 | 8/2000 |
| WO | WO 00/61775 A1 | 10/2000 |
| WO | WO 01/00876 A1 | 1/2001 |
| WO | WO 2001/07657 | 2/2001 |
| WO | WO 2001/07690 | 2/2001 |
| WO | WO 01/53539 A1 | 7/2001 |
| WO | WO 2001/56955 | 8/2001 |
| WO | WO 2001/90414 | 11/2001 |
| WO | WO 2002/03067 | 1/2002 |
| WO | WO 2002/10186 | 2/2002 |
| WO | WO 2002/34948 | 5/2002 |
| WO | WO 2002/40664 | 5/2002 |
| WO | WO 02/074929 A1 | 9/2002 |
| WO | WO 2002/074929 | 9/2002 |
| WO | WO 2002/074978 | 9/2002 |
| WO | WO 02/083951 A | 10/2002 |
| WO | WO2002090581 | 11/2002 |
| WO | WO 02/102820 A1 | 12/2002 |
| WO | WO 02/103008 A2 | 12/2002 |
| WO | WO 2002/099078 | 12/2002 |
| WO | WO 2002/103008 | 12/2002 |
| WO | WO-02103008 A2 * | 12/2002 ........... C07D 405/04 |
| WO | WO 2003/008972 | 1/2003 |
| WO | WO 03/025567 A2 | 3/2003 |
| WO | WO 2003/062417 | 7/2003 |
| WO | WO 03/078050 A2 | 9/2003 |
| WO | WO 03/078445 A2 | 9/2003 |
| WO | WO 03/078446 A2 | 9/2003 |
| WO | WO 03/078625 A2 | 9/2003 |
| WO | WO 03/078626 A2 | 9/2003 |
| WO | WO 03/078627 A2 | 9/2003 |
| WO | WO 03/082901 A2 | 10/2003 |
| WO | WO 2004/001042 A2 | 12/2003 |
| WO | WO 2004/009814 A1 | 1/2004 |
| WO | WO 2004/013070 A2 | 2/2004 |
| WO | WO 2004/016767 A2 | 2/2004 |
| WO | WO 2004/024929 | 3/2004 |
| WO | WO 2004/024929 A2 | 3/2004 |
| WO | WO-2004024929 A2 * | 3/2004 ......... C12N 15/1068 |
| WO | WO 2004/039825 A2 | 5/2004 |
| WO | WO 2004/056994 A2 | 7/2004 |
| WO | WO 2004/074429 A2 | 9/2004 |
| WO | WO 2004/074501 A2 | 9/2004 |
| WO | WO 2004/083427 A2 | 9/2004 |
| WO | WO 2004/099441 A2 | 11/2004 |
| WO | WO 2004/110964 A2 | 12/2004 |
| WO | WO 2005/003778 A2 | 1/2005 |
| WO | WO 2005/008240 | 1/2005 |
| WO | WO 2005/026387 A1 | 3/2005 |
| WO | WO 2006/048025 A1 | 5/2006 |
| WO | WO 2006/053571 A2 | 5/2006 |
| WO | WO 2007/053358 | 5/2007 |
| WO | WO 2007/062664 | 6/2007 |
| WO | WO 2007/124758 | 11/2007 |
| WO | WO 2008/014238 | 1/2008 |
| WO | WO 2008/036273 | 3/2008 |
| WO | WO 2008/054600 | 5/2008 |
| WO | WO2008/094599 | 8/2008 |
| WO | WO 2009/018003 | 2/2009 |
| WO | WO 2009/077173 | 6/2009 |
| WO | WO 2009/152824 | 12/2009 |
| WO | WO 2011/127933 | 10/2011 |

OTHER PUBLICATIONS

Canne et al. "Chemical Protein Synthesis by Solid Phase Ligation of Unprotected Peptide Segments", *J. Am. Chem. Soc.*, 121, 8720-8727 (1999).

Chen, et al. "Enzyme Engineering for Nonaqueous Solvents: Random Mutagenesis to Enchance Activity of Subtilisin E in Polar Organic Media"; *Bio/Technology 9*, 1073-1077 (1991)—Abstract.

Chen, et al. "Enzymes in Nonaqueous Solvents; Applications in Carbohydrate and Peptide Preparation", *Methods in Biotechnology*, vol. 15, 373-374 (2001).

Chu et al. "Ligation of oligonucleotides to nucleic acids or proteins via disulfide bonds." *Nucleic Acids Research*. vol. 16. No. 9. pp. 3671-3691 (1998).

Clark et al. "Design, synthesis and selection of DNA-encoded small-molecule libraries", *Nat Chem Biol* 5, 647 (2009).

Clark, Matthew A. "Selecting chemicals: the emerging utility of DNA-encoded libraries", *Molecular Discovery Research, GlaxoSmithKline*, Waltham, MA, USA. Current Opinion in Chemical Biology (2010), 14(3), 396-403. Publisher: Elsevier B.V.

Colombo, R. et al. "Synthesis of leucin-enkephalin and methionineenkephalin . . . ", *Hoppe-Seyler's Z.Physiol. Chem.* vol. 363 (1981).

Constantino, L et al. "Privileged structures as leads in medicinal chemistry", *Curr Med Chem* 13, 65, (2006).

Cotton, et al. "Reactivity of cytosine and thymine in single-base-pair mismatches withhydroxylamine and osmium tetroxide and its application to the study of mutations", *Proc Natl Acad Sci (US)*, 85, 4397-401 (1988).

Czarnik, A. W. "Encoding strategies in combinatorial chemistry", *Proc. Natl. Acad. Sci. USA*, vol. 94, pp. 12738-12739 (Nov. 1997).

(56) References Cited

OTHER PUBLICATIONS

Czarnik, et al. "Encoding methods for combinatorial chemistry", *Current Opinion in Chemical Biology*, vol. 1, ISS 1, p. 60-66 (Jun. 1997).

Degn, Hans, et al. "Enzyme Activity in Organic Solvent as a Function of Water Activity Determined by Membrane Inlet Mass Spectometry"; *Biotechnology Techniques* vol. 6; No. 2; pp. 161-164 (Mar./Apr. 1992).

Denapoli, et al. "PEG-supported Synthesis of Cyclic Oligodeoxyribonucleotides", *Nucleosides & Nucleotides*, vol. 12, No. 1 (1993).

DNA Phosphoramidites & CPG's; http://www.qualitysystems.com.tw/proligo/dna%20phosphoamidites%20&%20cpg's.htm Dec. 2, 2010.

Dokl Akad Nauk SSSR, vol. 258, 1242-1245, Krynetskya NF Tumanov YV (1981).

Dolinnaya, et al. "Chemical ligation as a method for the assembly of double-stranded nucleic acids: Modifications and local structure studies", *Russian Chemical Bulletin*, vol. 45, No. 8 (1996).

Dolinnaya, et al. "Structural and kinetic aspects of chemical reactions in DNA duplexes. Information on DNA local structure obtained from chemical ligation data", Nucleic Acids Research, vol. 19, No. 11, 3073-3080 (1991).

Douglas, et al. "Polymer-supported solution synthesis of oligosaccharides", J. Am. Chem. Soc., vol. 113 (1991).

Doyon, J.B et al. "Highly sensitive in vitro selections for DNA-linked synthetic small molecules with protein binding affinity and specificity", J. Am. Chem. Soc., vol. 125, 12372-12373 (2003).

Drabovich, et al. "Selection of Smart Small-Molecule Ligands: The Proof of Principle", Analytical Chemistry, vol. 81, No. 1, 490-494 (2009).

Drews "Drug Discovery: A Historical Perspective", Science vol. 287, pp. 1960-1964 (2000).

Dreyer, et al. "Enzyme Catalysis in Nonaqueous Media: Past, Present and Future" in Patel (ed.), "Biocatalysis in the Pharmaceutical and Biotechnology Industries", 819-820 (2006).

Ecker, David J, et al. "Rational screening of oligonucleotide combinatorial libraries for drug discovery", Nucleic Acids Research, vol. 21, No. 8, pp. 1853-1856 (1993).

Fack, Fred, et al. "Heteroduplex mobility assay (HMA) pre-screening: An improved strategy for the rapid identification of inserts selected from phage-displayed peptide libraries", *Molecular Diversity*, vol. 5, No. 1; pp. 7-12 (2000).

Fegan et al. "Rigid cyanine dye nucleic acid labels", *Chem Commun* May 7; (17) 2004-6 (2008).

Ficht, Simon, et al. "As Fast and Selective as Enzymatic Ligations: Upalred Nucleobases Increase the Selectivity of DNA-Controlled Native Chemical PNA Ligation"; *ChemBioChem*: vol. 6, Issue 11, pp. 2098-2103 (2005).

Fredriksson, et al. "Protein detection using proximity-dependent DNA ligation assays", *Nature Biotechnology*, vol. 20, p. 473-477 (May 2002).

Furka, A, "Combinatorial Chemistry: 20 years on . . . ", *Drug Discovery* today vol. 7, No. 1, p. 1-4 (2002).

Furka, et al. "Combinatorial Libraries by Portioning and Mixing", *Combinatorial Chemistry & High Throughput Screening*, 2, 105-122 (1999).

Geysen, et al. "Combinatorial Compound Libraries for Drug Discovery: An Ongoing Challenge", *Nature Reviews, Drug Discovery*, vol. 2, p. 222-223, (Mar. 2003).

Gorin, et al. "Reactivity-Dependent PCR: Direct, Solution-Phase in Vitro Selection for Bond Formation", *J. Am. Chem. Soc.* 131, pp. 9189-9191 (2009).

Grange, et al. "Detection of point mutations in type I collagen by RNase digestion of RNA/RNA hybrids", *Nucleic Acids Research* 18: 4227-36 (1990).

Gruen, et al. "An In Vivo Selection System for Homing Endonuclease Activity", *Nucleic Acids Research* 30, e29 (2002).

Gumport, et al. "T4 RNA Ligase as a Nucleic Acids Synthesis and Modification Reagent", *Elsevier North Holland, Inc.*, 314-345 (1981).

Guo, T. et al. "Preparation of Encoded Combinatorial Libraries for Drug Discovery", *Methods in Molecular Biology, Combinatorial Library Methods and Protocols*, pp. 23-39 (2002).

Hansen, M. "A Yoctoliter-scale DNA reactor for small-molecule evolution", *J Am Chem Soc*. 131, 1322 (2009).

Harada "In vitro selection of optimal DNS substrates for ligation by a water-soluble carbodiimide", *J Mol Evol*., 38, 6, 558-560 (1994).

Harada, et al. "In vitro selection of optimal DNA substrates for t4 RNA ligase", *Proc. Natl. Acad. Sci. USA*, vol. 90, pp. 1576-1579 (Feb. 1993).

Harada, et al. "Unexpected substrate specificity of T4 Dna ligase revealed by in vitro selection", *Nucleic Acids Research*, vol. 21, No. 10, 2287-2291 (1993).

Herpin, et al. "Synthesis of a 10000 member 1, 5-Benzodiazepine-2-one Library by the Directed Sorting Method", *J. Comb. Chem*., 2, 513-521 (2000).

Higgins, et al. "Addition of Oligonucleotides to the 5'-Terminus of DNA by T4 RNA Ligase", *Nucleic Acids Research*, 6(3): 1013-1024 (1979).

Higgins, et al. "DNA-joining Enzymes: A Review", *Methods in Enzymology*, vol. 68, pp. 50-71 (1979).

Hinton, et al. "T4 Rna Ligase Joins 2'-Deoxyribonucleoside 3', 5'-Bisphosphates to Oligodeoxyribonucleotides", *Biochemistry* vol. 17, No. 24, pp. 5091-5097 (1978).

Holmes, CP "Model Studies for New o-Nitrobenzyl Photolabile Linkers: Substituent Effects on the Rates of Photochemical Cleavage", *J. Org. Chem*. 62, 2370-2380 (1997).

Housby, Nicholas J, et al. "Fidelity of DNA ligation: a novel experimental approach based on the polymerisation of libraries of oligonucleotides", *Nucleic Acids Research*, vol. 26, No. 18, pp. 4259-4266 (1998).

Hsu "Detection of DNA point mutations with DNA mismatch repair enzymes" *Carcinogenesis* 15:1657-62 (1994).

Ito et al. Tag-reporter and Resin Capture ± Release Strategy in Oligosaccharide Synthesis. Chemistry—A European Journal 8(14):3077-3084 (2002).

James, Kenneth D. et al. "The Fidelity of Template-Directed Oligonucleotide Ligation and the Inevitability of Polymerase Function", Origins of Life and Evolution of the Biosphere 29, 1999 *Kluwer Academic Publishers*; pp. 375-390.

Janda, Kim D. "Tagged versus untagged libraries: Methods for the generation and screening of combinatorial chemical libraries", *Proc. Natl. Acad. Sci. USA*, vol. 91, pp. 10779-10785 (Nov. 1994).

Jäschke, Andres, et al. "Evolution of DNA and RNA as catalysts for chemical reactions"; Current Opinion in Chemical Biology 4; pp. 257-262 (2000).

Jäschke, et al. "Synthesis and properties of oligodeoxyribonucleotide—polyethylene glycol conjugates", *Nucleic Acids Research*, vol. 22, No. 22, pp. 4810-4817 (1994).

Jones, et al. "Enzymes in organic synthesis 22. Effects of organic solvents on horse liver alcohol dehydrogense-catalyzed reduction"; *Can. J. Chem*. 60 pp. 335-338 (1982).

Kanagawa, Takahiro Bias and Artifacts in Multitemplate Polymerase Chain Reactions (PCR), *Journal of Bioscience and Bioengineering*, vol. 96, No. 4, pp. 317-323 (2003).

Kanan, et al. "Reaction Discovery Enabled by DNA-Templated Synthesis and In Vitro Selection", Supplementary Information, pp. 1-20.

Kerr, JM et al. "Encoded Combinatorial Peptide Libraries Containing Non-Natural Amino Acids", *J. Am. Chem. Soc*.115, 2529-2531 (1993).

Kinoshita, et al. "Enzymatic Synthesis of Code Regions for Encoded Combinatorial Chemistry", *Nucleic Acids Symposium Series*, 34: 201-202 (1995).

Kinoshita, Y. et al. "Strand ligation in a double-stranded DNA by T4 RNA ligase", *Department of Functional Materials Science*, Saitama University, Urawa, Japan. Chemistry Letters (9), 797-798 (1996).

Klibanov, Alexander M. "Why are enzymes less active in organic solvent than water?"; *Trends in Biotechnology*, vol. 15, Issue 3, 97-101; 1 (Mar. 1997)—Abstract.

Krishna, Saja Hari "Developments and trends in enzyme catalysis in nonconventional media", *Biotechnology Advances*; vol. 20; Issues 3-4; pp. 239-267 (Nov. 2002)—Abstract.

(56) References Cited

OTHER PUBLICATIONS

Krug, et al. "Reversal of T4 RNA Ligase", *Biochemistry* vol. 21, No. 8, pp. 1858-1864 (1982).
Kurz, M. et al. "cDNA—protein fusions: covalent protein—gene conjugates for the in vitro selection of peptides and proteins", *ChemBioChem—A European Journal of Chemical Biology*, Wiley VCH, Weinheim, DE, vol. 2, No. 9, Sep. 3, 2001 (Sep. 3, 2001), pp. 666-672, XP002332971, ISSN: 1439-4227.
Lebl, Michal "Parallel Personal Comments on "Classical" Papers in Combinatorial Chemistry", *J. Comb. Chem.* 1, pp. 3-24 (1999).
Lehman, I.R. "DNA ligase: Structure, Mechanism, and Function; The joining of DNA chains by DNA ligase is an essential component of DNA repair, replication, and recombination", *Science* vol. 186; pp. 790-797: (1974).
Lim, Carols S. et al. "Syntehsis of DNA Dumbbells: Chemical vs. Enzymatic Ligation of Self-Complementary Oligonucleotides", Abstract only, Nucleotides and Nucleic Acids; vol. 16, Issue 1 & 2; pp. 41-51 (Jan. 1997).
Lindström; Ulf M. et al. "An orthogonal oligonucleotide protecting group strategy that enables assembly of repetitive or highly structured DNAs"; *Nucleic Acids Research* 30(19), e101; 2002 Oxford University Press (Oct. 1, 2002).
Liu, D.R. "The Chemistry and Chemical Biology of molecular Evolution", Liu Group Research Summary from the website of Professor David R. Liu, obtained from the website in Feb. 2005.
Liu, W, et al. "Denaturing high performance liquid chromatography (DHPLC) used in the detection of germline and somatic mutations" Nucleic Acids Research. vol. 26. pp. 1396-1400 (1998).
Lobanov *Trends in Biotechnology*, vol. 20, No. 2, pp. 86-87 (Feb. 2002).
Lockhart, et al. "Expression monitoring by hybridization to high-density oligonucleotide arrays", Bio/Technology, Nature publishing co., New York, US, vol. 14, No. 13, p. 1675-1680 (Dec. 1, 1996).
Loughlin, Wendy A. "Biotransformations in organic synthesis"; Bioresource Technology 74, pp. 49-62 (2000).
Lowe, et al. "Combinatorial Libraries for Studying Molecular Recognition", URL: iupac.org/symposia/proceedings/phuket97/lowe.html, downloaded in Jun. 2005.
Luebke, Kevin J. et al. "Nonenzymatic ligation of double-helical DNA by alternate-strand triple helix formation"; Nucleic Acids Research; vol. 20, No. 12; pp. 3005-3009 (1992).
Maclean, Derek, et al. "Encoded Combinatorial Chemistry: Synthesis and screening of a library of highly functionalized pyrrolidines", Proc. Natl. Acad. Sci. USA, vol. 94, pp. 2805-2810 (Apr. 1997).
Magliery, et al. "Expanding the Genetic Code In Vitro and In Vivo", The Genetic Code and the Origin of Life, Ed. Ribas de Pouplana, L. Landes Bioscience, in Press (2004).
Makara, Gergely M. et al. "Improving Success rates for lead generation using affinity binding technologies", Current Opinion in Biotechnology 16:666-673 (2005).
Mannocci, L. "DNA-Encoded affinity maturation libraries", Proc Natl Acad Sci USA 105, 17670 (2008).
Mannocci, Lucca "DNA-Encoded Chemical Libraries", Diss. ETH No. 18153 (2009).
Margulies, M. et al., "Genome sequencing in microfabricated high-density picolitre reactors", Nature 437, 376 (2005).
Mashal, et al. "Detection of mutations by cleavage of DNA heteroduplexes with bacteriophage resolvases", Nature Genetics 9:177-83 (1995).
Matsuda, et al. "Low Fidelity DNA Synthesis by Human DNA Polymerase-? ", *Nature*, 404: 1011-1013 (Apr. 27, 2000).
Matsuura, K., et al. "Construction of glyco-clusters by self-organization of site-specifically glycosylated oligonucleotides and their cooperative amplification of lectin-recognition." *Journal of the American Chemical Society*, vol. 123, No. 2, pp. 357-358 (Jan. 17, 2001).
McCoy, et al. "T4 Ribonucleic Acid Ligase Joins Single-Strand Oligo(deoxyribonucleotides)", *Biochemistry* vol. 19, No. 4, 635-642 (1980).

McGregor, et al. "Interaction-Dependent PCR: Identification of Ligand-Target Pairs from Libraries of Ligands and Libraries of Targets in a Single Solution-Phase Experiment", *J. Am. Chem. Soc.* 132, pp. 15522-15524 (2010).
Melkko, Samu. et al. "Lead discovery by DNA-encoded chemical libraries", *Drug Discovery Today*, vol. 12, No. 11/12, pp. 465-471 (Jun. 2007).
Miller, Scott J. "DNA as a template for reaction discovery", *Nature Biotechnology*, vol. 22, No. 11, pp. 1378-1379 (Nov. 2004).
Mudrakovskaya, et al. "Solid-Phase Enzymatic Synthesis of Oligoribonucleotides", *Bioorg Khim* vol. 17, No. 6, pp. 469-472 (1991).
Mutter, M. et al. "Functionalized polyethylene glycols and polypeptides in organic synthesis and catalysis", Reactive Polymers, vol. 6, pp. 99-107 (1987).
Myers, et al. "Detection of single base substitutions by ribonuclease cleavage at mismatches in RNA:DNA duplexes" *Science* 230: 1242-6 (1985).
Needels, CM, et al. "Generation and screening of an oligonucleotide-encoded synthetic peptide library", *Proc. Natl. Acad. Sci., USA*, vol. 90, pp. 10700-10704. (Nov. 1993).
Nestler, HP et al. "A General Method for Molecular Tagging of Encoded Combinatorial Chemistry Libraries", *J. Org. Chem.*, 59, 4723-4724 (1994).
Nielsen "Combinatorial chemistry and automation", DDT, vol. 1, No. 11, pp. 458-460 (Nov. 1996).
Nikolaiev, V et al. "Peptide-Encoding for structure determination of nonsequenceable polymers within libraries synthesized and tested on solid-phase supports", *Peptide Research*, vol. 6, No. 3, pp. 161-170 (1993).
Nishigaki, Koichi, et al. "Y-ligation: an efficient method for ligating single stranded DNAs and RNAs with T4 RNA ligase", Department of Functional Materials Science, Saitama University, Urawa, Japan. *Molecular Diversity* vol. 4(3), 187-190 (2000).
O'Donovan MC, et al. "Blind analysis of denaturing high-perfomance liquid chromatography as a tool for mutation detection", *Genomics*. 52:4449 (1998).
Organic Chemistry, Wikipedia, [accessed Dec. 10, 2009]: http://en.wikipedia.org/wiki/organic_chemistry (10 pages).
Orthogonal Protection Protecting Group, Wikipedia: http://en.Wikipedia.org/wiki/protecting_group#Orthogonal_protection [accessed Apr. 15, 2010].
Persichetti, et al. "Cross-Linked Enzyme Crystals (CLECs) of Thermolysin in the Synthesis of Peptides", *Journal of the American Chemical Society*, 117: 2732-2737 (1995).
Pochet, et al. "Solid-Supported Ligation Primer", *Nucleic Acids Research*, 16(4): 1619 (1988).
Polsky-Cynkin et al. "Use of DNA immobilized on platic and agarose supports to detect DNA by sandwich hybridization", *Clin. Chem.* 31(9): 1438-43 (Sep. 1985).
Porco, Jr. "Synthesis Undressed", *Nature* 446, 383-5 (Mar. 22, 2007).
Purmal, Andrei A., et al. "A new affinity reagent for the site-specific, covalent attachment of DNA to active-site nucleophiles: application to the EcoRI and RsrI restriction and modification enzymes", *Nucleic Acids Research*; vol. 20, No. 14; Oxford University Press; pp. 3713-3719 (1992).
Robertson, Dan "Direct Evolution Process for Robust Enzyme Catalysis in Organic Solvents"; Report date: Sep. 1996. pp. 1-14.
Robinson "A Synthesis of Tropinone", *Journal of the Chemical Society Transactions*, vol. 111, pp. 762-768, (1917).
Romaniuk, et al. "Joining of RNA molecules with RNA ligase", *Methods in Enzymology*, vol. 100, pp. 52-59, (1983).
Saiki et al. "Genetic analysis of amplified DNA with immobilized sequence-specific oligonucleotide probes" *PNAS* 86(16): 6230-6234 (1989).
Sarmento, et al. "Cardosins A and B, Two New Enzymes Available for Peptide Synthesis", *Journal of Molecular Catalysis B: Enzymatic*, 5: 327-330 (1998).
Scheuermann, Jörg, et al. "DNA-encoded chemical libraries", *Journal of Biotechnology* 126 568-581 (2006).

(56) References Cited

OTHER PUBLICATIONS

Scheuermann, Jörg, et al. "DNA-encoded chemical libraries: A tool for drug discovery and for chemical biology", *ChemBioChem* 0000, 00, 1-8 (2010).
Schmidt, JG, et al., "Information transfer from peptide nucleic acids to RNA by template-directed syntheses", *Nucleic Acids Res.*, vol. 25 (23), pp. 4792-4796 (Dec. 1, 1997).
Schmitz, et al. "Solid-Phase Enzymatic Synthesis of Oligonucleotides", *Organic Letters*, 1(11): 1729-1731 (1999).
Schoenleber, R.O. et al. "Photochemical release of amines by C,N-bond cleavage", *Synlett* 501-504 (2003).
Schultz, et al. "The Combinatorial Library: A Multifunctional Resource", *Biotechnol. Prog.* 12, 729-743 (1996).
Shabarova, et al. "Chemical ligation of DNA: the first non-enzymatic assembly of a biologically active gene", Nucl. Acids Res., 19:4247-51 (1991).
Sharifian, Hoda. "Errors induced during PCR amplification", May 30, 2010.
Shchepinov, et al. "Trityl tags for encoding in combinatorial synthesis", *Tetrahedron* 56 2713-2724 (2000).
Shuman, Stewart. "DNA ligases: Progress and Prospects"; jbc.org/content/284/26/17365. full downloaded Feb. 10, 2009.
Snyder, T. "Ordered multistep synthesis in a single solution directed by DNA templates", *Angew Chem* Int Ed Engl 44, 7379 (2005).
Sokolova, N.I., et al. "Chemical reactions within DNA duplexes; Cyanogen bromide as an effective oligodeoxyribonucleotide coupling agent"; *FEBS letters*, vol. 232, No. 1, pp. 153-155 (May 1988).
Still, W. Clark "Career-In-Review (CIR)", BJ Wright, Synthesis Literacy Group, Columbia University Chemistry, Mar. 30, 2007.
Tabor, Stanley "DNA-ligases"; *Current Protocols in Molecular Biology* 3.14.1-3.14.4 (1987).
Takemori, Shigeki, et al. "Stabilization of Enzyme Activity by an Organic Solvent", Abstract only, *Nature* 215, 417-419 (Jul. 22, 1967).
Tan et al. "Natural-product inhibitors of human DNA ligase I", *Biochemical Journal* 314: 993-1000 (1996).
Tan, Derek S. et al. "Ligand discovery using encoded combinatorial libraries", *Current Opinion in Drug Discovery & Development*, 3(4), p. 439-53 (Jul. 2000).
Tessier, et al. "Ligation of Single-Stranded Oligodeoxyribonucleotides by T4 RNA Ligase". *Analytical Biochemistry* 158, 171-178 (1986).
Tse, B. "Translation of DNA into a library of 13,000 synthetic small-molecule macrocycles suitable for in vitro selection", *J Am Chem Soc* 130, 15611 (2008).
Unknown "Science & Technology: Concentrates", *Chem. & Eng. News* 82 [40] 31 (2004).
Uhlenbeck, et al. "T4 RNA Ligase", The Enzymes, vol. XV, pp. 31-58 (1982).
Vágner, et al. "Enzyme-mediated spatial segregation on individual polymeric support beads: Application to generation and screening of encoded combinatorial libraries", *Proc. Natl. Acad. Sci. USA*, vol. 93, pp. 8194-8199, (Aug. 1996).
Vaisman, et al. "Human DNA polymerase, promiscuous mismatch extension", JBC 276: 30615-30622 (2001).
Vratskikh, et al. "Solid-phase synthesis of oligoribonucleotides using T4 RNA ligase and T4 polynucleotide kinase", *Biochimie* 77, 227-232 (1995).
Wagner, et al. "Mutation detection using immobilized mismatch binding protein (MutS)" *Nucleic Acids Research* 22, 3944-3948 (1995).
Walder, JA., et al. "Complementary carrier Peptide Synthesis: General Strategy and Implications for Prebiotic Origin of Peptide Synthesis", *Department of Chemistry, and Department of Biochemistry and Molecular Biology, Northwestern University*, Evanston, Illinois 60201, vol. 76, No. 1, p. 51-55, (1979).
Wang, S., et al. "Circular RNA oligonucleotides. Synthesis, nucleic acid binding properties, and a comparison with circular DNAs"; *Nucleic Acids Research* , 1994, vol. 22, No. 12; Oxford University Press; pp. 2326-2333 (1994).

Washington, et al. "Mismatch extension ability of yeast and human DNA polymerase n", JBC 276: 2263-2266 (2001).
Weiss, et al. "Enzymatic Breakage and Joining of Deoxyribonucleic Acid, I. Repair of Single-Strand Breaks in DNA by an Enzyme System From *Escherichia coli* Infected With T4 Bacteriophage*'" *PNAS* 57, (4): 1021-1028 (1967).
Whitesides, et al. "Enzymes as Catalysts in Organic Synthesis", *Aldrichimica Acta.*, vol. 16, No. 2, pp. 27-34, (1983).
Winzeler, et al. "Fluorescence-based expression monitoring using microarrays", *Methods Enzymol.* 306: 3-18 (1999).
Wong, Daphne M. et al. "Branch capture reactions: displacers derived from assymmetric PCR"; 1991 Oxford University Press; *Nucleic Acids Research*; vol. 19; No. 9; pp. 2251-2259 (1991).
Xu, Y, et al. "A Novel 5'-Iodonucleoside Allows Efficient Non-enzymatic Ligation of Single-Stranded and Duplex DNA", Abstract, *Glen Research Catalog, Tetrahedron Letters* 38:5595-5598 (1997).
Xu, Y., et al. "High sequence fidelity in a non-enzymatic DNA autoligation reaction", *Nucleic Acids Research*, vol. 27, No. 3; pp. 875-881 (1999).
Zhu, et al. A Primer-dependent Polymerase Function of Pseudomonas aeruginosa ATP-dependent DNA ligase (LigD). *Journal of Biological Chemistry* 280(1): 418-427 (2005).
Website of prof. David R. Llu, publicly available Mar. 1, 2001.
Website of prof. David R. Liu, publicly available Mar. 11, 2000.
Website of prof. David R. Liu, publicly available Oct. 15, 2000.
Website of prof. David R. Liu, publicly available Oct. 15, 2003.
Website of prof. David R. Llu, publicly available Apr. 19, 2001.
Website of prof. David R. Liu, publicly available Nov. 20, 2002.
Website of prof. David R. Liu, publicly available Sep. 23, 2001.
Website of prof. David R. Liu, publicly available Sep. 24, 2002.
Website of prof. David R. Liu, publicly available Apr. 23, 2003.
Website of prof. David R. Liu, publicly available Aug. 1, 2003.
Website of prof. David R. Liu, publicly available Aug. 2, 2002.
Website of prof. David R. Liu, publicly available Feb. 8, 2003.
Website of prof. David R. Liu, publicly available Feb. 10, 2004.
Website of prof. David R. Liu, publicly available Feb. 15, 2001.
Website of prof. David R. Liu, publicly available Dec. 16, 2003.
Website of prof. David R. Liu, publicly available Jun. 4, 2002.
Website of prof. David R. Liu, publicly available Jun. 6, 2003.
Website of prof. David R. Liu, publicly available Mar. 27, 2003.
Website of prof. David R. Liu, publicly available Mar. 31, 2001.
Website of prof. David R. Liu, publicly available Nov. 29, 2002.
Website of prof. David R. Liu, publicly available Nov. 30, 2001.
Website of prof. David R. Liu, publicly available Oct. 17, 2002.
Decision to Grant from European Application No. EP 02740409.4 dated Jul. 26, 2007.
European Office Action from European Application No. EP 02740409.4 dated Sep. 1, 2005.
Reply to European Office Action from European Application No. EP 02740409.4 dated Jun. 16, 2006.
Intent to Grant from European Application No. EP 02740409.4 printed Oct. 13, 2006.
Extended European Search Report from European Application No. 07114663.3 dated May 25, 2009.
Extended European Search Report from European Application No. 10 18 4311 dated Feb. 28, 2011.
International Preliminary Examination Report from PCT No. PCT/DK02/00419 dated Jan. 28, 2004.
International Search Report from PCT No. PCT/DK02/00419 dated Jun. 25, 2003.
Restriction Requirement from U.S. Appl. No. 10/175,539 dated Apr. 6, 2005.
Response to Restriction Requirement from U.S. Appl. No. 10/175,539 dated May 6, 2005.
Office Action (Non-Final Rejection) from U.S. Appl. No. 10/175,539 dated May 13, 2005.
Response to Office Action (Non-Final Rejection) from U.S. Appl. No. 10/175,539 dated Apr. 13, 2006.
Office Action (Non-Final Rejection) from U.S. Appl. No. 10/175,539 dated May 14, 2007.
Response to Office Action (Non-Final Rejection) from U.S. Appl. No. 10/175,539 dated Sep. 13, 2007.

(56) References Cited

OTHER PUBLICATIONS

Office Action (Final Rejection) from U.S. Appl. No. 10/175,539 dated May 19, 2006.
Notice of Appeal from U.S. Appl. No. 10/175,539 dated Nov. 20, 2006.
Request for Continued Examination from U.S. Appl. No. 10/175,539 dated Feb. 20, 2007.
Office Action (Ex Parte Quayle Action) from U.S. Appl. No. 10/175,539 dated Nov. 27, 2007.
Response to Ex Parte Quayle Action from U.S. Appl. No. 10/175,539, filed Feb. 27, 2008.
Notice of Allowance from U.S. Appl. No. 10/175,539 dated May 30, 2008.
Issue Notification U.S. Appl. No. 10/175,539 dated Jun. 1, 2010.
Office Action (Non-Final Rejection) from U.S. Appl. No. 12/330,709 dated Oct. 27, 2009.
Response to Office Action (Non-Final Rejection) from U.S. Appl. No. 12/330,709, filed Apr. 21, 2010.
Notice of Allowance from U.S. Appl. No. 12/330,709 dated Mar. 3, 2011.
Request for Continued Examination and supplemental IDS from U.S. Appl. No. 12/330,709, filed Jun. 2, 2011.
Office Action from European Application No. 03709676.5 dated Feb. 23, 2005.
Reply to 1st Office Action from European Application No. 03709676.5 dated Jun. 30, 2005.
2nd Office Action from European Application No. 03709676.5 dated Aug. 26, 2005.
Reply to 2nd Office Action from European Application No. 03709676.5 dated Sep. 13, 2005.
3rd Office Action from European Application No. 03709676.5 dated Sep. 30, 2005.
Reply to 3rd Office Action from European Application No. 03709676.5 dated May 19, 2006.
Intent to Grant from European Application No. 03709676.5 dated Oct. 10, 2006.
Amendment after Intention to Grant from European Application No. 03709676.5 dated Nov. 16, 2007.
Decision to Grant from European Application No. 03709676.5 dated Oct. 23, 2008.
European Search Report from European Application No. 08 16 9346 dated Apr. 13, 2010.
1st Office Action from European Application No. 08169346.7 dated Apr. 19, 2011.
Response filed in European Application No. 08169346.7 dated Mar. 23, 2011.
International Search Report for PCT Application No. PCT/DK03/00172 dated Nov. 3, 2003.
Office Action (Non-Final) for U.S. Appl. No. 10/507,121 dated Feb. 8, 2007.
Response to Office Action for U.S. Appl. No. 10/507,121 dated Jun. 7, 2007.
Office Action (Final Rejection) for U.S. Appl. No. 10/507,121 dated Sep. 7, 2007.
Request for Continued Examination and supplemental amendment for US Serial No. 10/507,121 filed Feb. 13, 2008.
Notice of Allowance for U.S. Appl. No. 10/507,121 dated Mar. 20, 2008.
Issue Notification for U.S. Appl. No. 10/507,121 dated Jul. 30, 2008.
Office Action (Non-Final) from U.S. Appl. No. 12/179,323 dated Jan. 27, 2010.
Response to Office Action from U.S. Appl. No. 12/179,323, filed Jun. 24, 2010.
Office Action (Final Rejection) for U.S. Appl. No. 12/179,323 dated Sep. 15, 2010.
Notice of Appeal from U.S. Appl. No. 12/179,323, filed Mar. 15, 2011.
1st Office Action from European Application No. 03766117.0 dated Mar. 24, 2009.
Reply to 1st Office Action from European Application No. 03766117.0 dated Jan. 8, 2010.
2nd Office Action from European Application No. 03766117.0 dated Feb. 16, 2010.
Reply to 2nd Office Action from European Application No. 03766117.0 dated Aug. 20, 2010.
3rd Office Action from European Application No. 03766117.0 dated Nov. 19, 2010.
Reply to 3rd Office Action from European Application No. 03766117.0 dated May 23, 2011.
4th Office Action from European Application No. 03766117.0 dated Jun. 9, 2011.
International Search Report from PCT Application No. PCT/DK03/00516 dated Feb. 18, 2004.
1st Restriction Requirement from U.S. Appl. No. 10/523,006 dated Apr. 4, 2008.
Response to 1st Restriction Requirement from U.S. Appl. No. 10/523,006, filed Oct. 1, 2008.
2nd Restriction Requirement from U.S. Appl. No. 10/523,006 dated Dec. 9, 2009.
Response to 2nd Restriction Requirement from U.S. Appl. No. 10/523,006, filed May 5, 2010.
3rd Restriction Requirement from U.S. Appl. No. 10/523,006 dated Aug. 3, 2010.
Response to 3rd Restriction Requirement from U.S. Appl. No. 10/523,006, filed Feb. 1, 2011.
Office Action (Non-Final) from U.S. Appl. No. 10/523,006 dated Mar. 16, 2011.
1st Office Action for European Application No. 03767480.1 dated May 7, 2007.
Reply to 1st Office Action for European Application No. 03767480.1 dated Mar. 19, 2008.
2nd Office Action for European Application No. 03767480.1 dated Jun. 18, 2008.
Reply to 2nd Office Action for European Application No. 03767480.1 dated Feb. 6, 2009.
Intent to Grant for European Application No. 03767480.1 dated Mar. 30, 2009.
Amendment after Intention to Grant for European Application No. 03767480.1 dated Jul. 22, 2009.
Decision to Grant for European Application No. 03767480.1 dated Nov. 5, 2009.
European Search Report for European Application No. 09 17 7376 dated Feb. 24, 2011.
International Search Report for PCT Application No. PCT/DK03/00921 Jun. 22, 2004.
Restriction Requirement for U.S. Appl. No. 10/539,288 dated Aug. 2, 2010.
Response to Restriction Requirement for U.S. Appl. No. 10/539,288, filed Jan. 31, 2011.
Office Action (Non-Final) for U.S. Appl. No. 10/539,288 dated Apr. 25, 2011.
1st Office Action for European Application No. 03729906.6 dated May 17, 2006.
Reply to 1st Office Action for European Application No. 03729906.6 dated Mar. 9, 2007.
2nd Office Action for European Application No. 03729906.6 dated Sep. 22, 2009.
Reply to 2nd Office Action for European Application No. 03729906.6 dated May 6, 2010.
International Search Report for PCT Application No. PCT/DK03/00417 Feb. 10, 2004.
Restriction Requirement for U.S. Appl. No. 10/518,056 dated Jan. 4, 2008.
Response to Restriction Requirement for U.S. Appl. No. 10/518,056, filed Jun. 2, 2008.
Office Action (Non-Final) for U.S. Appl. No. 10/518,056 dated Oct. 8, 2008.
Reply to Office Action for U.S. Appl. No. 10/518,056, filed Feb. 17, 2009.
Office Action (Final Rejection) for U.S. Appl. No. 10/518,056 dated May 27, 2009.

(56) References Cited

OTHER PUBLICATIONS

Notice of Appeal for U.S. Appl. No. 10/518,056 dated Oct. 27, 2009.
Amendment After Appeal for U.S. Appl. No. 10/518,056, filed Nov. 17, 2009.
Advisory Action for U.S. Appl. No. 10/518,056 dated Jan. 7, 2010.
Request for Continued Examination and IDS for U.S. Appl. No. 10/518,056, filed Mar. 22, 2010.
1st Office Action for European Application No. 04713515.7 dated Oct. 19, 2006.
Reply to 1st Office Action for European Application No. 04713515.7 dated Aug. 20, 2007.
2nd Office Action for European Application No. 04713515.7 dated Mar. 31, 2008.
Reply to 2nd Office Action for European Application No. 04713515.7 dated Dec. 5, 2008.
3rd Office Action for European Application No. 04713515.7 dated Sep. 6, 2010.
Reply to 3rd Office Action for European Application No. 04713515.7 dated Jun. 21, 2011.
International Search Report for PCT Application No. PCT/DK2004/000116 dated Aug. 23, 2004.
Office Action (Non-Final) for U.S. Appl. No. 10/545,795 dated Mar. 31, 2008.
Response filed for U.S. Appl. No. 10/545,795, filed Sep. 30, 2008.
Office Action for U.S. Appl. No. 10/545,795 dated Jan. 27, 2009.
Notice of Appeal filed for U.S. Appl. No. 10/545,795, filed Jul. 27, 2009.
Amendment after Appeal for U.S. Appl. No. 10/545,795, filed Sep. 28, 2009.
Office Action (Advisory Action) for U.S. Appl. No. 10/545,795 dated Sep. 29, 2009.
Request for Continued Examination and IDS for U.S. Appl. No. 10/545,795, filed Oct. 27, 2009.
Office Action (Non-Final) for U.S. Appl. No. 10/545,795 dated Nov. 16, 2009.
Office Action (Non-Final) for U.S. Appl. No. 10/545,795 dated Mar. 30, 2010.
Office Action (Interview Summary) for U.S. Appl. No. 10/545,795 dated Jul. 30, 2010.
Response filed for U.S. Appl. No. 10/545,795, filed Aug. 30, 2010.
Office Action (Final rejection) for U.S. Appl. No. 10/545,795 dated Feb. 1, 2011.
1st Office Action for European Application No. 04713517.3 dated Dec. 22, 2006.
Reply to 1st Office Action for European Application No. 04713517.3 dated Oct. 19, 2007.
2nd Office Action for European Application No. 04713517.3 dated Sep. 23, 2008.
Reply to 2nd Office Action for European Application No. 04713517.3 dated Jul. 13, 2009.
3rd Office Action for European Application No. 04713517.3 dated Feb. 14, 2011.
International Search Report for International Application No. PCT/DK2004/000117 dated Aug. 19, 2004.
Restriction Requirement for U.S. Appl. No. 10/546,538 dated Jul. 31, 2008.
Response to Restriction Requirement for U.S. Appl. No. 10/546,538, filed Dec. 24, 2008.
Office Action (Non-Final) for U.S. Appl. No. 10/546,538 dated Jun. 10, 2009.
Response to Office Action for U.S. Appl. No. 10/546,538, filed Dec. 9, 2009.
Office Action (Final Rejection) for U.S. Appl. No. 10/546,538 dated Jun. 8, 2010.
Response to Office Action (Notice of Appeal) for U.S. Appl. No. 10/546,538, filed Dec. 8, 2010.
Office Action (Communication re: Appeal) for U.S. Appl. No. 10/546,538 dated Jul. 20, 2011.
1st Office Action for European Application No. 04722237.7 dated Mar. 2, 2006.
Reply to 1st Office Action for European Application No. 04722237.7 dated Dec. 20, 2006.
2nd Office Action for European Application No. 04722237.7 dated Feb. 28, 2007.
Reply to 2nd Office Action for European Application No. 04722237.7 dated Oct. 19, 2007.
Intent to Grant for European Application No. 04722237.7 dated Jan. 18, 2008.
Amendment to Grant for European Application No. 04722237.7 dated Nov. 11, 2008.
Decision to Grant for European Application No. 04722237.7 dated Feb. 5, 2009.
European Search Report for European U.S. Appl. No. 09/154,197 dated Sep. 15, 2010.
International Search Report for International Application No. PCT/DK2004/000195 dated Dec. 27, 2004.
Restriction Requirement for U.S. Appl. No. 10/549,619 dated Apr. 21, 2008.
Response to Restriction Requirement for U.S. Appl. No. 10/549,619, filed Sep. 22, 2008.
Office Action (Non-Final) for U.S. Appl. No. 10/549,619 dated Apr. 28, 2009.
Response to Office Action for U.S. Appl. No. 10/549,619, filed Oct. 26, 2009.
Office Action (Interview Summary) for U.S. Appl. No. 10/549,619 dated Mar. 3, 2010.
Amendment filed for U.S. Appl. No. 10/549,619, filed Oct. 21, 2010.
Notice of Allowance for U.S. Appl. No. 10/549,619 dated Jul. 7, 2010.
Amendment After Allowance for U.S. Appl. No. 10/549,619, filed Oct. 6, 2010.
Issue Notification for U.S. Appl. No. 10/549,619 dated Mar. 9, 2011.
Australian Application No. 2003273792.
Examination Report for Australian Application No. 2003273792 dated May 6, 2011.
Reply to 1st Office Action for European Application No. 03757752.5 dated Jan. 12, 2006.
Amendment after ESP for European Application No. 03757752.5 dated Feb. 14, 2006.
1st Office Action for European Application No. 03757752.5 dated Mar. 16, 2006.
2nd Office Action for European Application No. 03757752.5 dated Feb. 15, 2007.
Reply to 2nd Office Action for European Application No. 03757752.5 dated Aug. 15, 2007.
Summons for European Application No. 03757752.5 dated Aug. 11, 2008.
Letter for Oral Proceeding for European Application No. 03757752.5 dated Dec. 15, 2008.
Telephone Summary for European Application No. 03757752.5 dated Dec. 23, 2008.
Letter for Oral Proceeding for European Application No. 03757752.5 dated Jan. 2, 2009.
Oral Proceedings for European Application No. 03757752.5 dated Jan. 8, 2009.
3rd Office Action for European Application No. 03757752.5 dated Jan. 14, 2009.
Reply to 3rd Office Action for European Application No. 03757752.5 dated Jul. 17, 2009.
Intent to Grant for European Application No. 03757752.5 dated Mar. 30, 2010.
Decision to Grant for European Application No. 03757752.5 dated May 19, 2011.
Request for Corrections for European Application No. 03757752.5 dated Nov. 9, 2010.
Office Action for Japanese Application No. 2005-501801 dated Apr. 6, 2010.
Office Action for Japanese Application No. 2005-501801 dated May 31, 2011.

(56) References Cited

OTHER PUBLICATIONS

International Search Report for International Application No. PCT/DK03/00739 dated Aug. 30, 2004.
Restriction Requirement for U.S. Appl. No. 10/525,817 dated May 9, 2007.
Response to Restriction Requirement for U.S. Appl. No. 10/525,817, filed Sep. 10, 2007.
Restriction Requirement for U.S. Appl. No. 10/525,817 dated Nov. 28, 2007.
Response to Restriction Requirement for U.S. Appl. No. 10/525,817, filed Feb. 28, 2008.
Restriction Requirement for U.S. Appl. No. 10/525,817 dated Jul. 7, 2009.
Response to Restriction Requirement for U.S. Appl. No. 10/525,817, filed Oct. 5, 2009.
Office Action (Non-Final) for U.S. Appl. No. 10/525,817 dated Apr. 1, 2010.
Supplemental Office Action for U.S. Appl. No. 10/525,817 dated Apr. 5, 2010.
Response filed for U.S. Appl. No. 10/525,817, filed Jul. 27, 2010.
Office Action (Non-Final) for U.S. Appl. No. 10/525,817 dated Jan. 5, 2011.
Office Action (Interview Summary) for U.S. Appl. No. 10/525,817 dated Jul. 1, 2011.
Response filed for U.S. Appl. No. 10/525,817, filed Jul. 5, 2011.
Restriction Requirement for U.S. Appl. No. 11/402,957 dated Jun. 25, 2008.
Response to Restriction Requirement for U.S. Appl. No. 11/402,957, filed Aug. 25, 2008.
Office Action (Non-Final) for U.S. Appl. No. 11/402,957 dated Nov. 28, 2008.
Response filed for U.S. Appl. No. 11/402,957, filed May 15, 2009.
Office Action (Non-Final) for U.S. Appl. No. 11/402,957 dated Jul. 6, 2009.
Response filed for U.S. Appl. No. 11/402,957 filed Dec. 7, 2009.
Office Action (Final Rejection) for U.S. Appl. No. 11/402,957 dated Feb. 16, 2010.
Response filed for U.S. Appl. No. 11/402,957, filed Jul. 28, 2010.
Notice of Appeal filed for U.S. Appl. No. 11/402,957, filed Aug. 16, 2010.
Notice of Allowance for U.S. Appl. No. 11/402,957 dated Sep. 2, 2010.
Request for Continued Examination filed for U.S. Appl. No. 11/402,957, filed Dec. 2, 2010.
Second Notice of Allowance for U.S. Appl. No. 11/402,957 dated Apr. 29, 2011.
1st Office Action for European Application No. 04762850.8 dated Dec. 6, 2006.
Reply to 1st Office Action for European Application No. 04762850.8 dated Oct. 18, 2007.
2nd Office Action for European Application No. 04762850.8 dated Jan. 24, 2008.
Reply to 2nd Office Action for European Application No. 04762850.8 dated Sep. 2, 2008.
Intent to Grant for European Application No. 04762850.8 dated Dec. 10, 2008.
Decision to Grant for European Application No. 04762850.8 dated Oct. 8, 2009.
Amendment after Grant for European Application No. 04762850.8 dated Jul. 17, 2009.
International Search Report for PCT/DK2004/000630 dated Feb. 14, 2005.
Restriction Requirement for U.S. Appl. No. 10/572,644 dated Feb. 4, 2009.
Response to Restriction Requirement for U.S. Appl. No. 10/572,644 dated Jul. 29, 2009.
Restriction Requirement for U.S. Appl. No. 10/572,644 dated Jul. 21, 2010.
Response to Restriction Requirement for U.S. Appl. No. 10/572,644, filed Jan. 19, 2011.
Office Action (Non-Final) for U.S. Appl. No. 10/572,644 dated Oct. 29, 2009.
Response to Office Action for U.S. Appl. No. 10/572,644, filed Apr. 28, 2010.
Office Action (Non-Final) for U.S. Appl. No. 10/572,644 dated Mar. 31, 2011.
1st Office Action for European Application No. 05715120.1 dated Apr. 12, 2007.
Reply to 1st Office Action for European Application No. 05715120.1 dated Feb. 1, 2008.
2nd Office Action for European Application No. 05715120.1 dated Mar. 25, 2008.
Reply to 2nd Office Action for European Application No. 05715120.1 dated Jan. 9, 2009.
Intent to Grant for European Application No. 05715120.1 dated May 7, 2009.
Amendment after Grant for European Application No. 05715120.1 dated Sep. 3, 2009.
Decision to Grant for European Application No. 05715120.1 dated Oct. 1, 2009.
International Search Report for International Application No. PCT/DK2005/000199 dated Jan. 23, 2006.
Office Action for U.S. Appl. No. 10/593,868 dated Mar. 30, 2009.
Response to Office Action for U.S. Appl. No. 10/593,868, filed Jul. 28, 2009.
Notice of Allowance for U.S. Appl. No. 10/593,868 dated Nov. 16, 2009.
Amendment after Allowance for U.S. Appl. No. 10/593,868, filed Feb. 16, 2010.
Issue Notification for U.S. Appl. No. 10/593,868 dated Apr. 7, 2010.
1st Office Action for European Application No. 05700655.3 dated Jun. 19, 2007.
Reply to 1st Office Action for European Application No. 05700655.3 dated Apr. 11, 2008.
2nd Office Action for European Application No. 05700655.3 dated Sep. 12, 2008.
Reply to 2nd Office Action for European Application No. 05700655.3 dated Jul. 9, 2009.
3rd Office Action for European Application No. 05700655.3 dated Aug. 12, 2009.
Reply to 3rd Office Action for European Application No. 05700655.3 dated Feb. 9, 2010.
Intent to Grant for European Application No. 05700655.3 dated Mar. 31, 2010.
Amendment after Grant for European Application No. 05700655.3 dated Nov. 11, 2010.
Decision to Grant for European Application No. 05700655.3 dated Dec. 2, 2010.
International Search Report for International Application No. PCT/DK2005/000106 dated Sep. 12, 2005.
Restriction Requirement for U.S. Appl. No. 10/589,551 dated Apr. 7, 2011.
1st Office Action for European Application No. 06818144.5 dated Dec. 11, 2008.
Reply to 1st Office Action for European Application No. 06818144.5 dated Oct. 30, 2009.
Intent to Grant for European Application No. 06818144.5 dated Feb. 23, 2010.
Amendment after Grant for European Application No. 06818144.5 dated Oct. 7, 2010.
Decision to Grant European Application No. 06818144.5 dated Nov. 5, 2010.
European Search Report for European Application No. 10 19 2716 dated May 24, 2011.
Invitation to Identify Subject Matter for European Application No. 10 192 717.6 dated Jun. 1, 2011.
International Search Report for International Application No. PCT/DK2006/000685 dated Jun. 14, 2007.
Communication pursuant to Rule 161(1) and 162 for European Application No. 09765460.2 dated Mar. 14, 2011.
Response to Rule 161(1) and 162 for European Application No. 09765460.2 dated Apr. 18, 2011.

(56) References Cited

OTHER PUBLICATIONS

International Search Report for International Application No. PCT/DK2009/050129 dated Aug. 21, 2009.
Annex I: Vipergen Technology Paper—The YoctoReactor drug discovery technology platform. 2 pages.
Annex II: Vipergen Technology Paper—The YoctoReactor drug discovery technology platform. 2 pages. Aug. 2008.
Anonymous. "DCI—A Logical Alternative Aviator", Glen Research Report, vol. 10, No. 1 (1997).
Millward, S.W. et al. "A General Route for Post-Translational Cyclization of mRNA Display Libraries", Journal of the American Chemical Society: vol. 127, 14142-14143, (2005).
Millward, S.W. et al. "Design of Cyclic Peptides That Bind Protein Surfaces with Antibody-Like Affinity", ACS Chemical Biology: vol. 2, No. 9, 625-634, (2007).
Giebel, L.B. et al. "Screening of Cyclic Peptide Phage Libraries Identifies Ligands That Bind Streptavidin with High Affinities", Biochemistry: vol. 34, No. 47; 15430-15435, (1995).
Ladner, R.C. "Constrained peptides as binding entities", Elsevier Science Ltd., Trends in Biotechnology: vol. 13, 426-430, (1995).
Koivunen, E. et al. "Phage Libraries Displaying Cyclic Peptides with Different Ring Sizes: Ligand Specificities of the RGD-Directed Integrins", Bio/Technology: vol. 13, 265-270, (1995).
Office Action in European patent application No. 10184311.8, dated Mar. 19, 2012, with Annex.
Office Action in Israel patent application No. 207672, dated Jan. 15, 2012, with English translation.
Response to OA in Israel patent application No. 207672, dated Jun. 14, 2012.
Office Action in Israel patent application No. 207673, dated Jan. 15, 2012, with English translation.
Response to OA in Israel patent application No. 207673, dated Jun. 14, 2012.
Response to OA in Canadian patent application No. 2,544,153, dated Mar. 26, 2012.
Appeal filed for Indian patent application No. 178/MUMNP/2007, dated Nov. 15, 2011.
Office Action in Chinese patent application No. 200380104764.5, dated Feb. 29, 2012, with translation of text of notification.
Response to OA in Chinese patent application No. 200380104764.5, dated Jul. 16, 2012.
Office Action in Japanese patent application No. P2010-226107, dated Jul. 10, 2012, with English translation.
Office Action in European patent application No. 10192716.8, dated Jul. 30, 2012.
Response to OA in European patent application No. 07114663.3, dated Jul. 4, 2012.
Office Action in European patent application No. 07114663.3, dated Jul. 23, 2012.
Official Communication in European patent application No. 09154197.9, dated Aug. 7, 2012.
Bunin et al., "The combinatorial synthesis and chemical and biological evaluation of a 1,4-benzodiazepine library," *Proc. Natl. Acad. Sci., USA*, vol. 19, pp. 4708-4712, May 1994.
Bunin et al., "[26] Synthesis and Evaluation of 1,4-Benzodiazepine Libraries," *Methods in Enzymology*, vol. 267, pp. 448-465 (1996).
Communication (office action) by the European Patent Office dated Mar. 24, 2016 in relation to European Patent Application No. 10741877.4.
Glen Research (Catalogue No. 10-1014-XX)—Mar. 8, 2005 + Material Safety Data Sheet on Catalogue No. 10-1014-xx—Sep. 11, 2004.
Glen Research (Catalogue No. 10-1054-XX)—Mar. 8, 2005 + Material Safety Data Sheet on Catalogue No. 10-1054-xx—Oct. 28, 2004.
Glen Research (Catalogue No. 10-1092-XX)—Apr. 28, 2005 + Material Safety Data Sheet on Catalogue No. 10-1092-xx—Oct. 28, 2004.
Glen Research (Catalogue No. 10-1590-XX)—Aug. 21, 2008 + Further Info on 10-1590-xx—Dec. 12, 2008.
Korshun et al., "5-(1-Pyrenylethynyl)-2'-Deoxyuridine, a N ovel Fluorescent Nucleosideanalog", Bioorganiceskaa himia, 22(12), 1996, pp. 923-925. (English abstract only).
Mullah et al., "Efficient synthesis of double dye-labeled oligodeoxyribonucleotide probes and their application in a real time PCR assay", Nucleic Acids Research, 1998, vol. 26, No. 4, pp. 1026-1031.
Thelwell, "Mode of action and application of Scorpion primers to mutation detection", Nucleic Acids Research, 2000, vol. 28, No. 19, pp. 3752-3761.
Third Party observation filed with the European Patent Office on Mar. 14, 2016 in relation to European Patent Application No. 10741877.4 (X-Chem Inc.).
Wagner, "Gene inhibition using antisense oligodeoxynucleotides", Nature, 1994, vol. 372, pp. 333-335.
Wagner, "Antisense gene inhibition by oligonucleotides containing C-5 propyne pyrimidines", Science, 1993, vol. 260, pp. 1510-1513.
Yamana et al., "Synthesis and Binding Properties of Oligonucleotides Containing an Azobenzene Linker", Nucleosides & Nucleotides, 1998, vol. 17, No. 1-3, pp. 233-242.
Blondal et al., "Isolation and characterization of a thermostable RNA ligase 1 from a Thermus scotoductus bacteriophage TS2126 with good single-stranded DNA ligation properties", Nucl. Acids. Res. 2005, vol. 33, No. 1, pp. 135-142.
Brennan & Gumport, "T4 RNA ligase catalyzed synthesis of base analogue-containing oligodeoxyribonucleotides and a characterization of their thermal stabilities", Nucleic Acids Res., 1985, vol. 13, No. 24, pp. 8665-8684.
Cummins et al., "Characterization of fully 2'-modified oligoribonucleotide hetero- and homoduplex hybridization and nuclease sensitivity", Nucl. Acids Res. 1995, vol. 23, No. 11, pp. 2019-2024.
Inoue et al., "Synthesis and hybridization studies on two complementary nona(2'-O-methyl)ribonucleotides", Nucleic Acids Res. 1987, vol. 15, No. 15, pp. 6131-6148.
Lesnik et al., "Oligodeoxynucleotides containing 2'-O-modified adenosine: Synthesis and effects on stability of DNA: RNA duplexes", Biochemistry, 1993, vol. 32, pp. 7832-7838.
Verma et al., "Functional tuning of nucleic acids by chemical modifications: tailored oligonucleotides as drugs, devices, and diagnostics", Chem Rec. 2003, 3(1), pp. 51-60.
Kahn, Jason. "DNA-ligases": www.adnadn.umd.edu/biochem/kahn/molmachines/replication/DNA%20ligase.htm 4 pages, downloaded Dec. 10, 2009.
1st Office Action in EP 07114663.3 dated Sep. 12, 2011.
Response to Office Action in EP 07114663.3 dated May 17, 2013.
3rd Office Action in European patent application No. 07114663.3 dated Jun. 3, 2013.
EESR Response to ESR dated Feb. 6, 2012.
Response to 1st Office Action of Mar. 19, 2012 in EP 10184311.8 submitted Jan. 18, 2013.
2nd Office action dated Feb. 6, 2013 in EP 10184311.8.
Response to Office Action filed Feb. 10, 2012.
2nd Office Action dated Feb. 24, 2012 with Annex.
Response to 2nd Office Action of Feb. 24, 2012 in EP 08169346.7 submitted Dec. 21, 2012.
3rd Office Action dated Jan. 29, 2013 in EP 08169346.7.
Response to 4th Office Action dated Jun. 9, 2011 in EP 03766117.0 submitted Mar. 14, 2012.
5th Office Action from European Application No. 03766117.0 dated May 31, 2012.
Office Action from European Application No. 03766117.0 dated Mar. 26, 2013.
EESR Response to Office Action filed Aug. 5, 2011.
Office Action w. Annex dated Sep. 12, 2011.
Decision to Grant dated Oct. 10, 2013 re European patent appliction No. 09154197.9.
Opposition against EP 1558744 filed by Strawman Limited on Mar. 15, 2012.
Opposition against EP 1558744 by HGF on Mar. 14, 2012.
Response to oppositions against EP 1558744 submitted Dec. 5, 2012.
Written submissions re EP 1558744 submitted Sep. 11, 2013 by proprietor.

(56) References Cited

OTHER PUBLICATIONS

Written submissions re EP 1558744 submitted Sep. 12, 2013 by opponent.
European Search Report dated Feb. 6, 2012 & Search Opinion.
Response to ESR of Feb. 6, 2012 re European Patent Application No. 10183942.1 submitted Jan. 9, 2013.
1st Office Action for European Patent Application No. 10183942.1 dated Feb. 11, 2013.
Decision to Grant EP 10183942.1 dated Nov. 14, 2013.
Communication re Partial European Seach Report dated Feb. 10, 2012.
Partial European Search Report dated Feb. 3, 2012.
European Search Report issued 2012-06-06 re EP 10184069.2.
Response dated Apr. 12, 2013 to European Search Report issued in European Patent Application No. 10184069.2.
1st Office Action for European Patent Application No. 10184069.2 dated Jul. 3, 2013.
EESR Office Action in European patent application No. 10192716.8 dated Jul. 3, 2013.
Invitation to identify subject matter for search Response to Invitation dated Aug. 5, 2011.
Invitation to identify subject matter for search Comm. re partial ESR w. partial European Search Report dated Oct. 7, 2011.
Invitation to identify subject matter for search Response to partial ESR dated Dec. 8, 2011.
Invitation to identify subject matter for search ESR and Search Opinion dated Jan. 16, 2012.
Invitation to identify subject matter for search Response to ESR dated Jan. 25, 2012 submitted Dec. 5, 2012.
Invitation to identify subject matter for search Office Action dated Jul. 16, 2013 re European patent application No. 10192717.6.
European Office Action from EP 09765460.2 dated May 7, 2012.
Response to office action re 09765460.2 submitted Feb. 22, 2013.
International Search Report dated Aug. 23, 2011.
Communication pursuant to Rule 161(1) and 162 for European Application No. 11720372.9 dated Dec. 12, 2012.
Notice of Acceptance for Australian Application No. 2003273792 dated Jun. 22, 2011.
Office action of Aug. 20, 2012 re Canadian patent application No. 2,544,153.
Notice of Allowance of Sep. 3, 2012 re Chinese patent application No. 200380104764.5.
Office Action in Israeli patent application No. 207672 dated May 28, 2013.
Office Action in Israeli patent application No. 207673 dated May 28, 2013.
Office Action of Feb. 8, 2013 re Japanese patent application No. 2010-226107.
Decision of dismissal of amendment dated Aug. 20, 2013 re Japanese patent application No. 2010-226107.
Restriction Requirement P101US00 Restriction Requirement dated Apr. 6, 2005 re U.S. Appl. No. 10/175,539.
O. L. Acevedo et al., "Non-enzymatic Transcription of an Oligodeoxynucleotide 14 Residues Long", *J. Mol. Biol.*, 197:187-193, 1987.
O. L. Acevedo et al., "Template-directed oligonucleotide ligation on hydroxylapatite", *Nature*, 321, 790-792, Jun. 19, 1986.
D. Albagli et al., "Chemical Amplification (CHAMP) by a Continuous, Self-Replicating Oligonucleotide-Based System", *J. Am. Chem. Soc.*, 121, 6954-6955, 1999.
S. A. Benner, "Expanding the genetic lexicon: incorporating non-standard amino acids into proteins by ribosome-based synthesis", *TIBTECH*, 12, 158-163, May 1994.
M. Berger et al., "Universal bases for hybridization, replication and chain termination", *Nucleic Acids Research*, 28(15), 2911-2914, 2000.
J. A. Bittker et al., "Recent advances in the in vitro evolution of nucleic acids", *Current Opinion in Chemical Biology*, 6:367-374, 2002.

C. Böhler et al., "Template switching between PNA and RNA oligonucleotides", *Nature*, 376:578-581, Aug. 17, 1995.
E. Braun et al., "DNA-templated assembly and electrode attachment of a conducting silver wire", *Nature*, 391:775-778, Feb. 19, 1998.
S. Brenner et al., "Encoded combinatorial chemistry", *Proc. Natl. Acad. Sci. USA.*, 89:5381-5383, Jun. 1992.
R. K. Bruick et al., "A simple procedure for constructing 5'-amino-terminated oligodeoxynucleotides in aqueous solution", *Nucleic Acids Research*, 25(6):1309-1310, 1997.
R. K. Bruick et al., "Template-directed ligation of peptides to oligonucleotides", *Chemistry & Biology*, 3:49-56, Jan. 1996.
C. T. Calderone et al., "Directing Otherwise Incompatible Reactions in a Single Solution by Using DNA-templated Organic Synthesis", *Angew. Chem. Int. Ed.*, 41(21): 4104-4108, 2002.
C. T. Calderone et al., "Nucleic-acid-templated synthesis as a model system for ancient translation", *Current Opinion in Chemical Biology*, 8:645-653, 2004.
C. B. Chen et al., "Template-directed Synthesis on Oligodeoxycytidylate and Polydeoxycytidylate Templates", *J. Mol. Biol.*, 181: 271-279, 1985.
B. Chan et al., "Intra-tRNA distance measurements for nucleocapsid protein-dependent tRNA unwinding during priming of HIV", *Proc. Natl. Acad. Sci. USA*, 96:459-464, Jan. 1999.
G. R. L. Cousins et al., "Identification and Isolation of a Receptor for N-Methyl Alkylammonium Salts: Molecular Amplification in a Pseudo-peptide Dynamic Combinatorial Library", *Angew. Chem. Int. Ed.* 40(2): 423-428, 2001.
J. L. Czlapinski et al., "Nucleic-acid Template-Directed Assembly of Metallosalen—DNA Conjugates", *J. Am. Chem. Soc.*, 123:8618-8619, 2001.
S. H. DeWitt et al., ""Diversomers": An approach to nonpeptide, nonoligomeric chemical diversity", *Proc. Natl. Acad. Sci. USA*, 90: 6909-6913, Aug. 1993.
W. J. Dower et al., "In vitro selection as a powerful tool for the applied evolution of proteins and peptides", *Current Opinion in Chemical Biology*, 6: 390-398, 2002.
J. B. Doyon et al., "Highly Sensitive In Vitro Selections for DNA-Linked Synthetic Small Molecules with Protein Binding Affinity and Specificity", *J. Am. Chem. Soc.*, 2 pages (including supporting information S1-S8), Sep. 16, 2003.
R. Elghanian et al., "Selective Colorimetric Detection of Polynucleotides Based on the Distance-Dependent Optical Properties of Gold Nanoparticles", *Science*, 227: 1078-1081, Aug. 22, 1997.
J. Ellman et al., "Biosynthetic Method for Introducing Unnatural Amino Acids Site-Specifically into Proteins", *Methods in Enzymology*, 202: 301-336, 1992.
A. G. Frutos et al., "Demonstration of a word design strategy for DNA computing on surfaces", *Nucleic Acids Research*, 25(23): 4748-4757, 1997.
K. Fujimoto et al., "Template-Driven Photoreversible Ligation of Deoxyoligonucleotides via 5-Vinyldeoxyuridine", *J. Am. Chem. Soc.*, 122:5646-5647, 2000.
K. Fujimoto et al., "Template-directed reversible photocircularization of DNA via 5-vinyldeoxycytidine", *Tetrahedron Letters*, 41: 6451-6454, 2000.
K. Fujimoto et al., "Template directed photochemical synthesis of branched oligodeoxynucleotides via 5-carboxyvinyldeoxyuridine", *Tetrahedron Letters*, 41: 9437-9440, 2000.
R. L. E. Furlan et al., "Molecular amplification in a dynamic combinatorial library using non-covalent interactions", *Chem. Commun.*, 1761-1762, 2000.
Z. J. Gartner et al., "DNA-templated Organic Synthesis and Selection of a Library of Macrocycles", *Science*, 305: 1601-1605 and 10 pages online supporting material, Sep. 10, 2004.
Z. J. Gartner et al., "Expanding the Reaction Scope of DNA-Templated Synthesis", *Angew. Chem. Int. Ed.*, 41(10): 1796-1800, 2002.
Z. J. Gartner et al., "The Generality of DNA-Templated Synthesis as a Basis for Evolving Non-Natural Small Molecules", *J. Am. Chem. Soc.*, 123: 6961-6963, 2001.
Z. J. Gartner et al., "Multistep Small-Molecule Synthesis Programmed by DNA Templates", *J. Am. Chem. Soc.*, 124: 10304-10306, 2002.

(56) References Cited

OTHER PUBLICATIONS

R. Grubina et al., "DNA-Templated Synthesis of a Synthetic Small Molecule Library", *The Nucleus*, 10-14, Jan. 2004.
Z. J. Gartner et al., "Two Enabling Architectures for DNA-Templated Organic Synthesis", *Angew. Chem. Int. Ed.*, 42(12): 1370-1375, 2003.
E. M. Gordon et al., "Applications of Combinatorial Technologies to Drug Discovery. 2. Combinatorial Organic Synthesis, Library Screening Strategies, and Future Directions", *J. Medicinal Chem.*, 37(10):1385-1401, May 13, 1994.
S. M. Gryaznov et al., "Chemical Ligation of Oligonucleotides in the Presence and Absence of a Template", *J. Am. Chem. Soc.*, 115: 3808-3809, 1993.
S. M. Gryaznov et al., "Template controlled coupling and recombination of oligonucleotide blocks containing thiophosphoryl groups", *Nucleic Acids Research*, 21(6): 1403-1408, 1993.
S. M. Gryaznov et al., "Enhancement of selectivity in recognition of nucleic acids via chemical autoligation", *Nucleic Acids Research*, 22(12): 2366-2369, 1994.
D. R. Halpin et al., "DNA Display I. Sequence-Encoded Routing of DNA Populations", *PLoS Biology*, 2(7): 0001-0006, Jul. 2004.
D. R. Halpin et al., "DNA Display II. Genetic Manipulation of Combinatorial Chemistry Libraries for Small Molecule Evolution", *PLoS Biology*, 2(7): 0001-0009, Jul. 2004.
D. R. Halpin et al., "DNA Display III. Solid-Phase Organic Synthesis on Unprotected DNA", *PLoS Biology*, 2(7): 0001-0006, Jul. 2004.
M. K. Herrlein et al., "Selective chemical autoligation on a double-stranded DNA template", *Nucleic Acids Research*, 22(23): 5076-5078, 1994.
T. Inoue et al., "A Nonenzymatic RNA Polymerase Model", *Science*, 219: 859-862, Feb. 18, 1983.
T. Inoue et al., "Oligomerization of (Guanosine 5'-phosphor)-2-methylimidazolide on Poly(C)", *J. Mol. Biol.*, 162: 201-217, 1982.
M. W. Kanan et al., "Reaction discovery enabled by DNA-templated synthesis and in vitro selection", *Nature*, 431:545-549, including Supplementary Information pp. 1-20, Sep. 30, 2004.
K. C. Keiler et al., "Role of a Peptide Taggin System in Degradation of Proteins Synthesized from Damaged Messenger RNA", *Science*, 271: 990-993, Feb. 16, 1996.
B. Klekota et al., "Selection of DNA-Binding Compounds via Multistage Molecular Evolution", *Tetrahedron*, 55:11687-11697, 1999.
M. Kurz et al., "An Efficient Synthetic Strategy for the Preparation of Nucleic Acid-Encloded Peptide and Protein Libraries for In Vitro Evolution Protocols", *Fourth International Electronic Conference on Synthetic Organic Chemistry (ECSOC-4)*, www.mdpi.org/ecsoc-4.htm 5 pages, Sep. 1-30, 2000.
M. Kurz et al., "Psoralen photo-crosslinked mRNA-puromycin conjugates: a novel template for the rapid and facile preparation of mRNA-protein fusions", *Nucleic Acids Research*, 28(18): 1-5, 2000.
J. C. Leitzel et al., "Template-Directed Ligation: From DNA Towards Different Versatile Templates", *Chem. Rec.*, 1(1): 53-62, 2001.
R. L. Letsinger et al., "Chemical and Photochemical Ligation of Oligonucleotide Blocks", *Nucleosides & Nucleotides*, 16(5&6): 643-652, 1997.
R. L. Lewis et al., "Ligation of oligonucleotides by pyrimidine dimers-a missing 'link' in the origin of life?", *Nature*, 298: 393-396, Jul. 22, 1982.
X. Li et al., "DNA-Catalyzed Polymerization", *J. Am. Chem. Soc.*, 124(5): 746-747, 2002.
X. Li et al., "DNA-Templated Organic Synthesis: Nature's Strategy for Controlling Chemical Reactivity Applied to Synthetic Molecules", *Angew. Chem. Int. Ed.*, 43: 4848-4870, 2004.
X. Li et al., "Stereoselectivity in DNA-Templated Organic Synthesis and Its Origins", *J. Am. Chem. Soc.*, 125: 10188-10189, 2003.
X. Li et al., "Translation of DNA into Synthetic N-Acyloxazolidines", *J. Am. Chem. Soc.*, 126: 5090-5092, 2004.

D. R. Liu et al., "DNA-Templated Synthesis as a Basis for the Evolution of Synthetic Molecules", *Abstracts of Papers of the Am. Chem. Soc.*, 225: 612-ORGN, Part 2, Mar. 2003.
D. R. Liu, "Development of Amplifiable and Evolvable Unnatural Molecules", website of Dr. D. R. Liu, publicly available Mar. 11, 2000. http://web.archive.org/web/20000311112631/http://evolve.harvard.edu.
D. R. Liu et al., "The Chemistry of Molecular Evolution", website of Dr. D. R. Liu, publicly available Oct. 15, 2000. http://web.archive.org/web/20001015144553/http://evolve.harvard.edu.
D. R. Liu et al., "The Chemistry and Chemical Biology of Molecular Evolution", website of Dr. D. R. Liu, publicly available Mar. 1, 2001. http://web.archive.org/web/20010301175107/http://evolve.harvard.edu.
D. R. Liu et al., "The Chemistry and Chemical Biology of Molecular Evolution", website of Dr. D. R. Liu, publicly available Nov. 20, 2002. http://web.archive.org/web/20021120104204/http://evolve.harvard.edu.
D. R. Liu et al., "The Chemistry and Chemical Biology of Molecular Evolution", website of Dr. D. R. Liu, publicly available Oct. 15, 2003. http://web.archive.org/web/20031015114255/http://evolve.harvard.edu.
D. R. Liu, "Development of Amplifiable and Evolvable Unnatural Molecules", Harvard Univ.Dept. of Chemistry and Chemical Biology, Report dated Aug. 4, 2003. OMB Form No. 0704-0188.
D. R. Liu et al., "Finding Reactions in a Haystack: Try 'em All, See What Works", *Science*, vol. 305, Sep. 40, 2004. Meeting: American Chemical Society.
D. R. Liu et al., "Engineering a tRNA and aminoacyl-tRNA synthetase for the site-specific incorporation of unnatural acids into proteins in vivo", *Proc. Natl. Acad. Sci. USA*, 94: 10092-10097, Sep. 1997.
D. R. Liu et al., "Progress toward the evolution of an organism with an expanded genetic code", *Proc. Natl. Acad. Sci. USA*, 96: 4780-4785, Apr. 1999.
D. R. Liu, "Primer: Translating DNA into Synthetic Molecules", *PLoS Biology*, 2(7): 0905-0906, Jul. 2004.
J. Liu et al., "Template-directed photoligation of oligodeoxyribonucleotides via 4-thiothymidine", *Nucleic Acids Research*, 26(13):3300-3304, 1998.
R. Liu et al., "Optimized Synthesis of RNA-Protein Fusions for in Vitro Protein Selection", *Methods in Enzymology*, vol. 318, 268-293, 2000.
C. J. Loweth et al., "DNA-Based Assembly of Gold Nanocrystals", *Angew. Chem. Int. Ed.*, 38(12), 1808-1812, 1999.
P. Luo et al., "Analysis of the Structure and Stability of a Backbone-Modified Oligonucleotide: Implications for Avoiding Product Inhibition in Catalytic Template-Directed Synthesis", *J. Am. Chem. Soc.*, 120: 3019-3031, 1998.
A. Luther et al., "Surface-promoted replication and exponential amplification of DNA analogues", *Nature*, 396: 245-248, Nov. 19, 1998.
D. Mendel, "Site-Directed Mutagenesis with an Expanded Genetic Code", *Annual Review Biophys. Biomol. Struct.*, 24:435-462, 1995.
C. A. Mirkin, "Programming the Assembly of Two- and Three-Dimensional Architectures with DNA and Nanoscale Inorganic Building Blocks", *Inorg. Chem.*, 39:2258-2272, 2000.
I. A. Nazarenko et al., "A closed tube format for amplification and detection of DNA based on energy transfer", *Nucleic Acids Research*, 25(12):2516-2521, 1997.
N. Nemoto et al., "In vitro virus: Bonding of mRNA bearing puromycin at the 3'-terminal end to the C-terminal end of its encoded protein on the ribosome in vitro", *FEBS Letters*, 414:405-408, 1997.
J. Nielsen et al., "Synthetic Methods for the Implementation of Encoded Combinatorial Chemistry", *J. Am. Chem. Soc.*, 115:9812-9813, 1993.
M. H. J. Ohlmeyer et al., Complex synthetic chemical libraries indexed with molecular tags, *Proc. Natl. Acad. Sci.*, 90:10922-10926, Dec. 1993.
Otto et al., "Recent developments in dynamic combinatorial chemistry", *Current Opinion in Chemical Biology*, 6:321-327, 2002.

(56) References Cited

OTHER PUBLICATIONS

M. R. Pavia, "The Chemical generation of Molecular Diversity", Network Science, http://www.netsci.org/Science/Combichem/feature01.html.

J. A. Piccirilli, "RNA seeks its maker", Nature, 376:548-549, Aug. 17, 1995.

O. Ramström et al., "In Situ Generation and Screening of a Dynamic Combinatorial Carbohydrate Library against Concanavalin A", Chembiochem, 1:41-48, 2000.

H. Rembold et al., "Single-Strand Regions of Poly(G) Act as Templates for Oligo(C) Synthesis", Journal of Molecular Evolution, 38:205-210, 1994.

R. W. Roberts et al., "RNA-peptide fusions for the in vitro selection of peptides and proteins", Proc. Natl. Acad. Sci., 94:12297-12302, Nov. 1997.

S. L. Roberts et al., "Simultaneous selection, amplification and isolation of a pseudo-peptide receptor by an immobilized N-methyl ammonium ion template", Chem. Commun., 938-939, 2002.

L. Rodriguez et al., "Template-Directed Extension of a Guanosine 5'-Phosphate Covalently Attached to an Oligodeoxycytidylate Template", Journal of Molecular Evolution, 33:477-482, 1991.

D. M. Rosenbaum et al., "Efficient and Sequence-Specific DNA-Templated Polymerization of Peptide Nucleic Acid Aldehydes", J. Am. Chem. Soc., 125:13924-13925, 2003.

K. Sakurai et al., "DNA-Templated Functional Group Transformations Enable Sequence-Programmed Synthesis Using Small-Molecule Reagents", J. Am. Chem. Soc., 127:1660-1661, 2005.

J. Salas et al., "Biosynthetic Polydeoxynucleotides as Direct Templates for Polypeptide Synthesis", J. Biol. Chem., 243(5):1012-1015, Mar. 10, 1968.

J. S. Schmidt et al., "Information transfer from DNA to peptide nucleic acids by template-directed syntheses", Nucleic Acids Research, 25(23):4792-4796, 1997.

A. W. Schwartz et al., "Template-Directed Synthesis of Novel, Nucleic Acid-Like Structures", Science, 228:585-587, 1985.

B. Smith et al., "DNA-Guided Assembly of Proteins as a Pathway to an Assembler", The 1997 Albany Conference, Biomolecular Motors and Nanomachines.

J. J. Storhoff et al., "Programmed Materials Synthesis with DNA", Chem. Rev. 99:1849-1862, 1999.

D. Summerer et al., "DNA-Templated Synthesis: More Versatile than Expected", Angew. Chem. Int. Ed., 41(1): 89-90, 2002.

K. Tamura et al., "Oligonucleotide-directed peptide synthesis in a ribosome- and ribozyme-free system", PNAS, 98(4):1393-1397, Feb. 13, 2001.

K. Tanaka et al., "Synthesis of a Novel Nucleoside for Alternative DNA Base Pairing through Metal Complexation", J. Org. Chem., 64:5002-5003, 1999.

J. Visscher et al., "Template-Directed Synthesis of Acyclic Oligonucleotide Analogues", J. Mol. Evol., 28:3-6, 1988.

J. Visscher et al., "Template-Directed Oligomerization Catalyzed by a Polynucleotide Analog", Science, 244:329-331, Apr. 21, 1989.

J. Visscher et al., "Oligomerization of Deoxynucleoside-Bisphosate Dimers: Template and Linkage Specificity", Originals of Life and Evolution of the Biosphere, 19:3-6, 1989.

J. A. Walder et al., "Complementary carrier peptide synthesis: General strategy and implications for prebiotic origin of peptide synthesis", Proc. Natl. Acad. Sci. USA, 76(1):51-55, Jan. 1979.

L. Wang et al., "A New Functional Suppressor tRNA/Aminoacyl-tRNA Synthetase Pair for the in Vivo Incorporation of Unnatural Amino Acids into Proteins", J. Am. Chem, Soc. 122:5010-5011, 2000.

H. Weizman et al., "2,2'-Bipyridine Ligandoside: A Novel Building Block for Modifying DNA with Intra-Duplex Metal", J. Am. Chem. Soc., 123:3375-3376, 2001.

S. M. Waybright et al., "Oligonucleotide-Directed Assembly of Materials: Defined Oligomers", J. Am. Chem. Soc., 123:1828-1833, 2001.

Y. Xu et al., "Nonenzymatic autoligation in direct three-color detection of RNA and DNA point mutations", Nature Biotechnology, 19:148-152, Feb. 2001.

Y. Xu et al., "Rapid and Selective Selenium-Mediated Autoligation of DNA Strands", J. Am. Chem. Soc., 122:9040-9041, 2000.

Z. J. Zhan et al., "Chemical Amplification through Template-Directed Synthesis", J. Am. Chem. Soc., 119:12420-12421, 1997.

R. N. Zuckermann et al., "Discovery of Nanomolar Ligands for 7-Transmembrane G-Protein-Coupled Receptors from a Diverse N-(Substituted)glycine Peptoid Library", J. Med. Chem., 37:2678-2685, 1994.

Amendments after Notice of Allowance Feb. 16, 2010 re U.S. Appl. No. 10/593,868.

Issue Notification dated Apr. 7, 2010 re U.S. Appl. No. 10/593,868.

Restriction Requirement dated Apr. 7, 2011 re U.S. Appl. No. 10/589,551.

Response submitted Oct. 7, 2011 to Restriction Requirement re U.S. Appl. No. 10/589,551.

Non-final rejection dated Oct. 26, 2011 re U.S. Appl. No. 10/589,551.

1st Restriction requirement of Oct. 5, 2011 re U.S. Appl. No. 12/095,778.

Response dated Mar. 5, 2012 to 1st Restriction Requirement re U.S. Appl. No. 12/095,778.

2nd Restriction requirement dated Jun. 27, 2012 re U.S. Appl. No. 12/095,778.

Response submitted Dec. 27, 2012 to 2nd Restriction Requirement re U.S. Appl. No. 12/095,778.

Office Action dated Apr. 15, 2013 re U.S. Appl. No. 12/095,778.

Response dated May 15, 2013 to Restriction Requirement re U.S. Appl. No. 12/095,778.

Non-final rejection dated Oct. 8, 2013 re U.S. Appl. No. 12/095,778.

Adang et al., "The Contribution of Combinatorial Chemistry to Lead Generation: An Interim Analysis", Current Medicinal Chemistry, 2001, 8, 985-998.

Affleck, "Solutions for library encoding to create collections of discrete compounds", Current Opinion in Chemical Biology, 2001, 5:257-263.

Bain et al., "Biosynthetic site-specific incorporation of a non-natural amino acid into a polypeptide", J. Am. Chem. Soc., 1989, 111, 8013-8014.

Barnes et al., "Recent developments in the encoding and deconvolution of combinatorial libraries", Current Opinion in Chemical Biology 2000, 4:346-350.

Chen et al., "Total Synthesis of Naturally Occurring Prostaglandin F2a on a Non-Cross-Linked Polystyrene Support", Tetrahedron Letters 39 (1998) 3943-3946.

Coe et al., "Solution-phase combinatorial chemistry", Molecular Diversity, 4: 31-38, 1999.

Dolle, "Comprehensive Survey of Combinatorial Library Synthesis: 2000", Journal of Combinatorial Chemistry, 2001, vol. 3, No. 6, pp. 477-517.

Dolle, "Comprehensive Survey of Combinatorial Library Synthesis: 2001", Journal of Combinatorial Chemistry, 2002, vol. 4, No. 5, pp. 369-418.

Dolle, "Comprehensive Survey of Combinatorial Library Synthesis: 2002", Journal of Combinatorial Chemistry, 2003, vol. 5, No. 6, pp. 693-753.

Furka et al., "General method for rapid synthesis of multicomponent peptide mixtures", Int. J. Peptide Protein Res., 37, 1991, 487-493.

Gallop et al., "Applications of Combinatorial Technologies to Drug Discovery. 1. Background and Peptide Combinatorial Libraries", Journal of Medicinal Chemistr-y, 1994, vol. 37, No. 9, pp. 1233-1251.

Guillen Schlippe et al.,"In Vitro Selection of Highly Modified Cyclic Peptides That Act as Tight Binding Inhibitors", J. Am. Chem. Soc. 2012, 134, 10469-10477.

Han et al., "Liquid-phase combinatorial synthesis", Proc. Natl. Acad. Sci. USA, vol. 92, pp. 6419-6423, Jul. 1995.

www.wikipedia.org/wiki/DNA-encoded chemical library Oct. 2, 2012, pp. 1-12.

http://www2.umt.edu/medchem/teaching/medchem/mclect14.htmThompson C. M., Medicinal Chemistry, lecture 14, Pharmaceutical Sciences 621 & Chemistry 569, 1995.

(56) References Cited

OTHER PUBLICATIONS

Li et al., "Kinetics of RNA Degradation by specific base catalysis of transesterification involving the 2'-hydroxyl group", J. Am. Chem. Soc., 1999, 121, pp. 5364-5372.
Ma et al., "In Vitro Selection of Unnatural Cyclic Peptide Libraries via mRNA Display", Book Ribosome Display and Related Technologies, ch. 21, pp. 367-390, 2012.
Maclean et al., "Glossary of terms used in combinatorial chemistry", Pure Appl. Chem., vol. 71, No. 12, pp. 2349-2365, 1999.
Meier et al, "Combinatorial Methods, Automated Synthesis and High-Throughput Screening in Polymer Research: The Evolution Continues", Macromol. Rapid Commun. 2004, 25, 21-33.
Chorghade, "Drug discovery and development", 2006, ISBN-13: 978-0-471-39848-6, Published by John Wiley & Sons, Inc., Hoboken, New Jersey.
Needels et al., "Generation and screening of an oligonucleotide-encoded synthetic peptide library", Proc. Natl. Acad. Sci. USA, vol. 90, pp. 10700-10704, 1993.
Ni et al., "Versatile Approach To Encoding Combinatorial Organic Syntheses Using Chemically Robust Secondary Amine Tags", J. Med. Chem. 1996, 39, 1601-1608.
Nicolaou et al., "Radiofrequency Encoded Combinatorial Chemistry", Angew. Chem. Int. Ed. Engl., 1995, 34, No. 20, pp. 2289-2291.
Noren et al., "A general method for site-specific incorporation of unnatural aminoacids into protein", Science, vol. 244, 1989, pp. 182-188.
Starck et al., "The puromycin route to assess stereo- and regiochemical constraints on peptide bond formation in eukaryotic ribosomes", J. Am. Chem. Soc., 2003, 125, 8090-8091.
Studer et al., "Fluorous Synthesis: A Fluorous-Phase Strategy for Improving Separation Efficiency in Organic Synthesis", 1997, Science 275, pp. 823-826.
Terrett et al., "Combinatorial synthesis-The design of compound libraries and their application to drug discovery", Tetrahedron, 1995, vol. 51, No. 30., pp. 8135-8173.
Website: "Combinatorial chemistry", http://www.ukessays.co.uk/essays/chemistry/combinatorial-chemistry.php, Oct. 29, 2012, pp. 1-11.
Wermuth et al., "Glossary of terms used in medical chemistry", Pure & Appl. Chem, 1998, vol. 70, No. 5, pp. 1129-1143.
Ymane et al., "Discrimination between D- and L-Tyrosyl transfer ribonucleic acids in peptide chain elongation", American Chemical Society, vol. 20, No. 25, 1981, pp. 7059-7064.
Lipinski et al., "Experimental and computational approaches to estimate solubility and permeability in drug discovery and development settings", Adv. Drug Deliv. Rev., vol. 46 (1-3), 2001, pp. 3-26.
Lipinski, "Lead- and drug-like compounds: the rule-of-five revolution", Drug Discovery Today: Technologies, vol. 1, No. 4, 2004, pp. 337-341.
Kleiner et al., "Small-molecule discovery from DNA-encoded chemical libraries", Chem. Soc. Rev., 2011, 40, pp. 5707-5717.
http://en.wikipedia.org/wiki/Scaffold_protein.
Balkenhohl et al., "Combinatorial synthesis of small organic molecules", Angew Chem Int. Ed Engl. 1996, 35, pp. 2288-2337.
Strachan, "Human Molecular Genetics", 2nd edition, textbook published by Wiley-Liss, 1999.
Barrio et al., "Synthesis of modified nucleoside 3',5'-bisphophates and their incorporation into oligoribonucleotides with T4 RNA Ligase", Biochemistry, vol. 17, No. 11, 1978.
Chan et al., "Altered DNA ligase I activity in Bloom's syndrome cells", Nature, vol. 325, pp. 357-359 , 1987.
Bain et al., "Regioselective Ligation of Oligoribonucleotides using DNA Splints", Nucl. Acids Res., vol. 20, No. 16, 4372, 1992.
Boger & Goldberg "Chapter 10: Multi-step Solution Phase Combinatorial Synthesis" in Combinatorial Chemistry, ed. Hicham Fenniri, Oxford University Press (Oxford, England), 2000, pp. 303-326.
Cheng et al., "Novel Solution Phase Strategy for the Synthesis of Chemical Libraries Containing Small Organic Molecules", J. Am. Chem. Soc., vol. 118, 2567-2573, 1996.

Clark et al., "Design, Synthesis and Selection of DNA-encoded Small-molecule Libraries", Nat. Chem. Biol., vol. 5, No. 9, 647-772, 2009.
Curran, "Strategy-Level Separations in Organic Synthesis: From Planning to Practice", Angew. Chem. Int. Ed., vol. 37, 1174-1196, 1998.
Declaration by Dr. Dennis Benjamin (including curriculum vitae).
Frutos et al. "Enzymatic Ligation Reactions of DNA "Words" on Surfaces for DNA Computing", J. Am. Chem. Soc., 10277-10282, 1998.
Gait, "Chapter 1: An Introduction to Modern Methods of DNA Synthesis": Van Boom & Wreesman, "Chapter 7:Chemical Synthesis of Small Oligoribonucleotides in solution"; and Beckett & Uhlenbeck, "Chapter 8: Enzymatic Synthesis of Oligoribonucleotides", in Oligonucleotide Synthesis: A Practical Approach, ed. M.J. Gait, IRL Press (Oxford, England and Washington, DC), 1984, pp. 1-22, 153-183, and 185-197.
Gartner et al., "Expanding the Reaction Scope of DNA-Templated Synthesis", Angew. Chem. Int. Ed., vol. 41, No. 10, 1796-1800, 2002.
Gartner et al., "Multistep Small-Molecule Synthesis Programmed by DNA Templates", J. Am. Chem. Soc., vol. 124, No. 35, 10304-10306 (including Supporting Information, pp. 1-4).
Glen Research Report, "Advances in RNA Synthesis and Structural Analysis", vol. 11, No. 2, Dec. 1998.
Harrison et al., "Synthesis and Hybridization Analysis of a Smal Library of Peptide-oligonucleotide Conjugates", Nucl. Acids Res., vol. 26, No. 13, 3136-3145, 1998.
Hausch et al., "Libraries of Multifunctional RNA Conjugates for the Selection of New RNA Catalysts", Bioconjugate Chem., vol. 8, 885-890, 1997.
Hill et al., "Diels-Alder Bioconjugation of Diene-Modified Oligonucleotides", J. Org. Chem., vol. 66, 5352-5358, 2001.
Itakura et al., "Expression in *Escherichia coli* of a Chemically Synthesized Gene for the Hormone Somatostatin", Science, vol. 198, 1056-1063, 1977.
Janda, "Tagged Versus Untagged Libraries: Methods for the Generation and Screening of Combinatorial Chemical Libraries, " PNAS USA, vol. 91, 10779-10785, 1994.
Kelemen et al., "Hypersensitive Substrate for Ribonucleases", Nucl. Acids. Res., vol. 27, No. 18, 3696-3701, 1999.
Kempe et al., "Chemical and Enzymatic Biotin-labeling of Oligodeoxyribonucleotides", Nucl. Acids Res., vol. 13, No. 1, 45-57, 1985.
Kinoshita et al., "Enzymatic Synthesis of Sequencing Primers Based on a Library of Tetramers", Chem. Express, 149-152, 1992.
Kinoshita et al., "Strand Ligation in a double-stranded DNA by T4 RNA Ligase", Chem. Lett., No. 9, 797-798, 1996.
Kitamura et al., "Construction of Block-Shuffled Libraries of DNA for Evolutionary Protein Engineering: Y-Ligation-Based Block Shuffling", Prot. Engineering, vol. 15, No. 10, 843-853, 2002.
Kitamura et al., "Development of Systemic in vitro Evolution and Its Application to Generation of Peptide-Aptamer-Based Inhibitors of Cathepsin E", J. Mol. Biol., vol. 387, 1186-1198, 2009.
Moore et al. "Site-specific Modification of Pre-mRNA: the 2'-hydroxyl Groups at the Splice Sites", Science, vol. 256, 992-997, 1992.
Nielsen et al., "Synthetic Methods for the Implementation of Encoded Combinatorial Chemistry", J. Am. Chem. Soc., vol. 115, 9812-9813, 1993 with supplementary Materials (pp. 1-7).
Nielsen et al., "Toward Chemical Implementation of Encoded Combinatorial Libraries", Methods: A Companion to Meth: Enzymol., vol. 6, 361-371, 1994.
Roux, "Optimization and troubleshooting in PCR", PCR Methods Appl., vol. 4, No. 5, S185-S194, 1995.
Schmitz et al., "Solid-phase Enzymatic Synthesis of Oligonucleotides", Org. Lett., vol. 1, 1729-1731, 1999.
Seelig et al., "Site-specific Modification of Enzymatically Synthesized RNA: Transcription Initiation and Diels-Alder Reaction," Tetrahed. Lett., vol. 38, 7729-7732, 1997.
Seo et al., "Click Chemistry to Construct Fluorescent Oligonucelotides for DNA sequencing", J. Org. Chem., vol. 68, 609-612, 2003.

(56) References Cited

OTHER PUBLICATIONS

Sherlin et al., "Chemical and Enzymatic Synthesis of tRNAs for High-throughput Crystallization", RNA, vol. 7, No. 11, 1671-1678, 2001.
Tabuchi et al., "An Efficient Ligation Method in the Making of an in vitro Virus for in vitro Protein Evolution," Biol., Proced. Online, vol. 4, No. 1, 49-54, 2002.
Verma et al., "Modified Oligonucleotides: Synthesis and Strategy for Users", Annu. Rev. Biochem., vol. 67, 99-134, 1998.
Woiwode et al., "Synthetic Compound Libraries Displayed in the Surface of Encoded Bacteriophage", Chem. Biol., 847-858, 2003.
Wojcewski et al., "Fluorescent Oligonucleotides—Versatile Tools as Probes and Primers for DNA and RNA Analysis", Synlett, No. 10, 1667-1678, 1999.
Wong & Whitesides, "Enzymes in Synthetic Organic Chemistry", Tetrahedron Organic Chemistry Series vol. 12, Pergamon, Elsevier Science Lrd. (Oxford, England) 1994, pp. Xiii-xv, 1-40, and 329-334.
Zhang et al., "Solution-Phase Preparation of a 560-Compound Library of Individual Pure Mappicine Analogous by Fluorous Mixture Synthesis", J. Am. Chem. Soc., vol. 124, 10443-10450, 2002.
Cranston et al., "Studies on ribonucleic acid ligase", J.Biol.Chem., vol. 249, No. 23, pp. 7447-7456, 1974.
England et al., "Enzymatic oligoribonucleotide synthesis with T4 RNA ligase", Biochemistry, vol. 17, No. 11., 1978.
Gassen et al., "Synthesis by polymer-bound ribonuclease of the termination codons U-A-A, U-A-G, and U-G-A" Biochemical and biophysical research communications, vol. 44, No. 6, pp. 1410-1415, 1971.
Haseth et al., "Interaction of *Escherichia coli* host factor protein with oligoriboadenylates", Biochemistry, 19, pp. 6138-6146, 1980.
Hoffman et al., "Polynucleotide phosphorylase covalently bound to cellulose and its use in the preparation of homopolynucleotides", Biochemical and biophysical research communications, vol. 41, No. 3, pp. 710-714, 1970.
Kiebom, "Enzymes that do not work in organic solvents: Too polar substrates give too tight enzyme-product complexes", Recl. Trav. Chim. Pays-Bas, 107, pp. 347-348, 1988.
Middleton et al., "Synthesis and purification of oligoribonucleotides using T4 RNA ligase and reverse-phase chromatography", Analytical Biochemistry, 144, pp. 110-117, 1985.
Narang, "DNA synthesis", Tetrahedron, vol. 39, No. 1, pp. 3-22, 1983.
Neilson et al., "Synthesis of biologically active portions of an intercistronic region by use of a new 3'-phosphate incorporation method to protect 3'-OH and their binding to ribosomes", Eur. J. Biochem., 99, pp. 429-437, 1979.
Ochoa et al., "Enzymatic synthesis of polynucleotides", J.Biol. Chem., vol. 236, 12, pp. 3303-3311, 1961.
Willis et al., "DNA ligase I deficiency in Bloom's syndrome", Nature, vol. 325, pp. 355-357, 1987.
D'Angelo et al., "HIV-1 integrase: the next target for AIDS therapy? ", Pathol. Biol. 2001, 49, pp. 237-246.
http://www.piercenet.com/method/avidin-biotin-interaction retrieved Nov. 5, 2013.
Response filed Sep. 22, 2008 to Restriction Requirement re U.S. Appl. No. 10/549,619.
Non-final Rejection Apr. 28, 2009 re U.S. Appl. No. 10/549,619.
Response after Non-final Rejection submitted Oct. 26, 2009 re U.S. Appl. No. 10/549,619.
Interview summary Mar. 3, 2010 re U.S. Appl. No. 10/549,619.
Notice of Allowance re U.S. Appl. No. 10/549,619.
Amendments after Notice of Allowance Oct. 6, 2010 re U.S. Appl. No. 10/549,619.
Second amendment after Notice of Allowance Oct. 21, 2010 re U.S. Appl. No. 10/549,619.
Issue Notification of Mar. 9, 2011 re U.S. Appl. No. 10/549,619.
First Restriction Requirement dated May 9, 2007 re U.S. Appl. No. 10/525,817.

Response submitted to First Restriction Requirement Sep. 10, 2007 re U.S. Appl. No. 10/525,817.
Second Restriction Requirement dated Nov. 28, 2007 re U.S. Appl. No. 10/525,817.
Response to second Restriction Requirement submitted Feb. 28, 2008 re U.S. Appl. No. 10/525,817.
Third Restriction Requirement dated Jul. 7, 2009 re U.S. Appl. No. 10/525,817.
Response to third Restriction Requirement submitted Oct. 5, 2009 re U.S. Appl. No. 10/525,817.
Non-final rejection dated Apr. 1, 2010 re U.S. Appl. No. 10/525,817.
Supplemental Non-final Action dated Apr. 5, 2010 re U.S. Appl. No. 10/525,817.
Response submitted Jul. 27, 2010 to Non-final Action Apr. 5, 2010 re U.S. Appl. No. 10/525,817.
Non-final rejection Jan. 5, 2011 re U.S. Appl. No. 10/525,817.
Interview Summary dated Jul. 1, 2011 re U.S. Appl. No. 10/525,817.
Response submitted Jul. 5, 2011 to Non-final Action re U.S. Appl. No. 10/525,817.
Examiner's amendment communication dated May 12, 2011 re U.S. Appl. No. 10/525,817.
Notice of Allowance dated Oct. 14, 2011 re U.S. Appl. No. 10/525,817.
Notice of Allowance dated Jan. 19, 2012 re U.S. Appl. No. 10/525,817.
RCE dated Mar. 19, 2012 re U.S. Appl. No. 10/525,817.
Notice of Allowance dated Mar. 30, 2012 re U.S. Appl. No. 10/525,817.
Issue Notification dated Jun. 6, 2012 re U.S. Appl. No. 10/525,817.
Restriction Requirement dated Jun. 25, 2008 re U.S. Appl. No. 11/402,957.
Response submitted Aug. 25, 2008 to Restriction Requirement re U.S. Appl. No. 11/402,957.
Non-final Rejection dated Nov. 28, 2008 re U.S. Appl. No. 11/402,957.
Response submitted May 14, 2009 to Non-final Rejection re U.S. Appl. No. 11/402,957.
Non-final Rejection dated Jul. 6, 2009 re U.S. Appl. No. 11/402,957.
Response submitted Dec. 7, 2009 to Non-final Rejection re U.S. Appl. No. 11/402,957.
Final Rejection dated Feb. 16, 2010 re U.S. Appl. No. 11/402,957.
Response submitted Jul. 28, 2010 to Final Rejection re U.S. Appl. No. 11/402,957.
Notice of Appeal dated Aug. 16, 2010 re U.S. Appl. No. 11/402,957.
Notice of Allowance dated Sep. 2, 2010 re U.S. Appl. No. 11/402,957.
RCE dated Dec. 2, 2010 re U.S. Appl. No. 11/402,957.
Second Notice of Allowance dated Apr. 29, 2011 re U.S. Appl. No. 11/402,957.
RCE dated Jul. 28, 2011 re U.S. Appl. No. 11/402,957.
Third Notice of Allowance dated Oct. 31, 2011 re U.S. Appl. No. 11/402,957.
RCE dated Dec. 12, 2011 re U.S. Appl. No. 11/402,957.
Preliminary amendment Nov. 21, 2012 re U.S. Appl. No. 11/402,957.
Non-final Rejection dated May 22, 2013 re U.S. Appl. No. 11/402,957.
Response to Non-final rejection submitted Sep. 23, 2013 re U.S. Appl. No. 11/402,957.
Restriction Requirement dated May 14, 2013 re U.S. Appl. No. 13/455,223.
Response submitted Aug. 14, 2013 to Restriction Requirement re U.S. Appl. No. 13/455,223.
Non-final rejection dated Nov. 15, 2013 re U.S. Appl. No. 13/455,223.
Non-final rejection dated Mar. 30, 2009 re U.S. Appl. No. 10/593,868.
Response submitted Jul. 28, 2009 to Non-final rejection re U.S. Appl. No. 10/593,868.
Notice of Allowance dated Nov. 16, 2009 re U.S. Appl. No. 10/593,868.
Response to Restriction Requirement submitted Jan. 31, 2011 re U.S. Appl. No. 10/539,288.
Non-final Rejection dated Apr. 25, 2011 re U.S. Appl. No. 10/539,288.
Response after Non-final rejection submitted Oct. 25, 2011 re U.S. Appl. No. 10/539,288.
Final rejection dated Dec. 22, 2011 re U.S. Appl. No. 10/539,288.
Notice of Appeal filed Jun. 18, 2012 re U.S. Appl. No. 10/539,288.
RCE filed Aug. 20, 2012 re U.S. Appl. No. 10/539,288.
Non final rejection dated Sep. 21, 2012 re U.S. Appl. No. 10/539,288.

(56) References Cited

OTHER PUBLICATIONS

Response after Non-final rejection submitted Feb. 28, 2013 re U.S. Appl. No. 10/539,288.
Non-final rejection dated Apr. 16, 2013 re U.S. Appl. No. 10/539,288.
Response to Non-final rejection submitted Sep. 16, 2013 re U.S. Appl. No. 10/539,288.
Non final rejection dated Nov. 15, 2013 re U.S. Appl. No. 10/539,288.
Restriction Requirement dated Jan. 4, 2008 re U.S. Appl. No. 10/518,056.
Response to Restriction Requirement submitted Jun. 2, 2008 re U.S. Appl. No. 10/518,056.
Non-final Rejection dated Oct. 8, 2008 re U.S. Appl. No. 10/518,056.
Response after Non-final Rejection submitted Feb. 17, 2009 re U.S. Appl. No. 10/518,056.
Final Rejection dated May 27, 2009 re U.S. Appl. No. 10/518,056.
Notice of Appeal filed Oct. 27, 2009 re U.S. Appl. No. 10/518,056.
Amendments after Notice of Appeal submitted Nov. 17, 2009 re U.S. Appl. No. 10/518,056.
Advisory Action dated Jan. 7, 2010 re U.S. Appl. No. 10/518,056.
RCE filed Mar. 22, 2010 re U.S. Appl. No. 10/518,056.
Non-final Rejection mailed Mar. 31, 2008 re U.S. Appl. No. 10/545,795.
Response after Non-final Rejection submitted Sep. 30, 2008.
Final Rejection dated Jan. 27, 2009 re U.S. Appl. No. 10/545,795.
Notice of Appeal filed Jul. 27, 2009 re U.S. Appl. No. 10/545,795.
Amendments after Notice of Appeal submitted Sep. 28, 2009 re U.S. Appl. No. 10/545,795.
Advisory Action dated Sep. 29, 2009 re U.S. Appl. No. 10/545,795.
Second amendment after Notice of Appeal submitted Oct. 27, 2009 re U.S. Appl. No. 10/545,795.
Advisory Action dated Oct. 21, 2009 re U.S. Appl. No. 10/545,795.
RCE submitted Oct. 27, 2009 re U.S. Appl. No. 10/545,795.
Non-final Rejection dated Nov. 16, 2009 re U.S. Appl. No. 10/545,795.
Non-final Rejection dated Mar. 30, 2010 re U.S. Appl. No. 10/545,795.
Interview summary dated Jul. 15, 2010 re U.S. Appl. No. 10/545,795.
Interview summary dated Jul. 30, 2010 re U.S. Appl. No. 10/545,795.
Response after Non-final Rejection dated Aug. 30, 2010 re U.S. Appl. No. 10/545,795.
Final Rejection dated Feb. 1, 2011 re U.S. Appl. No. 10/545,795.
Notice of Appeal filed Jul. 27, 2011 re U.S. Appl. No. 10/545,795.
Restriction Requirement dated Jul. 31, 2008 re U.S. Appl. No. 10/546,538.
Response to Restriction Requirement filed Dec. 24, 2008 re U.S. Appl. No. 10/546,538.
Non-final Rejection dated Jun. 10, 2009 re U.S. Appl. No. 10/546,538.
Response after Non-final Rejection submitted Dec. 9, 2009 re U.S. Appl. No. 10/546,538.
Final Rejection dated Jun. 8, 2010 re U.S. Appl. No. 10/546,538.
Notice of Appeal filed Dec. 8, 2010 re U.S. Appl. No. 10/546,538.
Appeal dismissed dated Jul. 20, 2011 re U.S. Appl. No. 10/546,538.
Restriction requirement mailed Apr. 24, 2012 re U.S. Appl. No. 13/179,283.
Response submitted Jul. 23, 2012 to restriction requirement re U.S. Appl. No. 13/179,283.
Non-final rejection dated Jul. 31, 2012 re U.S. Appl. No. 13/179,283.
Response of Jan. 30, 2013 to Non final rejection re U.S. Appl. No. 13/179,283.
Final rejection dated Apr. 11, 2013 re U.S. Appl. No. 13/179,283.
Notice of Appeal filed Sep. 11, 2013 re U.S. Appl. No. 13/179,283.
Restriction Requirement of Apr. 21, 2008 re U.S. Appl. No. 10/549,619.
Response to Restriction Requirement submitted May 6, 2005 re U.S. Appl. No. 10/175,539.
Non-final Rejection dated Oct. 13, 2005 re U.S. Appl. No. 10/175,539.
Response submitted Apr. 13, 2006 to Non-final Rejection re U.S. Appl. No. 10/175,539.
Final Rejection dated May 19, 2006 re U.S. Appl. No. 10/175,539.
Notice of Appeal filed Nov. 20, 2006 re U.S. Appl. No. 10/175,539.
RCE submitted Feb. 20, 2007 re U.S. Appl. No. 10/175,539.
Non-final Rejection dated May 14, 2007 re U.S. Appl. No. 10/175,539.
Response submitted Sep. 13, 2007 to Non-final Rejection to U.S. Appl. No. 10/175,539.
Quayle Action dated Nov. 27, 2007 re U.S. Appl. No. 10/175,539.
Response submitted Feb. 27, 2008 to Quayle Action re U.S. Appl. No. 10/175,539.
Notice of Allowance dated May 30, 2008 re U.S. Appl. No. 10/175,539.
Amendment after Notice of Allowance dated Oct. 16, 2008 re U.S. Appl. No. 10/175,539.
Amendment after Notice of Allowance dated May 13, 2009.
Issue Notification dated May 12, 2010 re U.S. Appl. No. 10/175,539.
Non-Final Rejection dated Oct. 27, 2009 re U.S. Appl. No. 12/330,709.
Response submitted Apr. 21, 2010 to Non-final Rejection re U.S. Appl. No. 12/330,709.
Supplemental response submitted Jun. 2, 2010 re U.S. Appl. No. 12/330,709.
Ex parte Quyale Action dated Jul. 27, 2010 re U.S. Appl. No. 12/330,709.
Response of Jan. 10, 2011 to Ex parte Quayle Action re U.S. Appl. No. 12/330,709.
Notice of Allowance dated Mar. 3, 2011 re U.S. Appl. No. 12/330,709.
RCE filed Jun. 2, 2011 re U.S. Appl. No. 12/330,709.
Office Action dated Sep. 17, 2012 re U.S. Appl. No. 12/330,709.
Response dated Feb. 18, 2013 to Office Action re U.S. Appl. No. 12/330,709.
Non-final rejection dated Mar. 27, 2013 re U.S. Appl. No. 12/330,709.
Response submitted Aug. 27, 2013 re U.S. Appl. No. 12/330,709.
Final rejection dated Oct. 28, 2013 re U.S. Appl. No. 12/330,709.
Non-final Rejection dated Feb. 8, 2007 re U.S. Appl. No. 10/507,121.
Response submitted Jun. 7, 2007 to Non-final Rejection re U.S. Appl. No. 10/507,121.
Final Rejection dated Sep. 7, 2007 re U.S. Appl. No. 10/507,121.
RCE filed Feb. 13, 2008 re U.S. Appl. No. 10/507,121.
Notice of Allowance dated Mar. 20, 2008 re U.S. Appl. No. 10/507,121.
Non-final Rejection dated Jan. 27, 2010 re U.S. Appl. No. 12/179,323.
Response submitted Jun. 24, 2010 to Non-final Rejection re U.S. Appl. No. 12/179,323.
Final Rejection dated Sep. 15, 2010 re U.S. Appl. No. 12/179,323.
Notice of Appeal submitted Mar. 15, 2011 re U.S. Appl. No. 12/179,323.
RCE submitted Oct. 17, 2011 re U.S. Appl. No. 12/179,323.
Non-final Rejection dated Jul. 3, 2013 re U.S. Appl. No. 12/179,323.
First Restriction Requirement dated Apr. 4, 2008 re U.S. Appl. No. 10/523,006.
Response to first Restriction Requirement dated Oct. 1, 2008 re U.S. Appl. No. 10/523,006.
Second Restriction Requirement dated Dec. 9, 2009 re U.S. Appl. No. 10/523,006.
Response to second Restriction Requirement dated May 5, 2010 re U.S. Appl. No. 10/523,006.
Third Restriction Requirement dated Aug. 3, 2010 re U.S. Appl. No. 10/523,006.
Response to third Restriction Requirement dated Feb. 1, 2011 re U.S. Appl. No. 10/523,006.
Non-final Rejection dated Mar. 16, 2011 re U.S. Appl. No. 10/523,006.
Response submitted Sep. 16, 2011 to non-final rejection re U.S. Appl. No. 10/523,006.
Final rejection dated Feb. 6, 2012 re U.S. Appl. No. 10/523,006.
RCE submitted Aug. 6, 2012 re U.S. Appl. No. 10/523,006.
Response submitted Oct. 11, 2013 re U.S. Appl. No. 10/523,006.
Restriction Requirement dated Aug. 2, 2010 re U.S. Appl. No. 10/539,288.

* cited by examiner

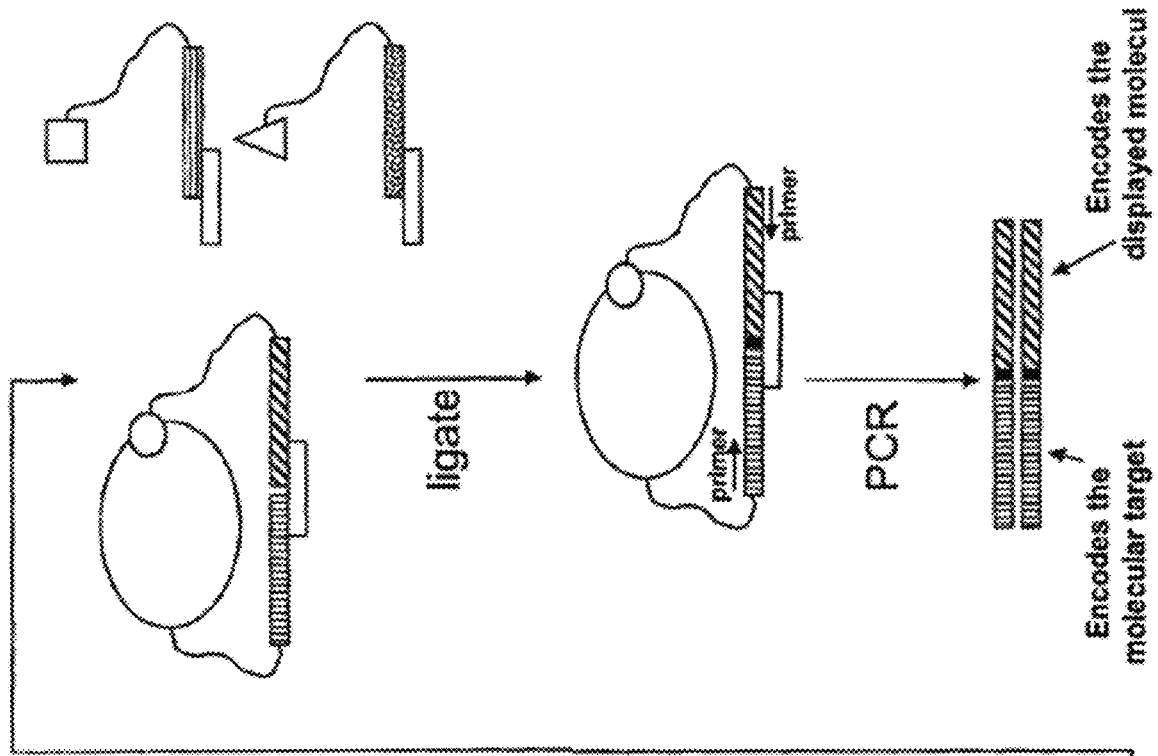
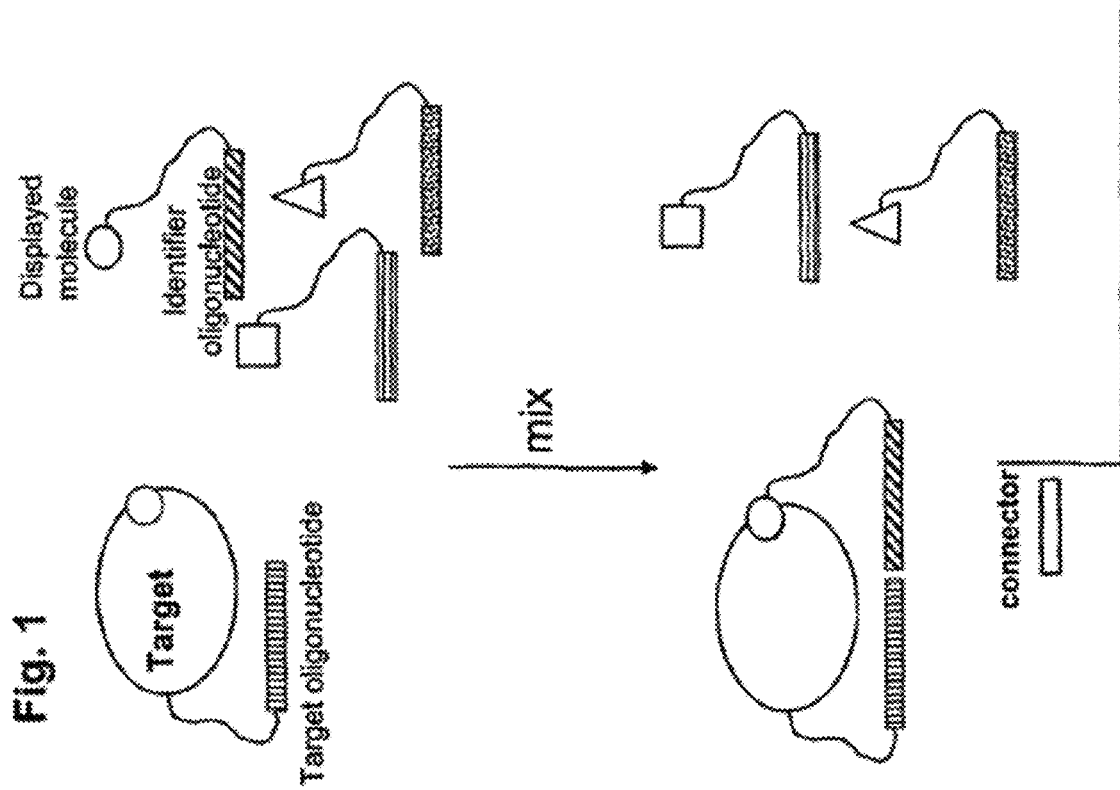
Fig. 1

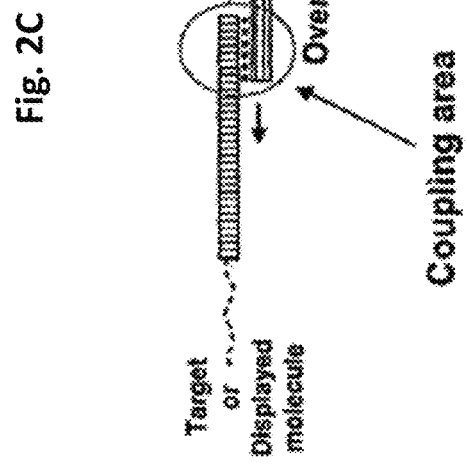
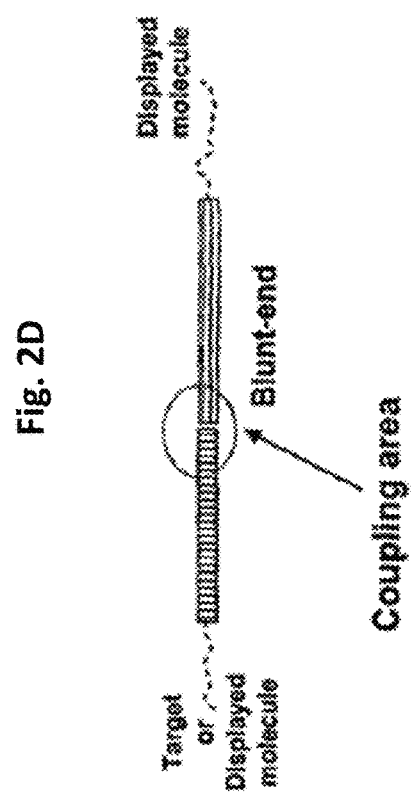
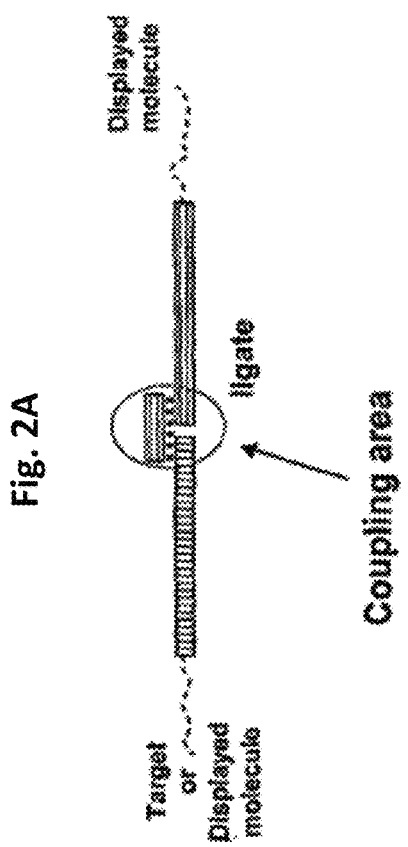
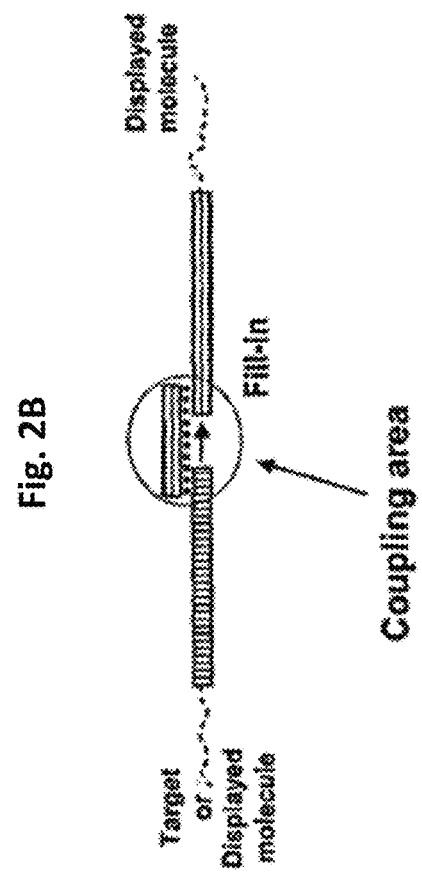

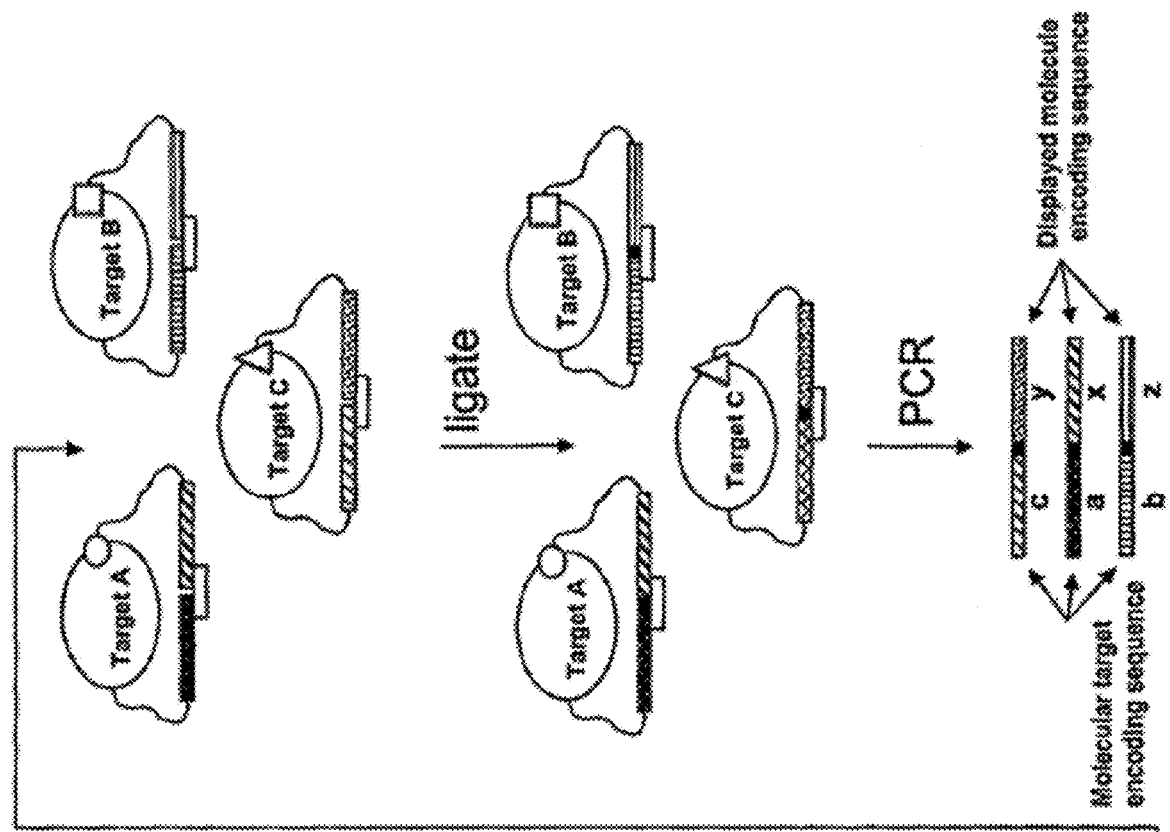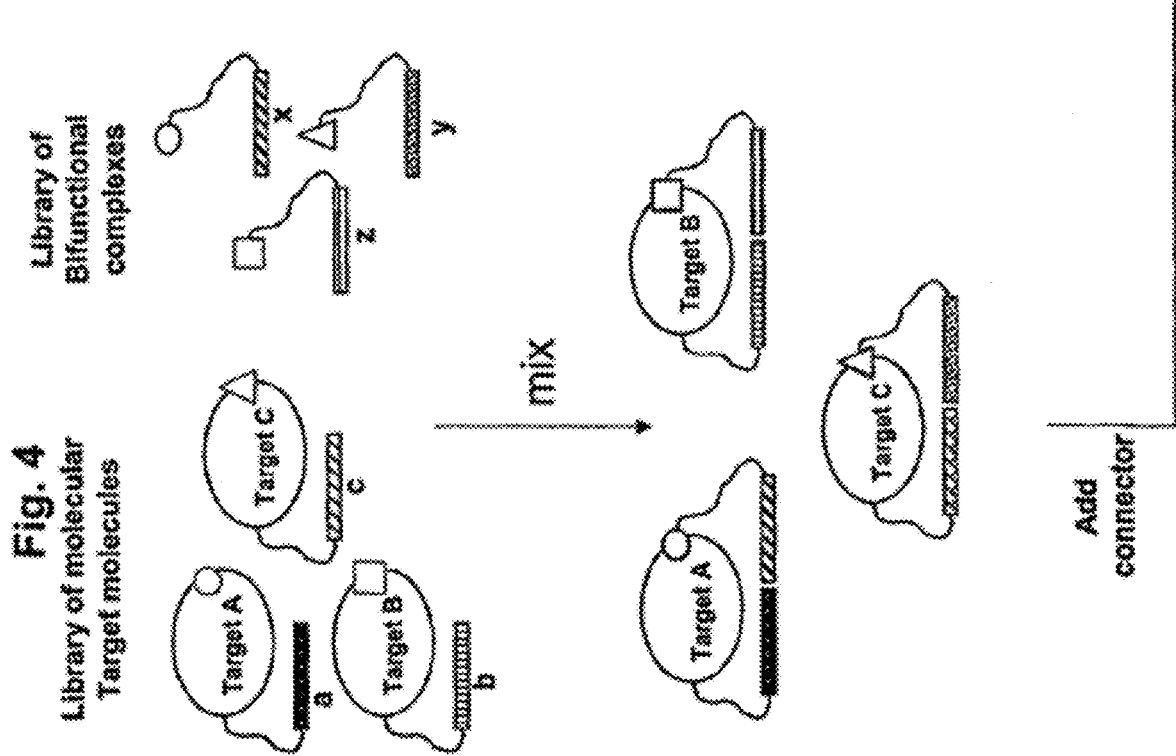

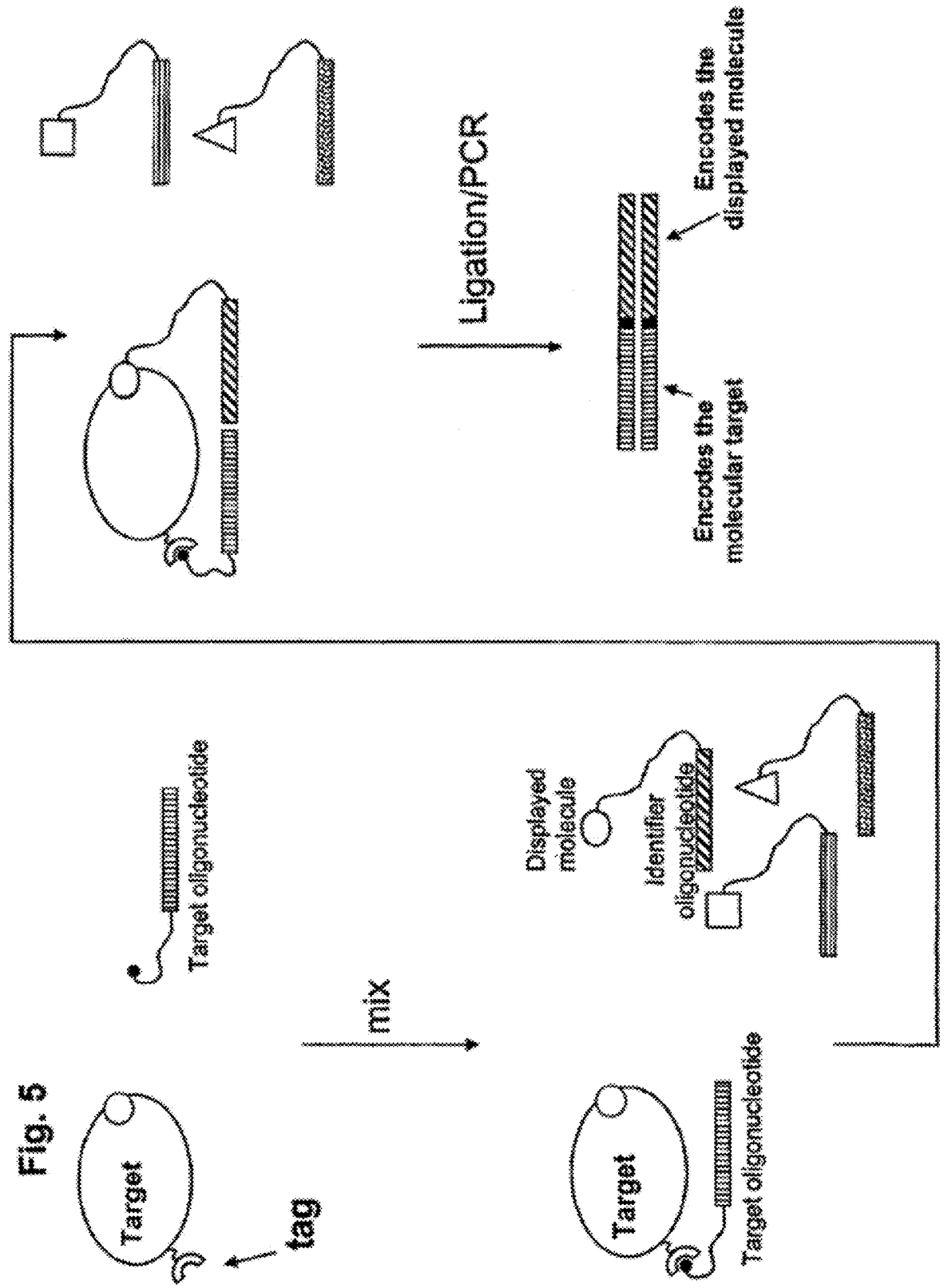

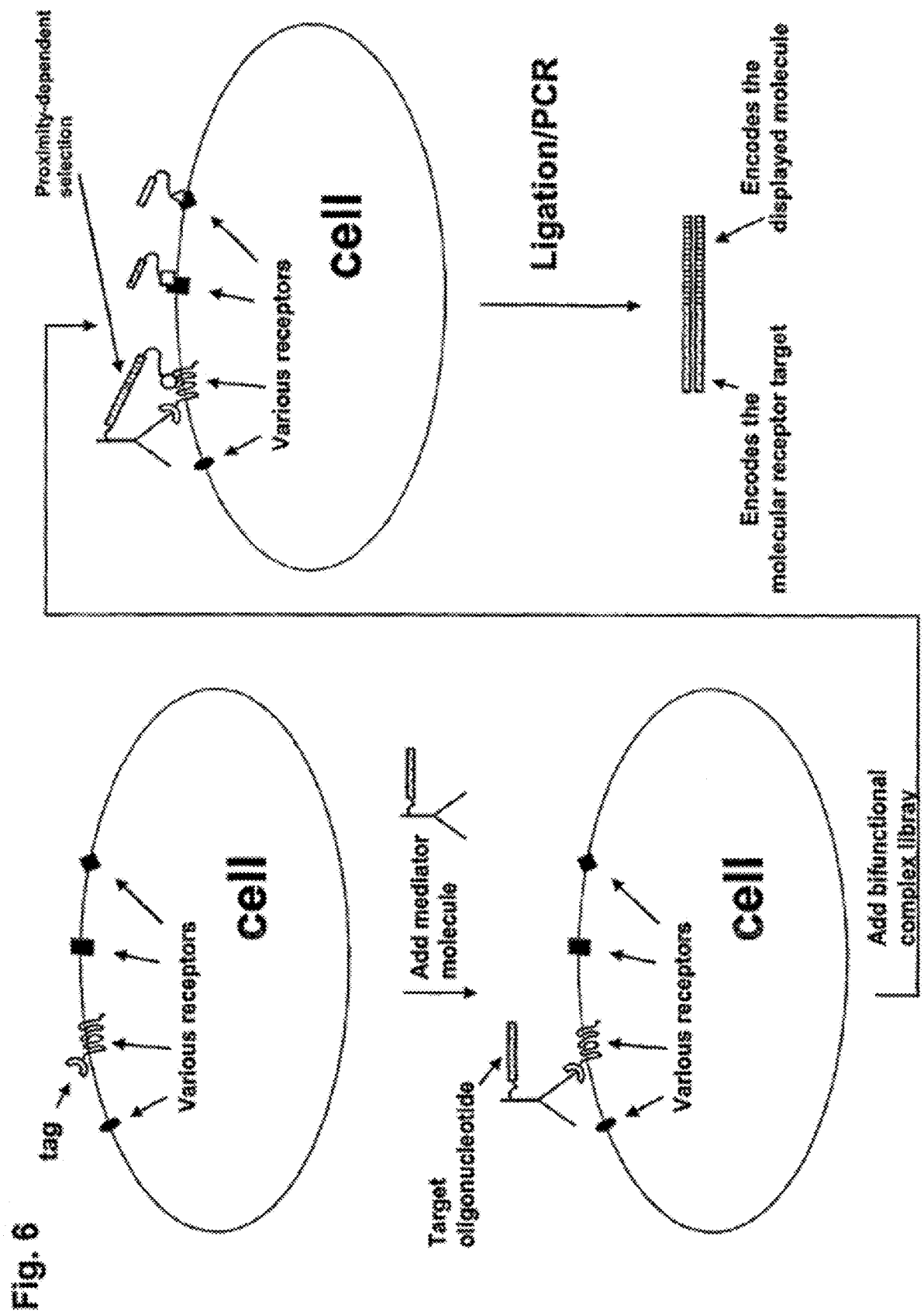

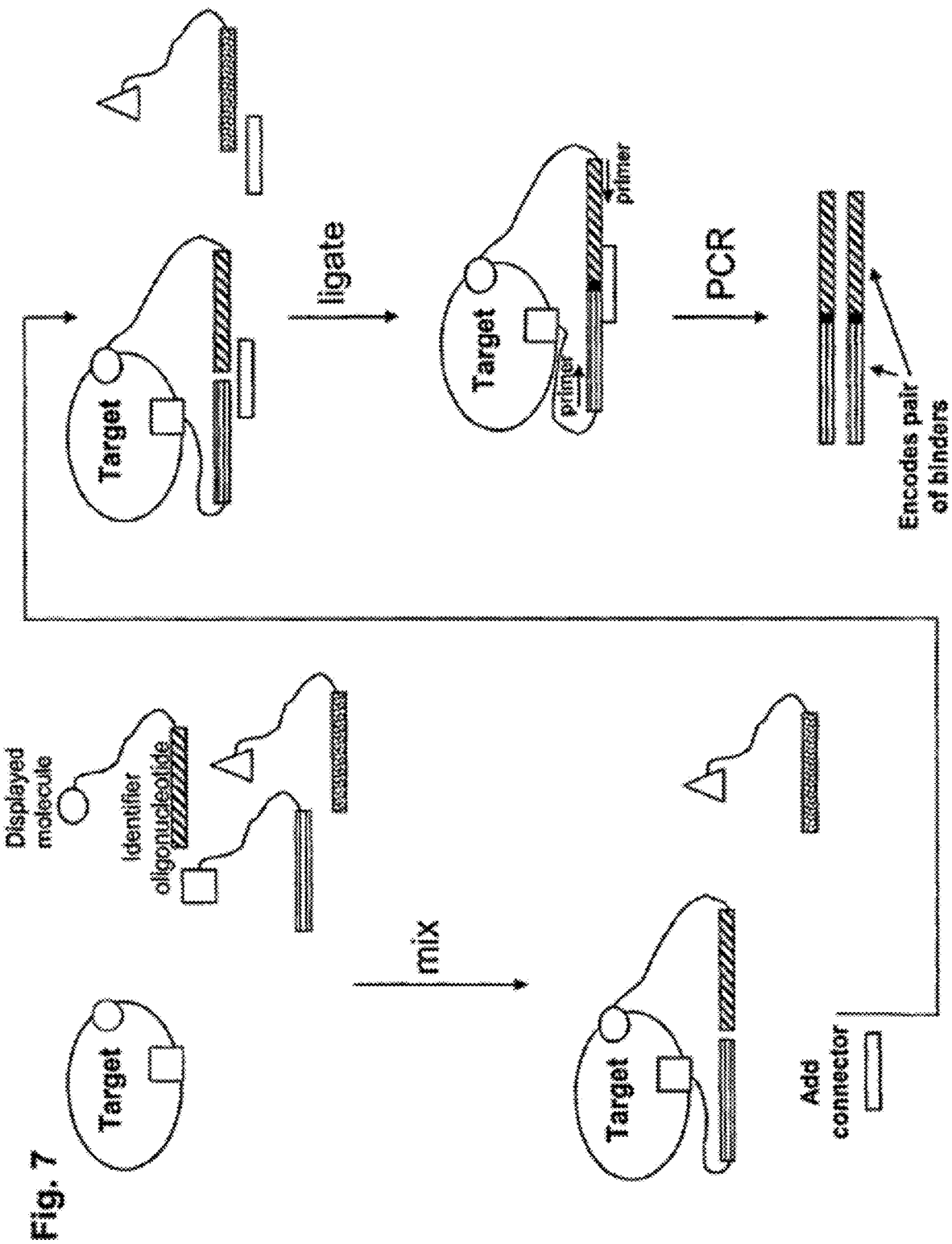

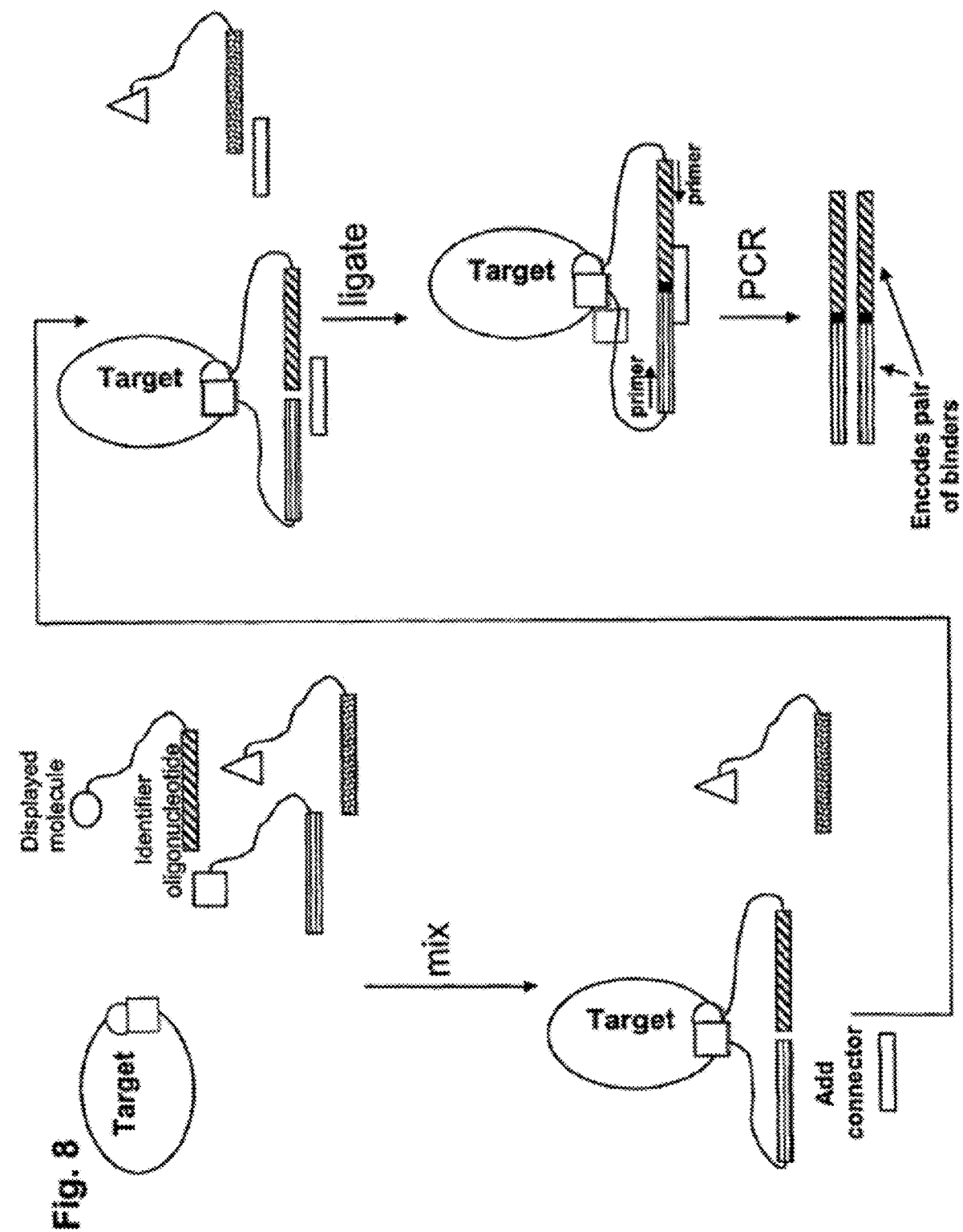

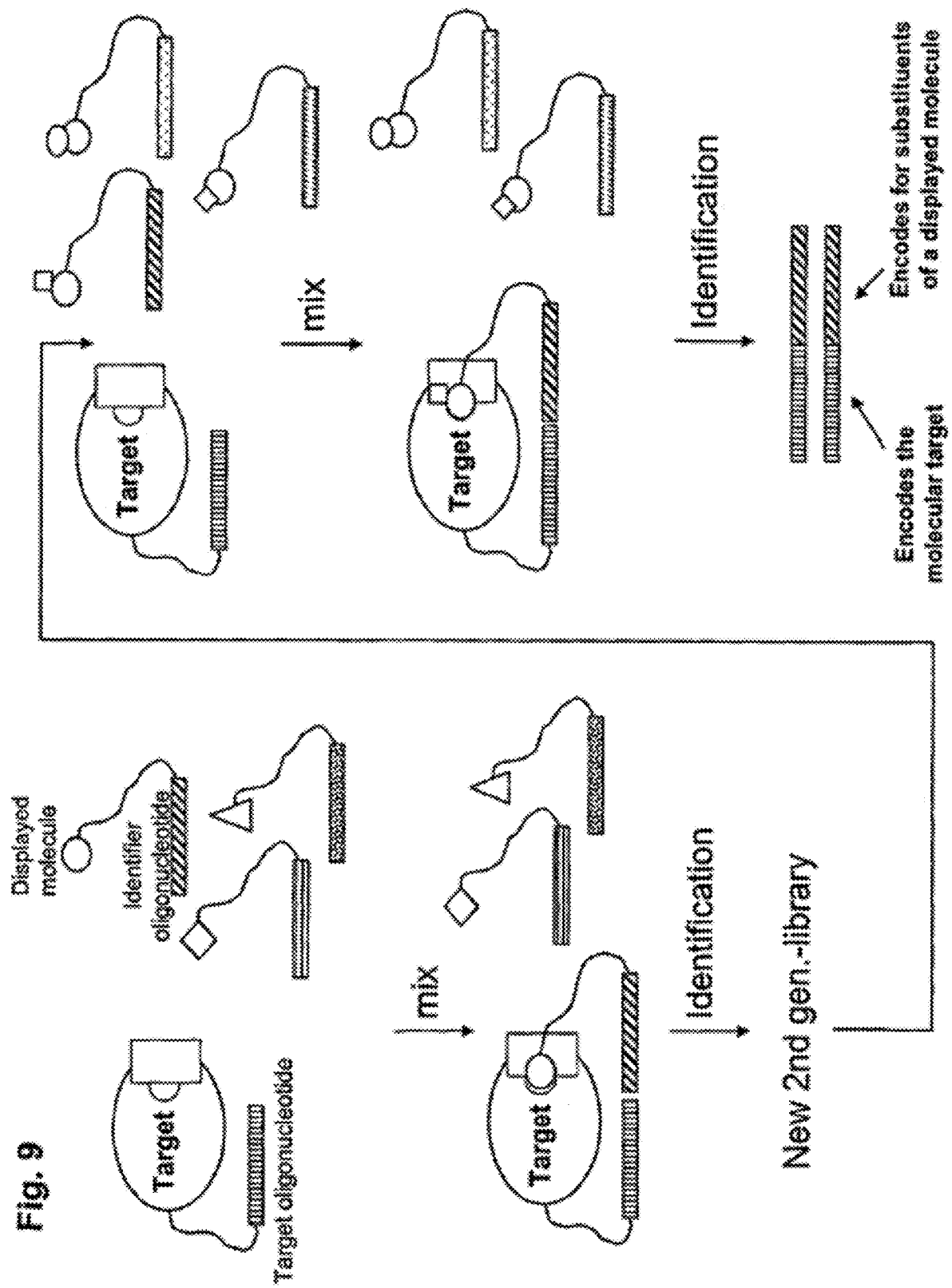

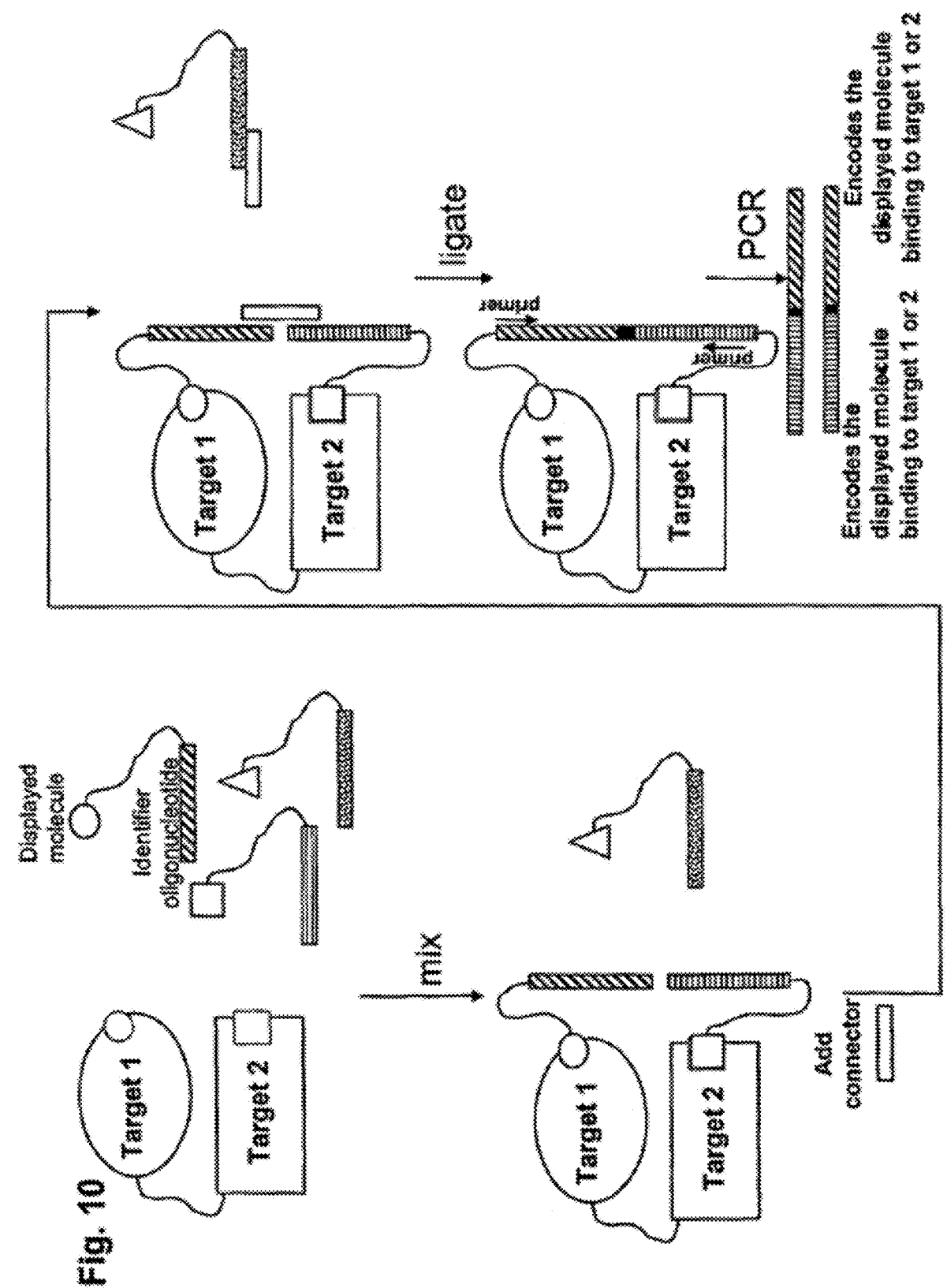

Fig. 13A
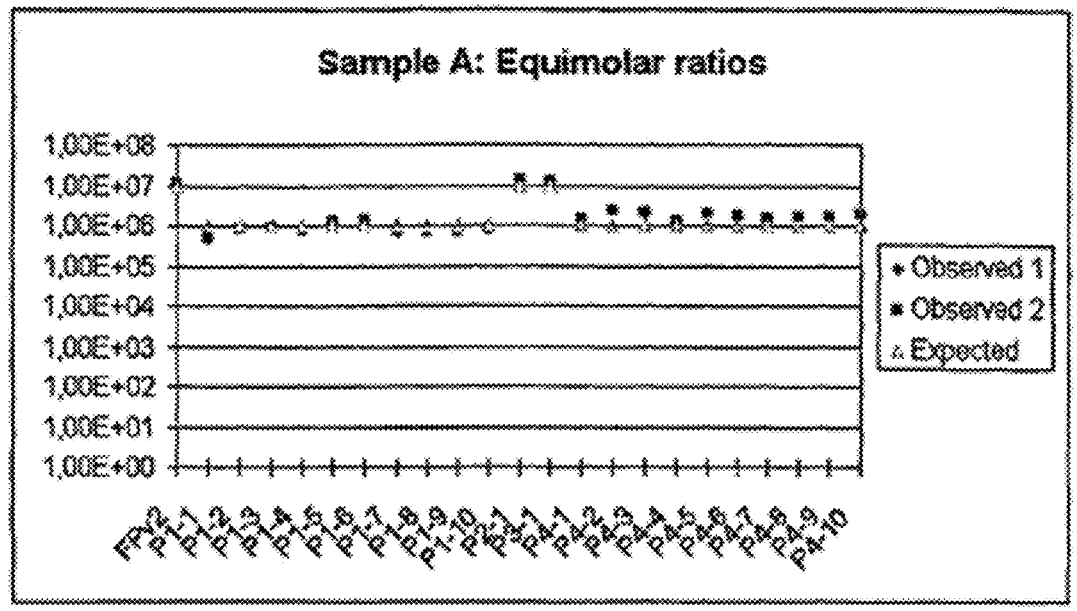
Fig. 13B  Sample B
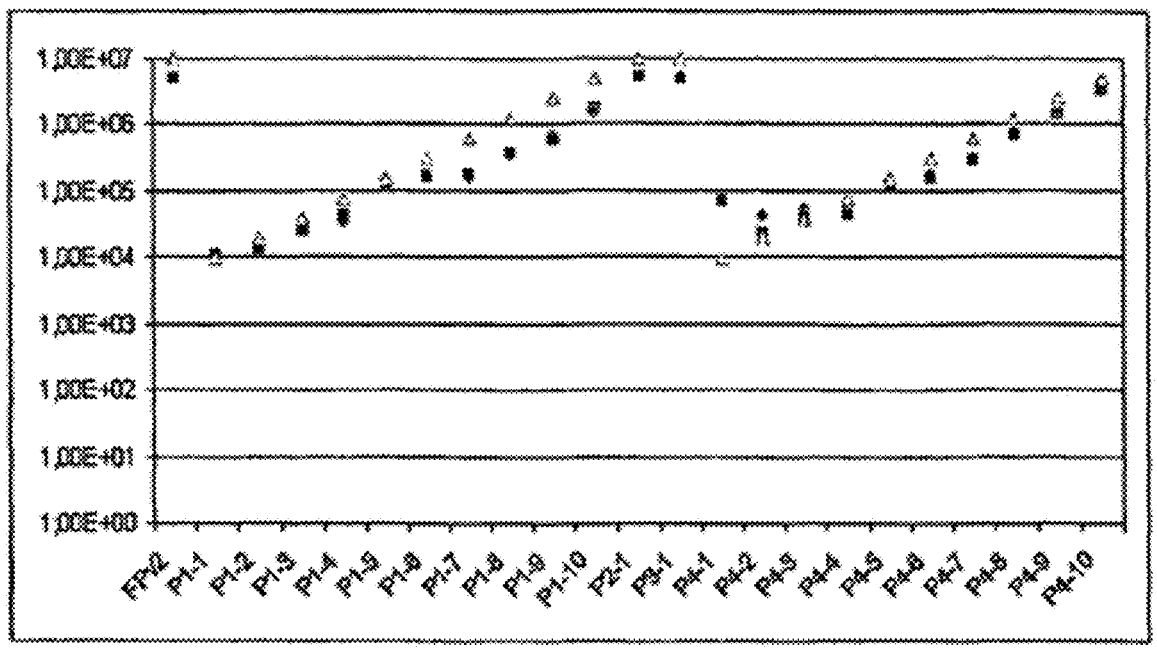

```
                           SEQUENCE LISTING

<160> NUMBER OF SEQ ID NOS: 82

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 1
aattccagct tctaggaaga c                                              21

<210> SEQ ID NO 2
<211> LENGTH: 139
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 2
cagcttggac accacgtcat actagctgct agagatgtgg tgatattagt gtgtgacgat     60
ggtacgcaca agtacgaacg tgcatcagag aggacgagca ggacctggaa cctggtgctt    120
cctccaccac gtctctgac                                                139

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 3
ggaagaagac agaagacctg                                                20

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 4
ctcgaccact gcaggtggag ctcc                                           24

<210> SEQ ID NO 5
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 5
tcaggagtcg agaactgaag                                              20

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 6
cgtgcttcct ctgctgcacc accg                                         24

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 7
tgtgtacgtc aacacgtcag                                              20

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 8
cctggtgtcg aggtgagcag cagc                                         24

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 9
tgtggaacta ccatccaagg                                              20

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 10
ctcgacgagg tccatcctgg tcgc                                         24

<210> SEQ ID NO 11
<211> LENGTH: 20
```

<212> TYPE: DNA
<213> ORGANISM: Artificial Sequence
<220> FEATURE:
<223> OTHER INFORMATION: Description of Artificial Sequence: Synthetic
      construct

<400> SEQUENCE: 11
ccatccaaca tcgttggaag                                                     20

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 12
cgtgaggagc aggtcctcct gtcg                                                24

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 13
aacctgtcct gtgagatctg                                                     20

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 14
cctgacactg gtcgtggtcg aggc                                                24

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 15
tcacgaagct ggatgatgag                                                     20

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 16
ccatctcgac gacctgctcc tggg                                                24

<210> SEQ ID NO 17
<211> LENGTH: 20
<212> TYPE: DNA

```
<213> ORGANISM: Artificial Sequence
<220> FEATURE:
<223> OTHER INFORMATION: Description of Artificial Sequence: Synthetic
      construct

<400> SEQUENCE: 17
tagcatcgat cgaacgtagg                                              20

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 18
ccacgaggtc tccactggtc cagg                                         24

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 19
tcgaagctac tgtcgagatg                                              20

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 20
ccactgagct gctcctccag gtgg                                         24

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 21
cagcttggac accacgtcat ac                                           22

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 22
gtcagagacg tggtggagga a                                            21

<210> SEQ ID NO 23
<211> LENGTH: 60
<212> TYPE: DNA
<213> ORGANISM: Artificial Sequence
```

-continued

```
<220> FEATURE:
<223> OTHER INFORMATION: Description of Artificial Sequence: Synthetic
      construct

<400> SEQUENCE: 23
cagcttggac accacgtcat actagctgct agagatgtgg tgatattagt gtgtgacgat       60

<210> SEQ ID NO 24
<211> LENGTH: 60
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 24
cagcttggac accacgtcat acggaagaag acagaagacc tgatattagt gtgtgacgat       60

<210> SEQ ID NO 25
<211> LENGTH: 60
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 25
cagcttggac accacgtcat actcaggagt cgagaactga agatattagt gtgtgacgat       60

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 26
cagcttggac accacgtcat actgtgtacg tcaacacgtc agatattagt gtgtgacgat       60

<210> SEQ ID NO 27
<211> LENGTH: 60
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 27
cagcttggac accacgtcat actgtggaac taccatccaa ggatattagt gtgtgacgat       60

<210> SEQ ID NO 28
<211> LENGTH: 60
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 28
cagcttggac accacgtcat acccatccaa catcgttgga agatattagt gtgtgacgat       60

<210> SEQ ID NO 29
<211> LENGTH: 60
<212> TYPE: DNA
<213> ORGANISM: Artificial Sequence
<220> FEATURE:
```

<223> OTHER INFORMATION: Description of Artificial Sequence: Synthetic
      construct

<400> SEQUENCE: 29
cagcttggac accacgtcat acaacctgtc ctgtgagatc tgatattagt gtgtgacgat    60

<210> SEQ ID NO 30
<211> LENGTH: 60
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 30
cagcttggac accacgtcat actcacgaag ctggatgatg agatattagt gtgtgacgat    60

<210> SEQ ID NO 31
<211> LENGTH: 60
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 31
cagcttggac accacgtcat actagcatcg atcgaacgta ggatattagt gtgtgacgat    60

<210> SEQ ID NO 32
<211> LENGTH: 60
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 32
cagcttggac accacgtcat actcgaagct actgtcgaga tgatattagt gtgtgacgat    60

<210> SEQ ID NO 33
<211> LENGTH: 54
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 33
gtcctctctg atgcacgttc gtacttgtgc gtaccatcgt cacacactaa tatc    54

<210> SEQ ID NO 34
<211> LENGTH: 65
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 34
gaacgtgcat cagagaggac gagcaggacc tggaacctgg tgcaattcca gcttctagga    60
agact    65

<210> SEQ ID NO 35
<211> LENGTH: 65
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 35
gaacgtgcat cagagaggac tcgaccactg caggtggagc tccaattcca gcttctagga    60
agact                                                                65

<210> SEQ ID NO 36
<211> LENGTH: 65
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 36
gaacgtgcat cagagaggac gtgcttcctc tgctgcacca ccgaattcca gcttctagga    60
agact                                                                65

<210> SEQ ID NO 37
<211> LENGTH: 65
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 37
gaacgtgcat cagagaggac ctggtgtcga ggtgagcagc agcaattcca gcttctagga    60
agact                                                                65

<210> SEQ ID NO 38
<211> LENGTH: 65
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 38
gaacgtgcat cagagaggac tcgacgaggt ccatcctggt cgcaattcca gcttctagga    60
agact                                                                65

<210> SEQ ID NO 39
<211> LENGTH: 65
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 39
gaacgtgcat cagagaggac gtgaggagca ggtcctcctg tcgaattcca gcttctagga    60
agact                                                                65

<210> SEQ ID NO 40
<211> LENGTH: 65
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 40
gaacgtgcat cagagaggac ctgacactgg tcgtggtcga ggcaattcca gcttctagga    60
agact                                                               65

<210> SEQ ID NO 41
<211> LENGTH: 65
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 41
gaacgtgcat cagagaggac catctcgacg acctgctcct gggaattcca gcttctagga    60
agact                                                               65

<210> SEQ ID NO 42
<211> LENGTH: 65
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 42
gaacgtgcat cagagaggac cacgaggtct ccactggtcc aggaattcca gcttctagga    60
agact                                                               65

<210> SEQ ID NO 43
<211> LENGTH: 65
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 43
gaacgtgcat cagagaggac cactgagctg ctcctccagg tggaattcca gcttctagga    60
agact                                                               65

<210> SEQ ID NO 44
<211> LENGTH: 42
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 44
gtcagagacg tggtggagga agtcttccta gaagctggaa tt                       42

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 45
gtcatactag ctgctagaga tgtggtgata                                     30

<210> SEQ ID NO 46

```
<211> LENGTH: 28
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 46
catacggaag aagacagaag acctgata                                            28

<210> SEQ ID NO 47
<211> LENGTH: 29
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 47
tcatactcag gagtcgagaa ctgaagata                                           29

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 48
catactgtgt acgtcaacac gtcagata                                            28

<210> SEQ ID NO 49
<211> LENGTH: 28
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 49
catactgtgg aactaccatc caaggata                                            28

<210> SEQ ID NO 50
<211> LENGTH: 22
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 50
ccatccaaca tcgttggaag at                                                  22

<210> SEQ ID NO 51
<211> LENGTH: 28
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 51
catacaacct gtcctgtgag atctgata                                            28

<210> SEQ ID NO 52
<211> LENGTH: 27
```

```
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 52
atactcacga agctggatga tgagata                                            27

<210> SEQ ID NO 53
<211> LENGTH: 28
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 53
catactagca tcgatcgaac gtaggata                                           28

<210> SEQ ID NO 54
<211> LENGTH: 29
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 54
tcatactcga agctactgtc gagatgata                                          29

<210> SEQ ID NO 55
<211> LENGTH: 26
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 55
atattagtgt gtgacgatgg tacgca                                             26

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 56
acaagtacga acgtgcatca gaga                                               24

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 57
cgagcaggac ctggaacct                                                     19

<210> SEQ ID NO 58
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      construct

<400> SEQUENCE: 58
tcgaccactg caggtgga                                                    18

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: misc_feature
<222> LOCATION: (1)..(1)
<223> OTHER INFORMATION: 6-FAM tag

<400> SEQUENCE: 59
tccagcttct aggaagac                                                    18

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 60

Met Gly Asx Asn Phe Gln
1               5

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 61
gcttcctctg ctgcacca                                                    18

<210> SEQ ID NO 62
<211> LENGTH: 19
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 62
ggtgtcgagg tgagcagca                                                   19

<210> SEQ ID NO 63
<211> LENGTH: 19
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 63
cgacgaggtc catcctggt                                                   19
```

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 64
gtgaggagca ggtcctcctg t                                            21

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 65
ctgacactgg tcgtggtcga                                              20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 66
catctcgacg acctgctcct                                              20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 67
acgaggtctc cactggtcca                                              20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 68
actgagctgc tcctccaggt                                              20

<210> SEQ ID NO 69
<211> LENGTH: 40
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 69
tagtcgatgt agctagctag tgcgccaatg ccttatcagc                        40

<210> SEQ ID NO 70
<211> LENGTH: 40
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 70
gatcgatgac tgacgccggt aaatctaccg tctaagctgy                    40

<210> SEQ ID NO 71
<211> LENGTH: 59
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 71
gatcgatgac tgacgccggt gacgtcgtag atatcgatgc aaatctaccg tctaagctg    59

<210> SEQ ID NO 72
<211> LENGTH: 28
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 72
aaaaggaata gtcgctagct actgtttt                                28

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 73
tagtcgatgt agctagctag                                         20

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 74
cagcttagac ggtagattt                                          19

<210> SEQ ID NO 75
<211> LENGTH: 4
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 75

Tyr Trp Thr Asp
1

```
<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 76

Asp Asp Asp Asp Lys
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      construct
<220> FEATURE:
<221> NAME/KEY: MOD_RES
<222> LOCATION: (7)..(7)
<223> OTHER INFORMATION: G or S

<400> SEQUENCE: 77

Glu Asn Leu Tyr Phe Gln Xaa
1               5

<210> SEQ ID NO 78
<211> LENGTH: 6
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 78

Leu Val Pro Ala Gly Ser
1               5

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 79

Ile Glu Gly Arg
1

<210> SEQ ID NO 80
<211> LENGTH: 6
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 80 gaattc                                                                     6

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
               construct

<400> SEQUENCE: 81
tagtcgatgt agctagctag                                          20

<210> SEQ ID NO 82
<211> LENGTH: 19
<212> TYPE: DNA
<213> ORGANISM: Artificial Sequence
<220> FEATURE:
<223> OTHER INFORMATION: Description of Artificial Sequence: Synthetic
               construct

<400> SEQUENCE: 82
cagcttagac ggtagattt                                           19
```

METHOD FOR OBTAINING STRUCTURAL INFORMATION CONCERNING AN ENCODED MOLECULE AND METHOD FOR SELECTING COMPOUNDS

CROSS-REFERENCE TO RELATED APPLICATIONS

This is a Continuation of U.S. patent application Ser. No. 10/572,644, filed Aug. 25, 2008, which is a National Stage of International Patent Application No. PCT/DK2004/000630, filed Sep. 17, 2004, which claims benefit of U.S. Provisional Patent Application No. 60/509,268, filed Oct. 8, 2003, U.S. Provisional Patent Application No. 60/504,748, filed Sep. 22, 2003, Danish Patent Application No. PA 2003 01485, filed Oct. 8, 2003 and Danish Patent Application No. PA 2003 01356, filed Sep. 18, 2003, which applications are incorporated herein by reference. To the extent appropriate, a claim of priority is made to each of the above-disclosed applications.

SEQUENCE LISTING

The instant application contains a Sequence Listing which has been submitted electronically in ASCII format and is hereby incorporated by reference in its entirety. Said ASCII copy, created on Mar. 22, 2022, is named 18598_0013FPC1_SL.txt and is 19,531 bytes in size.

TECHNICAL FIELD OF THE INVENTION

In one aspect, the present invention relates to a method for obtaining structural information about an encoded molecule. The encoded molecule may be produced by a reaction of a plurality of chemical entities and may be capable of being connected to an identifier oligonucleotide containing codons informative of the identity of the chemical entities which have participated in the formation of the encoded molecule. In a certain embodiment, primers are designed complementary to the codons appearing on the identifier oligonucleotide, and the presence, absence or relative abundance of a codon is evaluated by mixing a primer with the identifier oligonucleotide in the presence of a polymerase and substrate (deoxy)ribonucleotide triphosphates and measuring the extension reaction. In another aspect, the invention provides a method for selecting compounds which binds to a target. More specifically, the invention relates to a method in which a target associated with an oligonucleotide initially is mixed with a library of complexes, each complex comprising a display molecule and an oligonucleotide identifying said display molecule. Next, due an increased proximity, the target oligonucleotide is coupled to the identifier oligonucleotide of complexes having a display molecule with affinity towards the target. In a final stage the coupled nucleotides are analysed to deduce at least the identity of the display molecule.

A Method for Obtaining Structural Information Concerning an Encoded Molecule

The below paragraphs up to the section entitled "Method for identifying a display molecule" relate to the first aspect of the invention.

The first aspect of the present invention relates to a method for obtaining structural information about an encoded molecule. The encoded molecule is usually produced by a process that comprises the reaction of a plurality of chemical entities. The synthesis of the encoded molecule is recorded or programmed in an identifier oligonucleotide which is attached to the encoded molecule. The structural information obtained by the present method may be used to obtain the entire structure of the encoded molecule or a part thereof.

BACKGROUND OF THE INVENTION

The generation of molecules carrying new properties remains a challenging task. Recently, a number of procedures have been suggested that should allow a more efficient generation and screening of a huge number of molecules. The approach taken may involve the encoding and/or templating of molecules other than natural biopolymers and a coupling of the molecules to respective templates or identifier parts containing information about the reactants that have participated in the formation of the molecule. These approaches allow the researcher to generate and screen a huge number of molecules at the same time.

In U.S. Pat. No. 5,723,598 it is suggested to prepare libraries of bifunctional molecules, in which one part of the bifunctional molecule comprises an encoded part and the other part of the molecule contains an identifying part. The identifying part is segregated into codons, i.e. a stretches of nucleotides, which codes for reactants that have been involved in the synthesis of the encoded molecule. The libraries of bifunctional molecules are generally prepared by a split-and-mix method, which involves the initial reaction between a nascent bifunctional molecule and a range of different reactants in separate compartments at one end of the nascent bifunctional molecule and a corresponding range of identifier unit oligonucleotides (codons) and the other end. Subsequently, the contents of the compartments are mixed and the mixture is disposed in separate compartments and reacted again with another range of reactants and corresponding codons. Following the generation of a library of the bifunctional molecules, a partitioning with respect to affinity towards a target is conducted and the identifier part of the bifunctional molecule is decoded to establish the chemical structure of the compounds in the library that is likely to be a ligand to the target. The decoding step implies that the identifier oligonucleotides initially are amplified by PCR. The PCR product is subsequently incorporated in to a suitable vector which is transformed to a host organism, usually *E. coli*. Following the incubation of the *E. coli*, colonies are picked and sequenced.

Halpin and Harbury have in WO 00/23458 suggested an improvement to the approach stipulated above. The approach is based on the same split-and-mix strategy for synthesis of combinatorial libraries comprising two or more synthetic steps. A plurality nucleic acid templates are used, each having at one end a chemical reactive site and dispersed throughout the stand a plurality of codon regions, each of said codon regions in turn specifying different codons. Separately, each of the strands, identified by a first codon region, is reacted at the chemical reaction sites with specific selected reagents. Subsequently, all the strands are pooled and subjected to a second partitioning based on a second codon region. The split-and-combine method is conducted an appropriate number of times to produce a library of typically between $10^3$ and $10^6$ different compounds. The decoding is performed utilizing the process depicted above.

Recently, a new method for encoding molecules has been suggested, which can be performed in a single "pot". WO 02/00419 and WO 02/103008 disclose methods for preparing virtually any molecule connected to a template coding for chemical entities which have reacted to form the molecule. In short, a template segregated into a plurality of codons and a plurality of building blocks comprising a transferable chemical entity and an anticodon are initially provided. Under hybridisation conditions, the template and building blocks are annealed together and the chemical entities are subsequently reacted to form the molecule. However, after a sufficient number of rounds of selections have been performed, the template must be decoded to establish the identity of the encoded molecule. The decoding step implies that the template oligonucleotides initially are amplified by PCR. The PCR product is subsequently incorporated in to a suitable vector which is transformed to a host organism, usually *E. coli*. Following the incubation of the *E. coli*, colonies are picked and sequenced.

In an aspect of the invention, it is the object to facilitate the decoding of the coding oligonucleotide in order to obtain at least partial structural information of the encoded molecule being a ligand towards a target. In another aspect of the invention, it is desired to obtain information about which chemical entities that result in encoded molecules successful in a selection process. Such chemical entities may be used in the formation of a second generation library.

SUMMARY OF THE INVENTION

The first aspect of the present invention concerns a method for obtaining structural information about an encoded molecule produced by a process comprising reaction of a plurality of chemical entities, said encoded molecule being capable of forming part of a complex also comprising an identifier oligonucleotide containing codons informative of the identity of chemical entities which have participated in the formation of the encoded molecule, the method comprises mixing a primer oligonucleotide with the identifier oligonucleotide, subjecting the mixture to a condition allowing for an extension reaction to occur when the primer is sufficient complementary to a part of the identifier oligonucleotide, and evaluating, based on measurement of the extension reaction, the presence, absence, or relative abundance of one or more codons.

The method according to the invention may be performed on a single identifier oligonucleotide or a composition of identifier oligonucleotides to obtain structural information about the encoded molecule or a composition of encoded molecules, respectively, that have been attached to the identifier oligonucleotide(s).

A single identifier may be analysed using the above method to verify the incorporation into the encoded molecule of one or more chemical entities or to deconvolute the identity of the entire encoded molecule. A composition of two or more identifier oligonucleotides generally results from a selection process, i.e. a process involving subjecting a library of different complexes to a condition partitioning the composition from the remainder of the library. Usually the partitioning condition includes an affinity assay in which the library of complexes is contacted with a target and the identifier oligonucleotides of the binding complexes are harvested.

The conditions allowing for an extension reaction to occur may be selected from a enzymatic or chemical means. Suitably, the condition involves one or more enzymes. In a certain embodiment of the invention, the condition which allows for an extension reaction to occur includes a polymerase or a ligase as well as suitable substrates for the enzyme used. Preferred is a polymerase together with a blend of (deoxy)ribonucleotide triphosphates. Suitably, the blend include one or more of dATP, dGTP, dCTP, and dTTP.

A library of complexes can have any appropriate size. Typically, the size is above $10^3$, typically above $10^6$ different complexes. An effective, extensive, and rapid decoding is therefore desirable. The method of the present invention may be used at various stages of the process of finding a ligand to a certain target. As examples, the method of the invention may be used for controlling the quality of a starting library. The information acquired may be used to verify which codons being present, absent, and, in some embodiments, also the relative abundance. Thus, the method of the invention delivers a reliable picture of the process which has produced the library. If, for some reason, a chemical entity has not been incorporated into the encoded molecules, the absence of a codon for this chemical entity will in certain embodiments of the invention indicate this fact.

Another example of the use of the present method is following the selection. After the selection has been performed the codon profile is indicative of the chemical entities that have been used in the synthesis of encoded molecules having an affinity towards the target. In the event the selection has been sufficiently effective it may be possible directly to deduce a part or the entire structure of binding encoded molecules. Alternatively, it may be possible to deduce a structural unit appearing more frequently among the encoded molecules after the selection, which gives important information to the structure-activity-relationship (SAR). If the selection process has not narrowed the size of the library to a manageable number, the formation of a second generation library may be contemplated. In the formation of the second generation library chemical entities which have not been involved in the synthesis of encoded molecules that have been successful in the selection may be omitted, thus limiting the size of the new library and at the same time increasing the concentration of binding complexes. The second generation library may then be subjected to more stringent selection conditions to allow only the encoded molecules with a higher affinity to bind to the target. The second generation library may also be spiked with certain chemical entities suspected of increasing the performance of the final encoded molecule. The indication of certain successful chemical entities may be obtained from the SAR. The use in a second generation library of chemical entities, which have proved to be interesting for further investigation in a preceding library, may thus entail a shuffling with new chemical entities that may focus the second generation library in a certain desired direction.

The relative abundance of codons may make it possible to decode a plurality of identifiers simultaneously, even in the case when two or more identifiers contain the same codon. Thus, following the formation and selection of a first, second or further generation library, the identity of binding encoded molecules may be partly or entirely deconvoluted by the present method.

In a practical approach the library comprises complexes with identifier oligonucleotides having n codon positions each. In a certain aspect of the invention n is an integer independently selected from of 2 to 8. It may be preferred that n is constant among all the complexes in the library to facilitate the decoding process. Each of the codons in a certain position is in an aspect of the invention selected from a set of m different codons. m may vary for each codon position or may be constant among the various codon positions. It may be preferred in some embodiments to have all the codons in each position selected from the same set of m codons. However, in other embodiments, especially such involving hybridisation in the recognition between the codon and the anticodon, it may be preferred that all the codons are different.

Preferably, any member of the codon set differs from any other codons in the set with the identity of at least one nucleotide, i.e. at least one nucleotide position occurs. In some aspects of the invention it is preferred that any member of the codon set differs with at least two nucleotides nucleotide positions from any other member of the set to increase the fidelity of the method. In general, it is desired to maximize the differences between individual codons of the set. In some embodiments of the invention, a set of primers comprising a sequence of complementing the set of codons are prepared.

In a preferred aspect of the method a framing sequence is related to each of the n codon positions in a particular complex, said framing sequence positions the reaction of a chemical entity in the synthesis history of the encoded molecule. Typically, the framing sequence is identical among the complexes for each of the reaction rounds and is selected from a group of n different nucleotide sequences. In a certain aspect of the invention n×m different primers fully or in part complementing any combination of the set of m different codons and the set of n different framing sequences is prepared. The n×m primers may be used in separate compartments to reveal the identity of a chemical entity as well as the point in time of the synthesis of the encoded molecule is has reacted.

In a particular aspect, the invention concerns a method for identifying the chemical entities utilized in the formation of an encoded molecule or a composition of encoded molecules, wherein in separate compartments, n×m primers individually are mixed with an aliquot of a composition obtained by subjecting a library of different complexes to a condition partitioning said composition from the remainder of the library, subjected to a mixture of polymerase and substrate (deoxy)ribonucleotide triphosphates under conditions allowing for an extension reaction to occur when a primer is sufficient complementary to a part of one or more identifier oligonucleotides present in the aliquot, and evaluation, based on measurement of the extension reaction, the presence, absence, or relative abundance of one or more codons in each compartment.

The invention also concerns a set comprising a collection of oligonucleotide primers, a polymerase, a composition of (deoxy)ribonucleotide triphosphates (dNTPs), and a library of complexes composed of a display molecule part and an identifier oligonucleotide, said oligonucleotide comprising codons informative of the identity of the chemical entities which has participated in the formation of the display molecule, wherein the oligonucleotide primers are sufficiently complementary to codons appearing on the identifier oligo nucleotides in the library to allow for an extension to occur.

BRIEF DESCRIPTION OF THE FIGURES

FIG. 1 discloses an embodiment for proximity-dependent selection,

FIGS. 2A-2D disclose different approaches for accomplishing coupling,

FIG. 4 discloses a library versus library screening,

FIG. 5 discloses an embodiment in which a target oligonucleotide association is performed in solution.

FIG. 6 discloses a target oligonucleotide association on cell surface.

FIG. 7 discloses a target with multiple binding sites which may associate with members of the bifunctional molecule library.

FIG. 8 discloses a target with one binding site for association with a pair of displayed molecules.

FIG. 9 discloses a 2nd generation-library driven proximity selection.

FIG. 10 discloses multiple targets for simultaneously subjected to a library of complexes.

FIGS. 13A-13B disclose the result of two experiments reported in example 3.

DETAILED DESCRIPTION OF THE INVENTION

Complex

Figure 3D:
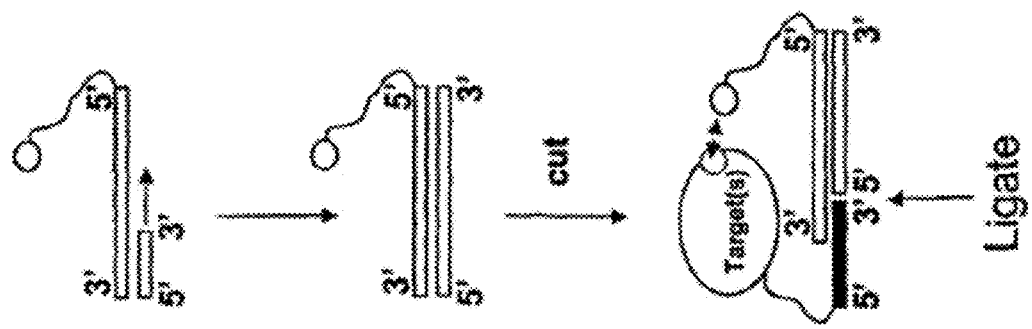
FIGS. 3A-3D disclose four different approaches for producing a coupling
Figure 3C:
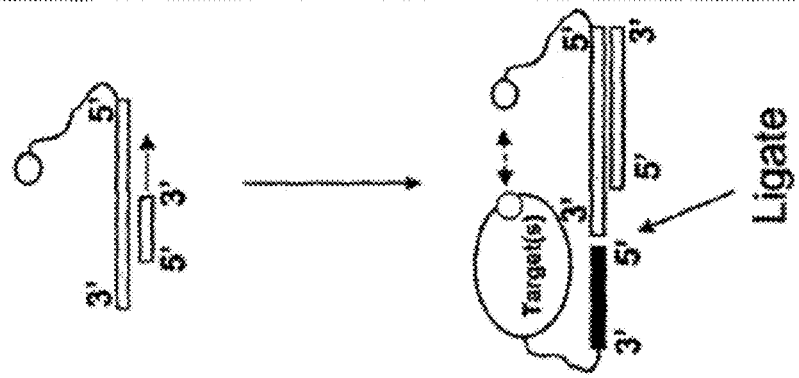
Figure 3B:
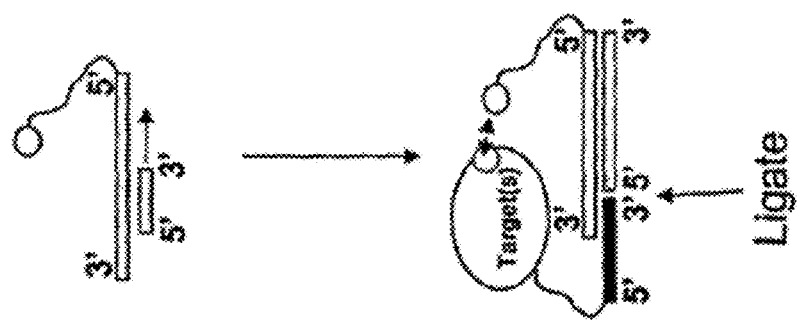
Figure 3A:
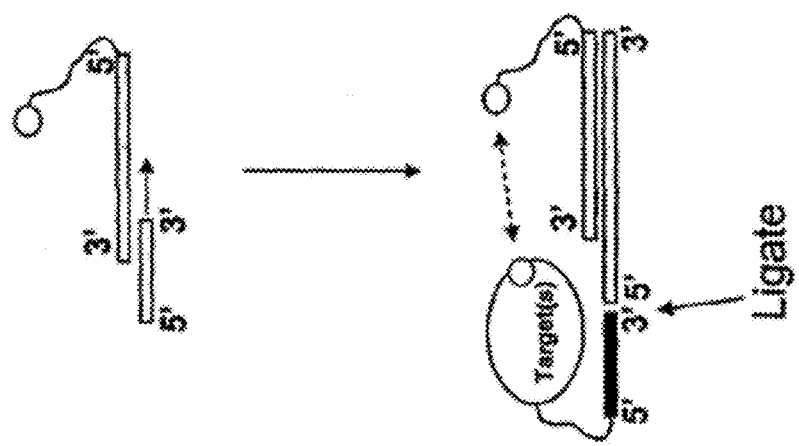

The complex comprises an encoded molecule and an identifier oligonucleotide. The identifier comprises codons that identify the encoded molecule. Preferably, the identifier oligonucleotide identifies the encoded molecule uniquely, i.e. in a library of complexes a particular identifier is capable of distinguishing the molecule it is attached to from the rest of the molecules.

The encoded molecule and the identifier may be attached directly to each other or through a bridging moiety. In one aspect of the invention, the bridging moiety is a selectively cleavable linkage.

The identifier oligonucleotide may comprise two or more codons. In a preferred aspect the identifier oligonucleotide comprises three or more codons. The sequence of each codon can be decoded utilizing the present method to identify reactants used in the formation of the encoded molecule. When the identifier comprises more than one codon, each member of a pool of chemical entities can be identified and the order of codons is informative of the synthesis step each member has been incorporated in.

In a certain embodiment, the same codon is used to code for several different chemical entities. In a subsequent identification step, the structure of the encoded molecule can be deduced taking advantage of the knowledge of different attachment chemistries, steric hindrance, deprotection of orthogonal protection groups, etc. In another embodiment, the same codon is used for a group of chemical entities having a common property, such as a lipophilic nature, a certain attachment chemistry etc. In a preferred embodiment, however, the codon is unique i.e. a similar combination of nucleotides does not appear on the identifier oligonucleotide coding for another chemical entity. In a practical approach, for a specific chemical entity, only a single combination of nucleotides is used. In some aspects of the invention, it may be advantageous to use several codons for the same chemical entity, much in the same way as Nature uses up to six different codons for a single amino acid. The two or more codons identifying the same chemical entity may carry further information related to different reaction conditions.

The sequence of the nucleotides in each codon may have any suitable length. The codon may be a single nucleotide or a plurality of nucleotides. In some aspects of the invention, it is preferred that each codon independently comprises four or more nucleotides, more preferred 4 to 30 nucleotides. In some aspects of the invention the lengths of the codons vary.

A certain codon may be distinguished from any other codon in the library by only a single nucleotide. However, to facilitate a subsequent decoding process and to increase the ability of the primer to discriminate between codons it is in general desired to have two or more mismatches between a particular codon and any other codon appearing on identifier oligonucleotide. As an example, if a codon length of 5 nucleotides is selected, more than 100 nucleotide combinations exist in which two or more mismatches appear. For a certain number of nucleotides in the codon, it is generally desired to optimize the number of mismatches between a particular codon relative to any other codon appearing in the library.

The identifier oligonucleotide will in general have at least two codons arranged in sequence, i.e. next to each other. Two neighbouring codons may be separated by a framing sequence. Depending on the encoded molecule formed, the identifier may comprise further codons, such as 3, 4, 5, or more codons. Each of the further codons may be separated by a suitable framing sequence. Preferably, all or at least a majority of the codons of the identifier are separated from a neighbouring codon by a framing sequence. The framing sequence may have any suitable number of nucleotides, e.g. 1 to 20. Alternatively, codons on the identifier may be designed with overlapping sequences.

The framing sequence, if present, may serve various purposes. In one setup of the invention, the framing sequence identifies the position of the codon.

Usually, the framing sequence either upstream or downstream of a codon comprises information which positions the chemical entity and the reaction conditions in the synthesis history of the encoded molecule. The framing sequence may also or in addition provide for a region of high affinity. The high affinity region may ensure that a hybridisation event with an anti-codon will occur in frame. Moreover, the framing sequence may adjust the annealing temperature to a desired level.

A framing sequence with high affinity can be provided by incorporation of one or more nucleobases forming three hydrogen bonds to a cognate nucleobase. Examples of nucleobases having this property are guanine and cytosine. Alternatively, or in addition, the framing sequence may be subjected to backbone modification. Several back bone modifications provides for higher affinity, such as 2'-O-methyl substitution of the ribose moiety, peptide nucleic acids (PNA), and 2'-4' O-methylene cyclisation of the ribose moiety, also referred to as LNA (Locked Nucleic Acid).

The sequence comprising a codon and an adjacent framing sequence has in a certain aspect of the invention a total length of 11 nucleotides or more, preferably 15 nucleotides or more. A primer may be designed to complementary to the codon sequence as well as the framing sequence. The presence of an extension reaction under conditions allowing for such reaction to occur is indicative of the presence of the chemical entity encoded in the codon as well as the position said chemical entity has in the entire synthesis history of the encoded molecule.

The identifier may comprise flanking regions around the coding section. The flanking regions can also serve as priming sites for amplification reactions, such as PCR or as binding region for oligonucleotide probe. The identifier may in certain embodiments comprise an affinity region having the property of being able to hybridise to a building block.

It is to be understood that when the term identifier oligonucleotide is used in the present description and claims, the identifier oligonucleotide may be in the sense or the anti-sense format, i.e. the identifier can be a sequence of codons which actually codes for the encoded molecule or can be a sequence complementary thereto. Moreover, the identifier may be single-stranded or double-stranded, as appropriate.

The encoded molecule part of the complex is generally of a structure expected of having an effect on a target. When the target is of pharmaceutical importance, the encoded molecule is generally a possible drug candidate. The complex may be formed by tagging a library of different possible drug candidates with a tag, e.g. a nucleic acid tag identifying each possible drug candidate. In another embodiment of the invention, the molecule formed by a variety of reactants which have reacted with each other and/or a scaffold molecule. Optionally, this reaction product may be post-modified to obtain the final molecule displayed on the complex. The post-modification may involve the cleavage of one or more chemical bonds attaching the encoded molecule to the identifier in order more efficiently to display the encoded molecule.

The formation of an encoded molecule generally starts by a scaffold, i.e. a chemical unit having one or more reactive groups capable of forming a connection to another reactive group positioned on a chemical entity, thereby generating an addition to the original scaffold. A second chemical entity may react with a reactive group also appearing on the original scaffold or a reactive group incorporated by the first chemical entity. Further chemical entities may be involved in the formation of the final reaction product. The formation of a connection between the chemical entity and the nascent encoded molecule may be mediated by a bridging molecule. As an example, if the nascent encoded molecule and the chemical entity both comprise an amine group a connection between these can be mediated by a dicarboxylic acid. A synthetic molecule is in general produced in vitro and may be a naturally occurring or an artificial substance. Usually, a synthetic molecule is not produced using the naturally translation system in an in vitro process.

The chemical entities that are precursors for structural additions or eliminations of the encoded molecule may be attached to a building block prior to the participation in the formation of the reaction product leading the final encoded molecule. Besides the chemical entity, the building block generally comprises an anti-codon. In some embodiments the building blocks also comprise an affinity region providing for affinity towards the nascent complex.

Thus, the chemical entities are suitably mediated to the nascent encoded molecule by a building block, which further comprises an anticodon. The anti-codon serves the function of transferring the genetic information of the building block in conjunction with the transfer of a chemical entity. The transfer of genetic information and chemical entity may occur in any order. The chemical entities are preferably reacted without enzymatic interaction in some aspects of the invention. Notably, the reaction of the chemical entities is preferably not mediated by ribosomes or enzymes having similar activity. In other aspects of the invention, enzymes are used to mediate the reaction between a chemical entity and a nascent encoded molecule.

According to certain aspects of the invention the genetic information of the anti-codon is transferred by specific hybridisation to a codon on a nucleic acid template. Another method for transferring the genetic information of the anti-codon to the nascent complex is to anneal an oligonucleotide complementary to the anti-codon and attach this oligonucleotide to the complex, e.g. by ligation. A still further method involves transferring the genetic information of the anti-codon to the nascent complex by an extension reaction using a polymerase and a mixture of dNTPs.

The chemical entity of the building block may in most cases be regarded as a precursor for the structural entity eventually incorporated into the encoded molecule. In other cases the chemical entity provides for the eliminations of chemical units of the nascent encoded molecule. Therefore, when it in the present application with claims is stated that a chemical entity is transferred to a nascent encoded molecule it is to be understood that not necessarily all the atoms of the original chemical entity is to be found in the eventually formed encoded molecule. Also, as a consequence of the reactions involved in the connection, the structure of the chemical entity can be changed when it appears on the nascent encoded molecule. Especially, the cleavage resulting in the release of the entity may generate a reactive group which in a subsequent step can participate in the formation of a connection between a nascent complex and a chemical entity.

The chemical entity of the building block comprises at least one reactive group capable of participating in a reaction which results in a connection between the chemical entity of the building block and another chemical entity or a scaffold associated with the nascent complex. The number of reactive groups which appear on the chemical entity is suitably one to ten. A building block featuring only one reactive group is used i.a. in the end positions of polymers or scaffolds, whereas building blocks having two reactive groups are suitable for the formation of the body part of a polymer or scaffolds capable of being reacted further. One, two or more reactive groups intended for the formation of connections, are typically present on scaffolds. Non-limiting examples of scaffolds are opiates, steroids, benzodiazepines, hydantoines, and peptidylphosphonates.

The reactive group of the chemical entity may be capable of forming a direct connection to a reactive group of the nascent complex or the reactive group of the building block may be capable of forming a connection to a reactive group of the nascent complex through a bridging fill-in group. It is to be understood that not all the atoms of a reactive group are necessarily maintained in the connection formed. Rather, the reactive groups are to be regarded as precursors for the structure of the connection.

The subsequent cleavage step to release the chemical entity from the building block can be performed in any appropriate way. In an aspect of the invention the cleavage involves usage of a chemical reagent or an enzyme. The cleavage results in a transfer of the chemical entity to the nascent encoded molecule or in a transfer of the nascent encoded molecule to the chemical entity of the building block. In some cases it may be advantageous to introduce new chemical groups as a consequence of linker cleavage. The new chemical groups may be used for further reaction in a subsequent cycle, either directly or after having been activated. In other cases it is desirable that no trace of the linker remains after the cleavage.

In another aspect, the connection and the cleavage is conducted as a simultaneous reaction, i.e. either the chemical entity of the building block or the nascent encoded molecule is a leaving group of the reaction. In some aspects of the invention, it is appropriate to design the system such that the connection and the cleavage occur simultaneously because this will reduce the number of steps and the complexity. The simultaneous connection and cleavage can also be designed such that either no trace of the linker remains or such that a new chemical group for further reaction is introduced, as described above.

The attachment of the chemical entity to the building block, optionally via a suitable spacer can be at any entity available for attachment, e.g. the chemical entity can be attached to a nucleobase or the backbone. In general, it is preferred to attach the chemical entity at the phosphor of the internucleoside linkage or at the nucleobase. When the nucleobase is used for attachment of the chemical entity, the attachment point is usually at the 7 position of the purines or 7-deaza-purins or at the 5 position of pyrimidines. The nucleotide may be distanced from the reactive group of the chemical entity by a spacer moiety. The spacer may be designed such that the conformational spaced sampled by the reactive group is optimized for a reaction with the reactive group of the nascent encoded molecule.

The encoded molecules may have any chemical structure. In a preferred aspect, the encoded molecule can be any compound that may be synthesized in a component-by-component fashion. In some aspects the synthetic molecule is a linear or branched polymer. In another aspect the synthetic molecule is a scaffolded molecule. The term "encoded molecule" also comprises naturally occurring molecules like α-polypeptides etc, however produced in vitro usually in the absence of enzymes, like ribosomes. In certain aspects, the synthetic molecule of the library is a non-α-polypeptide.

The encoded molecule may have any molecular weight. However, in order to be orally available, it is in this case preferred that the synthetic molecule has a molecular weight less than 2000 Daltons, preferably less than 1000 Dalton, and more preferred less than 500 Daltons.

The size of the library may vary considerably pending on the expected result of the inventive method. In some aspects, it may be sufficient that the library comprises two, three, or four different complexes. However, in most events, more than two different complexes are desired to obtain a higher diversity. In some aspects, the library comprises 1,000 or more different complexes, more preferred 1,000,000 or more different complexes. The upper limit for the size of the library is only restricted by the size of the vessel in which the library is comprised. It may be calculated that a vial may comprise up to $10^{14}$ different complexes.

Extension Reaction

The extension reaction requires a primer, a polymerase as well as a collection of deoxyribonucleotide triphosphates (abbreviated dNTP's herein) to proceed. An extension product may be obtained in the event the primer is sufficient complementary to an identifier oligonucleotide for a polymerase to recognise the double helix as a substrate. After binding of the polymerase to the double helix, the deoxyribonucleotide triphosphates (blend of dATP, dCTP, dGTP, and dTTP) are incorporated into the extension product using the identifier oligonucleotide as template. The conditions allowing for the extension reaction to occur usually includes a suitable buffer. The buffer may be any aqueous or organic solvent or mixture of solvents in which the polymerase has a sufficient activity. To facilitate the extension process the polymerase and the mixture of dNTP's are generally included in a buffer which is added to the identifier oligonucleotide and primer mixture. An exemplary kit comprising the polymerase and the nNTP's for performing the extension process comprises the following: 50 mM KCl, 10 mM Tris-HCl at pH 8.3; 1.5 mM MgCl2; 0.001% (wt/vol)

gelatin, 200 µM dATP; 200 µM dTTP; 200 µM dCTP; 200 µM dGTP; and 2.5 units *Thermus aquaticus* (Taq) DNA polymerase I (U.S. Pat. No. 4,889,818) per 100 microliters (pi) of buffer.

The primer may be selected to be complementary to one or more codons or parts of such codons. The length of the primers may be determined by the length of the codons, however, the primers usually are at least about 11 nucleotides in length, more preferred at least 15 nucleotides in length to allow for an efficient extension by the polymerase. The presence or absence of one or more codons is indicated by the presence of or absence of an extension product. The extension product may be measured by any suitable method, such as size fractioning on an agarose gel and staining with ethidium bromide.

In a preferred embodiment the admixture of identifier oligonucleotide and primer is thermocycled to obtain a sufficient number of copies of the extension product. The thermocycling is typically carried out by repeatedly increasing and decreasing the temperature of the mixture within a temperature range whose lower limit is about 30 degrees Celsius (30° C.) to about 55° C. and whose upper limit is about 90° C. to about 100° C. The increasing and decreasing can be continuous, but is preferably phasic with time periods of relative temperature stability at each of temperatures favouring polynucleotide synthesis, denaturation and hybridization.

When a single complex is analysed in accordance with the present method, the result may be used to verify the presence or absence of a specific chemical entity during the formation of the display molecule. The formation of an extension product is indicative of the presence of an oligonucleotide part complementary to the primer in the identifier oligonucleotide. Conversely, the absence of an extension product is indicative of the absence of an oligonucleotide part complementary to the primer in the identifier oligonucleotide. Selecting the sequence of the primer such that it is complementary to one or more codons will therefore provide information of the structure of the encoded molecule coded for by this codon(s).

In a preferred aspect of the invention, in the mixture of the identifier oligonucleotide and the primer oligonucleotide, a second primer complementary to a sequence of the extension product is included. The second primer is also termed reverse primer and ensures an exponential increase of the number of produced extension products. The method using a forward and reverse primer is well known to skilled person in the art and is generally referred to as polymerase chain reaction (abbreviated PCR) in the present application with claims. In one embodiment of the invention the reverse primer is annealed to a part of the extension product downstream, i.e. near the 3"end of the extension product, or a part complementing the coding part of the identifier oligonucleotide. In another embodiment, the first primer (forward primer) anneals to an upstream position of the identifier oligonucleotide, preferably before the coding part, and the reverse primer anneals to a sequence of the extension product complementing one or more codons or parts thereof.

The amplicons resulting from the PCR process may be stained during or following the reaction to ease the detection. A staining after the PCR process may be prepared with e.g. ethidium bromide or a similar staining agent. As an example, amplicons from the PCR process is run on an agarose gel and subsequently stained with ethidium bromide. Under UV illumination bands of amplicons becomes visible. It is possible to incorporate the staining agent in the agarose gel or to allow a solution of the staining agent to migrate through the gel. The amplicons may also be stained during the PCR process by an intercalating agent, like CYBR. In presence of the intercalating agent while the amplification proceeds it will incorporate in the double helix. The intercalation agent may then be made visible by irradiation by a suitable source.

The intensity of the staining is informative of the relative abundance of a specific amplicon. Thus, it is possible to quantify the occurrence of a codon in an identifier oligonucleotide. When a library of bifunctional complexes has been subjected to a selection the codons in the pool of identifier oligonucleotides which has been selected can be quantified using this method. As an example a sample of the selected identifier oligonucleotides is subjected to various PCR amplifications with different primers in separate compartments and the PCR product of each compartment is analysed by electrophoresis in the presence of ethidium bromide. The bands that appear can be quantified by a densitometric analysis after irradiation by ultraviolet light and the relative abundance of the codons can be measured.

Alternatively, the primers may be labelled with a suitable small molecule, like biotin or digoxigenin. A PCR-ELISA analysis may subsequently be performed based on the amplicons comprising the small molecule. A preferred method includes the application of a solid support covered with streptavidin or avidin when biotin is used as label and anti-digoxigenin when digoxigenin is used as the label. Once captured, the amplicons can be detected using an enzyme-labelled avidin or anti-dixigenin reporter molecule similar to a standard ELISA format.

To avoid laborious post-FOR handling steps required to evaluate the amplicons, it is in a certain embodiment preferred to measure the extension process "real time". Several real time PCR processes has been developed and all the suitable real time PCR process available to the skilled person in the art can be used in the evaluating step of the present invention and are include in the present scope of protection. The PCR reactions discussed below are of particular interest.

The monitoring of accumulating amplicons in real time has been made possible by labelling of primers, probes, or amplicons with fluorogenic molecules. The real time PCR amplification is usually performed with a speed faster than the conventional PCR, mainly due to reduced cycles time and the use of sensitive methods for detection of emissions from the fluorogenic labels. The most commonly used fluorogenic oligoprobes rely upon fluorescent resonance energy transfer (FRET) between fluorogenic labels or between one flourophor and a dark or "black-hole" non-fluorescent quencher (NFQ), which disperse energy as heat rather than fluorescence. FRET is a spectroscopic process by which energy is passed between molecules separated by 10-100 Å that have overlapping emission and absorption spectra. An advantage of many real time PCR methods is that they can be carried out in a closed system, i.e. a system which does not need to be opened to examine the result of the PCR. A closed system implies a reduced result turn-around, minimisation of the potential for carry-over contamination and the ability to closely scrutinise the essay's performance.

The present real time PCR methods currently available to the skilled person can be classified into either amplicon sequence specific or non-specific methods. The basis for the non-specific detection methods is a DNA-binding fluorogenic molecule. Included in this class are the earliest and simplest approaches to real time PCR. Ethidium bromide, YO-PRO-1, and SYBR® green 1 all fluorescence when associated with double stranded DNA which is exposed to a suitable wavelength of light. This approach requires the fluorescent agent to be present during the PCR process and provides for a real time detection of the fluorescent agent as it is incorporated into the double stranded helix.

The amplicons sequence specific methods includes, but are not limited to, the TaqMan®, hairpin, LightCycler®, Sunrise®, and Scorpion® methods. The LightCycler® method also designated "HybProbes" make use of a pair of adjacent, fluorogenic hybridisation oligonucleotide probes. A first, usually the upstream oligoprobe is labelled with a 3' donor fluorophore and the second, usually the downstream probe is commonly labelled with either a Light cycler Red 640 or Red 705 acceptor fluorophore a the 5' terminus so that when both oligoprobes are hybridised the two fluorophores are located in close proximity, such as within 10 nm, of each other. The close proximity provides for the emission of a fluorescence when irradiated with a suitable light source, such a blue diode in case of the LightCycler®. The region for annealing of the probes may be any suitable position that does not interfere with the primer annealing. In a suitable setup, the site for binding the probes are positioned downstream of the codon region on the identifier oligonucleotide. Alternatively, when a reverse primer is used, the region for annealing the probes may be at the 3' end of the strand complementing the identifier oligonucleotide. Another embodiment of the LightCycler method includes that the pair of oligonucleotide probes are annealed to one or more codons and primer sites exterior to the coding part of the identifier oligonucleotide are used for PCR amplification.

The TagMan® method, also referred to as the 5' nuclease or hydrolysis method, requires an oligoprobe, which is attached to a reporter flourophor, such as 6-carboxy-fluoroscein, and a quencher fluorophore, such as 6-carboxy-tetramethyl-rhodamine, at each end. When in close proximity, i.e. annealed to an identifier oligonucleotide, or a sequence complementing the identifier oligonucleotide, the quencher will "hijack" the emissions that have resulted from the excitation of the reporter. As the polymerase progresses along the relevant strand, it displaces and the hydrolyses the oligoprobe via its 5'→3' endonuclease activity. Once the reporter is removed from the extinguishing influence of the quencher, it is able to release excitation energy at a wavelength that can be monitored by a suitable instrument, such as ABI Prism® 7700. The fractional cycle number at which the real-time fluorescence signal mirrors progression of the reaction above the background noise is normally used as an indicator of successful identifier oligonucleotide amplification. This threshold cycle ($C_T$) is defined as the PCR cycle in which the gain in fluorescence generated by the accumulating amplicons exceeds 10 standard deviations of the mean base line fluorescence. The $C_T$ is proportional to the number of identifier oligonucleotide copies present in the sample. The TaqMan probe is usually designed to hybridise at a position downstream of a primer binding site, be it a forward or a reverse primer. When the primer is designed to anneal to one or more codons of the identifier oligonucleotide, the presence of these one or more codons is indicated by the emittance of light. Furthermore, the quantity of the identifier oligonucleotides comprising the one or more codons may be measured by the $C_T$ value.

The Hairpin method involves an oligoprobe, in which a fluorophore and a quencher are positioned at the termini. The labels are hold in close proximity by distal stem regions of homologous base pairing deliberately designed to create a hairpin structure which result in quenching either by FRET or a direct energy transfer by a collisional mechanism due to the intimate proximity of the labels. When direct energy transfer by a collision mechanism is used the quencher is usually different from the FRET mechanism, and is suitably 4-(4'-dimethylamino-phenylazo)-benzene (DABCYL). In the presence of a complementary sequence, usually downstream of a primer, or within the bounds of the primer binding sides in case of more than one a single primer, the oligoprobe will hybridise, shifting into an open configuration. The fluorophore is now spatially removed from the quencher's influence and fluorescence emissions are monitored during each cycle. In a certain aspect, the hairpin probe may be designed to anneal to a codon in order to detect this codon if present on the identifier oligonucleotide. This embodiment may be suitable if codons only differs from each other with a single or a few nucleotides, because is in well-known that the occurrence of a mismatch between a hairpin oligoprobe and its target sequence has a greater destabilising effect on the duplex than the introduction of an equivalent mismatch between the target oligonucleotide and a linear oligoprobe. This is probably because the hairpin structure provides a highly stable alternate conformation.

The Sunrise and Scorpion methods are similar in concept to the hairpin oligoprobe, except that the label becomes irreversible incorporated in to the PCR product. The Sunrise method involves a primer (commercially available as Amplifluor™ hairpin primers) comprising a 5' fluorophore and a quencher, e.g. DABCYL. The labels are separated by complementary stretches of sequence that create a stem when the sunrise primer is closed. At the 3' terminus is a target specific primer sequence. In a preferred embodiment the target sequence is a codon, optionally more codons. The sunrise primer's sequence is intended to be duplicated by the nascent complementary stand and, in this way, the stem is destabilised, the two fluorophores are held apart, usually between 15 and 25 nucleotides, and the fluorophore is free to emit its excitation energy for monitoring. The Scorpion primer resembles the sunrise primer, but derivate in having a moiety that blocks duplication on the signalling portion of the scorpion primer. The blocking moiety is typically hexethylene glycol. In addition to the difference in structure, the function of the scorpion primers differs slightly in that the 5' region of the oligonucleotide is designed to hybridise to a complementary region within the amplicons. In a certain embodiment the complementary region is a codon on the identifier oligonucleotide. The hybridisation forces the labels apart disrupting the hairpin and permitting emission in the same way as the hairpin probes.

Methods for Forming a Library of Complexes

The complexes comprising an identifier part having two or more codons that code for reactants that have reacted in the formation of the encoded molecule part of the complex may be formed by a variety of processes. Generally, the preferred methods can be used for the formation of virtually any kind of encode molecule. Suitable examples of processes include prior art methods disclosed in WO 93/20242, WO 93/06121, WO 00/23458, WO 02/074929, and WO 02/103008, the content of which being incorporated herein by reference as well as methods of the present applicant not yet public available, including the methods disclosed in DK PA 2002 01955 filed 19 Dec. 2002, and DK PA 2003 00430 filed 20 Mar. 2003. Any of these methods may be used, and the entire content of the patent applications are included herein by reference.

Below four preferred embodiments are described. A first embodiment disclosed in more detail in WO 02/103008 is based on the use of a polymerase to incorporate unnatural nucleotides as building blocks. Initially, a plurality of template oligonucleotides is provided. Subsequently primers are annealed to each of the templates and a polymerase is extending the primer using nucleotide derivatives which have appended chemical entities. Subsequent to or simultaneously with the incorporation of the nucleotide derivatives, the chemical entities are reacted to form a reaction product. The encoded molecule may be post-modified by cleaving some of the linking moieties to better present the encoded molecule.

Several possible reaction approaches for the chemical entities are apparent. First, the nucleotide derivatives can be incorporated and the chemical entities subsequently polymerised. In the event the chemical entities each carry two reactive groups, the chemical entities can be attached to adjacent chemical entities by a reaction of these reactive groups. Exemplary of the reactive groups are amine and carboxylic acid, which upon reaction form an amide bond. Adjacent chemical entities can also be linked together using a linking or bridging moiety. Exemplary of this approach is the linking of two chemical entities each bearing an amine group by a bi-carboxylic acid. Yet another approach is the use of a reactive group between a chemical entity and the nucleotide building block, such as an ester or a thioester group. An adjacent building block having a reactive group such as an amine may cleave the interspaced reactive group to obtain a linkage to the chemical entity, e.g. by an amide linking group.

A second embodiment for obtainment of complexes pertains to the use of hybridisation of building blocks to an identifier oligonucleotide and reaction of chemical entities attached to the building blocks in order to obtain a reaction product. This approach comprises that templates are contacted with a plurality of building blocks, wherein each building block comprises an anti-codon and a chemical entity. The anti-codons are designed such that they recognise a sequence, i.e. a codon, on the template. Subsequent to the annealing of the anti-codon and the codon to each other a reaction of the chemical entity is effected.

The template may be associated with a scaffold. Building blocks bringing chemical entities in may be added sequentially or simultaneously and a reaction of the reactive group of the chemical entity may be effected at any time after the annealing of the building blocks to the template.

A third embodiment for the generation of a complex includes chemical or enzymatical ligation of building blocks when these are lined up on a template. Initially, templates are provided, each having one or more codons. The templates are contacted with building blocks comprising anti-codons linked to chemical entities. The two or more anti-codons annealed on a template are subsequently ligated to each other and a reaction of the chemical entities is effected to obtain a reaction product. The method is disclosed in more detail in DK PA 2003 00430 filed 20 Mar. 2003.

A fourth embodiment makes use of the extension by a polymerase of an affinity sequence of the nascent complex to transfer the anti-codon of a building block to the nascent complex. The method implies that a nascent complex comprising a scaffold and an affinity region is annealed to a building block comprising a region complementary to the affinity section. Subsequently the anti-codon region of the building block is transferred to the nascent complex by a polymerase. The transfer of the chemical entity may be transferred prior to, simultaneously with or subsequent to the transfer of the anti-codon. This method is disclosed in detail in DK PA 2002 01955 filed 19 Dec. 2002.

After or simultaneously with the formation of the reaction product some of the linkers to the template may be cleaved, however at least one linker must be maintained to provide for the complex.

Nucleotides

The nucleotides used in the present invention may be linked together in a sequence of nucleotides, i.e. an oligonucleotide. Each nucleotide monomer is normally composed of two parts, namely a nucleobase moiety, and a backbone. The back bone may in some cases be subdivided into a sugar moiety and an internucleoside linker.

The nucleobase moiety may be selected among naturally occurring nucleobases as well as non-naturally occurring nucleobases. Thus, "nucleobase" includes not only the known purine and pyrimidine hetero-cycles, but also heterocyclic analogues and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosin, $N^6,N^6$-ethano-2,6-diamino-purine, 5-methylcytosine, 5-($C^3$-$C^6$)-alkynylcytosine, 5-fluorouracil, 5-bromouracil, pseudoisocytosine, 2-hydroxy-5-methyl-4-triazolopyridine, isocytosine, isoguanine, inosine and the "non-naturally occurring" nucleobases described in Benner et al., U.S. Pat. No. 5,432,272. The term "nucleobase" is intended to cover these examples as well as analogues and tautomers thereof. Especially interesting nucleobases are adenine, guanine, thymine, cytosine, 5-methylcytosine, and uracil, which are considered as the naturally occurring nucleobases in relation to therapeutic and diagnostic application in humans.

Examples of suitable specific pairs of nucleobases are shown below:

Natural Base Pairs

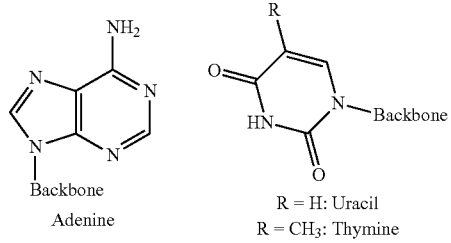

R = H: Uracil
R = CH$_3$: Thymine

Adenine

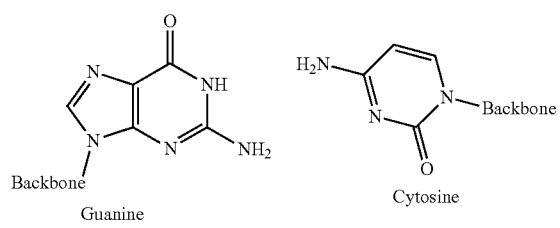

Guanine

Cytosine

Synthetic Base Pairs
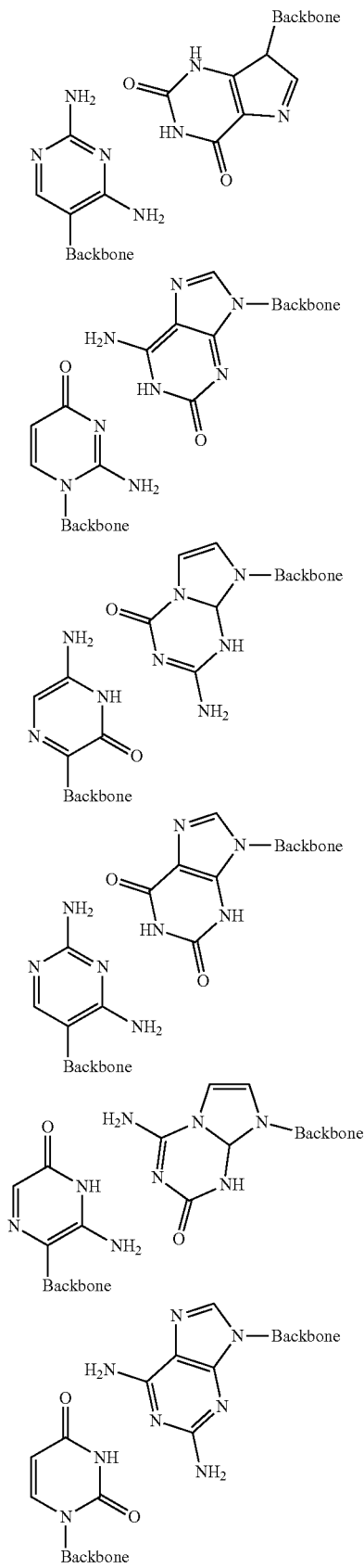
Synthetic Purine Bases Pairing with Natural Pyrimidines
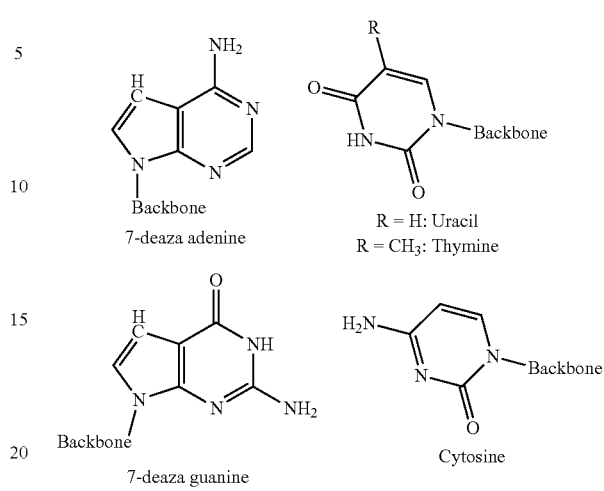
Suitable examples of backbone units are shown below (B denotes a nucleobase):
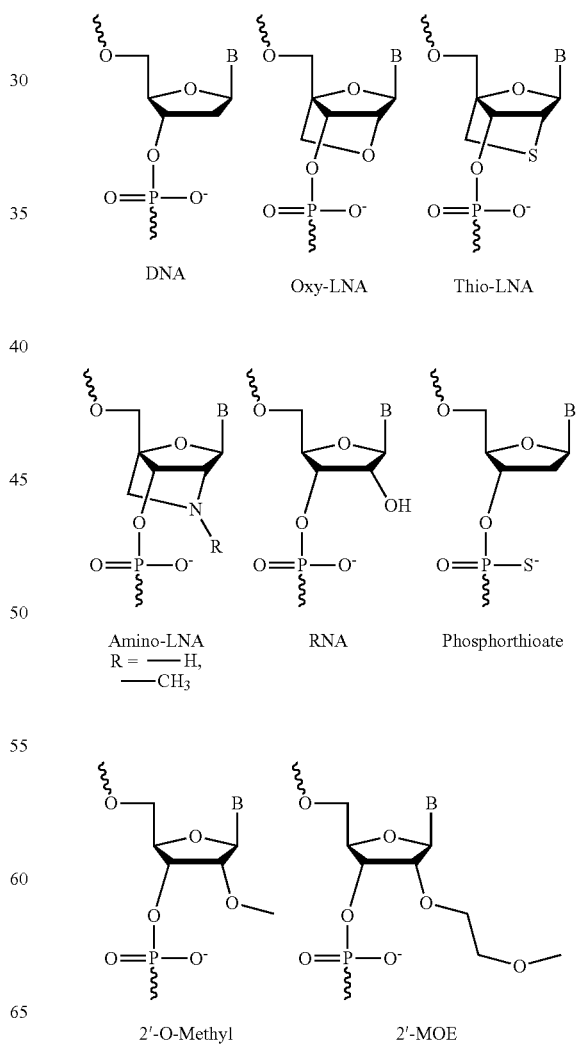

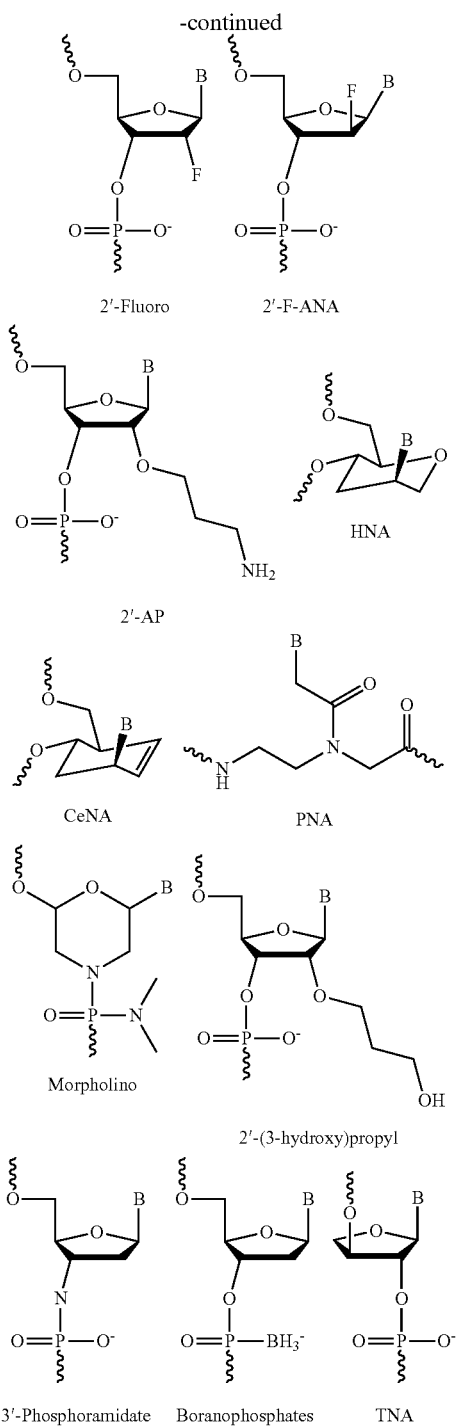

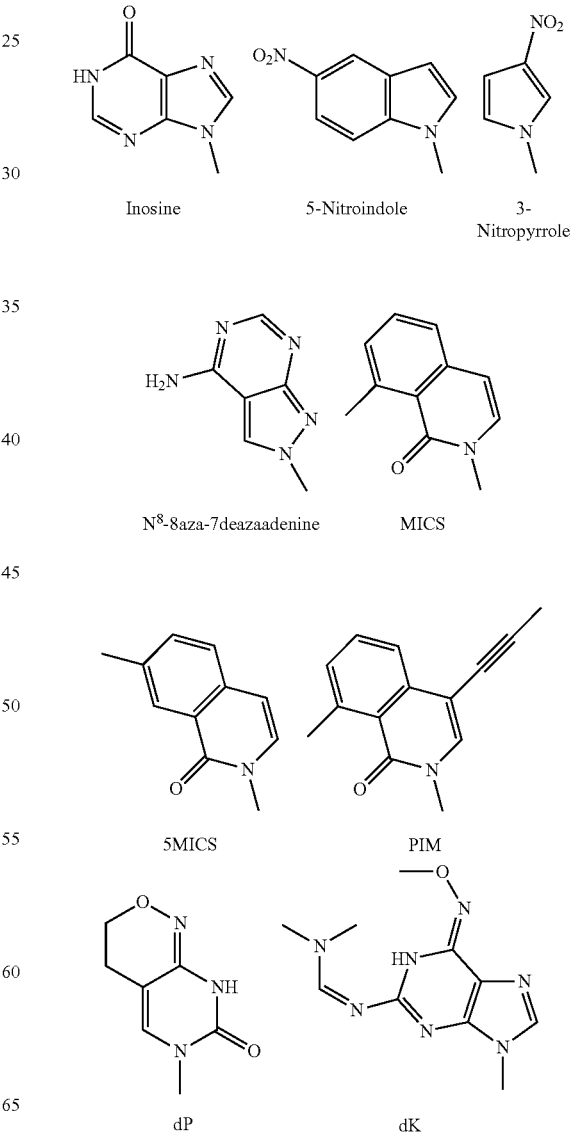

ioate, methylphosphonate, phosphoramidate, phosphotriester, and phosphodithioate. Furthermore, the internucleoside linker can be any of a number of non-phosphorous-containing linkers known in the art.

Preferred nucleic acid monomers include naturally occurring nucleosides forming part of the DNA as well as the RNA family connected through phosphodiester linkages. The members of the DNA family include deoxyadenosine, deoxyguanosine, deoxythymidine, and deoxycytidine. The members of the RNA family include adenosine, guanosine, uridine, cytidine, and inosine. Inosine is a non-specific pairing nucleoside and may be used as universal base because inosine can pair nearly isoenergetically with A, T, and C. Other compounds having the same ability of non-specifically base-pairing with natural nucleobases have been formed. Suitable compounds which may be utilized in the present invention includes among others the compounds depicted below Examples of Universal Bases The sugar moiety of the backbone is suitably a pentose but may be the appropriate part of an PNA or a six-member ring. Suitable examples of possible pentoses include ribose, 2'-deoxyribose, 2'-O-methyl-ribose, 2'-flour-ribose, and 2'-4'-O-methylene-ribose (LNA). Suitably the nucleobase is attached to the 1' position of the pentose entity.

An internucleoside linker connects the 3' end of preceding monomer to a 5' end of a succeeding monomer when the sugar moiety of the backbone is a pentose, like ribose or 2-deoxyribose. The internucleoside linkage may be the natural occurring phospodiester linkage or a derivative thereof. Examples of such derivatives include phosphoroth-

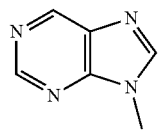

Nebularine

Building Block

The chemical entities that are precursors for structural additions or eliminations of the encoded molecule may be attached to a building block prior to the participation in the formation of the reaction product leading the final encoded molecule. Besides the chemical entity, the building block generally comprises an anti-codon.

The chemical entity of the building block comprises at least one reactive group capable of participating in a reaction which results in a connection between the chemical entity of the building block and another chemical entity or a scaffold associated with the nascent complex. The connection is facilitated by one or more reactive groups of the chemical entity. The number of reactive groups which appear on the chemical entity is suitably one to ten. A building block featuring only one reactive group is used i.a. in the end positions of polymers or scaffolds, whereas building blocks having two reactive groups are suitable for the formation of the body part of a polymer or scaffolds capable of being reacted further. One, two or more reactive groups intended for the formation of connections, are typically present on scaffolds.

The reactive group of the building block may be capable of forming a direct connection to a reactive group of the nascent complex or the reactive group of the building block may be capable of forming a connection to a reactive group of the nascent complex through a bridging fill-in group. It is to be understood that not all the atoms of a reactive group are necessarily maintained in the connection formed. Rather, the reactive groups are to be regarded as precursors for the structure of the connection.

The subsequent cleavage step to release the chemical entity from the building block can be performed in any appropriate way. In an aspect of the invention the cleavage involves usage of a reagent or an enzyme. The cleavage results in a transfer of the chemical entity to the nascent encoded molecule or in a transfer of the nascent encoded molecule to the chemical entity of the building block. In some cases it may be advantageous to introduce new chemical groups as a consequence of linker cleavage. The new chemical groups may be used for further reaction in a subsequent cycle, either directly or after having been activated. In other cases it is desirable that no trace of the linker remains after the cleavage.

In another aspect, the connection and the cleavage is conducted as a simultaneous reaction, i.e. either the chemical entity of the building block or the nascent encoded molecule is a leaving group of the reaction. In general, it is preferred to design the system such that the connection and the cleavage occur simultaneously because this will reduce the number of steps and the complexity. The simultaneous connection and cleavage can also be designed such that either no trace of the linker remains or such that a new chemical group for further reaction is introduced, as described above.

The attachment of the chemical entity to the building block, optionally via a suitable spacer can be at any entity available for attachment, e.g. the chemical entity can be attached to a nucleobase or the backbone. In general, it is preferred to attach the chemical entity at the phosphor of the internucleoside linkage or at the nucleobase. When the nucleobase is used for attachment of the chemical entity, the attachment point is usually at the 7 position of the purines or 7-deaza-purins or at the 5 position of pyrimidines. The nucleotide may be distanced from the reactive group of the chemical entity by a spacer moiety. The spacer may be designed such that the conformational space sampled by the reactive group is optimized for a reaction with the reactive group of the nascent encoded molecule or reactive site.

The anticodon complements the codon of the identifier sequence and generally comprises the same number of nucleotides as the codon. The anti-codon may be adjoined with a fixed sequence, such as a sequence complementing a framing sequence.

Various specific building blocks are envisaged. Building blocks of particular interest are shown below.

Specific Building Blocks

Building Blocks Transferring a Chemical Entity to a Recipient Nucleophilic Group The building block indicated below is capable of transferring a chemical entity (CE) to a recipient nucleophilic group, typically an amine group. The bold lower horizontal line illustrates the building block and the vertical line illustrates a spacer. The 5-membered substituted N-hydroxysuccinimid (NHS) ring serves as an activator, i.e. a labile bond is formed between the oxygen atom connected to the NHS ring and the chemical entity. The labile bond may be cleaved by a nucleophilic group, e.g. positioned on a scaffold

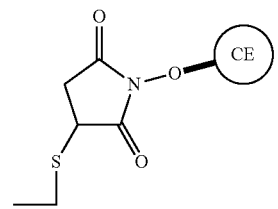

The 5-membered substituted N-hydroxysuccinimid (NHS) ring serves as an activator, i.e. a labile bond is formed between the oxygen atom connected to the NHS ring and the chemical entity. The labile bond may be cleaved by a nucleophilic group, e.g. positioned on a scaffold, to transfer the chemical entity to the scaffold, thus converting the remainder of the fragment into a leaving group of the reaction. When the chemical entity is connected to the activator through an carbonyl group and the recipient group is an amine, the bond formed on the scaffold will an amide bond. The above building block is the subject of the Danish patent application No. PA 2002 01946 and the US provisional patent application No. 60/434,439, the content of which are incorporated herein in their entirety by reference.

Another building block which may form an amide bond is

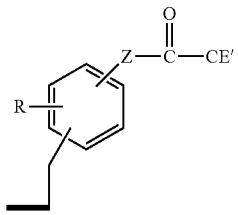

R may be absent or NO$_2$, CF$_3$, halogen, preferably Cl, Br, or I, and Z may be S or O. This type of building block is disclosed in Danish patent application No. PA 2002 0951 and US provisional patent application filed 20 Dec. 2002 with the title "A building block capable of transferring a functional entity to a recipient reactive group". The content of both patent application are incorporated herein in their entirety by reference.

A nucleophilic group can cleave the linkage between Z and the carbonyl group thereby transferring the chemical entity —(C=O)—CE' to said nucleophilic group.

Building Blocks Transferring a Chemical Entity to a Recipient Reactive Group Forming a C=C Bond A building block as shown below are able to transfer the chemical entity to a recipient aldehylde group thereby forming a double bond between the carbon of the aldehyde and the chemical entity

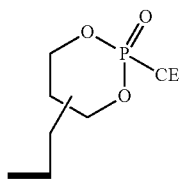

The above building block is comprised by the Danish patent application No. DK PA 2002 01952 and the US provisional patent application filed 20 Dec. 2002 with the title "A building block capable of transferring a functional entity to a recipient reactive group forming a C=C double bond". The content of both patent applications are incorporated herein in their entirety by reference.

Building Blocks Transferring a Chemical Entity to a Recipient Reactive Group Forming a C—C Bond The below building block is able to transfer the chemical entity to a recipient group thereby forming a single bond between the receiving moiety, e.g. a scaffold, and the chemical entity.

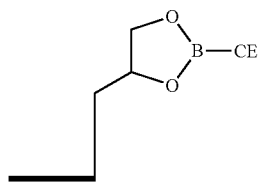

The above building block is comprised by the Danish patent application No. DK PA 2002 01947 and the U.S. provisional patent application No. 60/434,428. The content of both patent applications are incorporated herein in their entirety by reference.

Another building block capable of transferring a chemical entity to a receiving reactive group forming a single bond is

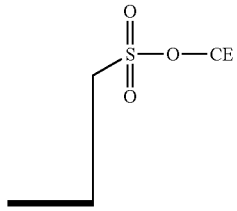

The receiving group may be a nucleophile, such as a group comprising a hetero atom, thereby forming a single bond between the chemical entity and the hetero atom, or the receiving group may be an electronegative carbon atom, thereby forming a C—C bond between the chemical entity and the scaffold.

The chemical entity attached to any of the above building blocks may be a selected from a large arsenal of chemical structures. Examples of chemical entities are H or entities selected among the group consisting of a $C_1$-$C_6$ alkyl, $C_2$-$C_6$ alkenyl, $C_2$-$C_6$ alkynyl, $C_4$-$C_8$ alkadienyl, $C_3$-$C_7$ cycloalkyl, $C_3$-$C_7$ cycloheteroalkyl, aryl, and heteroaryl, said group being substituted with 0-3 $R^4$, 0-3 $R^5$ and 0-3 $R^9$ or $C_1$-$C_3$ alkylene-$NR^4{}_2$, $C_1$-$C_3$ alkylene-$NR^4$C(O)$R^8$, $C_1$-$C_3$ alkylene-$NR^4$C(O)O$R^8$, $C_1$-$C_2$ alkylene-O—$NR^4{}_2$, $C_1$-$C_2$ alkylene-O—$NR^4$C(O)$R^8$, $C_1$-$C_2$ alkylene-O—$NR^4$C(O)O$R^8$ substituted with 0-3 $R^9$.

where $R^4$ is H or selected independently among the group consisting of $C_1$-$C_6$ alkyl, $C_2$-$C_6$ alkenyl, $C_2$-$C_6$ alkynyl, $C_3$-$C_7$ cycloalkyl, $C_3$-$C_7$ cycloheteroalkyl, aryl, heteroaryl, said group being substituted with 0-3 $R^9$ and $R^5$ is selected independently from —N$_3$, —CNO, —C(NOH)NH$_2$, —NHOH, —NHNHR$^6$, —C(O)R$^6$, —SnR$^6{}_3$, —B(OR$^6$)$_2$, —P(O)(OR$^6$)$_2$ or the group consisting of $C_2$-$C_6$ alkenyl, $C_2$-$C_6$ alkynyl, $C_4$-$C_8$ alkadienyl said group being substituted with 0-2 $R^7$, where $R^6$ is selected independently from H, $C_1$-$C_6$ alkyl, $C_3$-$C_7$ cycloalkyl, aryl or $C_1$-$C_6$ alkylene-aryl substituted with 0-5 halogen atoms selected from —F, —Cl, —Br, and —I; and $R^7$ is independently selected from —NO$_2$, —COOR$^6$, —COR$^6$, —CN, —OSiR$^6{}_3$, —OR$^6$ and —NR$^6{}_2$.

$R^8$ is H, $C_1$-$C_6$ alkyl, $C_2$-$C_6$ alkenyl, $C_2$-$C_6$ alkynyl, $C_3$-$C_7$ cycloalkyl, aryl or $C_1$-$C_6$ alkylene-aryl substituted with 0-3 substituents independently selected from —F, —C$_1$, —NO$_2$, —R$^3$, —OR$^3$, —SiR$^3{}_3$ $R^9$ is =O, —F, —Cl, —Br, —I, —CN, —NO$_2$, —OR$^6$, —NR$^6{}_2$, —NR$^6$—C(O)R$^8$, —NR$^6$—C(O)OR$^8$, —SR$^6$, —S(O)R$^6$, —S(O)$_2$R$^6$, —COOR$^6$, —C(O)NR$^6{}_2$ and —S(O)$_2$NR$^6{}_2$.

Cross-Link Cleavage Building Blocks

It may be advantageous to split the transfer of a chemical entity to a recipient reactive group into two separate steps, namely a cross-linking step and a cleavage step because each step can be optimized. A suitable building block for this two step process is illustrated below:

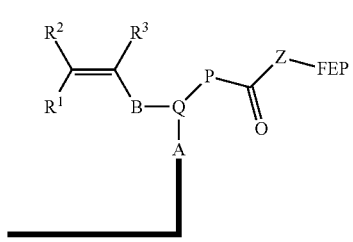

Initially, a reactive group appearing on the functional entity precursor (abbreviated FEP) reacts with a recipient reactive group, e.g. a reactive group appearing on a scaffold, thereby forming a cross-link. Subsequently, a cleavage is performed, usually by adding an aqueous oxidising agent such as $I_2$, $Br_2$, $Cl_2$, $H^+$, or a Lewis acid. The cleavage results in a transfer of the group HZFEP-to the recipient moiety, such as a scaffold.

In the above formula

Z is O, S, $NR^4$

Q is N, $CR^1$

P is a valence bond, O, S, $NR^4$, or a group $C_{5-7}$arylene, $C_{1-6}$ alkylene, $C_{1-6}$O-alkylene, $C_{1-6}$S-alkylene, $NR^1$-alkylene, $C_{1-6}$alkylene-O, $C_{1-6}$alkylene-S option said group being substituted with 0-3 $R^4$, 0-3 $R^5$ and 0-3 $R^9$ or $C_1$-$C_3$ alkylene-$NR^4{}_2$, $C_1$-$C_3$ alkylene-$NR^4C(O)R^8$, $C_1$-$C_3$ alkylene-$NR^4C(O)OR^8$, $C_1$-$C_2$ alkylene-O—$NR^4{}_2$, $C_1$-$C_2$ alkylene-O—$NR^4C(O)R^8$, $C_1$-$C_2$ alkylene-O—$NR^4C(O)OR^8$ substituted with 0-3 $R^9$, B is a group comprising D-E-F, in which D is a valence bond or a group $C_{1-6}$ alkylene, $C_{1-6}$ alkenylene, $C_{1-6}$alkynylene, $C_{5-7}$arylene, or $C_{5-7}$heteroarylene, said group optionally being substituted with 1 to 4 group $R^{11}$, E is, when present, a valence bond, O, S, $NR^4$, or a group $C_{1-6}$ alkylene, $C_{1-6}$ alkenylene, $C_{1-6}$ alkynylene, $C_{5-7}$arylene, or $C_{5-7}$heteroarylene, said group optionally being substituted with 1 to 4 group $R^{11}$, F is, when present, a valence bond, O, S, or $NR^4$, A is a spacing group distancing the chemical structure from the complementing element, which may be a nucleic acid, $R^1$, $R^2$, and $R^3$ are independent of each other selected among the group consisting of H, $C_1$-$C_6$ alkyl, $C_2$-$C_6$ alkenyl, $C_2$-$C_6$ alkynyl, $C_4$-$C_8$ alkadienyl, $C_3$-$C_7$ cycloalkyl, $C_3$-$C_7$ cycloheteroalkyl, aryl, and heteroaryl, said group being substituted with 0-3 $R^4$, 0-3 $R^5$ and 0-3 $R^9$ or $C_1$-$C_3$ alkylene-$NR^4{}_2$, $C_1$-$C_3$ alkylene-$NR^4C(O)R^8$, $C_1$-$C_3$ alkylene-$NR^4C(O)OR^8$, $C_1$-$C_2$ alkylene-O—$NR^4{}_2$, $C_1$-$C_2$ alkylene-O—$NR^4C(O)R^8$, $C_1$-$C_2$ alkylene-O—$NR^4C(O)OR^8$ substituted with 0-3 $R^9$, FEP is a group selected among the group consisting of H, $C_1$-$C_6$ alkyl, $C_2$-$C_6$ alkenyl, $C_2$-$C_6$ alkynyl, $C_4$-$C_8$ alkadienyl, $C_3$-$C_7$ cycloalkyl, $C_3$-$C_7$ cycloheteroalkyl, aryl, and heteroaryl, said group being substituted with 0-3 $R^4$, 0-3 $R^5$ and 0-3 $R^9$ or $C_1$-$C_3$ alkylene-$NR^4{}_2$, $C_1$-$C_3$ alkylene-$NR^4C(O)R^8$, $C_1$-$C_3$ alkylene-$NR^4C(O)OR^8$, $C_1$-$C_2$ alkylene-O—$NR^4{}_2$, $C_1$-$C_2$ alkylene-O—$NR^4C(O)R^8$, $C_1$-$C_2$ alkylene-O—$NR^4C(O)OR^8$ substituted with 0-3 $R^9$, where $R^4$ is H or selected independently among the group consisting of $C_1$-$C_6$ alkyl, $C_2$-$C_6$ alkenyl, $C_2$-$C_6$ alkynyl, $C_3$-$C_7$ cycloalkyl, $C_3$-$C_7$ cycloheteroalkyl, aryl, heteroaryl, said group being substituted with 0-3 $R^9$ and $R^5$ is selected independently from —$N_3$, —CNO, —C(NOH)$NH_2$, —NHOH, —$NHNHR^6$, —C(O)$R^6$, —$SnR^6{}_3$, —B(OR$^6$)$_2$, —P(O)(OR$^6$)$_2$ or the group consisting of $C_2$-$C_6$ alkenyl, $C_2$-$C_6$ alkynyl, $C_4$-$C_8$ alkadienyl said group being substituted with 0-2 $R^7$, where $R^6$ is selected independently from H, $C_1$-$C_6$ alkyl, $C_3$-$C_7$ cycloalkyl, aryl or $C_1$-$C_6$ alkylene-aryl substituted with 0-5 halogen atoms selected from —F, —Cl, —Br, and —I; and $R^7$ is independently selected from —$NO_2$, —$COOR^6$, —$COR^6$, —CN, —$OSiR^6{}_3$, —$OR^6$ and —$NR^6{}_2$.

$R^8$ is H, $C_1$-$C_6$ alkyl, $C_2$-$C_6$ alkenyl, $C_2$-$C_6$ alkynyl, $C_3$-$C_7$ cycloalkyl, aryl or $C_1$-$C_6$ alkylene-aryl substituted with 0-3 substituents independently selected from —F, —$C_1$, —$NO_2$, —$R^3$, —$OR^3$, —$SiR^3{}_3$ $R^9$ is =O, —F, —Cl, —Br, —I, —CN, —$NO_2$, —$OR^6$, —$NR^6{}_2$, —$NR^6$—$C(O)R^8$, —$NR^6$—$C(O)OR^8$, —$SR^6$, —S(O)$R^6$, —S(O)$_2R^6$, —$COOR^6$, —C(O)$NR^6{}_2$ and —S(O)$_2NR^6{}_2$.

In a preferred embodiment Z is O or S, P is a valence bond, Q is CH, B is $CH_2$, and $R^1$, $R^2$, and $R^3$ is H. The bond between the carbonyl group and Z is cleavable with aqueous 12.

Partitioning

The partitioning step, by which the library of bifunctional molecules is subjected to a condition partitioning one or more complexes having a certain property from the remainder of the library, may be referred to as the enrichment step or the selection step, as appropriate, and includes the screening of the library for encoded molecules having predetermined desirable characteristics. Predetermined desirable characteristics can include binding to a target, catalytically changing the target, chemically reacting with a target in a manner which alters/modifies the target or the functional activity of the target, and covalently attaching to the target as in a suicide inhibitor.

In theory, molecules of interest can be selected based on their properties using either physical or physiological procedures. The method preferred according to the present invention is to enrich molecules with respect to binding affinity towards a target of interest. In a certain embodiment, the basic steps involve mixing the library of complexes with the immobilized target of interest. The target can be attached to a column matrix or microtitre wells with direct immobilization or by means of antibody binding or other high-affinity interactions. In another embodiment, the target and displayed molecules interact without immobilisation of the target. Displayed molecules that bind to the target will be retained by a filter, size-exclusion chromatography etc, while non-binding displayed molecules will be removed during a single or a series of wash steps. The identifiers of complexes bound to the target can then be separated by cleaving a physical connection to the encoded molecule or the entire complex may be eluted. It may be considered advantageously to perform a chromatography step after or instead of the washing step. After the cleavage of the physical link between the synthetic molecule and the identifier, the identifier may be recovered from the media and optionally amplified before the decoding step.

A significant reduction in background binders may be obtained with increased washing volumes, repeating washing steps, higher detergent concentrations and prolonged incubation during washing. Thus, the more volume and number of steps used in the washing procedure together with more stringent conditions will more efficiently remove non-binders and background binders. The right stringency in the washing step can also be used to remove low-affinity specific binders. However, the washing step will also remove wanted binders if too harsh conditions are used.

A blocking step, such as incubation of solid phase with skimmed milk proteins or other inert proteins and/or mild detergent such as Tween-20 and Triton X-100, may also be used to reduce the background. The washing conditions should be as stringent as possible to remove background binding but to retain specific binders that interact with the immobilized target. Generally, washing conditions are adjusted to maintain the desired affinity binders, e.g. binders in the micromolar, nanomolar, or pocomolar range.

The target can be any compound of interest. E.g. the target can be a protein, peptide, carbohydrate, polysaccharide, glycoprotein, hormone, receptor, antigen, antibody, virus, substrate, metabolite, transition state analogue, cofactor, inhibitor, drug, dye, nutrient, growth factor, cell, tissue, etc. without limitation. Suitable targets include, but are not limited to, angiotensin converting enzyme, renin, cyclooxygenase, 5-lipoxygenase, IIL-1 0 converting enzyme, cytokine receptors, PDGF receptor, type II inosine monophosphate dehydrogenase, β-lactamases, integrin, proteases like factor VIIa, kinases like Bcr-Abl/Her, phosphotases like PTP-1B, and fungal cytochrome P-450. Targets can include, but are not limited to, bradykinin, neutrophil elastase, the HIV proteins, including tat, rev, gag, int, RT, nucleocapsid etc., VEGF, bFGF, TGFβ, KGF, PDGF, GPCR, thrombin, substance P, IgE, sPLA2, red blood cells, glioblastomas, fibrin clots, PBMCs, hCG, lectins, selectins, cytokines, ICP4, complement proteins, etc.

A target can also be a surface of a non-biological origin, such as a polymer surface or a metal surface. The method of the invention may then be used to identify suitable coatings for such surfaces.

In a preferred embodiment, the desirable synthetic molecule acts on the target without any interaction between the nucleic acid attached to the desirable encoded molecule and the target. In one embodiment, the bound complex-target aggregate can be partitioned from unbound complexes by a number of methods. The methods include nitrocellulose filter binding, column chromatography, filtration, affinity chromatography, centrifugation, and other well known methods. A preferred method is size-exclusion chromatography.

Briefly, the library of complexes is subjected to the target, which may include contact between the library and a column onto which the target is immobilised. Identifiers associated with undesirable encoded molecules, i.e. synthetic molecules not bound to the target under the stringency conditions used, will pass through the column. Additional undesirable encoded molecules (e.g. encoded molecules which cross-react with other targets) may be removed by counter-selection methods. Desirable complexes are bound to the column. The target may be immobilized in a number of ways. In one embodiment, the target is immobilized through a cleavable physical link, such as one more chemical bonds. The aggregate of the target and the complex may then be subjected to a size exclusion chromatography to separate the aggregate from the rest of the compounds in the media. The complex may then be eluted from the target by changing the conditions (e.g., salt, pH, surfactant, temperature etc.). Alternatively, the complex may be provided with a cleavable linker, preferable orthogonal to a cleavable linker that attaches the target to the solid support, at a position between the synthetic molecule and the identifier. Subsequent to the size exclusion chromatography this cleavable linker is cleaved to separate the identifiers of complexes having affinity towards the targets. Just to mention a single type of orthogonal cleavable linkages, one could attach the target to the solid support through a linkage that can be cleaved by a chemical agent, and the linker separating the synthetic molecule and the identifier may be selected as a photocleavable linkage. More specifically, the former linkage may be a disulphide bond that can be cleaved by a suitable reducing agent like DTT (dithiothreitol) and the latter linkage may be a o-nitrophenyl group.

There are other partitioning and screening processes which are compatible with this invention that are known to one of ordinary skill in the art. In one embodiment, the products can be fractionated by a number of common methods and then each fraction is assayed for activity. The fractionization methods can include size, pH, hydrophobicity, etc.

Inherent in the present method is the selection of encoded molecules on the basis of a desired function; this can be extended to the selection of molecules with a desired function and specificity. Specificity can be required during the selection process by first extracting complexes which are capable of interacting with a non-desired "target" (negative selection, or counter-selection), followed by positive selection with the desired target. As an example, inhibitors of fungal cytochrome P-450 (fungicides) are known to cross-react to some extent with mammalian cytochrome P-450 (resulting in serious side effects). Highly specific inhibitors of the fungal cytochrome could be selected from a library by first removing those complexes capable of interacting with the mammalian cytochrome, followed by retention of the remaining products which are capable of interacting with the fungal cytochrome.

Experimental Example: The 10 Templates Used for Q-PCR Quantification

```
                        Taqman MGB probe binding region: *=AATTCCAGCTTCTAGGAAGAC (SEQ ID NO: 1)
           P1           P2              P3              P4

(SEQ ID NO: 2)
5'-

CAGCTTGGACACCACGTCATACTAGCTGCTAGAGATGTGGTGATATTAGTGTGTGACGATGG-
TACGCACAAGTACGAACGTGCATCAGAGAGGACGAGCAGGACCTGGAACCTGGTGC*TTCCTCCACCACGTCTCTGAC-3'   (SEQ ID NO: 2)

GGAAGAAGACAGAAGACCTG (SEQ ID NO: 3)           CTCGACCACTGCAGGTGGAGCTCC (SEQ ID NO: 4)

TCAGGAGTCGAGAACTGAAG (SEQ ID NO: 5)           CGTGCTTCCTCTGCTGCACCACCG (SEQ ID NO: 6)
```

-continued

| | |
|---|---|
| TGTGTACGTCAACACGTCAG (SEQ ID NO: 7) | CCTGGTGTCGAGGTGAGCAGCAGC (SEQ ID NO: 8) |
| TGTGGAACTACCATCCAAGG (SEQ ID NO: 9) | CTCGACGAGGTCCATCCTGGTCGC (SEQ ID NO: 10) |
| CCATCCAACATCGTTGGAAG (SEQ ID NO: 11) | CGTGAGGAGCAGGTCCTCCTGTCG (SEQ ID NO: 12) |
| AACCTGTCCTGTGAGATCTG (SEQ ID NO: 13) | CCTGACACTGGTCGTGGTCGAGGC (SEQ ID NO: 14) |
| TCACGAAGCTGGATGATGAG (SEQ ID NO: 15) | CCATCTCGACGACCTGCTCCTGGG (SEQ ID NO: 16) |
| TAGCATCGATCGAACGTAGG (SEQ ID NO: 17) | CCACGAGGTCTCCACTGGTCCAGG (SEQ ID NO: 18) |
| TCGAAGCTACTGTCGAGATG (SEQ ID NO: 19) | CCACTGAGCTGCTCCTCCACGTGG (SEQ ID NO: 20) |

Oligos for Template Synthesis

```
                                                                    (SEQ ID NO: 21)
FPv2: CAGCTTGGACACCACGTCATAC (SEQ ID NO: 22)
RPv2: GTCAGAGACGTGGTGGAGGAA (SEQ ID NO: 23)
Temp1-1: CAGCTTGGACACCACGTCATACTAGCTGCTAGAGATGTGGTGATATTAGTGTGTGACGAT (SEQ ID NO: 24)
Temp1-2: CAGCTTGGACACCACGTCATACGGAAGAAGACAGAAGACCTGATATTAGTGTGTGACGAT (SEQ ID NO: 25)
Temp1-3: CAGCTTGGACACCACGTCATACTCAGGAGTCGAGAACTGAAGATATTAGTGTGTGACGAT (SEQ ID NO: 26)
Temp1-4: CAGCTTGGACACCACGTCATACTGTGTACGTCAACACGTCAGATATTAGTGTGTGACGAT (SEQ ID NO: 27)
Temp1-5: CAGCTTGGACACCACGTCATACTGTGGAACTACCATCCAAGGATATTAGTGTGTGACGAT (SEQ ID NO: 28)
Temp1-6: CAGCTTGGACACCACGTCATACCCATCCAACATCGTTGGAAGATATTAGTGTGTGACGAT (SEQ ID NO: 29)
Temp1-7: CAGCTTGGACACCACGTCATACAACCTGTCCTGTGAGATCTGATATTAGTGTGTGACGAT (SEQ ID NO: 30)
Temp1-8: CAGCTTGGACACCACGTCATACTCACGAAGCTGGATGATGAGATATTAGTGTGTGACGAT (SEQ ID NO: 31)
Temp1-9: CAGCTTGGACACCACGTCATACTAGCATCGATCGAACGTAGGATATTAGTGTGTGACGAT (SEQ ID NO: 32)
Temp1-10: CAGCTTGGACACCACGTCATACTCGAAGCTACTGTCGAGATGATATTAGTGTGTGACGAT (SEQ ID NO: 33)
Temp2: GTCCTCTCTGATGCACGTTCGTACTTGTGCGTACCATCGTCACACACTAATATC (SEQ ID NO: 34)
Temp3-1: GAACGTGCATCAGAGAGGACGAGCAGGACCTCGAACCTGGTGCAATTCCAGCTTCTAGGAAGACT
```

```
                                                                (SEQ ID NO: 35)
Temp3-2:  GAACGTGCATCAGAGAGGACTCGACCACTG-    CAGGTGGAGCTCCAATTCCAGCTTCTAGGAAGCCT (SEQ ID NO: 36)
Temp3-3:  GAACGTGCATCAGAGAGGACGTGCTTCCTCTGCTGCACCACGGAATTCCAGCTTCTAGGAAGACT (SEQ ID NO: 37)
Temp3-4:  GAACGTGCATCAGAGAGGACCTGCTGTCGAGGTGAGCAGCAGCAATTCCAGCTTCTAGGAAGACT (SEQ ID NO: 38)
Temp3-5:  GAACGTGCATCAGAGAAGGACTCGACGAGGTCCATCCTGGTCGCAATTCCAGCTTCTAGGAAGACTT (SEQ ID NO: 39)
Temp3-6:  GAACGTGCATCAGAGAGGACGTGAGGAGCAGGTCCTCCTGTCGAATTCCAGCTTCTAGGAAGACT (SEQ ID NO: 40)
Temp3-7:  GAACGTGCATCAGAGAGGACCTGACACTGGTCGTGGTCGACGCAATTCCAGCTTCTAGGAAGACTT (SEQ ID NO: 41)
Temp3-8:  GAACGTGCATCAGAGAGGACCATCTCGACGACCTGCTCCTGGGAATTCCAGCTTCTAGGAAGACT (SEQ ID NO: 42)
Temp3-9:  GAACGTTGCATCAGAGAGGACCACGAGGTCTCCACTGGTCCAGGAATTCCAGCTTCTAGGAAGACT (SEQ ID NO: 43)
Temp3-10: GAACGTGCATCAGAGAGGACCACTGAGCTGCTCCTCCAGGTGGAATTCCAGCTTCTAGGAAGACT (SEQ ID NO: 44)
Temp4:    GTCAGAGACGTGGTGGAGGAAGTCTTCCTAGAAGCTGGAATT
```

Synthesis of Identifier Oligonucleotides

The 10 identifier oligonucleotides were assembled in 10 separate 50 µl PCR reactions each containing 0.05 pmol of the oligos Q-Temp1-X, Q-Temp2, Q-Temp3-X and Q-Temp4 (x=1 through 10) and 25 pmol of the external primers FPv2 and RPv2 with TA=53° C. The 160 bp products were gel-purified using QIAquick Gel Extraction Kit from QIAGEN (Cat. No. 28706) and quantified on spectrophotometer. As a control, 20 ng of each of the templates (as estimated from these measurements) were loaded on an agarose gel.

Preparation of Samples for Q-PCR:

Sample A: Generated by mixing 20 ng from each identifier oligonucleotide prep. Volume was adjusted to 50 µl. Concentration: 4 ng/µl=38.46 fmol/µl (160 bp×650 Da/bp=1.04×105 g/mol. 1 ng=9.615 fmol). Diluted to $10^7$ copies/5 µl (0.00332 fmol/µl).

Sample B: 20 ng/20 µl stocks of each template were prepared. The sample was mixed as follows:

5 µl undil. Template #10
5 µl 2× dil. Template #9
5 µl 4× dil. Template #8
5 µl 8× dil. Template #7
5 µl 16× dil. Template #6
5 µl 32× dil. Template #5
5 µl 64× dil. Template #4
5 µl 128× dil. Template #3
5 µl 256× dil. Template #2
5 µl 512× dil. Template #1

Concentration: 10 ng/50 µl=0.20 ng/µl=1.923 fmol/µl. Diluted 579.2-fold to $10^7$ copies/5 µl (0.00332 fmol/µl).

Figure 12:
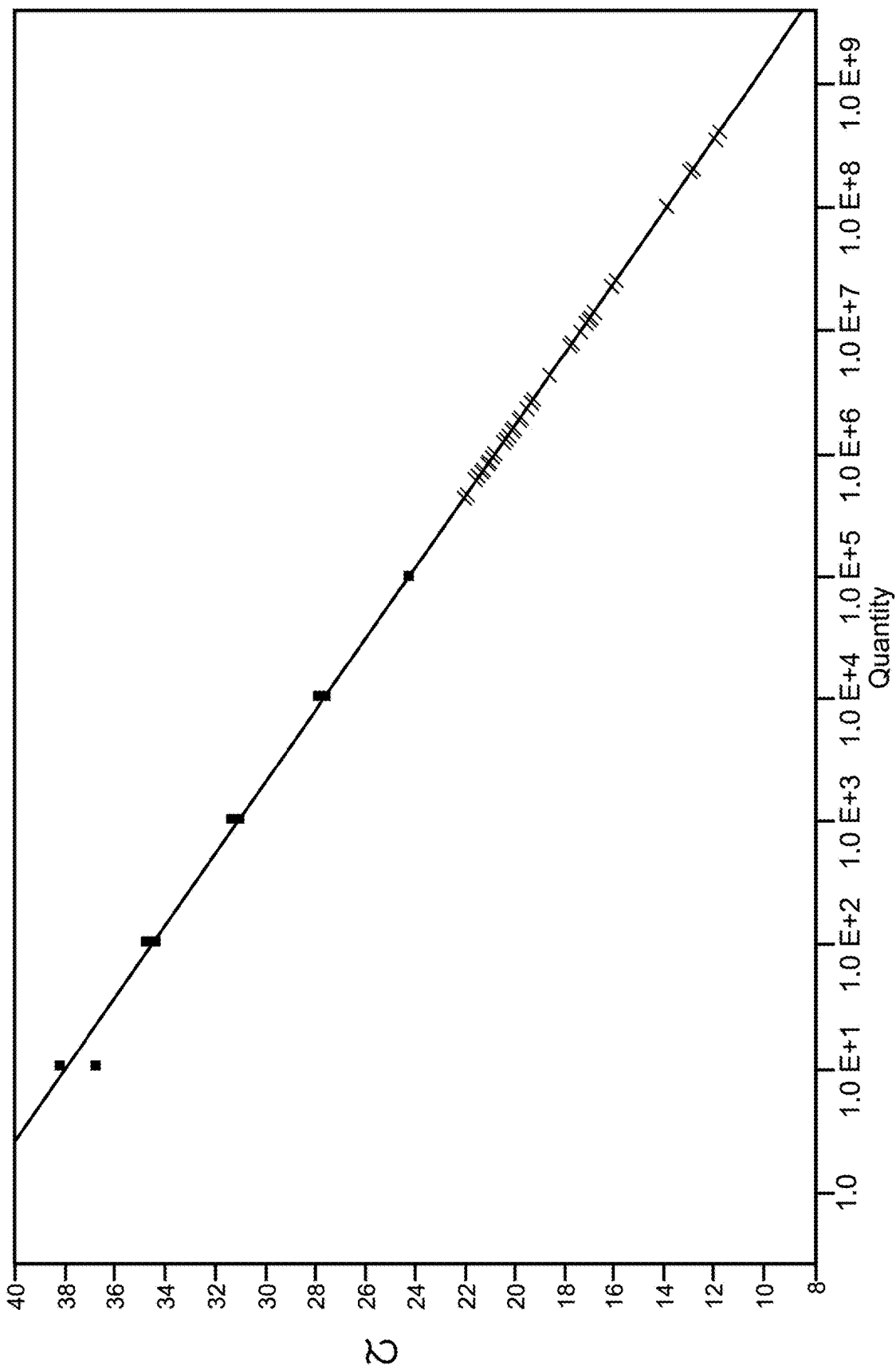
FIG. 12 discloses a standard curve used in example 3.

Standard curve: The samples for the standard curve was prepared by diluting Sample A 116.55-fold to $10^9$ copies/5 µl (0.33 fmol/µl) and subsequently performing a 10-fold serial dilution of this sample. 5 µl was used for each PCR reaction. The standard curve is shown in FIG. 12.

Q-PCR reactions

For 5 ml premix (for one 96-well plate):

2.5 ml Taqman Universal PCR Master Mix (Applied Biosystems; includes Taq polymerase, dNTPs and optimized Taq pol. buffer)

450 µl RPv2 (10 pmol/ul)

25 µl Taqman probe (6-FAM-TCCAGCTTCTAGGAA-GAC ((SEQ ID NO: 59)-MGBNFQ; (SEQ ID NO: 60) 50 µM; Applied Biosystems)

1075 µl $H_2O$ 40.5 µl premix was aliquoted into each well and 4.5 µl of relevant upstream PCR primer (FPv2 (for standard curve) or one of the codon specific primers listed below; 10 pmol/µl) and 5 µl sample ($H_2O$ in wells for negative controls) was added. The codon-specific PCR primers were: (Tm calculations shown are from Vector NTI; matched to Tm for RPv2 (67.7° C.))

```
P1-1:
                                                      (SEQ ID NO: 45)
GTCATACTAGCTGCTAGAGATGTGGTGATA   66.8° C.

P1-2:
                                                      (SEQ ID NO: 46)
CATACGGAAGAAGACAGAAGACCTGATA    67.8° C.
```

-continued

P1-3:
(SEQ ID NO: 47)
TCATACTCAGGAGTCGAGAACTGAAGATA 67.6° C.

P1-4:
(SEQ ID NO: 48)
CATACTGTGTACGTCAACACGTCAGATA 67.4° C.

P1-5:
(SEQ ID NO: 49)
CATACTGTGGAACTACCATCCAAGGATA 68.0° C.

P1-6:
(SEQ ID NO: 50)
CCATCCAACATCGTTGGAAGAT 67.8° C.

P1-7:
(SEQ ID NO: 51)
CATACAACCTGTCCTGTGAGATCTGATA 67.7° C.

P1-8:
(SEQ ID NO: 52)
ATACTCACGAAGCTGGATGATGAGATA 67.3° C.

P1-9:
(SEQ ID NO: 53)
CATACTAGCATCGATCGAACGTAGGATA 68.1° C.

P1-10:
(SEQ ID NO: 54)
TCATACTCGAAGCTACTGTCGAGATGATA 68.2° C.

P2-1:
(SEQ ID NO: 55)
ATATTAGTGTGTGACGATGGTACGCA 67.8° C.

P3-1:
(SEQ ID NO: 56)
ACAAGTACGAACGTGCATCAGAGA 67.7° C.

P4-1:
(SEQ ID NO: 57)
CGAGCAGGACCTGGAACCT 67.7° C.

P4-2:
(SEQ ID NO: 58)
TCGACCACTGCAGGTGGA 68.3° C.

P4-3:
(SEQ ID NO: 61)
GCTTCCTCTGCTGCACCA 66.7° C.

P4-4:
(SEQ ID NO: 62)
GGTGTCGAGGTGAGCAGCA 69.1° C.

P4-5:
(SEQ ID NO: 63)
CGACGAGGTCCATCCTGGT 68.6° C.

P4-6:
(SEQ ID NO: 64)
GTGAGGAGCAGGTCCTCCTGT 68.0° C.

P4-7:
(SEQ ID NO: 65)
CTGACACTGGTCGTGGTCGA 68.8° C.

P4-8:
(SEQ ID NO: 66)
CATCTCGACGACCTGCTCCT 67.9° C.

P4-9:
(SEQ ID NO: 67)
ACGAGGTCTCCACTGGTCCA 68.3° C.

P4-10:
(SEQ ID NO: 68)
ACTGAGCTGCTCCTCCAGGT 66.5° C.

Thermocycling/measurement of fluorescence was performed on an Applied Biosystems ABI Prism 7900HT real-time instrument utilizing the standard cycling parameters:

95° C. 10 min;
40 cycles of
95° C. 15 sec;
60° C. 1 min
All samples were run in duplicate.

Results

FIG. 12 shows the standard curve calculated by the 7900HT system software. The log of the starting copy number was plotted against the measured $C_T$ value. The relationship between $C_T$ and starting copy number was linear in the range from 10 to $10^9$ template copies.

This standard curve was utilized by the system software to calculate the quantity in the "unknown" samples as shown below.

TABLE I

Sample A (Shown graphically in FIG. 13A)

| Sample A: Equimolar ratios | Observed A | Observed B | Expected |
|---|---|---|---|
| FPv2 | 12539947.00 | 11977503.00 | 10000000 |
| P1-1 | 445841.90 | 480382.03 | 1000000 |
| P1-2 | 884840.70 | 847478.56 | 1000000 |
| P1-3 | 1013073.56 | 948770.00 | 1000000 |
| P1-4 | 764187.94 | 741304.40 | 1000000 |
| P1-5 | 1352874.60 | 1275155.50 | 1000000 |
| P1-6 | 1284075.60 | 1337928.50 | 1000000 |
| P1-7 | 658161.80 | 747371.56 | 1000000 |
| P1-8 | 742187.20 | 653874.00 | 1000000 |
| P1-9 | 824587.75 | 705785.75 | 1000000 |
| P1-10 | 813550.75 | 836037.90 | 1000000 |
| P2-1 | 13145159.00 | 14482606.00 | 10000000 |
| P3-1 | 13263911.00 | 12773780.00 | 10000000 |
| P4-1 | 1430704.80 | 1472576.80 | 1000000 |
| P4-2 | 2681652.00 | 2481824.80 | 1000000 |
| P4-3 | 1933106.80 | 2085476.40 | 1000000 |
| P4-4 | 1359684.40 | 1364621.40 | 1000000 |
| P4-5 | 2206709.80 | 2065813.60 | 1000000 |
| P4-6 | 1652718.10 | 1873777.20 | 1000000 |
| P4-7 | 1468208.10 | 1416153.00 | 1000000 |
| P4-8 | 1664467.50 | 1581067.00 | 1000000 |
| P4-9 | 1462520.60 | 1594593.80 | 1000000 |
| P4-10 | 2020088.20 | 1912277.40 | 1000000 |

TABLE II

Sample B (Shown graphically in FIG. 13B)

| Sample B: 2-fold dil. | Observed A | Observed B | Expected |
|---|---|---|---|
| FPv2 | 4.97E+06 | 5.05E+06 | 10000000 |
| P1-1 | 9955.07 | 10899.97 | 9765.625 |
| P1-2 | 12732.32 | 13469.12 | 19531.25 |
| P1-3 | 25542.8 | 25419.85 | 39062.5 |
| P1-4 | 34748.89 | 44070.81 | 78125 |
| P1-5 | 110881.41 | 123734.13 | 156250 |
| P1-6 | 163687.44 | 166220.5 | 312500 |
| P1-7 | 156993.81 | 172005.64 | 625000 |
| P1-8 | 343176.78 | 374809.13 | 1250000 |
| P1-9 | 646619.44 | 576151 | 2500000 |
| P1-10 | 1.49E+06 | 1.72E+06 | 5000000 |
| P2-1 | 5.19E+06 | 5.37E+06 | 10000000 |
| P3-1 | 5.29E+06 | 5.09E+06 | 10000000 |
| P4-1 | (no signal) | 70223.8 | 9765.625 |
| P4-2 | 42103.32 | 22733.17 | 19531.25 |
| P4-3 | 54480.62 | 39663.62 | 39062.5 |
| P4-4 | 51293.07 | 43950.9 | 78125 |

TABLE II-continued

Sample B (Shown graphically in FIG. 13B)

| Sample B: 2-fold dil. | Observed A | Observed B | Expected |
|---|---|---|---|
| P4-5 | 137946.95 | 115027.34 | 156250 |
| P4-6 | 174134.64 | 156442.55 | 312500 |
| P4-7 | 316505.78 | 283856.84 | 625000 |
| P4-8 | 737661.44 | 691296.75 | 1250000 |
| P4-9 | 1.42E+06 | 1.45E+06 | 2500000 |
| P4-10 | 3.72E+06 | 3.52E+06 | 5000000 |

The results of the experiments show the possibility of accurately quantification of identifier oligonucleotides down to or even below 10 copies with a 9 fold dynamic range, and reliable relative quantification of the tested codons in various positions in the identifier oligonucleotide.

While the invention has been described with references to specific methods and embodiments, it will be appreciated that various modifications and changes may be made without departing from the invention. All patent and literature references cited herein are hereby incorporated by reference in their entirety.

The following items describe embodiments of the first aspect of the present invention:

Item 1: A method for obtaining structural information about an encoded molecule produced by a process comprising reaction of a plurality of chemical entities, said encoded molecule being capable of forming part of a complex also comprising an identifier oligonucleotide containing codons informative of the identity of chemical entities which have participated in the formation of the encoded molecule, the method comprises
  a) mixing a primer oligonucleotide with the identifier oligonucleotide,
  b) subjecting the mixture to a condition allowing for an extension reaction to occur when the primer is sufficient complementary to a part of the identifier oligonucleotide, and
  c) evaluating, based on measurement of the extension reaction, the presence, absence, or relative abundance of one or more codons.

Item 2: The method according to Item 1, wherein a composition of one, two, or more identifier oligonucleotides are processed simultaneously.

Item 3: The method according to Item 2, the composition is a result of subjecting a library of different complexes to a condition partitioning one or more complexes having a certain property from the remainder of the library.

Item 4: The method according to Item 1, wherein the condition which allows for an extension reaction to occur includes a polymerase or a ligase as well as suitable substrates.

Item 5: The method according to Item 4, wherein the condition includes a polymerase and a substrate comprising a blend of (deoxy)ribonucleotide triphosphates.

Item 6: The method according to any of the preceding Items, wherein the chemical entities are precursors for structural units appearing in the encoded molecule.

Item 7: The method according to any of the Items 1 to 6, wherein the process of producing the one or more encoded molecules comprises transferring one or more chemical entities to a nascent encoded molecule by a building block which further comprises an anti-codon.

Item 8: The method of Item 7, wherein the information of the anti-codon is transferred in conjunction with the chemical entity to the nascent encoded molecule.

Item 9: The method according to any of the preceding Items 1 to 8, wherein the identifier comprises two or more codons.

Item 10: The method according to any of the preceding Items 1 to 8, wherein the identifier comprises three or more codons.

Item 11: The method according to any of the preceding Items, wherein neighbouring codons of the identifier are spaced by a framing sequence.

Item 12: The method according to Item 11, wherein the framing sequence positions the reaction of a chemical entity in the synthesis history of the encoded molecule.

Item 13: The method according to any of the Items 1 to 12, wherein at least a part of the primer is complementary to a codon.

Item 14: The method according to any of Items 1 to 13, wherein at least a part of the primer is complementary to a codon and an adjacent framing sequence.

Item 15: The method according to any of the Items 1 to 13, wherein the codons have a length of four or more nucleotides.

Item 16: The method according to any of the Items 1 to 15, wherein the sequence comprising the codon and an adjacent framing sequence has a total length of 11 nucleotides or more.

Item 17: The method according to any of the Items 1 to 16, wherein the extension reaction is measured using the polymerase chain reaction (PCR), wherein the primer of Item 1 is involved in said PCR.

Item 18: The method according to any of the Items 1 to 17, wherein a primer is labelled.

Item 19: The method according to Item 18, wherein the primer is labelled with a small molecule, a radio active component, or a fluorogenic molecule.

Item 20: The method according to Item 19, wherein the small molecule label is selected from biotin, dinitrophenol, and digoxigenin, and the PCR amplicons are detected using an enzyme labelled streptavidin, anti-dinitrophenol. or anti-digoxigenin, respectively, reporter molecule.

Item 21: The method according to any of the Items 1 to 19, wherein extension reaction is measured by real-time PCR.

Item 22: The method according to Item 21, wherein the real-time PCR involves the use of an oligonucleotide probe responsible for the generation of a detectable signal during the propagation of the PCR reaction.

Item 23: The method according to any of the Items 1 to 21, wherein the probe is designed to hybridise at a position downstream of a primer binding site.

Item 24: The method according to Item 22 or 23, wherein the probe is a 5' nuclease oligoprobe or a hairpin oligoprobe.

Item 25: The method according to Items 2 or 3, wherein the library comprises complexes with identifier oligonucleotides having n codon positions and the codons in said codon positions being selected from a set of m different codons.

Item 26: The method according to Item 25, wherein a framing sequence is related to each of the n codon positions in a particular complex, said framing sequence positions the reaction of a chemical entity in the synthesis history of the encoded molecule.

Item 27: The method according to Item 25, wherein each codon in the set of m different codons differs from any other codons in the set in at least two nucleotide positions.

Item 28: The method according to Item 26, wherein each framing sequence in a set of n different framing sequences differs from any other framing sequences in the set in at least two nucleotide positions.

Item 29: A method for identifying the chemical entities utilized in the formation of an encoded molecule or a composition of encoded molecules, wherein in separate compartments, n×m primers individually are mixed with an aliquot of a composition obtained by subjecting a library of different complexes to a condition partitioning said composition from the remainder of the library, subjected to a mixture of polymerase and substrate (deoxy)ribonucleotide triphosphates under conditions allowing for an extension reaction to occur when a primer is sufficient complementary to a part of one or more identifier oligonucleotides present in the aliquot, and evaluation, based on measurement of the extension reaction, the presence, absence, or relative abundance of one or more codons in each compartment.

Item 30: A set comprising a collection of oligonucleotide primers, a polymerase, a composition of (deoxy)ribonucleotide triphosphates (dNTPs), and a library of complexes composed of a display molecule part and an identifier oligonucleotide, said oligonucleotide comprising codons informative of the identity of the chemical entities which has participated in the formation of the display molecule, wherein the oligonucleotide primers are sufficient complementary to codons appearing on the identifier oligo nucleotides in the library to allow for an extension reaction to occur.

Item 31: An encoded molecule identified by a method according to Items 1 to 28.

Method for Identifying a Display Molecule

The following pages will describe the second aspect of the invention: A METHOD FOR IDENTIFYING A DISPLAY MOLECULE, in which various patent and non-patent references cited in the present application are hereby incorporated by reference in their entirety. It is envisaged that any of the embodiments of the first aspect of the present invention may be used in combination with any of the embodiments of the second aspect of the present invention; indeed any of the features described in relation to the first aspect of the present invention may be used in combination with any of the embodiments or features of the second aspect of the present invention, and vice versa.

The second aspect of the present invention relates to a method for identifying from a library a display molecule having affinity towards one or more molecular targets. The display molecule is a part of a complex also comprising an identifier oligonucleotide that codes for said display molecule.

Traditional drug discovery begins with a pathological phenomenon in an organism and the development of a therapeutic theory to combat this. A chemical concept follows to produce compounds for screening. Most of the processes for curing the pathological phenomenon originate with the understanding of some biological pathways and screening for an effect in tissues or cells. This may or may not eventually reveal a "target". The target can be identified by various conventional methods, including protein expressing, protein chemistry, structure-functional studies, knowledge of biochemical pathways, and genetic studies.

In recent years, genetic information has increasingly guided the identification of molecular targets. These are derived from the knowledge of the genes of specific cell phenotypes that encode proteins that may be involved in the pathogenesis of a particular disease state.

A lead is a compound, usually a small organic molecule that demonstrates a desired biological activity on a target. Usually, a collection of compounds, referred to as a "library", is screened before a useful lead is identified. Today, many libraries are commercially available or open to public. Most pharmaceutical companies house their own compilation of compounds that have been synthesised over several years and screened against a variety of targets.

Each compound in a library must be screened by an appropriate assay against the target. Techniques for handling the screening of several thousands compounds simultaneously have been developed and are generally referred to as high-throughput screening techniques. To push the limit of compounds possible to screen simultaneously, different manufactures have been developing instrumentation capable of handling multiple micro titer plate formats on the same platform using 384 and 1536-well plates. Advances in small volume liquid dispensing and pipetting, reliable handling of standardized plates and simplified assay formats all have made an impact on the reliability of the high-throughput screening process.

However, high-throughput screening has the disadvantage that each of the compounds has to be positioned in spatially discrete regions, usually in wells of a micro titer plate in order to observe an interaction with a target. If more than a single compound is present, it is not feasible to discern which compound displaying the appropriate biological activity. Thus, the full power of combinatorial chemistry cannot be applied because a collection of compounds usually is produced in a single container.

To be able to select a possible lead compound in a collection of compounds placed in the same container, libraries of bifunctional complexes have been evolved. Each bifunctional complex in the library comprises a potential lead compound coupled to an identifier oligonucleotide sequence. The identifier oligonucleotide sequence is suitably a nucleic acid which identifies the potential lead compound. When a library of bifunctional complexes is screened against a target, one or more of the potential leads may bind to the target. After removal of the remainder of the library, the binding bifunctional complexes can be eluated and the lead compound identified by sequencing the identifier oligonucleotide.

Various techniques for producing bifunctional complexes are known from the prior art. Some attempts to form the complex comprising a molecule as well as the identifier oligonucleotide that codes therefore, are based on the split-and-mix principle known from combinatorial chemistry, see e.g. WO 93/06121 A1, EP 643 778 B1, and WO 00/23458.

Other attempts have focused on the formation of encoded proteins using the natural machinery of a cell and connecting the formed protein with the template nucleic acid that has coded for the amino acid components of the protein. Examples of suitable systems are phage display, *E. coli* display, ribosome display (WO 93/03172), and protein-mRNA-fusions (WO 98/31700). The genetic information of the nucleic acid, usually mRNA or DNA, may not necessarily be decoded between each round of selection to establish the identity of the chemical entities that has formed the protein because the nucleic acid can be amplified by known means, such as PCR, and processed for the formation of a new library enriched in respect of suitable binding proteins.

Recently, a method for encoding molecules has been suggested, which can be performed in several selection rounds without intermediate decoding, wherein the encoded molecule is not restricted to peptides and proteins. WO 02/00419 and WO 02/103008 disclose methods for preparing virtually any molecule connected to an identifier oligonucleotide coding for chemical entities which have reacted to form the display molecule. In short, a template segregated into a plurality of codons and a plurality of building blocks comprising a transferable chemical entity and an anticodon are initially provided. Under hybridisation conditions, the template and building blocks are annealed together and the chemical entities are subsequently reacted to form the molecule.

The present invention aims at providing an efficient method for identifying display molecules having affinity towards a target using a library of bifunctional complexes.

The second aspect of the present invention concerns a method for identifying display molecule(s) having affinity towards molecular target(s), comprising the steps of mixing one or more molecular target(s) associated with target oligonucleotide(s) and a library of bifunctional complexes, each bifunctional complex of the library comprising a display molecule attached to an identifier oligonucleotide, which codes for said display molecule, coupling to the target oligonucleotide(s) the identifier oligonucleotide of complexes comprising display molecules binding to the target, and deducing the identity of the binding display molecule(s) and/or the molecular target(s) from the coupled product between the identifier oligonucleotide(s) and the target oligonucleotide(s).

The second aspect of the present invention is based on the realization that a close proximity of the identifier oligonucleotides relative to the target oligonucleotide is obtained when a display molecule has binding affinity towards a target and therefore, will be more prone to be coupled to the target oligonucleotide compared to identifier oligonucleotides of complexes not comprising a display molecule having affinity toward the target. The tendency to be coupled together depends on various factors such as (1) the affinity of the displayed molecule towards the target, (2) the length between the displayed molecule and the coupling point on the identifier oligonucleotide sequence as well as the length between the target molecule and the coupling point on the target sequence, and (3) possible steric effects resulting from the nature of the target or the oligonucleotides. The proximity effect, and thus the power of selectivity, will increase with higher local concentration of ends of nucleotides to be coupled together. Thus, various embodiments of the present invention may be envisaged to fine-tune the local concentration of the ends of the oligonucleotides, including appropriately selected lengths of target and identifier oligonucleotides, site of attachment of the target oligonucleotide to the target relative to the binding site of the display molecule, and size of target.

The molecular target may be of a biological origin or may be a synthetic molecular target. Typically, the molecular target stems from an organism selected from human and animals, especially vertebras. However, in other embodiments the target may originate from a plant. In the quest for a compound with therapeutical effect on the human or animal body, the target is usually expected to have an importance in a therapeutically theory that combats a certain disease. In the quest for discovering compounds with plant protective effect, the target is usually expected to originate from an organism that harms the crop or a competing undesired plant. The organism may be a fungus when a compound with fungicide effect is searched for or an insect when a compound having insecticide effect is desired. Optionally, a protein target stemming from a biological origin may be derivatised by altering, adding, or deleting one or more amino acids.

The molecular target may be a protein, a small molecular hormone, a lipid, a polysaccharide, a whole cell, a nucleic acid, a metabolite, a heme group, etc. In a preferred aspect the target is a protein. The protein may serve the function in the organism of being an enzyme, a hormone, a structural element, a regulatory protein, a membrane channel or pump, a part of a signal transducing cascade, an antibody, etc. Suitable target enzymes include kinases, phosphatases, and proteases. The protein may occur as an independent entity or may be dimers, trimers, tetramers, or polymers and the protein may comprise a prosthetic group. Also, the target may be a fusion protein having two or more functionalities. Furthermore, the molecular target may be a soluble or insoluble agglomerate of one or more proteins and one or more substituents occurring in the body or artificial components. In another preferred embodiment, the molecular target is a nucleic acid, such as DNA or RNA aptamer or ribozyme.

The target may be immobilized to a support or be present as a solution or a emulsion, as appropriate. The target optionally immobilized on the support, may also form a stable or quasi-stable dispersion in the media. In a certain embodiment, the target is in solution and all the reactions occur in the solution too. The absence of an immobilization step reduces the background noise because there is no background surface to associate to. Thus the result of the assay may be more sensitive. In solution, the only background noise imaginable is when the oligonucleotides or display molecules of the library of complexes binds unspecific to the target molecules or the target oligonucleotides. The absence of an immobilization step generally necessitates a subsequent recovery step, eg. by chromatography.

In certain aspects of the invention, it is preferred to immobilize the molecular target on a solid support. The solid support may be beads of a column or the surface of a container. The immobilisation of the molecular target may ease the removal of the non-binding complexes by washing or similar means. In a certain embodiment, a cleavable linkage between the molecular target and the solid support is present. The cleavable linker is preferably selectively cleavable, that is, the linkage can be cleaved without cleaving other linkages in the target or the complexes. The cleavage of the linkage between the molecular target and the solid support may reduce the contribution from the background, such as complexes associated with the surface of the solid support and not binding to the molecular target.

A single or a multitude of different molecular targets may be mixed with the library of complexes. If two or more different targets are mixed with the library of complexes it is appropriate to provide the molecular targets with a genetic sequence coding for the identity of the target in question. Proving the targets with identifying oligonucleotides allows for a simultaneous decoding of the binding partners, i.e. the molecular target and the display molecule. The simultaneous decoding is not only suitable for finding binding partners. It is also valuable for finding a possible cross-binding interaction or to find other dis-μlay molecules competing for the same target. Furthermore, appropriate selection of display molecules and/or molecular targets, can generate useful information for preparing a structure-activity relationship (usually abbreviated SAR).

The molecular target may be obtained in any suitable way. A variety of targets are commercially available, either as purified protein or as the corresponding cDNA. Other protein or peptide targets may be isolated from tissues or mRNA (or the corresponding cDNA) may be extracted from a tissue. Smaller peptides may be synthesised chemically using the standard solid-phase Fmoc peptide synthesis. When nucleic acids are used or included in the molecular target, it may be synthesised using the standard amedite synthesis method or by using the natural machinery.

The target can be associated with the target oligonucleotide using any suitable means and the association may involve a covalent or non-covalent linkage. In an aspect of the invention the oligonucleotide is associated with the target utilizing a chemical synthesis. A protein usually comprises several groups that may be functionalized and used as attaching point. As examples the side chain of lysine contains an amino group, the side chain of serine contains a hydroxyl group and the side chain of cystein contains a thiol group, all of which may serve as anchoring point for a target oligonucleotide comprising e.g. a carboxylic acid group. In another aspect of the invention, the protein target is fused to a tag, such as a His-tag, Flag-tag, antibody, or streptavidin. The tag can be selectively recognized by an anti-body or small molecule such as biotin or dinitrophenol. The antibody or the small molecule is attached to the target oligonucleotide, thereby ensuring an efficient coupling of the molecular target to the target oligonucleotide.

The target oligonucleotide can be associated to the molecular target through a cleavable linker. The cleavable linkage can be used to separate the target oligonucleotide from the molecular target or the coupled product from the target at a point in time following the contacting between the target and library of complexes. The target oligonucleotide can be distanced from the molecular target by a suitable linker, such as a polyethylene linker or a noncoding nucleotide sequence. A linker may remedy any interaction that possible can be between the molecular target and the target oligonucleotide and at the same time provide suffice space for an enzyme to perform its action.

A variety or methods for association of an oligonucleotide to a target is available for the skilled person in the art. An option involves the association of a target protein with the mRNA responsible for the formation thereof. This method is generally referred to as mRNA display. Optionally, the mRNA may be substituted with the corresponding cDNA. A method for generation such a single or a library of fusions between a protein and the mRNA responsible for the formation thereof is disclosed in WO 98/31700. The corresponding DNA strand may be attached to the protein using the method disclosed in WO 00/32823. The contents of both patent applications being incorporated in their entirety by reference herein. The method of WO 98/31700 includes providing a RNA stand comprising a translation initiation sequence, a start codon operable linked to a protein encoding sequence, and a peptide acceptor at the 3' end and translating the protein encoding sequence to produce a RNA-protein fusion. According to WO 00/32823 a DNA primer is covalently connected to the 3' end of the mRNA strand and extended by reverse transcriptase a to prepare the complementing DNA strand. The original RNA strand may be digested by RNase H. Another suitable method for generating a target library is disclosed in WO 01/90414, the content of which is incorporated herein by reference.

In accordance with another option, the target oligonucleotide is associated with a target using a method generally referred to as ribosome display. Ribosome display is disclosed in WO 93/03172, the content of which is included herein by reference. A still further option for association is a variation of the phage display, in which a target is displayed on the capsule of the phage and a target oligonucleotide is connected to the same capsule. Suitably, the target oligonucleotide is connected to the capsule via reactive groups positioned on proteins expressed on the capsule. A suitable reactive group is —SH emanating from cystein.

A further option for associating the target with an oligonucleotide includes the method disclosed in M. Yonezawa et al, Nucleic acid research, 2003, vol. 31, No. 19 e118 (included by reference). The method includes the initial provision of a target oligonucleotide connected to biotin and compartmentalization thereof together with a transcription and translation system. The target oligonucleotide comprises a fusion gene coding for streptavidin and a target. After the formation of the fusion protein in each compartment, the streptavidin part of the fusion protein binds to the biotin moiety of the target oligonucleotide, thereby associating the target with the target oligonucleotide.

In case the target is a nucleic acid, it may be of the aptamer type, i.e. an aptamer or a library of aptamers comprising constant nucleic acid regions flanking a random oligonucleotide part. The random oligonucleotide part serves the function of a molecular target in the present invention and one or both the constant region serves as target oligonucleotides. Alternatively, an additional oligonucleotide sequence can be adhered to one or both the constant regions to serve as the target oligonucleotide. The present invention also allows for the selection of pairs of aptamers that either binds to each other or binds to the same target but to different epitopes. The latter embodiment is of particular relevance when evolving detection assays, where aptamers that bind to different epitopes on the same target may be desired.

In certain embodiments, a bifunctional complex having a display molecule binding to the molecular target constitutes the target oligonucleotide associated with the molecular target. The bifunctional complexes binding to the target and serving to associate an oligonucleotide to the molecular target may be provided prior to or during with the mixing step. In case the target oligonucleotide is associated with the molecular target during the mixing step the bifunctional complex may be a member of the library or may be a complex added to the mixture. In some aspects of the invention, the display molecule is a compound known to bind to the target. The display molecule may be known to bind to the target from the prior art or from preceding screening procedures. To find a second or further binding compound, the target is generally saturated with the known display molecule prior to the mixing step. The known binding molecule may or may not be attached to a nucleic acid sequence.

In case the target oligonucleotide emanates from an identifier oligonucleotide in the library of complexes, two bifunctional complexes of a library of bifunctional complexes are associated with a common molecular target and can be discovered simultaneously. The bifunctional complexes may bind to the same binding site of the molecular target or the bifunctional complexes may bind to different binding sites. In case the bifunctional complexes bind to the same binding sites, the display molecules may be connected to each other through a covalent or non-covalent chemical bond, e.g. by a technique known as click chemistry. By way of example only, the two display molecules can be connected through a disulphide bridge. In aspects of the invention in which the display molecules binds to discrete binding domains on the same target molecule they are usually adhered together after the identification process of the present invention by a suitable linker in order to form the effective compound.

In a certain aspects of the invention an iterative method for finding the desired compound is applied. An initial display molecule or a pool of display molecules with affinity towards a target is found using the present method or another method. In the event the affinity is in the lower range of what is desired, the initial display molecule is amended by reaction with one or more chemical entities to form a second generation library, said second generation library being used in the method of the present invention.

In Nature, biochemical components interact. In a certain aspect of the present invention, two or more targets interacting in a biological context are separately subjected to the method of the invention, whereupon the identified display molecules binding to the two or more targets are linked via a suitable linker. By way of example only, blood factors, such as factor VIIa and Xa may be prevented or promoted in the their interaction with each other using a compound having a part binding to a first blood factor and a part binding to a second blood factor. In other aspects of the invention, targets are linked by a suitable linker, as disclosed in FIG. 10.

A library of molecular targets may be generated by starting out from a library of DNA molecules, usually cDNA molecules, and preparing the corresponding RNA strands by a suitable RNA polymerase. In according with a certain aspect of the invention, the mixture step therefore includes that a molecular target library comprising different peptides each attached to the nucleic responsible for the formation thereof is mixed with a library of complexes.

The coupling of the target oligonucleotide and the identifier oligonucleotide is promoted due to the relative high local concentration of the ends of oligonucleotides. The complexes in solution, i.e. complexes not bund to the target, are relatively remote from the target oligonucleotide and the tendency of the target oligonucleotides to be coupled to such unspecific complexes is reduced. Among other things, the unspecific coupling depends on the concentration of the complexes in solution.

In an aspect of the invention the non-binding library members are either diluted or at least partly removed prior to the coupling step. Dilution may be performed by adding a suitable buffer and the removal may be preformed by washing one or more times with a suitable liquid, such as a buffer. In the event the target molecule is immobilized on a bead, the beads may be retained on a filter while non-binding complexes is transported through the filter. In case the target is in solution or made in solution by cleavage of a bond immobilising the target, optional following one or more washing step, the removal can be performed by chromatography, such as size-exclusion chromatography.

Thus, in a certain aspect of the invention, the mixing step includes the removal of non-binding library members prior to the coupling of the target oligonucleotide and the identifier nucleotide together.

It may be an advantage to have all or at least a part of the nucleotides on a double stranded form during the contacting with the molecular target, as certain nucleic acids may perform a binding interaction or a catalytical action on the components present during the mixing step. Thus, in one embodiment of the invention, the target oligonucleotide and/or the identifier oligonucleotide partly or fully is hybridised to a complementing oligonucleotide.

The coupling may be performed using any suitable means that ensures a physical connection. Suitably, the coupling is performed using means selected from the group consisting of chemical means, enzymatic means, and design means.

The chemical means for coupling the ends together can be selected from a large plethora. Suitable examples include that a) a first oligonucleotide end comprises a 3'-OH group and the second oligonucleotide end comprises a 5'-phosphor-2-imidazole group. When reacted a phosphodiester internucleoside linkage is formed, b) a first oligonucleotide end comprising a phosphoimidazolide group and the 3'-end and a phosphoimidazolide group at the 5'- and. When reacted together a phosphodiester internucleoside linkage is formed, c) a first oligonucleotide end comprising a 3'-phosphorothioate group and a second oligonucleotide comprising a 5'-iodine. When the two groups are reacted a 3'-O—P(=O)(OH)—S-5' internucleoside linkage is formed, and d) a first oligonucleotide end comprising a 3'-phosphorothioate group and a second oligonucleotide comprising a 5'-tosylate. When reacted a 3'-O—P(=O)(OH)—S-5' internucleoside linkage is formed.

Suitably, the target oligonucleotide or a complementing target oligonucleotide and the identifier oligonucleotide or a complementing identifier oligonucleotide operatively are joined together, so that as to allow a nucleic acid active enzyme to recognize the coupling area a substrate. Notably, in a preferred embodiment, the coupling is performed so as to allow a polymerase to recognise the coupled strand as a template. Thus, in a preferred aspect, a chemical reaction strategy for the coupling step generally includes the formation of a phosphodiester internucleoside linkage. In accordance with this aspect, method a) and b) above is preferred.

The enzymatic means is in some instances preferred because the coupling reaction is specific, i.e. the risk of side reactions in virtually not present. The enzymatic means is in general selected from the enzymes of the polymerase type, ligase type, and restriction enzymes, as well as any combination thereof.

Ligases are useful means for the coupling step. Suitable examples include Taq DNA ligase, T4 DNA ligase, T7 DNA ligase, and *E. coli* DNA ligase. The choice of the ligase depends to a certain degree on the design of the ends to be joined together. Thus, if the ends are blunt, T4 DNA ligase may be preferred, while a Taq DNA ligase may be preferred for a sticky end ligation, i.e. a ligation in which an overhang on each end is a complement to each other.

In a certain aspect of the invention, a connector oligonucleotide is used. The connector oligonucleotide has a region complementing a distal part of the target oligonucleotide and a region complementing a distal part of the identifier oligonucleotide. If the ends of the target and identifier oligonucleotides abut each other a ligase can ligate the ends together. If a gap exists between the ends, a polymerase may be used to fill the gap and a ligase may subsequently perform a ligation. The regions of the connector oligonucleotide complementing the identifier oligonucleotide and target oligonucleotide, respectively, may independently be chose, e.g. in the range of 6 to 16 nucleotides, preferably in the range of 8 to 12 nucleotides. In a particular aspect of the invention the connector oligonucleotide is added in excess relative to the total target and identifier oligonucleotides to saturate the ends of complexes not bound to a target.

In another aspect of the invention the coupling is performed by design means. As an example, the regions at the distal ends of the target and identifier oligonucleotides are designed to be complementary to each other. Under hybridisation conditions polymerase is then allowed to extend the target oligonucleotide as well as the identifier oligonucleotide to obtain a double stranded coupled product.

Still another coupling means include the design of the ends of one or more oligonucleotides with sticky ends. In a certain aspect, the target oligonucleotide and/or the identifier oligonucleotide is provided with a sticky end to allow a ligase or a polymerase or a mixture thereof to adjoin the oligonucleotides. Suitably, the sticky ends can be formed by a restriction nuclease. In a practical approach, the target and the identifier oligonucleotides are initially double stranded and provide at the ends with a restriction site. Following the initial contact, the mixture is treated with a restriction nuclease to form the sticky ends. After subsequent removal of the restriction enzyme from the mixture, a ligase is allowed to perform its enzymatic action to form a ligation product.

The coupled product of the identifier and target oligonucleotides comprises the information necessary for decoding the identity of the display molecule and optionally also of the molecular target. The coupled product may be analysed directly in some instances to reveal the identity of the display molecules that have performed an interaction with the molecular target. As an example, the coupled product may be detached from the target-display molecule interaction using a cut by a restriction nuclease at positions of the coupled product flanking the informative part. The informative part can be decoded in a standard sequencing machine. In general however, it is preferred to include the informative part of the coupled product in to a suitable vector and transfer the vector to a host organism. The host organisms may then be cultivated on a suitable substrate and allowed to form colonies. Samples from the colonies may be used for sequencing in a sequencing machine.

In another approach, the target and/or the identifier oligonucleotides or sequences complementary thereto at the proximal end is provided with a priming site. The priming site may be used for annealing a primer to allow a polymerase to extent the primer using the coupled product as template. Appropriately, the extended strand is designed with another priming site which may allow a second (reverse) primer to anneal thereto and subsequently a polymerase to perform an extension of the primer to produce a sequence identical to the coupled product. The extension product or the amplification product may be analysed directly or be incorporated into a vector which subsequently is transformed into a host organism as explained above. In a certain aspect of the invention, the coupled oligonucleotide is amplified by PCR using priming sites positioned proximal to the display molecule and the molecular target, respectively, and flanking the informative part of the coupled product.

Following the coupling step, the target-display molecule conjugate may be recovered. Any method that result in a recovery may in principle be used, including filtering, washing, elution, chromatography, etc. In a preferred aspect the target-display molecule conjugate is recovered by chromatography following the coupling of the target and the identifier oligonucleotides. Optionally, the various recovering methods may be combined. As an example, a washing or elution step may precede the chromatography step. A presently preferred chromatography method is size-exclusion chromatography. The chromatography is usually performed on a sample in which the target-display molecule conjugate is in solution. In one aspect of the invention, the target has been cleaved from a solid support prior to the chromatography step.

In an aspect of the invention, selective cleavable chemical moieties at each end of the coupled oligonucleotides are cleaved to liberate the coupled oligonucleotides prior to amplification. Usually, the cleavage is preceded of a step removing the non-binding complexes. The liberated product may be recovered as described above and subjected to amplification.

The invention also pertains to a conjugate comprising a molecular target associated with an oligonucleotide and a bifunctional complex comprising a display molecule attached to an identifier oligonucleotide, which codes for said molecule. Usually, the display molecule part of the complex is bound to the target. The target oligonucleotide and/or the identifier oligonucleotide of the conjugate are in a certain embodiment joined to the molecular target and/or the display molecule, respectively, through a selectively cleavable linkage. In an embodiment of the invention, the target oligonucleotide and the identifier oligonucleotide are coupled together, whereby a product is obtained wherein a display molecule is bound to the molecular target and the identifier and target oligonucleotides are coupled together. In a certain aspect, the coupled oligonucleotide is amplifiable. The amplifiability is usually obtained through a coupling that involves a phospodiester internucleoside linkage.

The present invention also extends to a display molecule identified by any of the methods disclosed herein.

DETAILED DESCRIPTION

Complex

The complex used in the present invention comprises a display molecule and an identifier oligonucleotide. The identifier oligonucleotide comprises identifying moieties that identifies the display molecule. Preferably, the identifier oligonucleotide identifies the molecule uniquely, i.e. in a library of complexes a particular identifier oligonucleotide is capable of distinguishing the molecule it is attached to from the rest of the display molecules.

The display molecule and the identifier oligonucleotide may be attached directly to each other or through a bridging moiety. In one aspect of the invention, the bridging moiety is a selectively cleavable linkage.

The method may in certain embodiments be performed without amplification after the coupling step. However, when larger libraries are used and the amount of separated coupled product oligonucleotide is relatively low, it is in general preferred to use an identifier oligonucleotide and a coupled product which is amplifiable. Identifier oligonucleotides comprising a sequence of nucleotides may be amplified using standard techniques, like PCR.

The identifier oligonucleotide may comprise two or more codons. The sequence of codons can be decoded to identify reactants used in the formation of the molecule. When the identifier oligonucleotide comprises more than one codon, each member of a pool of chemical entities can be identified and the order of codons is informative of the synthesis step each member has been incorporated in.

The sequence of the nucleotides in each codon may have any suitable length. The codon may be a single nucleotide or a plurality of nucleotides. In some aspects of the invention, it is preferred that each codon independently comprises four or more nucleotides, more preferred 4 to 30 nucleotides.

The identifier oligonucleotide will in general have at least two codons arranged in sequence, i.e. next to each other. Two neighbouring codons may be separated by a framing sequence. Depending on the encoded molecule formed, the identifier oligonucleotide may comprise further codons, such as 3, 4, 5, or more codons. Each of the further codons may be separated by a suitable framing sequence. Preferably, all or at least a majority of the codons of the identifier oligonucleotide are separated from a neighbouring codon by a framing sequence. The framing sequence may have any suitable number of nucleotides, e.g. 1 to 20. Alternatively, codons on the identifier oligonucleotide may be designed with overlapping sequences.

The framing sequence, if present, may serve various purposes. In one setup of the invention, the framing sequence identifies the position of the codon. Usually, the framing sequence either upstream or downstream of a codon comprises information which allows determination of the position of the codons. In another setup, the frames have alternating sequences, allowing for addition of building blocks from two pools in the formation of the library. The framing sequence may also or in addition provide for a region of high affinity. The high affinity region may ensure that the hybridisation of the template with an anti-codon will occur in frame. Moreover, the framing sequence may adjust the annealing temperature to a desired level.

A framing sequence with high affinity can be provided by incorporation of one or more nucleobases forming three hydrogen bonds to a cognate nucleobase. Examples of nucleobases having this property are guanine and cytosine. Alternatively, or in addition, the framing sequence may be subjected to backbone modification. Several back bone modifications provides for higher affinity, such as 2'-O-methyl substitution of the ribose moiety, peptide nucleic acids (PNA), and 2'-4' O-methylene cyclisation of the ribose moiety, also referred to as LNA (Locked Nucleic Acid).

The identifier oligonucleotide may comprise one or two flanking regions. The flanking region can encompass a signal group, such as a flourophor or a radio active group to allow for detection of the presence or absence of a complex or the flanking region may comprise a label that may be detected, such as biotin. When the identifier oligonucleotide comprises a biotin moiety, the identifier oligonucleotide may easily be recovered.

The flanking region(s) can also serve as priming sites for amplification reactions, such as PCR. The identifier oligonucleotide may in certain embodiments comprise an affinity region having the property of being able to hybridise to a building block.

It is to be understood that when the term identifier oligonucleotide is used in the present description and claims, the identifier oligonucleotide may be in the sense or the anti-sense format, i.e. the identifier oligonucleotide can be a sequence of codons which actually codes for the molecule or can be a sequence complementary thereto. Moreover, the identifier oligonucleotide may be single-stranded or double-stranded, as appropriate.

The display molecule part of the complex is generally of a structure expected of having an effect on the target. When the target is of pharmaceutical importance, the molecule is generally a possible drug candidate. The complex may be formed by tagging a library of different possible drug candidates with a tag, e.g. a nucleic acid tag identifying each possible drug candidate. In another embodiment of the invention, the molecule is encoded, i.e. formed by a variety of reactants which have reacted with each other and/or a scaffold molecule. Optionally, this reaction product may be post-modified to obtain the final molecule displayed on the complex. The post-modification may involve the cleavage of one or more chemical bonds attaching the encoded molecule to the identifier in order more efficiently to display the encoded molecule. In still another embodiment the display molecule is a polypeptide formed using the natural machinery, such as the methods disclosed in WO 92/02536, WO 91/05058, and U.S. Pat. No. 6,194,550.

The formation of a synthetic encoded molecule generally starts by a scaffold, i.e. a chemical unit having one or more reactive groups capable of forming a connection to another reactive group positioned on a chemical entity, thereby generating an addition to the original scaffold. A second chemical entity may react with a reactive group also appearing on the original scaffold or a reactive group incorporated by the first chemical entity. Further chemical entities may be involved in the formation of the final reaction product. The formation of a connection between the chemical entity and the nascent encoded molecule may be mediated by a bridging molecule. As an example, if the nascent encoded molecule and the chemical entity both comprise an amine group a connection between these can be mediated by a dicarboxylic acid. A display molecule is in general produced in vitro and may be a naturally occurring or an artificial substance. In an aspect of the invention, a display molecule is not produced using the naturally translation system in an in vitro process. In other aspects of the invention, the display molecule is a polypeptide produced using the natural translation machinery.

The chemical entities that are precursors for structural additions or eliminations of the encoded molecule may be attached to a building block prior to the participation in the formation of the reaction product leading to the final display molecule. Besides the chemical entity, the building block generally comprises an anti-codon. In some embodiments the building blocks also comprise an affinity region providing for affinity towards the nascent complex.

Thus, the chemical entities are suitably mediated to the nascent encoded molecule by a building block, which further comprises an anticodon. The anti-codon serves the function of transferring the genetic information of the building block in conjunction with the transfer of a chemical entity. The transfer of genetic information and chemical entity may occur in any order, however, it is important that a correspondence is maintained in the complex. The chemical entities are preferably reacted without enzymatic interaction in some aspects of the invention. Notably, the reaction of the chemical entities is preferably not mediated by ribosomes or enzymes having similar activity. In another aspect of the invention a ribosome is used to translate an mRNA into a protein using a tRNA loaded with a natural or unnatural amino acid. In still another aspect of the invention, enzymes having catalytic activities different from that of ribosomes are used in the formation of the display molecule.

According to certain aspects of the invention the genetic information of the anti-codon is transferred by specific hybridisation to a codon on a nucleic acid template. Another method for transferring the genetic information of the anti-codon to the nascent complex is to anneal an oligonucleotide complementary to the anti-codon and attach this oligonucleotide to the complex, e.g. by ligation. A still further method involves transferring the genetic information of the anti-codon to the nascent complex by an extension reaction using a polymerase and a mixture of dNTPs.

The chemical entity of the building block may in certain cases be regarded as a precursor for the structural entity eventually incorporated into the encoded molecule. In other cases the chemical entity provides for the eliminations of chemical units of the nascent encoded molecule. Therefore, when it in the present application with claims is stated that a chemical entity is reacted with a nascent encoded molecule it is to be understood that not necessarily all the atoms of the original chemical entity is to be found in the eventually formed encoded molecule. Also, as a consequence of the reactions involved in the connection, the structure of the chemical entity can be changed when it appears on the nascent encoded molecule. Especially, the cleavage resulting in the release of the entity may generate a reactive group which in a subsequent step can participate in the formation of a connection between a nascent complex and a chemical entity.

The chemical entity of the building block comprises at least one reactive group capable of participating in a reaction which results in a connection between the chemical entity of the building block and another chemical entity or a scaffold associated with the nascent complex. The number of reactive groups which appears on the chemical entity is suitably one to ten. A building block featuring only one reactive group is used i.a. in the end positions of polymers or scaffolds, whereas building blocks having two reactive groups are suitable for the formation of the body part of a polymer or scaffolds capable of being reacted further. One, two or more reactive groups intended for the formation of connections, are typically present on scaffolds. Non-limiting examples of scaffolds are opiates, steroids, benzodiazepines, hydantoines, and peptidylphosphonates.

The reactive group of the chemical entity may be capable of forming a direct connection to a reactive group of the nascent complex or the reactive group of the building block may be capable of forming a connection to a reactive group of the nascent complex through a bridging fill-in group. It is to be understood that not all the atoms of a reactive group are necessarily maintained in the connection formed. Rather, the reactive groups are to be regarded as precursors for the structure of the connection.

The subsequent cleavage step to release the chemical entity from the building block can be performed in any appropriate way. In an aspect of the invention the cleavage involves usage of a chemical reagent or an enzyme. The cleavage results in a transfer of the chemical entity to the nascent encoded molecule or in a transfer of the nascent encoded molecule to the chemical entity of the building block. In some cases it may be advantageous to introduce new chemical groups as a consequence of linker cleavage. The new chemical groups may be used for further reaction in a subsequent cycle, either directly or after having been activated. In other cases it is desirable that no trace of the linker remains after the cleavage.

In another aspect, the connection and the cleavage is conducted as a simultaneous reaction, i.e. either the chemical entity of the building block or the nascent encoded molecule is a leaving group of the reaction. In some aspects of the invention, it is appropriate to design the system such that the connection and the cleavage occur simultaneously because this will reduce the number of steps and the complexity. The simultaneous connection and cleavage can also be designed such that either no trace of the linker remains or such that a new chemical group for further reaction is introduced, as described above.

The attachment of the chemical entity to the building block, optionally via a suitable spacer can be at any entity available for attachment, e.g. the chemical entity can be attached to a nucleobase or the backbone. In general, it is preferred to attach the chemical entity at the phosphor of the internucleoside linkage or at the nucleobase. When the nucleobase is used for attachment of the chemical entity, the attachment point is usually at the 7 position of the purines or 7-deaza-purins or at the 5 position of pyrimidines. The nucleotide may be distanced from the reactive group of the chemical entity by a spacer moiety. The spacer may be designed such that the conformational space sampled by the reactive group is optimized for a reaction with the reactive group of the nascent encoded molecule.

The display molecules of the invention may have any chemical structure. In a preferred aspect, the display molecule can be any compound that may be synthesized in a component-by-component fashion. In some aspects the display molecule is a linear or branched polymer. In another aspect the display molecule is a scaffolded molecule. The term "display molecule" also comprises naturally occurring molecules like α-polypeptides etc, however produced in vitro usually in the absence of enzymes, like ribosomes. In certain aspects, the display molecule of the library is a non-α-polypeptide.

The display molecule may have any molecular weight. However, in order to be orally available, it is in this case preferred that the display molecule has a molecular weight less than 2000 Daltons, preferably less than 1000 Dalton, and more preferred less than 500 Daltons.

The size of the library may vary considerably pending on the expected result of the inventive method. In some aspects, it may be sufficient that the library comprises two, three, or four different complexes. However, in most events, more than two different complexes are desired to obtain a higher diversity. In some aspects, the library comprises 1,000 or more different complexes, more preferred 1,000,000 or more different complexes. The upper limit for the size of the library is only restricted by the size of the vessel in which the library is comprised. It may be calculated that a vial may comprise up to $10^{14}$ different complexes.

Methods for Forming Libraries of Complexes

The complexes comprising an identifier oligonucleotide having two or more codons that codes for reactants that have reacted in the formation of the molecule part of the complex may be formed by a variety of processes. Generally, the preferred methods can be used for the formation of virtually any kind of encode molecule. Suitable examples of processes include prior art methods disclosed in WO 93/20242, WO 93/06121, WO 00/23458, WO 02/074929, and WO 02/103008, the content of which being incorporated herein by reference as well as methods of the present applicant not yet public available, including the methods disclosed in DK PA 2002 01955 filed 19 Dec. 2002, and DK PA 2003 00430 filed 20 Mar. 2003. Any of these methods may be used, and the entire content of the patent applications are included herein by reference.

Below four preferred embodiments are described. A first embodiment disclosed in more detail in WO 02/103008 is based on the use of a polymerase to incorporate unnatural nucleotides as building blocks. Initially, a plurality of template oligonucleotides is provided. Subsequently primers are annealed to each of the templates and a polymerase is extending the primer using nucleotide derivatives which have appended chemical entities. Subsequent to or simultaneously with the incorporation of the nucleotide derivatives, the chemical entities are reacted to form a reaction product. The encoded molecule may be post-modified by cleaving some of the linking moieties to better present the encoded molecule.

Several possible reaction approaches for the chemical entities are apparent. First, the nucleotide derivatives can be incorporated and the chemical entities subsequently polymerised. In the event the chemical entities each carry two reactive groups, the chemical entities can be attached to adjacent chemical entities by a reaction of these reactive groups. Exemplary of the reactive groups are amine and carboxylic acid, which upon reaction form an amide bond. Adjacent chemical entities can also be linked together using a linking or bridging moiety. Exemplary of this approach is the linking of two chemical entities each bearing an amine group by a bi-carboxylic acid. Yet another approach is the use of a reactive group between a chemical entity and the nucleotide building block, such as an ester or a thioester group. An adjacent building block having a reactive group such as an amine may cleave the interspaced reactive group to obtain a linkage to the chemical entity, e.g. by an amide linking group.

A second embodiment for obtainment of complexes pertains to the use of hybridisation of building blocks to a template and reaction of chemical entities attached to the building blocks in order to obtain a reaction product. This approach comprises that templates are contacted with a plurality of building blocks, wherein each building block comprises an anti-codon and a chemical entity. The anti-codons are designed such that they recognise a sequence, i.e. a codon, on the template. Subsequent to the annealing of the anti-codon and the codon to each other a reaction of the chemical entity is effected.

The template may be associated with a scaffold. Building blocks bringing chemical entities in may be added sequentially or simultaneously and a reaction of the reactive group of the chemical entity may be effected at any time after the annealing of the building blocks to the template.

A third embodiment for the generation of a complex includes chemical or enzymatical ligation of building blocks when these are lined up on a template. Initially, templates are provided, each having one or more codons. The templates are contacted with building blocks comprising anti-codons linked to chemical entities. The two or more anti-codons annealed on a template are subsequently ligated to each other and a reaction of the chemical entities is effected to obtain a reaction product. The method is disclosed in more detail in DK PA 2003 00430 filed 20 Mar. 2003.

A fourth embodiment makes use of the extension by a polymerase of an affinity sequence of the nascent complex to transfer the anti-codon of a building block to the nascent complex. The method implies that a nascent complex comprising a scaffold and an affinity region is annealed to a building block comprising a region complementary to the affinity section. Subsequently the anti-codon region of the building block is transferred to the nascent complex by a polymerase. The transfer of the chemical entity may be transferred prior to, simultaneously with or subsequent to the transfer of the anti-codon. This method is disclosed in detail in DK PA 2002 01955 filed 19 Dec. 2002 and DK PA 2003 01064, filed 11 Jul. 2003.

Thus, the codons are either pre-made into one or more templates before the encoded molecules are generated or the codons are transferred simultaneously with the formation of the encoded molecules.

After or simultaneously with the formation of the reaction product some of the linkers to the template may be cleaved, however at least one linker must be maintained to provide for the complex.

Nucleotides

The nucleotides used in the present invention may be linked together in a sequence of nucleotides, i.e. an oligonucleotide. Each nucleotide monomer is normally composed of two parts, namely a nucleobase moiety, and a backbone. The back bone may in some cases be subdivided into a sugar moiety and an internucleoside linker.

The nucleobase moiety may be selected among naturally occurring nucleobases as well as non-naturally occurring nucleobases. Thus, "nucleobase" includes not only the known purine and pyrimidine hetero-cycles, but also heterocyclic analogues and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosin, $N^6,N^6$-ethano-2,6-diamino-purine, 5-methyl-cytosine, 5-($C^3$-$C^6$)-alkynylcytosine, 5-fluorouracil, 5-bromouracil, pseudoisocytosine, 2-hydroxy-5-methyl-4-triazolopyridine, isocytosine, isoguanine, inosine and the "non-naturally occurring" nucleobases described in Benner et al., U.S. Pat. No. 5,432,272. The term "nucleobase" is intended to cover these examples as well as analogues and tautomers thereof. Especially interesting nucleobases are adenine, guanine, thymine, cytosine, 5-methylcytosine, and uracil, which are considered as the naturally occurring nucleobases in relation to therapeutic and diagnostic application in humans.

Examples of suitable specific pairs of nucleobases are shown on p 27 of this application, entitled "Natural base pairs", "synthetic base pairs", "synthetic purine bases pairing with natural pyrimidines".

Suitable examples of backbone units are shown diagrammatically on p 28 of this application (B denotes a nucleobase). The sugar moiety of the backbone is suitably a pentose but may be the appropriate part of an PNA or a six-member ring. Suitable examples of possible pentoses include ribose, 2'-deoxyribose, 2'-O-methyl-ribose, 2'-flour-ribose, and 2'-4'-O-methylene-ribose (LNA). Suitably the nucleobase is attached to the 1' position of the pentose entity.

An internucleoside linker connects the 3' end of preceding monomer to a 5' end of a succeeding monomer when the sugar moiety of the backbone is a pentose, like ribose or 2-deoxyribose. The internucleoside linkage may be the natural occurring phospodiester linkage or a derivative thereof. Examples of such derivatives include phosphorothioate, methylphosphonate, phosphoramidate, phosphotriester, and phosphodithioate. Furthermore, the internucleoside linker can be any of a number of non-phosphorous-containing linkers known in the art.

Preferred nucleic acid monomers include naturally occurring nucleosides forming part of the DNA as well as the RNA family connected through phosphodiester linkages. The members of the DNA family include deoxyadenosine, deoxyguanosine, deoxythymidine, and deoxycytidine. The members of the RNA family include adenosine, guanosine, uridine, cytidine, and inosine. Inosine is a non-specific pairing nucleoside and may be used as universal base because inosine can pair nearly isoenergetically with A, T, and C. Other compounds having the same ability of non-specifically base-pairing with natural nucleobases have been formed. Suitable compounds which may be utilized in the present invention includes among others the compounds depicted on p 30 of this application, entitled "Examples of Universal Bases".

Building Block

The chemical entities that are precursors for structural additions or eliminations of the encoded molecule may be attached to a building block prior to the participation in the formation of the reaction product leading the final encoded molecule. Besides the chemical entity, the building block generally comprises an anti-codon.

The chemical entity of the building block comprises at least one reactive group capable of participating in a reaction which results in a connection between the chemical entity of the building block and another chemical entity or a scaffold associated with the nascent complex. The connection is facilitated by one or more reactive groups of the chemical entity. The number of reactive groups which appear on the chemical entity is suitably one to ten. A building block featuring only one reactive group is used i.a. in the end positions of polymers or scaffolds, whereas building blocks having two reactive groups are suitable for the formation of the body part of a polymer or scaffolds capable of being reacted further. One, two or more reactive groups intended for the formation of connections, are typically present on scaffolds.

The reactive group of the building block may be capable of forming a direct connection to a reactive group of the nascent complex or the reactive group of the building block may be capable of forming a connection to a reactive group of the nascent complex through a bridging fill-in group. It is to be understood that not all the atoms of a reactive group are necessarily maintained in the connection formed. Rather, the reactive groups are to be regarded as precursors for the structure of the connection.

The subsequent cleavage step to release the chemical entity from the building block can be performed in any appropriate way. In an aspect of the invention the cleavage involves usage of a reagent or an enzyme. The cleavage results in a transfer of the chemical entity to the nascent encoded molecule or in a transfer of the nascent encoded molecule to the chemical entity of the building block. In some cases it may be advantageous to introduce new chemical groups as a consequence of linker cleavage. The new chemical groups may be used for further reaction in a subsequent cycle, either directly or after having been activated. In other cases it is desirable that no trace of the linker remains after the cleavage.

In another aspect, the connection and the cleavage is conducted as a simultaneous reaction, i.e. either the chemical entity of the building block or the nascent encoded molecule is a leaving group of the reaction. In general, it is preferred to design the system such that the connection and the cleavage occur simultaneously because this will reduce the number of steps and the complexity. The simultaneous connection and cleavage can also be designed such that either no trace of the linker remains or such that a new chemical group for further reaction is introduced, as described above.

The attachment of the chemical entity to the building block, optionally via a suitable spacer can be at any entity available for attachment, e.g. the chemical entity can be attached to a nucleobase or the backbone. In general, it is preferred to attach the chemical entity at the phosphor of the internucleoside linkage or at the nucleobase. When the nucleobase is used for attachment of the chemical entity, the attachment point is usually at the 7 position of the purines or 7-deaza-purins or at the 5 position of pyrimidines. The nucleotide may be distanced from the reactive group of the chemical entity by a spacer moiety. The spacer may be designed such that the conformational space sampled by the reactive group is optimized for a reaction with the reactive group of the nascent encoded molecule or reactive site.

The anticodon complements the codon of the identifier oligonucleotide sequence and generally comprises the same number of nucleotides as the codon. The anticodon may be adjoined with a fixed sequence, such as a sequence complementing a framing sequence.

Various specific building blocks are envisaged. Building blocks of particular interest are shown below.

Building Blocks Transferring a Chemical Entity to a Recipient Nucleophilic Group The building block indicated below is capable of transferring a chemical entity (CE) to a recipient nucleophilic group, typically an amine group. The bold lower horizontal line illustrates the building block and the vertical line illustrates a spacer. The 5-membered substituted N-hydroxysuccinimid (NHS) ring serves as an activator, i.e. a labile bond is formed between the oxygen atom connected to the NHS ring and the chemical entity. The labile bond may be cleaved by a nucleophilic group, e.g. positioned on a scaffold

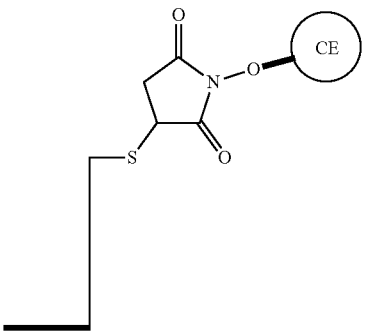

The 5-membered substituted N-hydroxysuccinimid (NHS) ring serves as an activator, i.e. a labile bond is formed between the oxygen atom connected to the NHS ring and the chemical entity. The labile bond may be cleaved by a nucleophilic group, e.g. positioned on a scaffold, to transfer the chemical entity to the scaffold, thus converting the remainder of the fragment into a leaving group of the reaction. When the chemical entity is connected to the activator through an carbonyl group and the recipient group is an amine, the bond formed on the scaffold will an amide bond. The above building block is the subject of WO03078627A2, the content of which is incorporated herein in their entirety by reference.

Another building block which may form an amide bond is

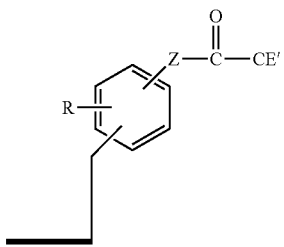

R may be absent or $NO_2$, $CF_3$, halogen, preferably Cl, Br, or I, and Z may be S or O. This type of building block is disclosed in WO03078626A2. The content of this patent application is incorporated herein in the entirety by reference.

A nucleophilic group can cleave the linkage between Z and the carbonyl group thereby transferring the chemical entity —(C=O)—CE' to said nucleophilic group.

Building Blocks Transferring a Chemical Entity to a Recipient Reactive Group Forming a C=C Bond A building block as shown below are able to transfer the chemical entity to a recipient aldehylde group thereby forming a double bond between the carbon of the aldehyde and the chemical entity

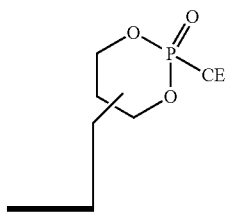

The above building block is disclosed in WO03078445A2, the content of which being incorporated herein in the entirety by reference.

Building Blocks Transferring a Chemical Entity to a Recipient Reactive Group Forming a C—C Bond The below building block is able to transfer the chemical entity to a recipient group thereby forming a single bond between the receiving moiety, e.g. a scaffold, and the chemical entity.

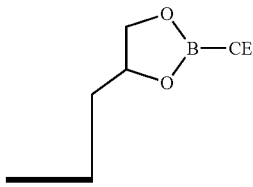

The above building block is disclosed in WO03078445A2, the content of which being incorporated herein in the entirety by reference.

Another building block capable of transferring a chemical entity to a receiving reactive group forming a single bond is

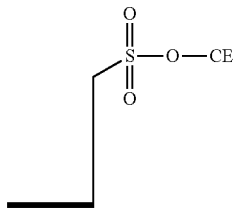

The receiving group may be a nucleophile, such as a group comprising a hetero atom, thereby forming a single bond between the chemical entity and the hetero atom, or the receiving group may be an electronegative carbon atom, thereby forming a C—C bond between the chemical entity and the scaffold. The above building block is disclose in WO03078446A2, the content of which is incorporated herein by reference.

The chemical entity attached to any of the above building blocks may be a selected from a large arsenal of chemical structures. Examples of chemical entities are H or entities selected among the group consisting of a $C_1$-$C_6$ alkyl, $C_2$-$C_6$ alkenyl, $C_2$-$C_6$ alkynyl, $C_4$-$C_8$ alkadienyl, $C_3$-$C_7$ cycloalkyl, $C_3$-$C_7$ cycloheteroalkyl, aryl, and heteroaryl, said group being substituted with 0-3 $R^4$, 0-3 $R^5$ and 0-3 $R^9$ or $C_1$-$C_3$ alkylene-$NR^4_2$, $C_1$-$C_3$ alkylene-$NR^4C(O)R^8$, $C_1$-$C_3$ alkylene-$NR^4C(O)OR^8$, $C_1$-$C_2$ alkylene-O—$NR^4_2$, $C_1$-$C_2$ alkylene-O—$NR^4C(O)R^8$, $C_1$-$C_2$ alkylene-O—$NR^4C(O)OR^8$ substituted with 0-3 $R^9$.

where $R^4$ is H or selected independently among the group consisting of $C_1$-$C_6$ alkyl, $C_2$-$C_6$ alkenyl, $C_2$-$C_6$ alkynyl, $C_3$-$C_7$ cycloalkyl, $C_3$-$C_7$ cycloheteroalkyl, aryl, heteroaryl, said group being substituted with 0-3 $R^9$ and $R^5$ is selected independently from —$N_3$, —CNO, —C(NOH)$NH_2$, —NHOH, —NHNHR$^6$, —C(O)R$^6$, —SnR$^6_3$, —B(OR$^6$)$_2$, —P(O)(OR$^6$)$_2$ or the group consisting of $C_2$-$C_6$ alkenyl, $C_2$-$C_6$ alkynyl, $C_4$-$C_8$ alkadienyl said group being substituted with 0-2 $R^7$, where $R^6$ is selected independently from H, $C_1$-$C_6$ alkyl, $C_3$-$C_7$ cycloalkyl, aryl or $C_1$-$C_6$ alkylene-aryl substituted with 0-5 halogen atoms selected from —F, —Cl, —Br, and —I; and $R^7$ is independently selected from —$NO_2$, —COOR$^6$, —COR$^6$, —CN, —OSiR$^6_3$, —OR$^6$ and —NR$^6_2$.

$R^8$ is H, $C_1$-$C_6$ alkyl, $C_2$-$C_6$ alkenyl, $C_2$-$C_6$ alkynyl, $C_3$-$C_7$ cycloalkyl, aryl or $C_1$-$C_6$ alkylene-aryl substituted with 0-3 substituents independently selected from —F, —Cl, —$NO_2$, —$R^3$, —$OR^3$, —$SiR^3_3$ $R^9$ is =O, —F, —Cl, —Br, —I, —CN, —$NO_2$, —OR$^6$, —NR$^6_2$, —NR$^6$—C(O)R$^8$, —NR$^6$—C(O)OR$^8$, —SR$^6$, —S(O)R$^6$, —S(O)$_2$R$^6$, —COOR$^6$, —C(O)NR$^6_2$ and —S(O)$_2$NR$^6_2$.

Cross-Link Cleavage Building Blocks

It may be advantageous to split the transfer of a chemical entity to a recipient reactive group into two separate steps, namely a cross-linking step and a cleavage step because each step can be optimized. A suitable building block for this two step process is illustrated below:

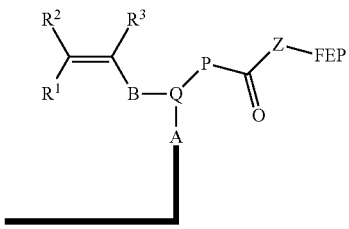

Initially, a reactive group appearing on the functional entity precursor (abbreviated FEP) reacts with a recipient reactive group, e.g. a reactive group appearing on a scaffold, thereby forming a cross-link. Subsequently, a cleavage is performed, usually by adding an aqueous oxidising agent such as $I_2$, $Br_2$, $Cl_2$, H$^+$, or a Lewis acid. The cleavage results in a transfer of the group HZ-FEP-to the recipient moiety, such as a scaffold.

In the above formula

Z is O, S, NR$^4$

Q is N, CR$^1$

P is a valence bond, O, S, NR$^4$, or a group $C_{5-7}$arylene, $C_{1-6}$ alkylene, $C_{1-6}$O-alkylene, $C_{1-6}$S-alkylene, NR$^1$-alkylene, $C_{1-6}$alkylene-O, $C_{1-6}$alkylene-S option said group being substituted with 0-3 $R^4$, 0-3 $R^5$ and 0-3 $R^9$ or $C_1$-$C_3$ alkylene-NR$^4_2$, $C_1$-$C_3$ alkylene-NR$^4$C(O)R$^8$, $C_1$-$C_3$ alkylene-NR$^4$C(O)OR$^8$, $C_1$-$C_2$ alkylene-O—NR$^4_2$, $C_1$-$C_2$ alkylene-O—NR$^4$C(O)R$^8$, $C_1$-$C_2$ alkylene-O—NR$^4$C(O)OR$^8$ substituted with 0-3 $R^9$, B is a group comprising D-E-F, in which D is a valence bond or a group $C_{1-6}$ alkylene, $C_{1-6}$ alkenylene, $C_{1-6}$ alkynylene, $C_{5-7}$arylene, or $C_{5-7}$heteroarylene, said group optionally being substituted with 1 to 4 group $R^{11}$, E is, when present, a valence bond, O, S, NR$^4$, or a group $C_{1-6}$alkylene, $C_{1-6}$ alkenylene, $C_{1-6}$ alkynylene, $C_{5-7}$arylene, or $C_{5-7}$heteroarylene, said group optionally being substituted with 1 to 4 group $R^{11}$, F is, when present, a valence bond, O, S, or $NR^4$, A is a spacing group distancing the chemical structure from the complementing element, which may be a nucleic acid, $R^1$, $R^2$, and $R^3$ are independent of each other selected among the group consisting of H, $C_1$-$C_6$ alkyl, $C_2$-$C_6$ alkenyl, $C_2$-$C_6$ alkynyl, $C_4$-$C_8$ alkadienyl, $C_3$-$C_7$ cycloalkyl, $C_3$-$C_7$ cycloheteroalkyl, aryl, and heteroaryl, said group being substituted with 0-3 $R^4$, 0-3 $R^5$ and 0-3 $R^9$ or $C_1$-$C_3$ alkylene-$NR^4{}_2$, $C_1$-$C_3$ alkylene-$NR^4C(O)R^8$, $C_1$-$C_3$ alkylene-$NR^4C(O)OR^8$, $C_1$-$C_2$ alkylene-O—$NR^4{}_2$, $C_1$-$C_2$ alkylene-O—$NR^4C(O)R^8$, $C_1$-$C_2$ alkylene-O—$NR^4C(O)OR^8$ substituted with 0-3 $R^9$, FEP is a group selected among the group consisting of H, $C_1$-$C_6$ alkyl, $C_2$-$C_6$ alkenyl, $C_2$-$C_6$ alkynyl, $C_4$-$C_8$ alkadienyl, $C_3$-$C_7$ cycloalkyl, $C_3$-$C_7$ cycloheteroalkyl, aryl, and heteroaryl, said group being substituted with 0-3 $R^4$, 0-3 $R^5$ and 0-3 $R^9$ or $C_1$-$C_3$ alkylene-$NR^4{}_2$, $C_1$-$C_3$ alkylene-$NR^4C(O)R^8$, $C_1$-$C_3$ alkylene-$NR^4C(O)OR^8$, $C_1$-$C_2$ alkylene-O—$NR^4{}_2$, $C_1$-$C_2$ alkylene-O—$NR^4C(O)R^8$, $C_1$-$C_2$ alkylene-O—$NR^4C(O)OR^8$ substituted with 0-3 $R^9$, where $R^4$ is H or selected independently among the group consisting of $C_1$-$C_6$ alkyl, $C_2$-$C_6$ alkenyl, $C_2$-$C_6$ alkynyl, $C_3$-$C_7$ cycloalkyl, $C_3$-$C_7$ cycloheteroalkyl, aryl, heteroaryl, said group being substituted with 0-3 $R^9$ and $R^5$ is selected independently from —$N_3$, —CNO, —C(NOH)$NH_2$, —NHOH, —$NHNHR^6$, —C(O)$R^6$, —$SnR^6{}_3$, —B(O$R^6$)$_2$, —P(O)(O$R^6$)$_2$ or the group consisting of $C_2$-$C_6$ alkenyl, $C_2$-$C_6$ alkynyl, $C_4$-$C_8$ alkadienyl said group being substituted with 0-2 $R^7$, where $R^6$ is selected independently from H, $C_1$-$C_6$ alkyl, $C_3$-$C_7$ cycloalkyl, aryl or $C_1$-$C_6$ alkylene-aryl substituted with 0-5 halogen atoms selected from —F, —Cl, —Br, and —I; and $R^7$ is independently selected from —$NO_2$, —COO$R^6$, —CO$R^6$, —CN, —OSi$R^6{}_3$, —O$R^6$ and —$NR^6{}_2$.

$R^8$ is H, $C_1$-$C_6$ alkyl, $C_2$-$C_6$ alkenyl, $C_2$-$C_6$ alkynyl, $C_3$-$C_7$ cycloalkyl, aryl or $C_1$-$C_6$ alkylene-aryl substituted with 0-3 substituents independently selected from —F, —Cl, —$NO_2$, —$R^3$, —O$R^3$, —Si$R^3{}_3$ $R^9$ is =O, —F, —Cl, —Br, —I, —CN, —$NO_2$, —O$R^6$, —$NR^6{}_2$, —$NR^6$—C(O)$R^8$, —$NR^6$—C(O)O$R^8$, —S$R^6$, —S(O)$R^6$, —S(O)$_2R^6$, —COO$R^6$, —C(O)$NR^6{}_2$ and —S(O)$_2NR^6{}_2$.

In a preferred embodiment Z is O or S, P is a valence bond, Q is CH, B is $CH_2$, and $R^1$, $R^2$, and $R^3$ is H. The bond between the carbonyl group and Z is cleavable with aqueous 12.

Contacting Between Target and Library

The contacting step, by which the library of bifunctional molecules is subjected under binding conditions to a target associated with a target oligonucleotide, may be referred to as the enrichment step or the selection step, as appropriate, and includes the screening of the library for display molecules having predetermined desirable characteristics. Predetermined desirable characteristics can include binding to a target, catalytically changing the target, chemically reacting with a target in a manner which alters/modifies the target or the functional activity of the target, and covalently attaching to the target as in a suicide inhibitor.

In theory, display molecules of interest can be selected based on their properties using either physical or physiological procedures. The method preferred according to the present invention is to enrich molecules with respect to binding affinity towards a target of interest. In a certain embodiment, the basic steps involve mixing the library of complexes with the immobilized target of interest. The target can be attached to a column matrix or microtitre wells with direct immobilization or by means of antibody binding or other high-affinity interactions. In another embodiment, the target and displayed molecules interact without immobilisation of the target. Displayed molecules that bind to the target will be retained on this surface, while nonbinding displayed molecules in a certain aspect of the invention will be removed during a single or a series of wash steps. The identifier oligonucleotides of complexes bound to the target can then be coupled to the target oligonucleotide. It may be considered advantageously to perform a chromatography step after or instead of the washing step, notably in cases where the target is not immobilized. After the coupling between the identifier oligonucleotide and the target oligonucleotide, the coupled oligonucleotide may be recovered and optionally amplified before the decoding step.

A significant reduction in background binders may be obtained with increased washing volumes, repeating washing steps, higher detergent concentrations and prolonged incubation during washing. Thus, the more volume and number of steps used in the washing procedure together with more stringent conditions the more efficiently the non-binders and background binders will be removed. The right stringency in the washing step can also be used to remove low-affinity specific binders. However, the washing step will also remove wanted binders if too harsh conditions are used.

A blocking step, such as incubation of solid phase with skimmed milk proteins or other inert proteins and/or mild detergent such as Tween-20 and Triton X-100, may also be used to reduce the background. The washing conditions should be as stringent as possible to remove background binding but to retain specific binders that interact with the immobilized target. Generally, washing conditions are adjusted to maintain the desired affinity binders, e.g. binders in the micromolar, nanomolar, or pocomolar range.

In traditional elution protocols, false positives due to suboptimal binding and washing conditions are difficult to circumvent and may require elaborate adjustments of experimental conditions. However, an enrichment of more than 100 to 1000 is rarely obtained. The present invention alleviates the problem with false positive being obtained because the non-specific binding complexes to a large extent remain in solution or attached to the reaction chamber such that the identifier oligonucleotide of non-binding complexes will be in a low concentration compared to the identifier oligonucleotides of binding complexes relative to the concentration of the target oligonucleotide.

The target can be any compound of interest. E.g. the target can be a protein, peptide, carbohydrate, polysaccharide, glycoprotein, hormone, receptor, antigen, antibody, virus, substrate, metabolite, transition state analogue, cofactor, inhibitor, drug, dye, nutrient, growth factor, cell, tissue, etc. without limitation. Suitable targets include, but are not limited to, angiotensin converting enzyme, renin, cyclooxygenase, 5-lipoxygenase, IIL-1 0 converting enzyme, cytokine receptors, PDGF receptor, type II inosine monophosphate dehydrogenase, β-lactamases, integrin, proteases like factor VIIa, kinases like BcrAbl/Her, phosphotases like PTP-1B, and fungal cytochrome P-450. Targets can include, but are not limited to, bradykinin, neutrophil elastase, the HIV proteins, including tat, rev, gag, int, RT, nucleocapsid etc., VEGF, bFGF, TGFβ, KGF, PDGF, GPCR, thrombin, substance P, IgE, sPLA2, red blood cells, glioblastomas, fibrin clots, PBMCs, hCG, lectins, selectins, cytokines, ICP4, complement proteins, etc.

Certain targets comprise one or more discrete binding domains. Proteins that contain these domains are involved in a variety of processes, such as cellular transporters, cholesterol movement, signal transduction and signaling functions which are involved in development and neurotransmission. See *Herz, Lipoprotein receptors: beacons to neurons?*, (2001) Trends in Neurosciences 24(4):193-195, Goldstein and Brown, The Cholesterol Quartet, (2001) Science 292: 1310-1312. The function of a discrete binding domain is often specific but it also contributes to the overall activity of the protein or polypeptide. For example, the LDL-receptor class A domain (also referred to as a class A module, a complement type repeat or an A-domain) is involved in ligand binding while the gamma-carboxyglumatic acid (Gla) domain which is found in the vitamin-K-dependent blood coagulation proteins is involved in high-affinity binding to phospholipid membranes. Other discrete binding domains include, e.g., the epidermal growth factor (EGF)-like domain in tissue-type plasminogen activator which mediates binding to liver cells and thereby regulates the clearance of this fibrinolytic enzyme from the circulation and the cytoplasmic tail of the LDL-receptor which is involved in receptor mediated endocytosis.

Individual target proteins can possess one or more discrete monomer domains, as discussed above. These proteins are often called mosaic proteins. For example, members of the LDL-receptor family contain four major structural domains: the cysteine rich A-domain repeats, epidermal growth factor precursor-like repeats, a transmembrane domain and a cytoplasmic domain. The LDL-receptor family includes members that: 1) are cell-surface receptors; 2) recognize extracellular ligands; and 3) internalize them for degradation by lysosomes. See Hussain et al., *The Mammalian Low-Density Lipoprotein Receptor Family*, (1999) Annu. Rev. Nutr. 19:141-72. For example, some members include very-low-density lipoprotein receptors (VLDL-R), apolipoprotein E receptor 2, LDLR-related protein (LRP) and megalin. Family members have the following characteristics: 1) cell-surface expression; 2) extracellular ligand binding consisting of A-domain repeats; 3) requirement of calcium for ligand binding; 4) recognition of receptor-associated protein and apolipoprotein (apo) E; 5), epidermal growth factor (EGF) precursor homology domain containing YWTD (SEQ ID NO: 75) repeats; 6) single membrane spanning region; and 7) receptor-mediated endocytosis of various ligands. See Hussain, supra. Yet, the members bind several structurally dissimilar ligands. The present invention offers the possibility of identifying two or more ligands against the same target as discussed elsewhere herein.

In some aspects of the invention, a dimer compound binding with two targets normally interacting in a biological context is identified using the methods of the present invention. Examples of such targets are factor Xa and factor VIIa. The method includes separately screening a library of bifunctional complexes and identifying suitable display molecules that binds to both targets. The two display molecules pools are then linked together. In the event m display molecules are identified having an affinity above a certain threshold (i.e. a low Kd) to a first target and n display molecules having an affinity above another or the same threshold, a dimer compound array of n times m molecules are formed. The dimer compound are subsequently screened for the ability to bind to the first and the second target molecule, thereby identifying a dimer or a range of dimers that specifically bind to the first and the second target molecule with a certain affinity.

A target can also be a surface of a non-biological origin, such as a polymer surface or a metal surface. The method of the invention may then be used to identify suitable coatings for such surfaces.

In a preferred embodiment, the desirable display molecule acts on the target without any interaction between the nucleic acid attached to the desirable encoded molecule and the target. In one embodiment, the bound complex-target aggregate can be partitioned from unbound complexes prior to or subsequent to the coupling step by a number of methods. The methods include nitrocellulose filter binding, column chromatography, filtration, affinity chromatography, centrifugation, and other well known methods. A preferred method is size-exclusion chromatography.

Briefly, the library of complexes is subjected to the target, which may include contact between the library and a column onto which the target is immobilised. Identifier oligonucleotides associated with undesirable display molecules, i.e. display molecules not bound to the target under the stringency conditions used, will pass through the column. Additional undesirable display molecules (e.g. display molecules which cross-react with other targets) may be removed by counter-selection methods. Desirable complexes are bound to the column. The target may be immobilized in a number of ways. In one embodiment, the target is immobilized through a cleavable physical link, such as one more chemical bonds. Following the interaction of the display molecule and the target, the respective oligonucleotides are coupled. The aggregate of the target and the complex may then be subjected to a size exclusion chromatography to separate the aggregate from the rest of the compounds in the media.

The complex may be provided with a cleavable linker at a position between the display molecule and the identifier oligonucleotide. When the target is immobilized the cleavable linker of the complex is preferable orthogonal to the cleavable linker that attached the target to the solid support. Subsequent to the optional size exclusion chromatography, this cleavable linker is cleaved to separate the identifier oligonucleotides of complexes having affinity towards the targets. Just to mention a single type of orthogonal cleavable linkages, one could attached to target to the solid support through a linkage that can be cleaved by a chemical agent, and the linker separating the display molecule and the identifier oligonucleotide may be selected as a photo-cleavable linkage. More specifically, the former linkage may be a disulphide bond that can be cleaved by a suitable reducing agent like DTT (dithiothreitol) and the latter linkage may be an o-nitrophenyl group.

There are other partitioning and screening processes which are compatible with this invention that are known to one of ordinary skill in the art. Such known process may be used in combination with the present inventive method. In one embodiment, the coupling products can be fractionated by a number of common methods and then each fraction is assayed for activity. The fractionization methods can include size, pH, hydrophobicity, etc.

Inherent in the present method is the selection of encoded molecules on the basis of a desired function; this can be extended to the selection of molecules with a desired function and specificity. Specificity can be required during the selection process by first extracting complexes which are capable of interacting with a non-desired "target" (negative selection, or counter-selection), followed by positive selection with the desired target. As an example, inhibitors of fungal cytochrome P-450 are known to cross-react to some extent with mammalian cytochrome P-450 (resulting in serious side effects). Highly specific inhibitors of the fungal cytochrome could be selected from a library by first removing those complexes capable of interacting with the mammalian cytochrome, followed by retention of the remaining products which are capable of interacting with the fungal cytochrome.

The present invention can be used to identify compounds that bind to different molecular targets. A small library of preferred compounds can be directly linked to an oligonucleotide that identifies the structure of the said compound. This can be done manually or using a more automatic system such as robotic equipments. These tagged compounds can then be mixed with one or more target molecules to select for compound and target pairs that bind to each other. For example, a library of compounds designed to bind preferably to protein kinases could be mixed with a library of various protein kinases to identify compounds that specifically interact with a certain protein kinase. The use of the present proximity selection procedure will in this instance generate an extensive structure activity relationship (SAR) where different binding compound are match simultaneously against different related target molecules. The above method can also be used for other target classes such as proteases, phosphatases, GPCRs, nuclear receptors and corresponding compound libraries. The information for these selections can be used to study the selectivity and specificity and to design sub-libraries with potential binding compounds.

In a prior art selection where the target is immobilized to a surface, for example in a well or a bead, the effective concentration of the target will be high locally on the surface but infinitively low in the solution. This restriction will result in low recovery of binding molecules because most of the binding molecules are free in the solution and removed in future washing steps. The present invention allows selection in solution at true equilibrium conditions between the molecular target and the binding molecules. The invention is not dependent on washing- or separation-step as is most prior art selection protocols. The amount of captured binding molecules can be varied using a suitable concentration of the target. Most of the binding molecules with a certain binding constant can be captured if the target concentration is higher than the binding constant of the binding molecules. Also the concentration of the target can be adjusted to capture binders with a certain binding constant. A high target concentration will also increase the likelihood of selecting specific binders that are present in low copy number. By using high concentration of target, the solution selection can also be used to identify binders with low binding affinity. This is especially important with screening for small fragments which normally possess low affinity but still holds important structural information that can be used in second generation library design.

In a certain embodiment, a binding platform may be constructed that can be used for almost any target. The binding platform should preferably be small enough to only allow association of a few or a single target molecule. This to ensure a solution based selection procedure with adjustable target concentration. The binding platform is primarily composed of two components; a small surface allowing association of the target molecule, and an association area/site for the target oligonucleotide. This binding platform may be designed to mediate the association of the target and target oligonucleotide to allow proximity selection in solution.

Cleavable Linkers

A cleavable linker may be positioned between the target and a solid support, between the potential drug candidate and the identifier oligonucleotide, between the molecular target and the target oligonucleotide or any other position that can provide for a separation of the identifier oligonucleotide from successful complexes from non-specific binding complexes. The cleavable linker may be selectively cleavable, i.e. conditions may selected that only cleave that particular linker.

The cleavable linkers may be selected from a large plethora of chemical structures. Examples of linkers includes, but are not limited to, linkers having an enzymatic cleavage site, linkers comprising a chemical degradable component, and linkers cleavable by electromagnetic radiation, such as light.

Examples of Linkers Cleavable by Electromagnetic Radiation (Light)

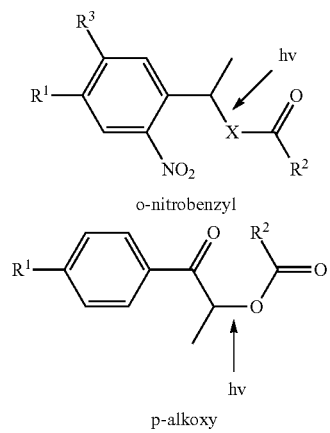

o-nitrobenzyl p-alkoxy o-nitrobenzyl in Exo Position

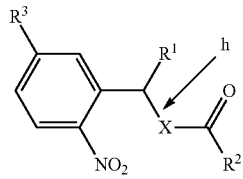

For more details see Holmes CP. J. Org. Chem. 1997, 62, 2370-2380

3-nitrophenyloxy

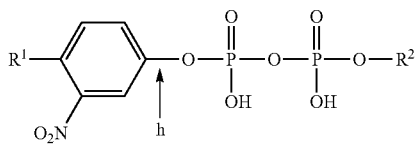

For more details see Rajasekharan Pillai, V. N. Synthesis. 1980, 1-26

Dansyl Derivatives

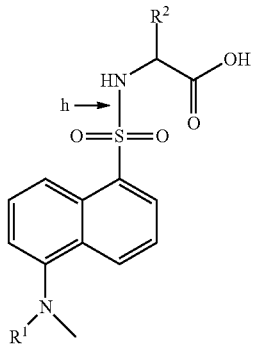

For more details see Rajasekharan Pillai, V. N. Synthesis. 1980, 1-26

Coumarin Derivatives

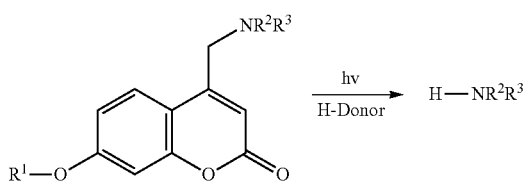

For more details see R. O. Schoenleber, B. Giese. Synlett 2003, 501-504

$R^1$ and $R^2$ can be either of the potential drug candidate and the identifier oligonucleotide, respectively. Alternatively, $R^1$ and $R^2$ can be either of the target or a solid support, respectively.

$R^3$=H or $OCH_3$

If X is O then the product will be a carboxylic acid

If X is NH the product will be a carboxamide

One specific example is the PC Spacer Phosphoramidite (Glen research catalog #10-4913-90) which can be introduced in an oligonucleotide during synthesis and cleaved by subjecting the sample in water to UV light (~300-350 nm) for 30 seconds to 1 minute.

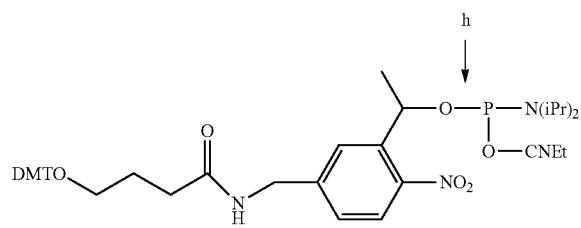

DMT=4,4'-Dimethoxytrityl
iPr=Isopropyl
CNEt=Cyanoethyl

The above PC spacer phosphoamidite is suitable incorporated in a library of complexes at a position between the identifier and the potential drug candidate. The spacer may be cleaved according to the following reaction.

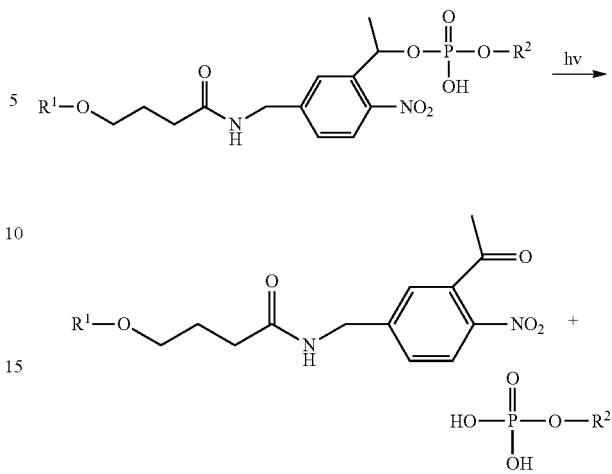

$R^1$ and $R^2$ can be either of the encoded molecule and the identifying molecule, respectively. In a preferred aspect $R^2$ is an oligonucleotide identifier and the $R^1$ is the potential drug candidate. When the linker is cleaved a phosphate group is generated allowing for further biological reactions. As an example, the phosphate group may be positioned in the 5"end of an oligonucleotide allowing for an enzymatic ligation process to take place.

Examples of Linkers Cleavable by Chemical Agents

Ester linkers can be cleaved by nucleophilic attack using e.g. hydroxide ions. In practice this can be accomplished by subjecting the target-ligand complex to a base for a short period.

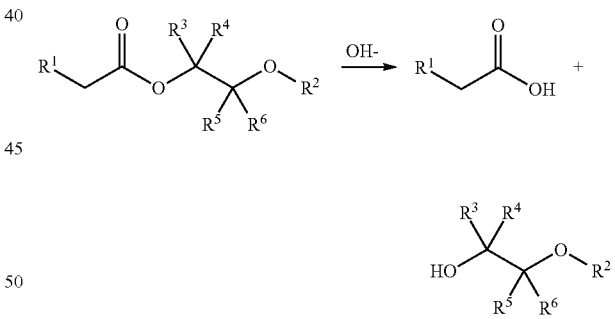

$R^1$ and $R^2$ can be the either of be the potential drug candidate or the identifier oligonucleotide, respectively. $R^{4-6}$ can be any of the following: H, CN, F, $NO_2$, $SO_2NR_2$.

Disulfide linkers can efficiently be cleaved/reduced by Tris (2-carboxyethyl) phosphine (TCEP). TCEP selectively and completely reduces even the most stable water-soluble alkyl disulfides over a wide pH range. These reductions frequently required less than 5 minutes at room temperature. TCEP is a nonvolatile and odorless reductant and unlike most other reducing agents, it is resistant to air oxidation. Trialkylphosphines such as TCEP are stable in aqueous solution, selectively reduce disulfide bonds, and are essentially unreactive toward other functional groups commonly found in proteins.

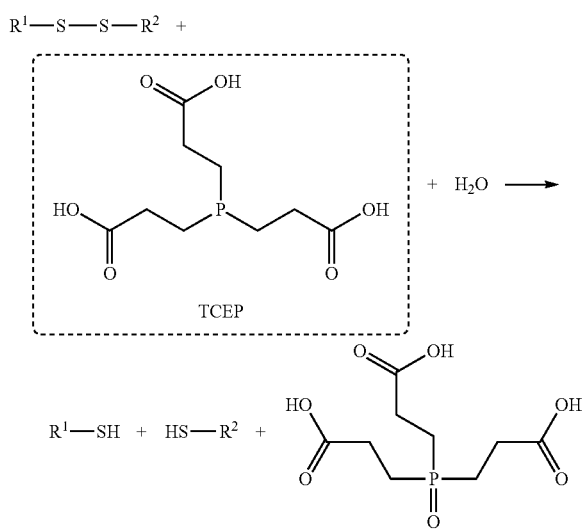

More details on the reduction of disulfide bonds can be found in Kirley, T. L. (1989), Reduction and fluorescent labeling of cyst(e)ine-containing proteins for subsequent structural analysis, *Anal. Biochem.* 180, 231 and Levison, M. E., et al. (1969), Reduction of biological substances by water-soluble phosphines: Gamma-globulin. *Experentia* 25, 126-127.

Linkers Cleavable by Enzymes

The linker connecting the potential drug candidate with the identifier oligonucleotide or the solid support and the target can include a peptide region that allows a specific cleavage using a protease. This is a well-known strategy in molecular biology. Site-specific proteases and their cognate target amino acid sequences are often used to remove the fusion protein tags that facilitate enhanced expression, solubility, secretion or purification of the fusion protein.

Various proteases can be used to accomplish a specific cleavage. The specificity is especially important when the cleavage site is presented together with other sequences such as for example the fusion proteins. Various conditions have been optimized in order to enhance the cleavage efficiency and control the specificity. These conditions are available and know in the art.

Enterokinase is one example of an enzyme (serine protease) that cut a specific amino acid sequence. Enterokinase recognition site is Asp-Asp-AspAsp-Lys (DDDDK) (SEQ ID NO: 76), and it cleaves C-terminally of Lys. Purified recombinant Enterokinase is commercially available and is highly active over wide ranges in pH (pH 4.5-9.5) and temperature (4-45° C.).

The nuclear inclusion protease from tobacco etch virus (TEV) is another commercially available and well-characterized proteases that can be used to cut at a specific amino acid sequence. TEV protease cleaves the sequence Glu-Asn-Leu-Tyr-Phe-Gln-Gly/Ser (ENLYFQG/S) (SEQ ID NO: 77) between Gln-Gly or Gln-Ser with high specificity.

Another well-known protease is thrombin that specifically cleaves the sequence Leu-Val-Pro-Arg-Gly-Ser (LVPAGS) (SEQ ID NO: 78) between Arg-Gly. Thrombin has also been used for cleavage of recombinant fusion proteins. Other sequences can also be used for thrombin cleavage; these sequences are more or less specific and more or less efficiently cleaved by thrombin. Thrombin is a highly active protease and various reaction conditions are known to the public.

Activated coagulation factor FX (FXa) is also known to be a specific and useful protease. This enzyme cleaves C-terminal of Arg at the sequence Ile-GluGly-Arg (IEGR) (SEQ ID NO: 79). FXa is frequently used to cut between fusion proteins when producing proteins with recombinant technology. Other recognition sequences can also be used for FXa.

Other types of proteolytic enzymes can also be used that recognize specific amino acid sequences. In addition, proteolytic enzymes that cleave amino acid sequences in an un-specific manner can also be used if only the linker contains an amino acid sequence in the complex molecule.

Other type of molecules such as ribozymes, catalytically active antibodies, or lipases can also be used. The only prerequisite is that the catalytically active molecule can cleave the specific structure used as the linker, or as a part of the linker, that connects the encoding region and the displayed molecule or, in the alternative the solid support and the target.

A variety of endonucleases are available that recognize and cleave a double stranded nucleic acid having a specific sequence of nucleotides. The endonuclease Eco RI is an example of a nuclease that efficiently cuts a nucleotide sequence linker comprising the sequence GAATTC (SEQ ID NO: 80) also when this sequence is close to the nucleotide sequence length. Purified recombinant Eco RI is commercially available and is highly active in a range of buffer conditions. As an example the Eco RI is working in in various protocols as indicted below (NEBuffer is available from New England Biolabs):

NEBuffer 1: [10 mM Bis Tris Propane-HCl, 10 mM MgCl2, 1 mM dithiothreitol (pH 7.0 at 25° C.)], NEBuffer 2: [50 mM NaCl, 10 mM Tris-HCl, 10 mM MgCl2, 1 mM dithiothreitol (pH 7.9 at 25° C.)], NEBuffer 3: [100 mM NaCl, 50 mM Tris-HCl, 10 mM MgCl2, 1 mM dithiothreitol (pH 7.9 at 25° C.)], NEBuffer 4: [50 mM potassium acetate, 20 mM Tris-acetate, 10 mM magnesium acetate, 1 mM dithiothreitol (pH 7.9 at 25° C.)].

Extension buffer: mM KCl, 20 mM Tris-HCl (Ph 8.8 at 25° C.), 10 mM (NH4)2 SO4, 2 mM MgSO 4 and 0.1% Triton X-100, and 200 µM dNTPs.

Determining the Identifier Oligonucleotide Sequence

The nucleotide sequence of the identifier sequence present in the coupled product is determined to identify the identity of the binding display molecule(s) and 7 or optionally the molecular target(s). In a certain embodiment of the invention, chemical entities that participated in the formation of the display molecules that binds to the target are identified. The synthesis method of the display molecule may be established if information on the chemical entities as well as the point in time they have been incorporated in the display molecule can be deduced from the identifier oligonucleotide. It may be sufficient to obtain information on the chemical structure of the various chemical entities that have participated in the display molecule to deduce the full molecule due to structural constraints during the formation. As an example, the use of different kinds of attachment chemistries may ensure that a chemical entity on a building block can only be transferred to a single position on a scaffold. Another kind of chemical constrains may be present due to steric hindrance on the scaffold molecule or the chemical entity to be transferred. In general however, it is preferred that information can be inferred from the identifier oligonucleotide sequence that enable the identification of each of the chemical entities that have participated in the formation of the encoded molecule along with the point in time in the synthesis history the chemical entities have been incorporated in the (nascent) display molecule.

Although conventional DNA sequencing methods are readily available and useful for this determination, the amount and quality of isolated bifunctional molecule may require additional manipulations prior to a sequencing reaction.

Where the amount is low, it is preferred to increase the amount of the coupled oligonucleotide sequence by polymerase chain reaction (PCR) using PCR primers directed to primer binding sites present in the identifier oligonucleotide sequence.

In one embodiment, the different coupled oligonucleotide sequences are cloned into separate sequencing vectors prior to determining their sequence by DNA sequencing methods. This is typically accomplished by amplifying the different coupled oligonucleotide sequences by PCR and then using a unique restriction endonuclease sites on the amplified product to directionally clone the amplified fragments into sequencing vectors. The cloning and sequencing of the amplified fragments then is a routine procedure that can be carried out by any of a number of molecular biological methods known in the art.

Alternatively, the bifunctional complex or the PCR amplified identifier oligonucleotide sequence can be analysed in a microarray. The array may be designed to analyse the presence of a single codon or multiple codons in a identifier oligonucleotide sequence.

In still another approach, the coupled oligonucleotide product is analysed by QPCR. Preferably, the QPCR affords information as to the chemical moieties that has participated in the formation of the display molecules and optionally the identity of the target. The QPCR approach also allows a direct investigation of the enrichment factor if two samples are analysed in parallel, one with target and the other with the target plus library. The difference in signal from these to samples will illustrate how much coupling that is due to the target mediated coupling compared to the background coupling. Various conditions can be investigated to obtain the most optimal selection procedure before the sequences are analysed to identify the precise structures of the binding molecules.

Synthesis of Nucleic Acids

Oligonucleotides can be synthesized by a variety of chemistries as is well known in the art. For synthesis of an oligonucleotide on a substrate in the direction of 3' to 5', a free hydroxy terminus is required that can be conveniently blocked and deblocked as needed. A preferred hydroxy terminus blocking group is a dimexothytrityl ether (DMT). DMT blocked termini are first deblocked, such as by treatment with 3% dichloroacetic acid in dichloromethane (DCM) as is well known for oligonucleotide synthesis, to form a free hydroxy terminus.

Nucleotides in precursor form for addition to a free hydroxy terminus in the direction of 3' to 5' require a phosphoramidate moiety having an aminodiisopropyl side chain at the 3' terminus of a nucleotide. In addition, the free hydroxy of the phosphoramidate is blocked with a cyanoethyl ester (OCNET), and the 5' terminus is blocked with a DMT ether. The addition of a 5' DMT-, 3' OCNET-blocked phosphoramidate nucleotide to a free hydroxyl requires tetrazole in acetonitrile followed by iodine oxidation and capping of unreacted hydroxyls with acetic anhydride, as is well known for oligonucleotide synthesis. The resulting product contains an added nucleotide residue with a DMT blocked 5' terminus, ready for deblocking and addition of a subsequent blocked nucleotide as before.

For synthesis of an oligonucleotide in the direction of 5' to 3', a free hydroxy terminus on the linker is required as before. However, the blocked nucleotide to be added has the blocking chemistries reversed on its 5' and 3' termini to facilitate addition in the opposite orientation. A nucleotide with a free 3' hydroxyl and 5' DMT ether is first blocked at the 3' hydroxy terminus by reaction with TBS-$C_1$ in imidazole to form a TBS ester at the 3' terminus. Then the DMT-blocked 5' terminus is deblocked with DCA in DCM as before to form a free 5' hydroxy terminus. The reagent (N,N-diisopropylamino)(cyanoethyl) phosphonamidic chloride having an aminodiisopropyl group and an OCNET ester is reacted in tetrahydrofuran (THF) with the 5' deblocked nucleotide to form the aminodiisopropyl-, OCNET-blocked phosphonamidate group on the 5' terminus. Thereafter the 3' TBS ester is removed with tetrabutylammonium fluoride (TBAF) in DCM to form a nucleotide with the phosphonamidate-blocked 5' terminus and a free 3' hydroxy terminus. Reaction in base with DMT-$C_1$ adds a DMT ether blocking group to the 3' hydroxy terminus.

The addition of the 3' DMT-, 5' OCNET-blocked phosphonamidated nucleotide to a linker substrate having a free hydroxy terminus then proceeds using the previous tetrazole reaction, as is well known for oligonucleotide polymerization. The resulting product contains an added nucleotide residue with a DMT-blocked 3' terminus, ready for deblocking with DCA in DCM and the addition of a subsequent blocked nucleotide as before.

DETAILED DISCLOSURE OF THE FIGURES

FIG. 1 outlines an embodiment for a proximity-dependent selection (PDS). The molecular target is linked to a target oligonucleotide, which in some embodiment may be unique for the target molecule. This target sequence comes in close proximity with a specific identifier oligonucleotide when the displayed molecule of a bifunctional complex binds to the target molecule. This proximity will promote the coupling between the bifunctional complex molecules that bind to the target compare to bifunctional complex in solution. Thus, there will be a selection for coupling products that contain display molecules that possess affinity for the target molecule. The final ligation product is amplified using two primers that only amplify ligated products.

In a first step, the target associate with a target oligonucleotide is mixed with a library of complexes, in which each complex comprises a display molecule attached to an identifier oligonucleotide. The display molecules are then incubated with the target. The display molecules which have an affinity towards the molecular target will bind, while the complexes not having affinity will remain in solution. Subsequent to the incubation, a connector oligonucleotide is added. The connector oligo nucleotide comprises parts that hybridise to sequences near the ends of the target and the identifier oligonucleotides, respectively. Subsequent to the addition of the connector oligonucleotide, a ligation is effected by chemical or enzymatic means. Preferably a ligase is used to ligate the target and the identifier oligonucleotides together. The connector oligonucleotide is generally added in excess to saturate the complexes in solution to avoid unspecific ligation.

After the ligation, the ligation product is amplified by PCR. Thus, a forward primer is annealed to the ligation product at the 3' end thereof and extended using a polymerase. The transcribed product comprises a site to which a second (or reverse) primer can anneal so as to provide for an extension of the second primer using the transcribed product as template. Using forward and reverse primers as indicated above together with a polymerase and suitable substrates produces amplicons, which comprises information about the display molecule as well as the molecular target. The ligated product can be introduced into a host organism using a suitable vector. The host vector may be allowed to form colonies and the colonies can be sequenced to establish the identity of the display molecule.

FIG. 2 shows various options to perform coupling between the target oligonucleotide and the identifier oligonucleotide. A. The ligation is promoted using a connector oligonucleotide that anneals both to the target oligonucleotide and the identifier oligonucleotide. The connector oligonucleotide is designed such that the ends of the identifier oligonucleotide and the target oligonucleotides are abutted. A ligase is subsequently allowed to ligate the ends together. B. A connector oligonucleotide is used to promote fill in of a gap using a polymerase and finally ligation using a ligase. C. The distal end of the target oligonucleotide overlaps the distal end of the identifier oligonucleotide, which allows a polymerase to extend the target oligonucleotide as well as the identifier oligonucleotide thereby forming a double stranded product. D. Blunt-ended ligation of single-stranded or double stranded DNA using a suitable enzyme like T4 DNA ligase.

FIG. 3 shows various methods for preparing a coupling area on an existing bifunctional complex. Conjugates between molecular targets associated with an oligonucleotide and complexes comprising a display molecule and an identifier oligonucleotide can be modified to allow a ligase to couple the oligonucleotides together. A. The identifier oligonucleotide is extended with a primer with an overhang that creates the coupling area. The extension is suitably conducted before the selection process to obtain the benefit of a double stranded nucleotide sequence. A target oligonucleotide can be ligated to the blunt end of the extended primer or a connector oligonucleotide can be used to connect the target oligonucleotide and the extended primer prior to ligation with a suitable ligase. B. The identifier oligonucleotide is annealed to a primer that binds internally. The primer is subsequently extended, suitably before the selection process. The extension forms a coupling area directly on the identifier oligonucleotide, which allows a target oligonucleotide to be annealed and ligated. C. The first step is identical to the procedure as describe in B but the target sequence has a free 5'-end that allow ligation to the 3'-end of the identifier oligonucleotide. A blunt ended single stranded ligation can be performed. Alternatively, this variation can be performed using a connector oligonucleotide and subsequent ligation. D. A primer is annealed to a identifier oligonucleotide and extended to produce a double-stranded DNA which is subsequently cut with an enzyme (e.g. restriction enzyme) to produce a single-stranded DNA portion that can be used as handle in the coupling process.

FIG. 4 shows a library versus library selection method. Different targets specifically encoded by the attached target oligonucleotides are mixed with a library of bifunctional complexes. The displayed molecules will bind to specific targets and promote the ligation through the proximity effect. This ligation will connect the target oligonucleotides with oligonucleotides that encodes for specific displayed molecules. The ligated oligonucleotides can be amplified and determined by sequencing procedures well known in the art. The ligated sequences will reveal which display molecules that bind to which target.

FIG. 5 discloses inter alia the association of the target oligonucleotide to the target. One way of associating the target oligonucleotide with the target molecule is to link the oligonucleotide through a tag introduced on the target molecule. The tag can be attached before the target is produced (e.g. a short amino acid sequence such as HIS-tag of FLAG-tag) or be modified after the target is produced. The target sequence can then be associated through the tag using a tag-binding molecule such as an antibody or other type of molecules that binds to the tag.

FIG. 6 discloses target oligonucleotide association on a cell surface. Specific receptors can be engineered to express a specific tag on the cell surface. Different tags can be used such as HIS- or FLAG-tags or other types of tags that become bound with the receptor. The tag will only be displayed on the cell surface together with the specific receptor. The target oligonucleotide is then associated with the receptor target using a mediator molecule that carries the target oligonucleotide and binds to the tag. A mediator molecule could be an antibody that binds to the tag (e.g. anti-HIS or anti-FLAG antibodies) that is associated with the target oligonucleotide. This procedure will specifically associate the target oligonucleotide with a receptor target on the cell surface which will promote a ligation between oligonucleotides of the binding displayed molecules and the target oligonucleotide.

FIG. 7 shows a target molecule with several sites for binding of ligands. The target is subjected to a library of complexes of bifunctional molecules. Display molecules of the complexes binds to the discrete sites of the molecular target thus promoting a high local concentration of the ends of the oligonucleotides which have bound to the target. Subsequently a connector oligonucleotide is added to adjoin the distal ends of the oligonucleotides together. Usually, the connector oligonucleotide is added in excess to saturate the ends of the identifier oligonucleotides free in the solution. The ends of the oligonucleotides kept together by the connector oligonucleotide are ligated together forming a coupled product. The coupled product is amplified by PCR using primers annealing to each end of the coupled product. The amplified coupled product is decoded to identify the display molecules which have bound to the in the target. In a step not shown on the figure, the two binding display molecules are coupled together via a suitable linker to form a ligand which binds to two sites of the target. Suitable, the dimer comprising the two revealed display molecules and the linker is synthesised by organic synthesis.

Libraries of bifunctional complexes can also be screened against each other using the present invention. Such an embodiment allows the detecting of pairs of displayed molecules that bind to the same target at different or the same binding site or pair of displayed molecules that bind to different targets. The power of the screening libraries in the above fashion is indicated by the fact that a library of e.g. $10^4$ different displayed molecules generates a total combination of display molecules of $10^8$ when pair of binders are searched for.

FIG. 8 discloses a library of bifunctional complexes which is presented to a target having a site possible to be occupied by two display molecules. Initially, the target is mixed with the library of bifunctional complexes under conditions which promote a binding interaction to take place. A first bifunctional complex associates with the target to form the target associated with the target oligonucleotide. Subsequently to or simultaneously with the binding of the first display molecule, a second complex binds to the same site of the target. The display molecules may or may not be reacted with each other to form a covalent linkage between the display molecules. In another embodiment, the two display molecules are connected via a suitable linker or reacted with an external reactant so as to form a single molecule. After the binding interaction of the library of complexes with the target, the ends of the complexes which comprises display molecules that binds to the target are joint together. In an aspect of the invention, the ends are joined together using a connector polynucleotide. The connector polynucleotide is preferably added in excess to saturate ends of identifier oligonucleotides which are not part of a binding complex. After the hybridisation event between the ends of the identifier oligonucleotides and the connector oligonucleotide a ligation is conducted. Suitably the ligation is performed by a ligase to form a coupled product, which can be used as a template by a polymerase. After the ligation, the coupled product is amplified by PCR to form PCR amplicons comprising information of the display molecules which have participated in the binding interaction.

FIG. 9 discloses a two (or more) step identification method. In a first step the method as disclosed in FIG. 1 is conducted and in the second step a new library prepared upon the knowledge harvested in the first library is used to generate the second generation library. Initially, a library of complexes are is presented to a target having a binding site. In the library, display molecules having a binding affinity above a certain threshold is not present, illustrated on the drawing with a display molecule only having a partial fit in the binding site of the target. In the synthesis of the second generation library components used in the synthesis of the low binding display molecule are shuffled with further components and/or the low binding display molecule is added or subtracted a structural unit. As an example, a further round of addition of chemical entities can be conducted. For systems for complex generation relying on the natural translation system a deletion, alteration or addition of nucleic acid can be performed. The second generation library is presented to the a target again. In the event the alteration of the initial low binding molecule has been successful display molecules are generated which binds with a higher affinity towards the target.

FIG. 10 discloses two targets which are attached to each other prior to the mixing with the library of complexes. The attachment can be natural, i.e. the association between target 1 and target 2 occur in a biological context or the attachment can be artificial, i.e. the association between target 1 and target 2 is obtained by a chemical synthesis. In the latter instance, the association between the targets may be obtained by any chemical or enzymatic means which ensure a linkage. The association of the targets may also be obtained by expressing target 1 and target 2 as a fusion protein, i.e. a single protein having two distinct targets or monomer domains. In an embodiment, one of the targets in the fusion protein is a capturing protein, like streptavidin. In the event the library is spiked with complexes having a ligand against the capturing protein, like biotin, it is feasible to form a connection between the fusion protein and a member of the library. The further functionality, i.e. target 2, of the fusion protein may be then be subjected to a screening process to find binder from the library.

During the mixing step, the two attached targets are contacted with the library of complexes under binding conditions. The library may be spiked with a complex comprising a compounds known to bind to the one of the targets in order to find suitable binders against another target. If the library comprises suitable binding display molecules, two ends of the binding complexes is positioned in close proximity. The addition of a connector oligonucleotide ensures that the ends are kept close together when a ligase is allowed to perform the action of ligating the ends together. The resulting PCR product comprises genetic information which encodes both the display molecules that have participated in the binding interaction with target 1 and target 2.

Examples Illustrating the Second Aspect of the Present Invention

Example 1

Oligonucleotide Sequences
Target Sequence (ES-1)

(SEQ ID NO: 69)
5'-X-TAGTC GATGT AGCTA GCTAG TGCGC CAATG CCTTA TCAGC

Identifier Sequence (IS-1) (Extension Part)

(SEQ ID NO: 70)
5'-GATCG ATGAC TGACG CCGGT AAATCTACCGTCTAAGCTG-Y-3'

Underlined sequence is reverse primer binding site
Control Identifier Sequence (CIS-1) (Extension Part)

(SEQ ID NO: 71)
5'-GATCG ATGAC TGACG CCGGT *gacgt cgtag atatc gatgc* AAATCTACCGTCTAAGCTG-Z-3'

Underlined sequence is reverse primer
Connector Sequence (CS-1)

(SEQ ID NO: 72)
5'-AAAAGGAATAGTCG-CTAGCTACTGTTTT

Primers (Forward PR-1 and Reverse PR-2)

PR-1:
(SEQ ID NO: 73)
5'-TAGTC GATGT AGCTA GCTAG

PR-2:
(SEQ ID NO: 74)
5'-CAGCT TAGAC GGTAG ATTT

Target Labelling with Oligonucleotide Sequence.

The target molecule (streptavidin) is modified with an oligonucleotide sequence using a terminus modifier that allow direct coupling to the target(s) molecule. The oligonucleotide sequence ES-1 is synthesised with the 5'-Thiol-Modifier (Glen Research, #10-1926-90) to produce a oligonucleotide that can be coupled to the target(s) through the 5'-end (designated X in the ES-1).

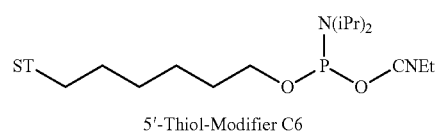

5'-Thiol-Modifier C6

The covalent attachment of the oligonucleotide at the target is carried out with the aid of the heterobispecific crosslinker Sulfosuccinimidyl-4-(N-maleimidomethyl)cyclohexane-1-carboxylate (sSMMCC). The 6-amino groups of lysine side chains of the target(s) are first derivatized with sSMCC cross linker to provide a maleimide functionality, which subsequently is reacted with the thiolated oligonucleotide.

Protecol: Dissolve approx. 2 mg of sSMCC in 60 μl of DMF. Add the sSMCC solution to 200 μl of a 100 μM solution of streptavidin in PBS buffer pH 7.3 and incubate in the dark at room temperature for about 1 hour. The excess sSMCC is removed using NAPS or NAP10 (Pharmacia) using a PBSE buffer. The thiolated oligo (ES-1) is activated in TE buffer, pH 7.4 using 1 mM DDT and excess removed using spin column (BioRad). The activated streptavidin and oligonucleotide are preferably used directly in the cross linking reaction by mixing and incubation for about 1 hour in the dark at room temperature. The modified streptavidin is preferably purified on a size-exclusion column or a anion-exchange column (MonoQ HR5/5, Pharmacia).

Bifunctional Complex Molecules.

Bifunctional complexes are preferably molecules that are composed of a nucleotide sequence that encodes for the displayed molecule. These complexes can be generated using various procedures, as disclosed elsewhere herein. The bifunctional complexes preferably contain an oligonucleotide that can be ligated or otherwise connected to the oligonucleotide sequence on the target mediated by the binding of the display molecule to the target.

Figure 14A:
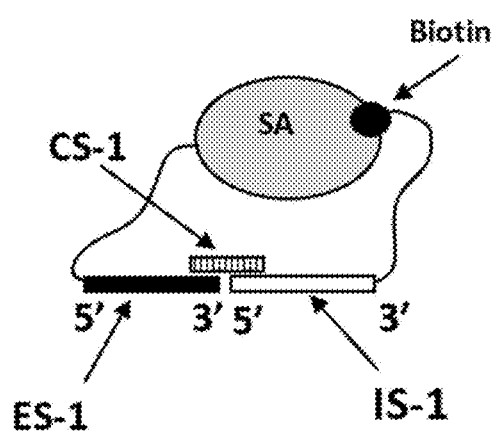
FIG. 14A discloses a bifunctional complex as the IS-1 sequence which is labelled with a biotin in the 3' end (designated Y in the sequence).

FIG. 14A describes the bifunctional complex as the IS-1 sequence which is labelled with a biotin in the 3' end (designated Y in the sequence). This oligonucleotide is synthesized using Biotin-dT (Glen Research, #10-1038-95), which will function as the display molecule and the oligonucleotide sequence encoding the biotin moiety. The displayed biotin molecule has high affinity for streptavidin which will bring the coding oligonucleotide (CS-1) in close proximity of the identifier sequence (IS-1). This will promote the ligation between the ES-1 and the IS-1 oligonucleotides as shown below. The ligation is mediated by the connector sequence (CS-1).

Figure 14B:
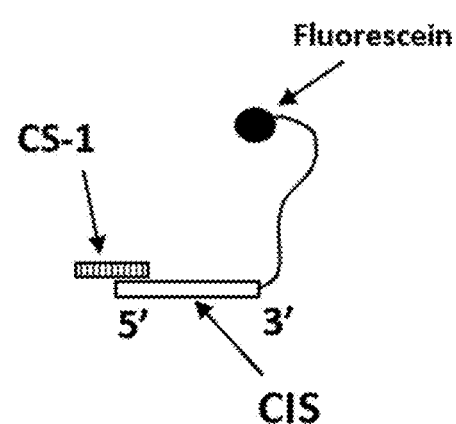
FIG. 14B discloses a different bifunctional complex with a Fluorescein as display molecule.

FIG. 14B describes a different bifunctional complex with a Fluorescein as display molecule. The flurorescein will not bind to the target molecule (streptavidin) resulting in no proximity ligation between the ES-1 and the IS-1 oligonucleotides.

Selection Through Proximity Ligation 20 pM bifunctional complex (IS-1) is mixed with 100 pM conjugated target molecule to allow binding of the biotin molecule to streptavidin. Another bifunctional complex (CIS-1) was used as a control (100 pM) with a different display molecule (Fluorescein) included in the synthesis of the oligonucleotide as a Fluorescein-dT (Glen Research, #10-1056-95). This displayed molecule is encoded by another unique sequence in the CIS-1 oligonucleotide. However, the ligation region is identical to the IS-1 oligonucleotide allowing ligation if proximity is achieved. The CIS-1 oligonucleotide is 10 nucleotides longer permitting the distinction from the 1S-1 oligonucleotide by running an agorose gel and determining the length of the oligonucleotides. The mixtures were incubated in 50 mM KCl, 10 mM Tris-HCl. pH 8.3, 1.5 mM MgCl2, 0.15 mM ATP. pH 7.4 for 1 hour to allow association of the Biotin (or Fluorescein) to streptavidin.

The connector sequence (CS-1) is then added at 400 nM concentration to promote the connection between the ES-1 and 1S-1 oligonucleotides together with 2 ∪ T4 DNA ligase to start the ligation. The reaction was keep at 30° C. for 5 min and then 80° C. for 20 min. The relatively high concentration of the connector oligonucleotide will saturate all 1S-1 that have not been brought into proximity of an encoding sequence.

Amplification of the ligated products was performed with the polymerase chain reaction (PCR) using primers corresponding to the 5'-end of the encoding sequence (PR-1: 5'-TAGTC GATGT AGCTA GCTAG) (SEQ ID NO: 81) and the 3'-end of the identifier oligonucleotide sequence (PR-2: 5'-CAGCT TAGAC GGTAG ATTT) (SEQ ID NO: 82). The primers are design to only amplify the ligated product. PCR was performed using Ready-To-Go (RTG) PCR beads (Amersham Biosciences) and 10 pmol of each primer in a reaction volume of 25 μl. The PCR reaction consisted of an initial denaturation step of 94° C. for 2 minutes followed by 20-45 cycles of denaturation at 94° C. for 30 seconds, annealing at 58° C. for 1 minute and extension at 72° C. for 1 minute. A final extension step of 2 minutes at 72° C. was included. The PCR products were resolved by agarose gel electrophoresis and the band corresponding to the expected size was cut from the gel and purified using QIAquick Gel Extraction Kit (QIAGEN).

The different length of the Biotin and Fluorescein identifier oligonucleotide sequences (1S-1 and CIS-1) is used to verify that the bifunctional complex with Biotin have been enriched through the binding to streptavidin.

This example describes a selection using two different bifunctional complexes. The same approach can be used for larger libraries, at least up to $10^{14}$ different molecules. The same approach is used when screening library versus library. In this case the targets are encoded by different sequences but with identical coupling area.

Cloning/Sequencing

To sequence individual PCR fragments the purified PCR products were cloned into the pCR4-TOPO vector (Invitrogen) according to the manufacturer's instructions. The resulting mixture was used for transformation of TOP10 *E. coli* cells (Invitrogen) using standard procedures. The cells were plated on growth medium containing 100 μg/ml ampicillin and left at 37° C. for 12-16 hours. Individual *E. coli* clones were picked and transferred to PCR wells containing 50 μl water. These wells were then boiled for 5 minutes and 20 μl mixture from each well was used in a PCR reaction using RTG PCR beads and 5 pmol each of M13 forward and reverse primers according to the manufacturer's instructions. A sample of each PCR product was then treated with Exonuclease I (USB) and Shrimp Alkaline Phosphatase (USB) to remove degrade single stranded DNA and dNTPs and sequenced using the DYEnamic ET cycle sequencing kit (Amersham Biosciences) according to the manufacturer's instructions and the reactions were analyzed on a MegaBace 4000 capillary sequencer (Amersham Biosciences). Sequence outputs were analyzed with Contig Express software (Informax Inc.).

Example 2: Library Versus Library

A library of bifunctional complexes is screened against another library of encoded peptides or proteins. Examples of other encoded peptides are ribosome displayed peptides or mRNA displayed peptides. This example describes the use of bifunctional complexes together with mRNA displayed targets to perform library versus library screening. Any other library, where the genotype is associated with the phenotype, can be used together with bifunctional complexes as described in this invention.

A freshly transcribed mRNA (0.5-2.5 nmol) is prepared from an appropriate library. The transcribed mRNA library is hybridized to biotinylated puromycin-linker (about 0.5 nmol) in 300 µl binding buffer (30 mM Tris, pH 7.0, 250 mM NaCl) by heating to 85° C. for 30 sec followed by cooling to 4° C. in 5 min. 100 µl pre-washed Neutravidin beads (Pierce) is then added to the hybridization mixture and incubated for 30 min at 4° C. under rocking. Subsequently, the beads are washed in 3× 100 µl binding buffer followed by centrifugation to remove the liquid phase. The moist beads were then irradiated for 15 min at room temperature with a 25 W UV-lamp (Pyrex-filter, λ>300 nm). Subsequently, the beads are washed with 100 µl µlain water to yield the photocrosslinked mRNA-puromycin template which is directly used for mRNA-peptide fusion formation in rabbit reticulocyte lysate to produce the mRNA-protein fusions library according to the literature (Kurz et al., Nucleic Acids Res. 2000, 28:83). The puromycin-linker is also prepared according to Kurz et al. and biotinylated by carbamate bond formation between the puromycin amino group (50 µM) and the photo-cleavable biotin-reagent (NHS-PC-Biotin, 5 mM, EZ-Link™-Biotin, Pierce Chemicals) in 25% DMSO/water for 2 h at room temperature followed by NaCl/EtOH precipitation.

The mRNA-peptide fusion library is then converted by a suitable primer to contain a coupling area. The coupling area is formed by a primer partly complementary to the distal region of the mRNA and which is able to promote an extension on the mRNA strand with the coupling area. This coupling area is then used in the selection procedure to couple the target oligonucleotide with the identifier oligonucleotide mediated by the binding of displayed molecules to the mRNA-peptide fusions.

1-100 pmol bifunctional complex library molecules are mixed with 1-100 pmol mRNA-peptide fusion library in a binding buffer (50 mM KCl, 10 mM Tris-HCl. pH 8.3, 1.5 mM MgCl2, 0.15 mM ATP. pH 7.4) for 1 hour to allow binding of the displayed molecules to the mRNA-peptide fusion molecules. The connector sequence (an oligonucleotide the is complementary to the coupling area is then added at about 400 nM concentration to promote the connection between the target and identifier oligonucleotides. Subsequently, 2 U T4 DNA ligase is added to start the ligation. The reaction is kept at 30° C. for 5 min and then 80° C. for 20 min. Amplification of the ligated products is performed using a polymerase chain reaction (PCR) using primers corresponding to the 5'-end of the target oligonucleotide and the 3'-end of the identifier oligonucleotide. The primers are design to only amplify the ligated product. PCR is performed using Ready-To-Go (RTG) PCR beads (Amersham Biosciences) and 10 pmol each primer in a reaction volume of 25 µl. The PCR reaction consisted of an initial denaturation step of 94° C. for 2 minutes followed by 20-45 cycles of denaturation at 94° C. for 30 seconds, annealing at 58° C. for 1 minute and extension at 72° C. for 1 minute. A final extension step of 2 minutes at 72° C. was included. The PCR products are resolved by agarose gel electrophoresis and the band corresponding to the expected size is cut from the gel and purified using QIAquick Gel Extraction Kit (QIAGEN).

Example 3—Illustrating the First Aspect of the Present Invention

A preferred embodiment of the invention utilizing a universal Taqman probe is shown in FIG. 11. Four codons are shown (P1 through P4, bold pattern) along with flanking regions (light pattern). A universal Taqman probe anneals to a region adjacent to the codon region, but within the amplicon defined by the universal PCR primers Pr. 1 and Pr. 2. These primers could be the same as used for amplification of the identifier oligonucleotides encoding binders after an enrichment process on a specific target. However, if minimal length templates are preferred during the encoding process, the region involved in Taqman probe annealing could be appended to the library identifier oligonucleotides by e.g. overlap PCR, ligation, or by employing a long downstream PCR primer containing the necessary sequences. The added length corresponding to the region necessary for annealing of the Taqman probe would be form 20 to 40 nts depending on the type of TaqMan probe and TA of the PCR primers. The Q-PCR reactions are preferably performed in a 96- or 384-well format on a real-time PCR thermocycling machine.

Figure 11A:
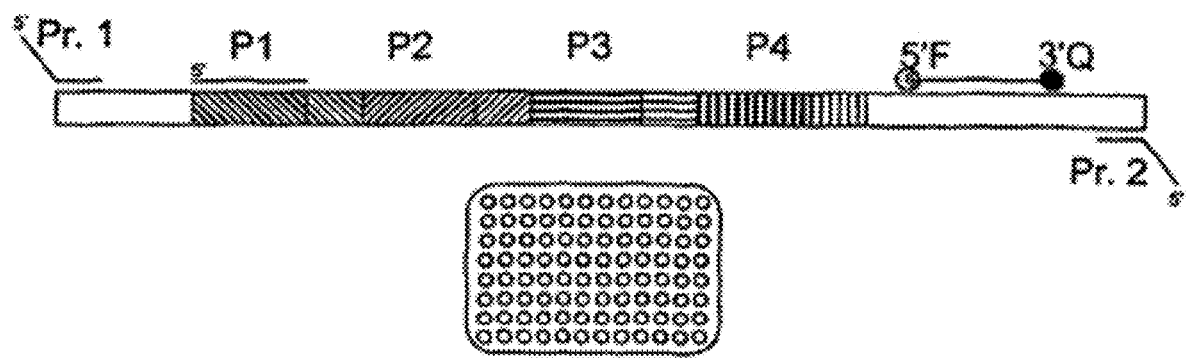
FIGS. 11A and B each disclose an embodiment of using a Taqman probe (5' nuclease probe) in the measurement of the presence or absence of a certain codon.

FIG. 11A shows the detection of abundance of a specific codon sequence in position one. Similar primers are prepared for all codon sequences. For each codon sequence utilized to encode a specific BB in the library a Q-PCR reaction is performed with a primer oligonucleotide complementary to the codon sequence in question. A downstream universal reverse primer Pr. 2 is provided after the Taqman probe to provide for an exponential amplification of the PCR amplicon. The setup is most suited for cases where the codon constitutes a length corresponding to a length suitable for a PCR primer.

Figure 11B:
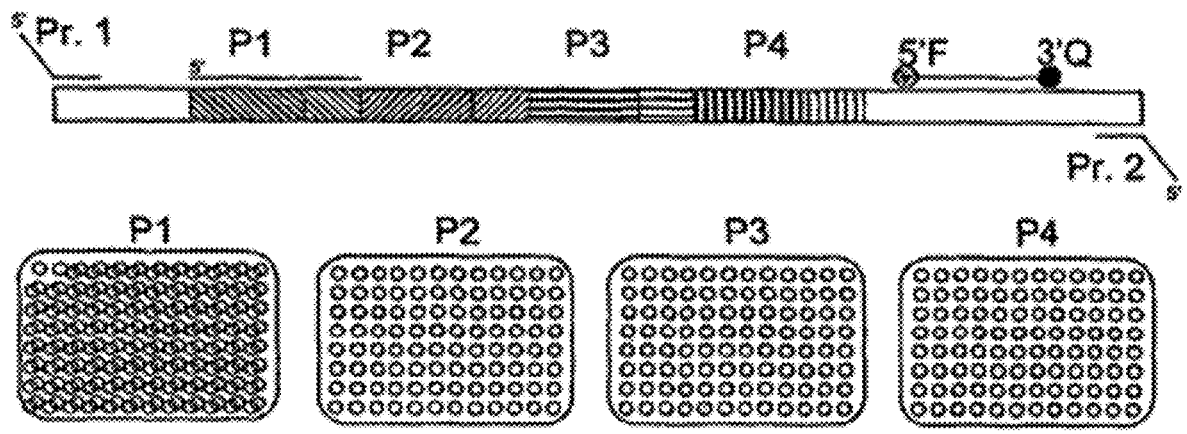

FIG. 11B shows the detection of abundance of a specific codon sequence in a specific codon position using a primer which is complementing a codon and a framing sequence. Similar primers are used for all the codons and framing sequences. For each codon sequence utilized to encode a specific BB at a specific codon position in the library a Q-PCR reaction is performed with an oligo complementary to the codon sequence in question as well as a short region up- or downstream of the codon region which ensures extension of the primer in a PCR reaction only when annealed to the codon sequence in that specific codon position. The number of specific primers and Q-PCR reactions needed to cover all codon sequences in all possible codon positions equals the number of codon sequences times the number of codon positions. Thus, monitoring the abundance of 96 different codon sequences in 4 different positions can be performed in a single run on four 96 wells micro titre plates (as shown in FIG. 11B) or a single 384 well plate on a suitable instrument. This architecture allows for the decoding of a $8.5 \times 10^7$ library of different encoded molecules.

Quantification is performed relative to the amount of full-length PCR product obtained in a parallel control reaction on the same input material performed with the two external PCR primers Pr. 1+Pr. 2. Theoretically, a similar rate of accumulation of this control amplicon compared to the accumulation of a product utilizing a single codon+ sequence specific primer would indicate a 100% dominance of this particular sequence in the position in question.

Although the setups shown in FIGS. 11A and 11B employ a Taqman probe strategy, other detection systems (SYBR green, Molecular Beacons etc.) could be utilized. In theory, multiplex reactions employing up to 4 different fluorofors in the same reaction could increase throughput correspondingly.

An example of how a deconvolution process of a library of encoded molecules occurs is described in the following. Imagine that at the end of a selection scheme a pool of 3 ligand families (and the corresponding coding templates) are dominating the population and present at approx. the same concentration. Three different chemical entities are present in the first position of the encoded compounds, and each of these chemical entities are present in combination with one unique chemical entity out of 3 different chemical entities in position P2. Only one chemical entity in position 3 gives rise to active binders, whereas any of a 20% subset of chemical entities (e.g. determined by charge, size or other characteristics) are present in position 4. The outcome of the initial codon profile analysis would be: 3 codon sequences are equally dominating in position P1, 3 other codon sequences in position P2, 1 unique codon sequence is dominant in P3 whereas somewhat similarly increased levels of 20% of the codon sequences (background levels of the remaining 80% sequences) are seen in P4. In such cases it could be relevant to use an iterative Q-PCR ("IQ-PCR") strategy to perform a further deconvolution of a library after selection. Again with reference to the example above, by taking the PCR products from the 3 individual wells that contained primers giving the high yields in position P1, diluting the product appropriately and performing a second round of Q-PCR on each of these identifier oligonucleotides separately, it would be possible to deduce which codon sequence(s) is preferred in P2 when a given codon sequence is present in P1.

The invention has been described in detail with reference to preferred embodiments thereof. However, it will be appreciated that those skilled in the art, upon consideration of this disclosure, may make modifications and improvements within the spirit and scope of the invention.

The invention claimed is:

1. A method of identifying a dimer compound that binds to different molecular targets, the method comprising the steps of:
   i) providing a first library of bifunctional complexes, each complex comprising a first display molecule and a first identifier oligonucleotide;
   ii) exposing the first library to an environment comprising a first target, and identifying first display molecules that bind to the first target with a predetermined binding affinity;
   iii) providing a second library of bifunctional complexes, each complex comprising a second display molecule and a second identifier oligonucleotide;
   iv) exposing the second library to an environment comprising a second target, and identifying second display molecules that bind to the second target with a predetermined binding affinity;
   v) forming dimer compounds by linking first and second display molecules identified in steps ii) and iv), respectively;
   vi) exposing the dimer compounds to an environment comprising the first and second targets; and
   vii) identifying dimer compounds binding the first and second targets with a predetermined binding affinity.

2. The method of claim 1, wherein the dimer compounds promote a binding of the first and second targets.

3. The method of claim 1, wherein the dimer compounds prevent the first and second targets from binding to each other.

4. The method of claim 1, wherein the dimer compounds are scaffolded molecules.

5. The method of claim 1, wherein the dimer compounds are formed by linking first and second display molecules by a linker.

6. The method of claim 1, wherein the dimer compounds are selected from the group consisting of molecules comprising one or more structures selected from the group consisting of monofunctional, difunctional, trifunctional and oligofunctional nonaromatic carbocycles;

molecules comprising one or more structures selected from the group consisting of monocyclic, bicyclic, tricyclic, polycyclic and bridged polycyclic hydrocarbons;

molecules comprising one or more structures selected from the group consisting of monofunctional, difunctional, trifunctional and oligofunctional nonaromatic heterocycles;

molecules comprising one or more structures selected from the group consisting of monocyclic, bicyclic, tricyclic, polycyclic and bridged polycyclic heterocycles;

molecules comprising one or more structures selected from the group consisting of monofunctional, difunctional, trifunctional and oligofunctional aromatic carbocycles;

molecules comprising one or more structures selected from the group consisting of monocyclic, bicyclic, tricyclic and polycyclic aromatic carbocycles; and molecules comprising one or more structures selected from the group consisting of monofunctional, difunctional, trifunctional and oligofunctional aromatic heterocycles.

7. The method of claim 1, wherein the dimer compounds are small non-peptide molecules.

8. The method of claim 1, wherein the dimer compounds are cyclic molecules comprising a plurality of covalently linked amino acid residues.

9. The method of claim 8, wherein the dimer compounds have a molecular weight of less than 1000 Dalton, preferably less than 500 Dalton.

10. The method of claim 1, wherein the dimer compounds are not nucleic acids or alpha-polypeptides.

11. The method of claim 1, wherein the targets are molecular targets of biological origin.

12. The method according to claim 11, wherein one of the molecular targets is immobilized on a solid support.

13. The method of claim 1, wherein the targets are selected from proteins, glycoproteins, peptides, carbohydrates, polysaccharides, hormones, viruses and cells.

14. The method of claim 1, wherein the identifier oligonucleotides are on a double-stranded form.

15. The method of claim 1, wherein at least one library of bifunctional complexes is prepared by split-and-mix synthesis.

16. The method of claim 1, wherein nucleotide monomers of the identifier oligonucleotides are composed of a nucleobase moiety and backbone units comprising sugar moieties and inter-nucleoside linkers.

17. The method of claim 16, wherein the nucleobases are selected from adenine, guanine, thymine, cytosine, uracil, purine, xanthine, diamino-purine, 8-oxo-N6-methyl-adenine, 7-deaza-xanthine, 7-deaza-guanine, N4,N4-ethano-cytosin, N6,N6-ethano-2,6-diamino-purine, 5-methyl-cytosine, 5-(C3-C6)-alkynyl-cytosine, 5-fluoro-uracil, 5-bromouracil, pseudo-isocytosine, 2-hydroxy-5-methyl-4-triazolo-pyridine, iso-cytosine, iso-guanine, and inosine.

18. The method of claim 16, wherein the backbone units are selected from the group consisting of

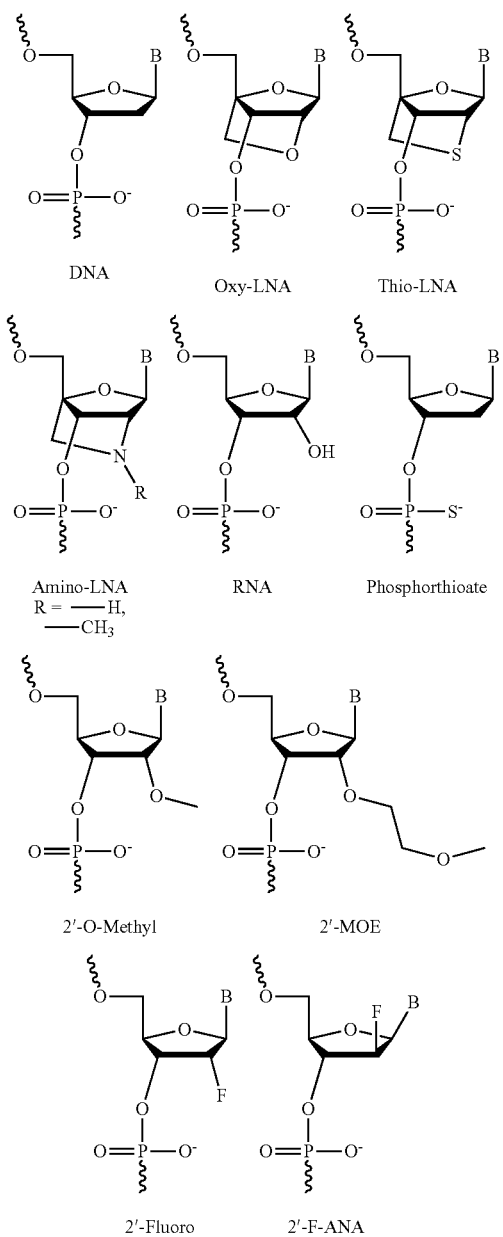

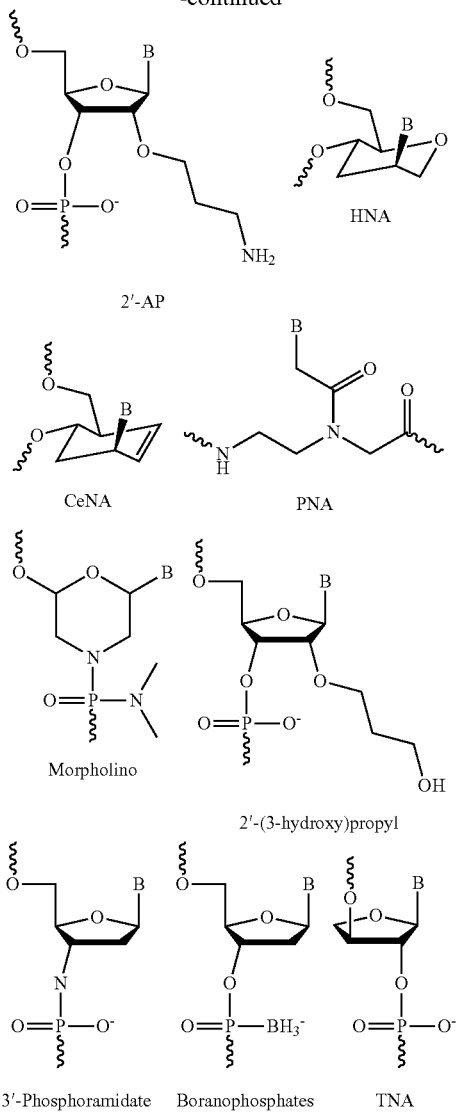

wherein B denotes a nucleobase.

19. The method of claim 16, wherein the sugar moieties of the backbone units are selected from the group of pentoses consisting of ribose, 2'-deoxyribose, 2'-O-methyl-ribose, 2'-flour-ribose, and 2'-4'-O-methylene-ribose (LNA).

20. The method of claim 16, wherein the internucleoside linkers are selected from phospodiester linkages, phosphorothioate linkages, methyl-phosphonate, linkages, phosphoramidate linkages, phosphotriester linkages, and phosphodithioate linkages.

* * * * *